(12) United States Patent
Parish et al.

(10) Patent No.: US 11,542,505 B1
(45) Date of Patent: Jan. 3, 2023

(54) SUBSTITUTED RIG-I AGONISTS: COMPOSITIONS AND METHODS THEREOF

(71) Applicants: Merck Sharp & Dohme Corp., Rahway, NJ (US); Craig A. Parish, Tenafly, NJ (US); Hongwu Wang, Westfield, NJ (US); Wonsuk Chang, Princeton, NJ (US); Quang T. Truong, Morganville, NJ (US); Tony Siu, Brookline, MA (US); Anne Mai Wassermann, Boston, MA (US)

(72) Inventors: Craig A. Parish, Tenafly, NJ (US); Hongwu Wang, Westfield, NJ (US); Wonsuk Chang, Princeton, NJ (US); Quang T. Truong, Morganville, NJ (US); Tony Siu, Brookline, MA (US); Anne Mai Wassermann, Boston, MA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 29 days.

(21) Appl. No.: 17/047,271

(22) PCT Filed: Apr. 15, 2019

(86) PCT No.: PCT/US2019/027423
§ 371 (c)(1),
(2) Date: Oct. 13, 2020

(87) PCT Pub. No.: WO2019/204179
PCT Pub. Date: Oct. 24, 2019

Related U.S. Application Data

(60) Provisional application No. 62/660,568, filed on Apr. 20, 2018.

(51) Int. Cl.
*C12N 15/113* (2010.01)
*C07H 21/02* (2006.01)

(52) U.S. Cl.
CPC ......... *C12N 15/1136* (2013.01); *C07H 21/02* (2013.01); *C12N 2310/17* (2013.01); *C12N 2310/315* (2013.01); *C12N 2310/321* (2013.01); *C12N 2310/322* (2013.01); *C12N 2310/33* (2013.01); *C12N 2310/346* (2013.01); *C12N 2310/531* (2013.01); *C12N 2310/533* (2013.01)

(58) Field of Classification Search
CPC ............... C07H 21/02; C12N 2310/17; C12N 2310/315; C12N 2310/321; C12N 2310/322; C12N 2310/33; C12N 2310/346; C12N 2310/531; C12N 2310/533
See application file for complete search history.

(56) References Cited

U.S. PATENT DOCUMENTS

| | | | |
|---|---|---|---|
| 7,488,802 | B2 | 2/2009 | Collins et al. |
| 7,521,051 | B2 | 4/2009 | Collins et al. |
| 7,655,785 | B1 | 2/2010 | Bentwich |
| 8,008,449 | B2 | 8/2011 | Korman et al. |
| 8,168,757 | B2 | 5/2012 | Finnefroch et al. |
| 8,354,509 | B2 | 1/2013 | Carven et al. |
| 8,383,796 | B2 | 2/2013 | Korman et al. |
| 9,439,962 | B2 | 9/2016 | Honjo et al. |
| 2008/0025979 | A1 | 1/2008 | Honjo et al. |
| 2009/0111765 | A1 | 4/2009 | Hartmann et al. |
| 2011/0271358 | A1 | 11/2011 | Freeman et al. |
| 2013/0037977 | A1 | 2/2013 | Burke et al. |
| 2016/0152983 | A1 | 6/2016 | Goldeck et al. |

FOREIGN PATENT DOCUMENTS

| | | |
|---|---|---|
| EP | 3045536 A1 | 7/2016 |
| WO | 2004004771 A1 | 1/2004 |
| WO | 2004056875 A1 | 7/2004 |
| WO | 2004072286 A1 | 8/2004 |
| WO | 2010027827 A2 | 3/2010 |
| WO | 2010077634 A1 | 7/2010 |
| WO | 2011066342 A2 | 6/2011 |
| WO | 2013019906 A1 | 2/2013 |
| WO | 2014159990 A1 | 10/2014 |
| WO | 2016179034 A2 | 11/2016 |
| WO | 2017173427 A1 | 10/2017 |
| WO | 2019204743 A1 | 10/2019 |

OTHER PUBLICATIONS

Kasumba et al (Trends Pharmacol Sci . Feb. 2019;40(2):116-127) (Year: 2019).*
Ablasser, Andrea et al., RIG-I-dependent sensing of poly(dA:dT) through the induction of an RNA polymerase III-transcribed RNA intermediate, Nature Immunology, 2009, 1065-1072, 10(10).
Chen, Y. Grace et al., Sensing Self and Foreign Circular RNAs by Intron Identity, Molecular Cell, 2017, 228-238 (e1-e5), 67(2).
Chiang, Cindy, Sequence-Specific Modifications Enhance the Broad-Spectrum Antiviral Response Activated by RIG-I Agonists, Journal of Virology, 2015, 8011-8025, vol. 89, No. 15.
Civril, Filiz et al., The RIG-I ATPase domain structure reveals insights into ATP-dependent antiviral signalling, EMBO reports, 2011, 1127-1134, 12(11).
Devarkar, Swapnil C. et al., Structural basis for m7G recognition and 2'-0-methyl discrimination in capped RNAs by the innate immune receptor RIG-I, PNAS, 2016, 596-601, 113(3).
Duewell, P. et al., RIG-I-like helicases induce immunogenic cell death of pancreatic cancer cells and sensitize tumors toward killing by CD8+ T cells, Cell Death and Differentiation, 2014, 1825-1837, 21(12).

(Continued)

*Primary Examiner* — Richard A Schnizer
(74) *Attorney, Agent, or Firm* — Steven C. Pageau; Anna L. Cocuzzo

(57) ABSTRACT

This invention provides compositions, compounds, and uses thereof, wherein said compounds comprise a single strand oligonucleotide that may form a short oligonucleotide hairpin or stem loop molecule with self complementary base pairing of less than 12 base pairs that bind to RIG-I and activate the RIG-I pathway.

19 Claims, No Drawings
Specification includes a Sequence Listing.

(56) References Cited

OTHER PUBLICATIONS

Durbin, Ann Fiegen et al., RNAs Containing Modified Nucleotides Fail to Trigger RIG-I Conformational Changes for Innate Immune Signaling, mBio, 2016, 1-11, 7(5): e00833-16.
Elion, David L. et al., Therapeutically Active RIG-I Agonist Induces Immunogenic Tumor Cell Killing in Breast Cancers, Cancer Research, 2018, 6183-6195, N/A.
Fitzgerald, Megan E. et al., Selective RNA targeting and regulated signaling by RIG-I is controlled by coordination of RNA and ATP binding, Nucleic Acids Research, 2017, 1442 1454, 45(3).
Goulet, Marie-Line et al., Systems Analysis of a RIG-I Agonist Inducing Broad Spectrum Inhibition of Virus Infectivity, PLoS Pathogens, 2013, 1-19, 9(4):e1003298.
Jiang, Fuguo et al., Structural basis of RNA recognition and activation by innate immune receptor RIG-I, Nature, 2011, 423-427, 479.
Kowalinski, Eva et al., Structural Basis for the Activation of Innate Immune Pattern-Recognition Receptor RIG-I by Viral RNA, Cell, 2011, 423-435, 147.
Lee, Mi-Kyung et al., Structural features of influenza A virus panhandle RNA enabling and activation of RIG-I independently of 5'-triphosphate, Nucleic Acids Research, 2016, 8407-8416, 44(17).
Linehan, Melissa M. et al., A minimal RNA ligand for potent RIG-I activation in living mice, Science Advances, 2018, 1-10, 4: e1701854.
Louber, Jade et al., Kinetic discrimination of self/non-self RNA by the ATPase activity of RIG-I and MDA5, BMC Biology, 2015, 1-16, 13:54.
Luo, Dahai et al., Structural Insights into RNA Recognition by RIG-I, Cell, 2011, 409-422, 147.
Nabet, Barzin Y. et al., Exosome RNA Unshielding Couples Stromal Activation to Pattern Recognition Receptor Signaling in Cancer, Cell, 2017, 352-366, 170(2).
Pichlmair, Andreas et al., RIG-I-Mediated Antiviral Responses to Single-Stranded RNA Bearing 5'-Phosphates, Science, 2006, 997-1001, 314.
Ranoa, Diana Rose E. et al., Cancer therapies activate RIG-I-like receptor pathway through endogenous non-coding RNAs, Oncotarget, 2016, 26496-26515, 7(18).
Schlee, Martin et al., Recognition of 5' Triphosphate by RIG-I Helicase Requires Short Blunt Double-Stranded RNA as Contained in Panhandle of Negative-Strand Virus, Immunity, 2009, 25-34, 31.
Schlee, Martin, Master sensors of pathogenic RNA-RIG-I like receptors, Immunobiology, 2013, 1322-1335, 218 (11).
Schuberth-Wagner, Christine et al., A Conserved Histidine in the RNA Sensor RIG-I Controls Immune Tolerance to N1-2'0-Methylated Self RNA, Immunity, 2015, 41-51, 43.
Wang, Yanli et al., Structural and functional insights into 5'-ppp RNA pattern recognition by the innate immune receptor RIG-I, Nature Structural & Molecular Biology, 2010, 781-787, 17(7).
Wu, Wenxin et al., RIG-I and TLR3 are both required for maximum interferon induction by influenza virus in human lung alveolar epithelial cells, Virology, 2015, 181-188, 482.
Xue, Feng et al., SRSF1 Facilitates Cytosolic DNA-Induced Production of Type I Interferons Recognized by RIG-I, PLoS One, 2015, 1-15, 10(2):e0115354.
Bruns, Annie M. et al., Activation of RIG-I-like receptor signal transduction, Critical Reviews in Biochemistry and Molecular Biology, 2011, 194-206, 47(2).
Lee, Janghyun et al., Retraction—Systematic editing of synthetic RIG-I ligands to produce effective antiviral and anti-tumor RNA immunotherapies, Nucleic Acids Research, 2018, 1635-1647, 46(4).
Patel, Jenish R. et al., Activation and regulation of pathogen sensor RIG-I, Cytokine & Growth Factor Reviews, 2014, 513-523, 25.
Shah, Neelam et al., Combined roles of ATP and small hairpin RNA in the activation of RIG-I revealed by solution-based analysis, Nucleic Acids Research, 2018, 3169-3186, 46(6).

* cited by examiner

SUBSTITUTED RIG-I AGONISTS: COMPOSITIONS AND METHODS THEREOF

CROSS-REFERENCE TO RELATED APPLICATIONS

This application is a National Stage application of International Patent Application No. PCT/US2019/027423, filed Apr. 15, 2019, which claims the benefit of priority to U.S. Provisional Patent Application No. 62/660,568, filed Apr. 20, 2018, the contents of each of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Jun. 22, 2021, is named 24588USPCT-SEQLIST-22JUN2021.txt and is 2320 Kb in size.

BACKGROUND OF THE INVENTION

Retinoic acid-inducible gene 1 (RIG-I) plays a crucial role in promoting the release of type I and type III interferons to fortify host anti-viral immunity (Wu et al., 2015, Virology 482: 181-188). The RIG-I pathway has been identified as an important innate immune sensing pathway of cytosolic 5'-triphosphate (5'ppp) dsRNA that drives the production of a variety of cytokines, including interferon β. In response to viral 5'ppp cytosolic double stranded RNA, RIG-I undergoes activation and recruits mitochondrial antiviral signaling protein (MAVS). Moreover, transcriptome analysis reveals a RIG-I-related signature covering the canonical pathway categories "IFN signaling", "activation of IRFs by cytosolic pattern recognition receptors (PRRs)", "TNFR2 signaling" and "antigen presentation" indicating that RIG-I bridges the innate and adaptive immune system (Goulet et al., 2013, PLoS Pathogens). Intriguingly, RIG-I-induced immunogenic tumor cell death triggers adaptive immunity, engaging dendritic cells and T-cells to kill tumors in vivo providing a second innate/adaptive immune system loop (Duewell et al., Cell death and differentiation 2014: 21(12) 1825-1837). Of note, RIG-I-induced apoptosis is restricted to tumor cells only (Duewell et al., 2014, 21(12) 1825-1837).

Recent studies identified key structural features for optimal RIG-I ligands. Short length, double-strandedness, 5'-triphosphorylation and blunt end base pairing characterize the prototypic RNA-based RIG-I agonist (Schlee et al., 2009, Immunity 31:25-34; Pichlmair et al., Science 2006, 314: 997-1001; Schlee, Immunobiology, 2013; 218(11), 1322-1335). Moreover, circular structures (Chen et al. Mol Cell 67 (2), 228-238.e5. 2017) and bent/KINK RNAs (Lee et al., 2016, Nucleic Acids Res, 44(17), 8407-8416) constitute another recently identified group of RIG-I ligands that do not require a triphosphate moiety. Nabet et al. (Cell 2017 Jul. 13; 170(2):352-366.e13. doi: 10.1016/j.cell.2017.06.031) reported that an unshielded endogenous RNA can activate RIG-I in tumor cells promoting aggressive features of cancer. Recent findings indicate also that endogenous small non-coding RNAs leaking to the cytoplasm can activate RIG-I during ionizing radiation therapy (Ranoa et al., Oncotarget 2016; 7(18), 26496-26515). In addition, a heterotrimeric complex of RIG-I/RNA polymerase III/serine-arginine-rich splicing factor 1 facilitates RIG-I activation in response to delocalized, cytosolic DNA via a 5'ppp RNA intermediate (Ablasser et al., Nat Immunol 2009; 10(10), 1065-1072; Xue et al., PLoS One 2015; 10920, E0115354).

Structural and functional analysis of RIG-I reveals that single amino acids and a lysine-rich patch located at the C-terminal domain (CTD) of RIG-I sense the structural properties of RNAs (Wang et al., Nat Struc Mol Biol 2010; 17(7), 781-787). Remarkably, a typical eukaryotic 2'-O-methylation pattern along with 7-methyl guanosine capping of the 5'-triphosphate group of RNAs prevent binding to RIG-I, thus distinguishing host from pathogenic non-self RNA. Specifically, modifications at the 5' end decrease RNA affinity and production of pro-inflammatory cytokines (Schuberth-Wagner et al., 2015, Immunity 43, 41-51; Devarkar et al., PNAS 2016; 113(3), 596-601). Modified RNAs containing modified nucleotides m6A, Ψ, mΨ, 2FdU, 2FdC, 5mC, 5moC, and 5hmC appear to lack stimulatory activity (Durbin et al., mBio 7(5):e00833-16. doi: 10.1128/mBio.00833-16). Moreover, illegitimate RIG-I activation by endogenous RNA is controlled by fast ATPase turnover which leads to dissociation of the RIG-I/RNA complex (Louber et al., BMC Biology 2015; 13:54). Interestingly, RIG-I mutations that correlate with a decreased ATPase activity appear to be constitutively active potentially due to signals from host RNA (Fitzgerald et al., 2017, Nucleic Acids Res, 45(3), 1442-1454).

Improvement in the understanding of how RIG-I recognizes RNA and utilizes ATP has resulted from structural studies of RIG-I truncations in mouse, human, and duck (Civril et al., 2011, EMBO Rep 12:1127-1134; Jiang et al., 2011, Nature 479:423-427; Kowalinski et al., 2011, Cell 147:423-435; Luo et al., 2011, Cell 147:409-422). However, in the only RIG-I structure with caspase activation and recruitment domains (CARD) present, the protein was in an inactive, apo-state, and lacked the CTD. This leads to questions regarding the role of both RNA and ATP in the innate immune response derived from RIG-I activation, and the relative positions of the CTD and CARDs in the active RIG-I conformation. Interestingly, the RIG-I CTD capped the 5' end of the RNA, regardless of the length of the bound duplex. The preference for the end of the duplex RNA in these structures was also independent of a 5'ppp. Recent publications, including those mentioned herein, have demonstrated that activation of the innate immune system through RIG-I leads to potent anti-tumor immunity. This new immunotherapeutic mechanism may be synergized with checkpoint inhibitors such as an anti-PD1 antibody to achieve greater anti-tumor responses. See also Elion et al., 2018, Cancer Research (DOI: 10.1158/0008-5472.CAN-18-0730).

Hence, there still remains a need for understanding RIG-I functionality and establishing RIG-I selectivity, boosting or abrogating RIG-I-driven immunity.

SUMMARY OF THE INVENTION

The present invention provides a composition comprising a nucleic acid capable of activating RIG-I. This invention provides compounds, and uses thereof, wherein said compounds comprise a short single strand oligonucleotide that optionally forms an oligonucleotide hairpin or stem loop molecule with self complementary base pairing of less than 12 base pairs that bind to RIG-I and activate the RIG-I pathway. An embodiment of this invention is realized when the short single strand oligonucleotide does not form an oligonucleotide hairpin or stem loop molecule.

An embodiment of this invention is realized when the short single strand oligonucleotide forms an oligonucleotide hairpin or stem loop molecule. An embodiment of this invention is realized when the short oligonucleotide hairpin molecule optionally comprises a 5'-terminus group selected from OH, diphosphate (pp) group and triphosphate (ppp) group. Another embodiment of this invention is realized when the short oligonucleotide hairpin molecule optionally comprises a 5'-terminus selected from functional groups that mimic the interactions of the triphosphate and diphosphate groups, sometimes referred to as 5' terminus pp mimic or ppp mimic. An embodiment of this invention is realized when in the absence of a 5'-terminus phosphate group the short oligonucleotide molecule comprises a 5'-terminus that is a 5'-OH. Another embodiment of this invention is realized when the short oligonucleotide hairpin molecule comprises a 5' terminus pp or 5' terminus pp mimic. Another embodiment of this invention is realized when the short oligonucleotide hairpin molecule comprises a 5'-terminus ppp, or a 5'-terminus ppp mimic.

An embodiment of this invention is realized when the short oligonucleotide molecule comprises a 5'-terminus ppp. Still another sub-embodiment of this invention is realized when the short oligonucleotide molecule comprises a 5'-terminus ppp mimic. In yet another embodiment the short oligonucleotide hairpin molecule comprises a 5'-terminus group selected from diphosphate and triphosphate, a self complementary base pairing region of less than 12 base pairs, and a blunt end. In another embodiment, the short oligonucleotide hairpin molecule comprises a 5'-terminus mimic group selected from diphosphate and triphosphate, a self complementary base pairing region of less than 12 base pairs, and a blunt end. In another embodiment, the short oligonucleotide hairpin molecule comprises a 5'-terminus mimic group selected from diphosphate and triphosphate, a self complementary base pairing region of less than 12 base pairs, a blunt end, and a non-base pairing stem loop. A subembodiment of this aspect of the invention is realized when the looped end is a non-base pairing tetraloop consisting of four nucleotides. Another subembodiment of this aspect of the invention is realized when a blunt end is at the 5'terminus end.

Still in another embodiment, the invention is directed to short oligonucleotide hairpin or stem loop molecules having a self complementary base pairing region of less than 12 base pairs, a blunt end, and a non-base pairing tetraloop, further comprising a modified phosphodiester backbone. A sub-embodiment of this aspect of the invention is realized when the modified phosphodiester backbone comprise at least one modified phosphate group comprising a phosphorothioate.

In another embodiment of this aspect of the invention, the short oligonucleotide hairpin molecules comprise at least one modified nucleotide base (nucleobase).

In yet another embodiment, disclosed is a method for inducing type I interferon production in a cell, or a method for treating a disease or disorder in a subject in need thereof by inducing type I interferon production in a cell of the subject. In another embodiment, use of one or more short oligonucleotide molecules in the potential treatment or prevention of RIG-I pathway-associated diseases or disorders is disclosed, wherein the molecule comprises a self-complementary base pairing region of less than 12 base pairs, a blunt end, and non base pairing tetraloop. In a sub-embodiment of this aspect of the invention, the disease or disorder is selected from the group consisting of a bacterial infection, a viral infection, a parasitic infection, cancer, an autoimmune disease, an inflammatory disorder, and a respiratory disorder.

In still another embodiment, compositions comprising one or more of short oligonucleotide molecules are disclosed. In another embodiment, a pharmaceutical composition comprising one or more of the short oligonucleotide hairpin molecules capable of inducing interferon production and a pharmaceutically acceptable carrier, wherein the molecule comprises a self complementary base pairing region of less than 12 base pairs, a blunt end and a non base pairing tetraloop. In a sub-embodiment of this aspect of the invention, the 5'-terminus of the short oligonucleotide hairpin molecules comprise at least one of the group consisting of 5'-OH, 5'-triphosphate, 5'-diphosphate, 5'-diphosphate mimic, and 5'-triphosphate mimic. In a sub-embodiment of this aspect of the invention, the pharmaceutical composition further comprises at least one agent selected from an immunostimulatory agent, an antigen, an anti-viral agent, an anti-bacterial agent, an anti-tumor agent, retinoic acid, IFN-α, and IFN-β.

DETAILED DESCRIPTION OF THE INVENTION

The present invention relates to novel oligonucleotides and analogues thereof and their use to bind and activate the RIG-I protein.

Embodiments of the disclosure include compounds of general Formula Ia and Formula I as well as synthesis and isolation of compounds of general Formula Ia and Formula I. Uses of compounds of general Formula Ia and Formula I are also disclosed. Other embodiments, aspects and features of the present disclosure are either further described in or will be apparent from the ensuing description, examples and appended claims.

The term "oligonucleotide" in the context of the present application encompasses compounds comprising a plurality, e.g., at least 4 nucleotide or nucleotide analogue building blocks, preferably, 6-100, e.g., 19-40, 19-30, and 19-25 building blocks. The nucleotide or nucleotide analogue building blocks may comprise nucleoside or nucleoside analogue subunits connected by inter-subunit linkages. The nucleoside subunits include deoxyribonucleoside subunits, ribonucleoside subunits and/or analogues thereof, particularly sugar- and/or nucleobase-modified nucleoside analogues. Further, the oligonucleotides may comprise non-nucleotidic building blocks and/or further terminal and/or side-chain modifications.

Examples of sugar-modified subunits are realized when $R_1$, $R_2$ $R_3$, and/or $R_4$ of a ribonucleoside subunit is replaced, for example, by a group as defined below. In other sugar-modified subunits, the ribose may be substituted, e.g., by another sugar, for example a pentose such as arabinose. This sugar modification may be combined with 2'-OH modifications as described above, such as in 2'-fluoroarabinonucleoside subunits. Still other sugar-modified subunits include locked nucleosides (LNA). A "locked nucleoside" is a nucleoside in which the robose moiety is modified with an extra bridge connecting a 2' oxygen and a 4' carbon. Still other nucleobase-modified nucleosidic building blocks, a non-standard, e.g., non-naturally occurring nucleobase, is used instead of a standard nucleobase. Examples of non-standard or modified nucleobases are uracils or cytosines modified at the 5-position, e.g., 5-(2-amino)propyl uracil or 5-bromouracil; hypoxanthine; 2,6-diaminopurine; adenines or guanines modified at the 8-position, e.g. 8-bromoguanine; deazanucleosides, e.g. 7-deazaguanine or 7-deazaadenine; or O- and N-alkylated nucleobases, e.g. $N^6$-methyladenine, or $N^6,N^6$-dimethyladenine. Further suitable nucleobase analogues may be selected from universal nucleobase analogues such as 5-nitroindole or inosine.

As used herein, the term "backbone" refers to the linkage between the subunits of the oligonucleotide. A "modified phosphodiester backbone" occurs when the inter-subunit linkage between subunits is be a phosphodiester linkage or a modified linkage, e.g. a phosphorothioate, phosphorodithioate, methylphosphonate, phosphoramidate, boranophosphate, and the like or another modified linkage described herein or known to a skilled person in the art.

As used herein, a "single stranded oligonucleotide" refers to an oligonucleotide in which the bases are not complementary to each other. A "hairpin" oligonucleotide structure refers to a single stranded oligonucleotide, wherein a portion of the oligonucleotide chain loops around and self complementary base pairing results in a portion of the oligonucleotide which is effectively double stranded.

As used herein, a "double stranded oligonucleotide," refers to an oligonucleotide of two strands, which is formed from complementary base pairsA double-stranded oligonucleotide as used herein can have terminal overhangs on either end or both ends. An oligonucleotide section is fully double-stranded when the two stretches of nucleic acid forming the section have the same length and have sequences which are 100% complementary to each other. As established in the art, two nucleotides are said to be complementary to each other if they can form a base pair, either a Waston-Crick base pair (A-U, G-C) or a wobble base pair (U-G, U-A, I-A, I-U, I-C).

As used herein, the term "blunt end" as used in a double stranded oligonucleotide refers to the 3' and 5' ends of the oligonucleotide of the invention, wherein the oligonucleoide terminates in a base pair. Oligonucleotides which do not have a blunt end are referred to as having an overhang, wherein one strand has a longer oligonucleotide chain than the other strand. A single stranded oligonucleotide may have a single blunt end or an overhang.

The oligonucleotide may be selected from deoxyribonucleotides, ribonucleotides and oligonucleotide analogues. The deoxyribonucleotides, ribonucleotides and/or oligonucleotide analogues may be chemically modified at the nucleoside and/or ribose subunit of the analogue, deoxyribonucleotide, ribonucleotide and/or oligonucleotide. Analogues of desoxyribonucleotides or ribonucleotides may comprise at least one desoxyribonucleoside or ribonucleoside subunit and at least one modified nucleosidic subunit and/or at least one modified inter-subunit linkage, e.g. as described above. Oligonucleotide analogues may also consist in their entirety of modified nucleosidic subunits.

The oligonucleotides of the present invention comprise short single strand oligonucleotides that optionally may fold to form a hairpin consisting of self complementary base pairings and an unpaired tetraloop. The self complementary base pairing hairpin structure is formed when intra-molecular base pairing forms a double helix that ends in an unpaired tetraloop opposite the 5' terminus end of the single strand. An embodiment of this aspect of the invention is realized when the self complementary base pairing is less than 12 base pairs and the unpaired loop is a tetraloop of four nucleotides. The hairpin molecules may be blunt ended or comprise at least one overhang, e.g., a 5'- or 3'-overhang. The hairpin molecules may optionally comprise a 5' OH group, 5'-terminus phosphate group or 5'-terminus phosphate mimic group.

The oligonucleotides of the present invention comprise single strands of a length of at least 24 nucleotides. In another embodiment, the single strand has a length of 24 nucleotides.

The oligonucleotide may comprise further terminal and/or side-chain modifications, e.g., cell specific targeting entities covalently attached thereto. Those entities may promote cellular or cell-specific uptake and include, for example lipids, small molecules, cholesterol, folate, vitamins, hormones, peptides, oligosaccharides and analogues thereof. Targeting entities may, e.g., be attached to modified nucleobases or non-nucleotidic building blocks by methods known to the skilled person.

Still in another embodiment, modifications establish and/or enhance the selectivity of the oligonucleotide towards a given target. In a particularly preferred embodiment the RIG-I selectivity of the oligonucleotide is enhanced. Methods to determine the RIG-I selectivity of a given oligonucleotide are described herein in detail (cf. Examples) and/or are known to the person skilled in the art.

Yet in another embodiment, the chemical modifications maintain or enhance the chemical stability of the oligonucleotide. A person skilled in the art knows methods for determining the chemical stability of a given oligonucleotide. Such methods are also described, e.g., in the Examples.

Chemical modifications of the oligonucleotide include those to the ribonucleoside subunit, phosphodiester backbone, and nucleobase. Non-limiting examples of such modifications are independently selected from the group comprising halogenation, (e.g., 2'-F-halogenation), 2'-O-alkylation (e.g., 2'-O-methylation), and/or phosphorothioate modifications of internucleotide linkages. Particularly, 2'-F-halogenation and phosphorothioate modifications may increase the stability of the oligonucleotide, while 2'-O-methylation may establish or increase RIG-I selectivity of the oligonucleotide. 2'-O-methylations may also be able to modify the immunogenicity of RNA.

The identification patterns of a given oligonucleotide depend on the sequence and the length of an oligonucleotide and can be determined for each given oligonucleotide. A person skilled in the art is well aware how to carry out this determination. As explained herein, such methods for determining RIG-I selectivity and/or stability of a given oligonucleotide are described in detail in the present application.

The present invention provides modified short oligonucleotide molecules of general Formula Ia:
Formula Ia
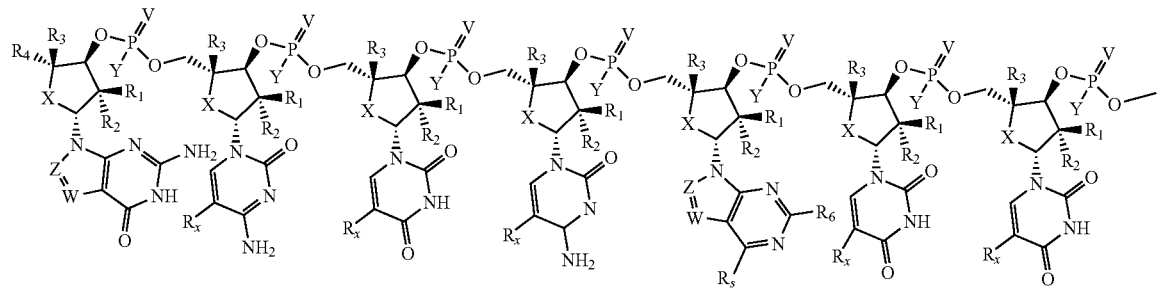
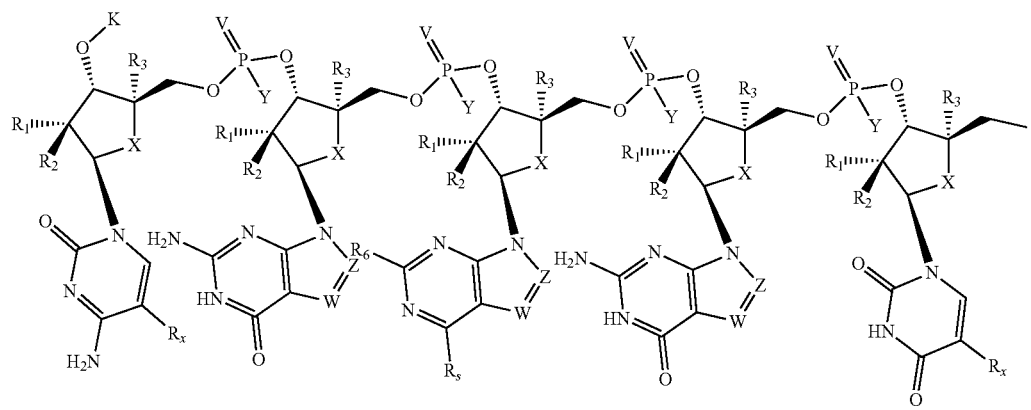
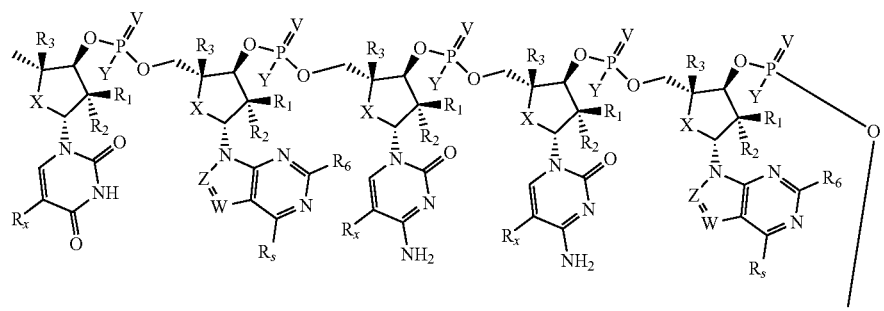
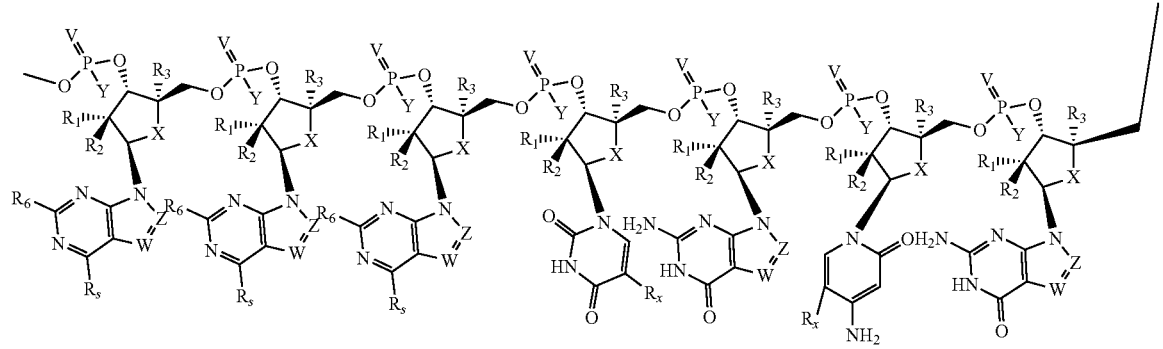

or pharmaceutically acceptable salts thereof, wherein:

each X is independently selected from the group consisting of O, S, —CH$_2$—, and —NH—;

each Y is independently selected from the group consisting of —OH, —SH, and

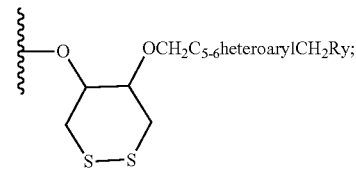

each V is independently O, or S;

K is H, or

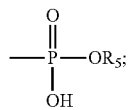

each W is independently N, —CH—, or —C(F)—;

each Z is independently N, or —CH—;

each $R_1$ is independently selected from the group consisting of H, halogen, —OH, —OC$_{1-6}$ alkyl, C$_{1-6}$ alkyl, —OC$_{1-3}$ haloalkyl, —OC$_{2-6}$ alkenyl, —OC$_{2-6}$ alkynyl, —NH$_2$, and —OCH$_2$C$_{5-6}$ heteroarylCH$_2$R$_y$, said alkyl, alkenyl, alkynyl and heteroaryl optionally substituted with 1 to 3 groups of $R_b$;

each $R_2$ is independently selected from the group consisting of H, halogen, —OH, —OC$_{1-6}$ alkyl, C$_{1-6}$ alkyl, —OC$_{1-3}$ haloalkyl;

or one or more adjacent $R_1$ and $R_2$ can combine to form =CH$_2$;

each $R_3$ is independently H, halogen, C$_{1-6}$ alkyl, or C$_{2-6}$ alkynyl;

or $R_1$ and $R_3$ on a sugar moiety can be linked to form —CH$_2$O, provided $R_2$ is hydrogen;

$R_4$ is selected from the group consisting of —CH$_2$OH,

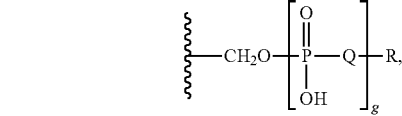

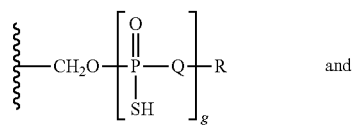
and

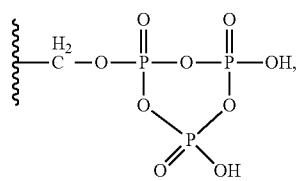

$R_5$ is selected from the group consisting of H, C$_{1-6}$ alkyl, —(CH$_2$CH$_2$O)$_p$CH$_2$CH$_3$, and —CH$_2$CH(OH)CH$_2$(O(CH$_2$)$_2$)$_n$CH$_2$NHC(O)R$_z$;

each $R_6$ is independently selected from H and NH$_2$;

$R_b$ is selected from C$_{1-6}$ alkyl, —OC$_{1-6}$ alkyl, halo, OH, CN, NO, NH$_2$, NHC$_{1-6}$alkyl, N(C$_{1-6}$alkyl)$_2$, SO$_3$H, SO$_4$, PO$_4$, C$_{1-3}$ haloalkyl, C$_{1-3}$ haloalkoxy, carboxyl, oxo, and S(O)$_g$alkyl;

R is H or —P(O)(OH)$_2$;

Q is independently selected from the group consisting of O, CH$_2$, and NH;

$R_s$ is NH$_2$ or —C(O)—;

$R_x$ is hydrogen or —C≡CH;

$R_y$ is —CH$_2$(O(CH$_2$)$_2$)$_n$(CH$_2$)$_k$NHC(O)—R$_z$, or —(CH$_2$OCH$_2$)$_n$CH$_2$C(O)N((CH$_2$)$_k$NHC(O)R$_z$)$_2$;

$R_z$ is cholesterol;

g is 1, 2, or 3;

k and n are independently selected from 1, 2, 3, 4, 5, and 6;

p is an integer from 1 to 50.

An embodiment of the invention of Formula Ia is represented by Formula I:

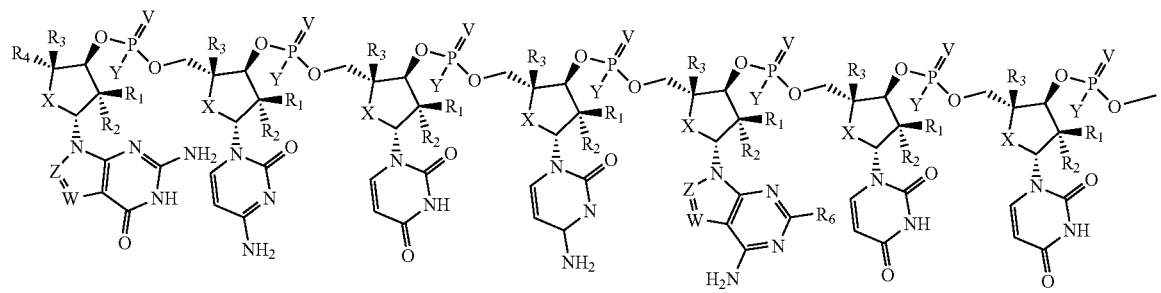

Formula I

-continued

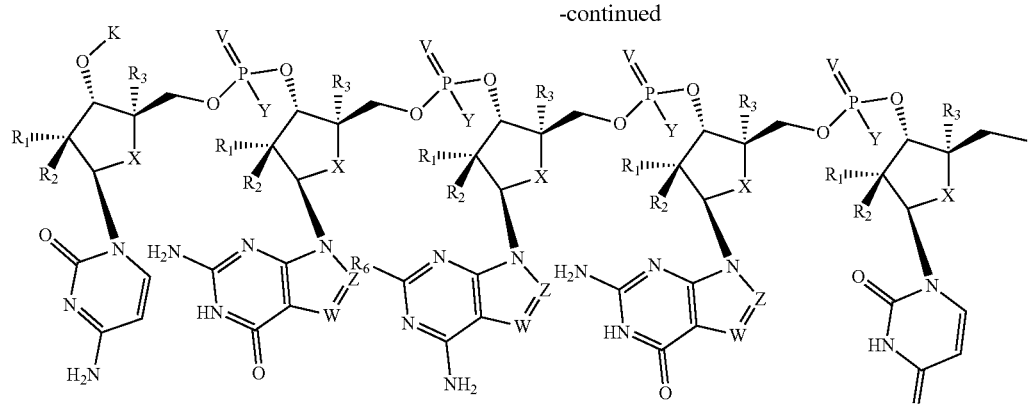

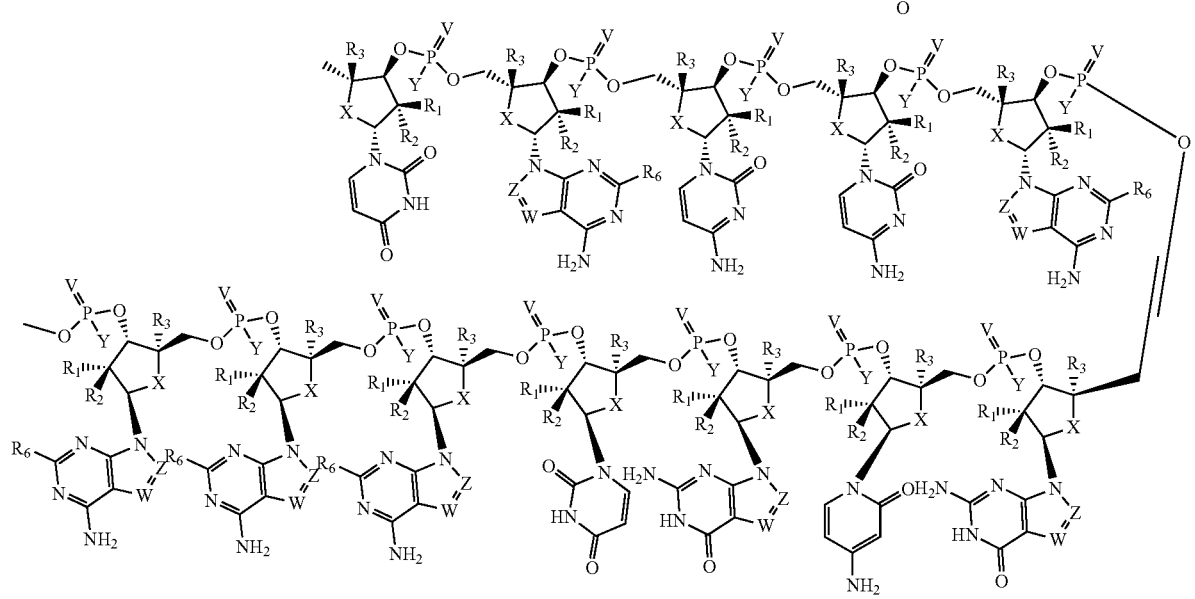

or pharmaceutically acceptable salts thereof, wherein:
each X is independently selected from the group consisting of O, S, —CH$_2$—, and —NH—;
each Y is independently selected from the group consisting of —OH, —SH, and

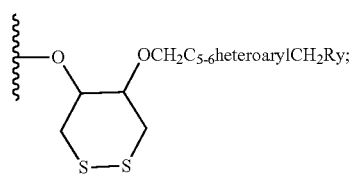

each V is independently O, or S;
K is H, or

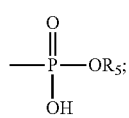

each W is independently N, —CH—, or —C(F)—;
each Z is independently N, or —CH—;

each R$_1$ is independently selected from the group consisting of H, halogen, —OH, —OC$_{1-6}$ alkyl, C$_{1-6}$ alkyl, —OC$_{1-3}$ haloalkyl, —OC$_{2-6}$ alkenyl, —OC$_{2-6}$ alkynyl, —NH$_2$, and —OCH$_2$C$_{5-6}$ heteroarylCH$_2$R$_y$, said alkyl, alkenyl, alkynyl and heteroaryl optionally substituted with 1 to 3 groups of R$_b$;

each R$_2$ is independently selected from the group consisting of H, halogen, —OH, —OC$_{1-6}$ alkyl, C$_{1-6}$ alkyl, —OC$_{1-3}$ haloalkyl;

or one or more adjacent R$_1$ and R$_2$ can combine to form =CH$_2$;

each R$_3$ is independently H, halogen, C$_{1-6}$ alkyl, or C$_{2-6}$ alkynyl;

or R$_1$ and R$_3$ on a sugar moiety can be linked to form —CH$_2$O, provided R$_2$ is hydrogen;

R$_4$ is selected from the group consisting of —CH$_2$OH,

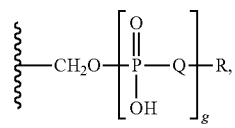

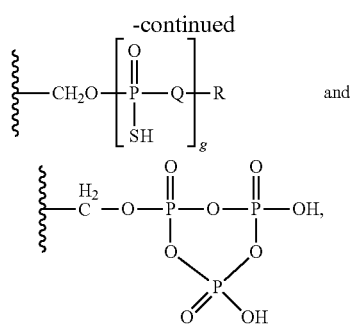

and

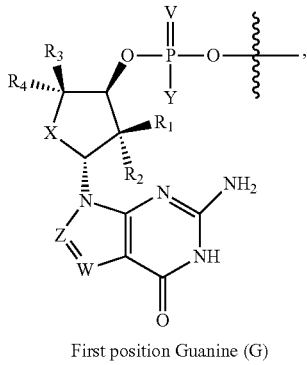

$R_5$ is selected from the group consisting of H, $C_{1-6}$ alkyl, —$(CH_2CH_2O)_pCH_2CH_3$, and —$CH_2CH(OH)CH_2(O(CH_2)_2)_nCH_2NHC(O)R_z$;

each $R_6$ is independently selected from H and $NH_2$;

$R_b$ is selected from $C_{1-6}$ alkyl, —$OC_{1-6}$ alkyl, halo, OH, CN, NO, $NH_2$, $NHC_{1-6}$alkyl, $N(C_{1-6}alkyl)_2$, $SO_3H$, $SO_4$, $PO_4$, $C_{1-3}$ haloalkyl, $C_{1-3}$ haloalkoxy, carboxyl, oxo, and $S(O)_g$alkyl;

R is H or —$P(O)(OH)_2$;

Q is independently selected from the group consisting of O, $CH_2$, and NH; $R_y$ is —$CH_2(O(CH_2)_2)_n(CH_2)_kNHC(O)$—$R_z$, or —$(CH_2OCH_2)_nCH_2C(O)N((CH_2)_kNHC(O)R_z)_2$;

$R_z$ is cholesterol;

g is 1, 2, or 3;

k and n are independently selected from 1, 2, 3, 4, 5, and 6;

p is an integer from 1 to 50.

For purposes of this invention, the compound of Formula Ia and I comprises 24 nucleotides selected from the group consisting of 1, 2, 3, 4, 5, and 6,

1

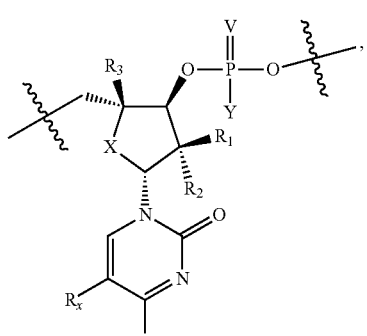

First position Guanine (G)

2

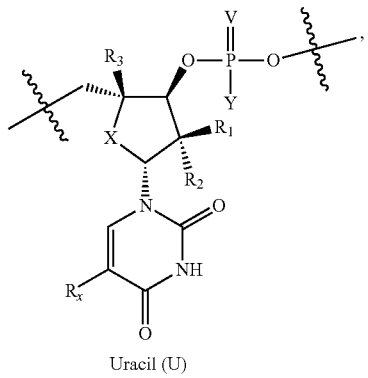

Position 2, 4, 10, 11, 14 Cytosine (C)

3

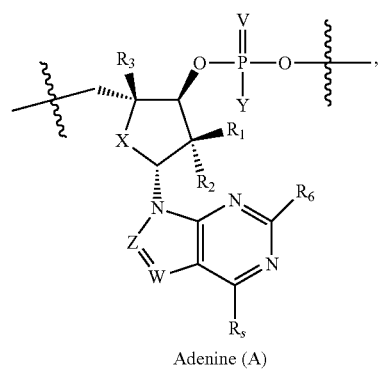

Uracil (U)

4

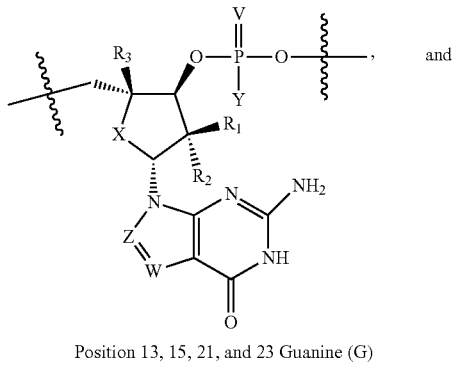

Adenine (A)

5 and

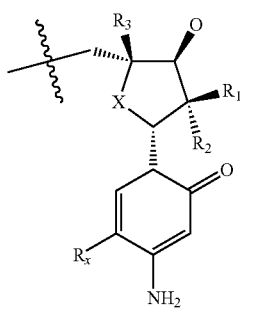

Position 13, 15, 21, and 23 Guanine (G)

6

Position 24 Cytosine (C)

wherein $R_1$, $R_2$, $R_3$, $R_4$, $R_6$, $R_x$, $R_s$, X, V, Y, K, Z, and W are as described herein. Adenine is present at positions 5, 9, 12, 17, 18, 19 and 22. Uracil is present at positions 3, 6, 7, 8, 16 and 20. When the hairpin is present, and reading from left to right, up to 10 self complementary base pairs are possible.

The compounds of the invention also include adenine derivative, inosine, or derivatives thereof, as depicted below:

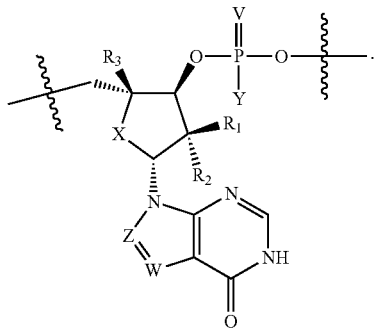

An embodiment of the invention of Formula Ia and I is realized when it is read from left to right beginning with guanine (G), which is at the 5' end, and ending with cytosine (C) at the 3' end.

Another embodiment of the invention is compounds of formula (I), or a pharmaceutically acceptable salt thereof, wherein any X is independently selected from O and S, any Y is independently selected from OH and SH, any V is independently selected from O or S; and any K is independently selected from H and OH

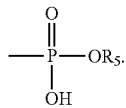

In another embodiment, any $R_1$ is independently selected from the group consisting of H, halogen, —OH, —OMe, Me, —OCF$_3$, O(CH$_2$)$_2$OCH$_3$, NH$_2$, —OCH$_2$C≡CH, any $R_2$ is independently selected from the group consisting of H, halogen, —OH, —OMe, Me, and —OCF$_3$.

In another embodiment, any X is independently selected from O and S, any Y is independently selected from OH and SH, any V is independently selected from O or S; K is H, any W and Z within a single nine membered bicycle is independently selected from W=N and Z=—CH—; W=—CH— and Z=N and W=—CH— and Z is CH, any $R_1$ is selected from the group consisting of H, halogen, —OH, —OMe, Me, —OCF$_3$, —O(CH$_2$)$_2$OCH$_3$, —NH$_2$, —OCH$_2$C≡CH, any $R_2$ is independently selected from the group consisting of H, halogen, —OH, —OMe, -Me, and —OCF$_3$, and any $R_3$ is independently selected from the group consisting of H, halogen, $C_{1-6}$ alkyl, and —C≡CH.

An embodiment of the invention of Formula Ia and I is realized when any X is independently selected from O, S, and —CH$_2$—. A subembodiment of this aspect of the invention is realized when any X is independently selected from O and S. A subembodiment of this aspect of the invention is realized when each X is O. A subembodiment of this aspect of the invention is realized when each X is S. A subembodiment of this aspect of the invention is realized when each X is —CH$_2$—.

Another embodiment of the invention of Formula Ia and I is realized when any Y is independently selected from OH and SH A subembodiment of this aspect of the invention is realized when each Y is SH. A subembodiment of this aspect of the invention is realized when each Y is OH.

An embodiment of this aspect of the invention is realized when one to three Y is

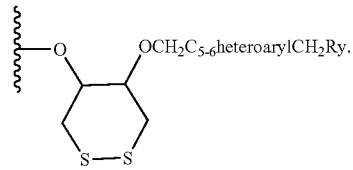

A further subembodiment of this aspect of the invention is realized when the heteroaryl is optionally substituted triazolyl, said triazolyl optionally substituted with 1 to 3 groups of $R_b$. Another embodiment of this aspect of the invention is realized when $R_y$ is —CH$_2$(O(CH$_2$)$_2$)$_n$(CH$_2$)$_k$NHC(O)—R$_z$. Still another subembodiment of this aspect of the invention is realized when $R_y$ is —(CH$_2$OCH$_2$)$_n$CH$_2$C(O)N((CH$_2$)$_k$NHC(O)R$_z$)$_2$. Another subembodiment of this aspect of the invention is realized when Y is

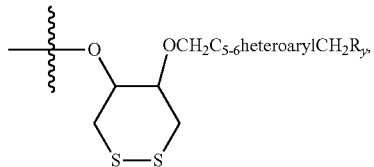

selected from

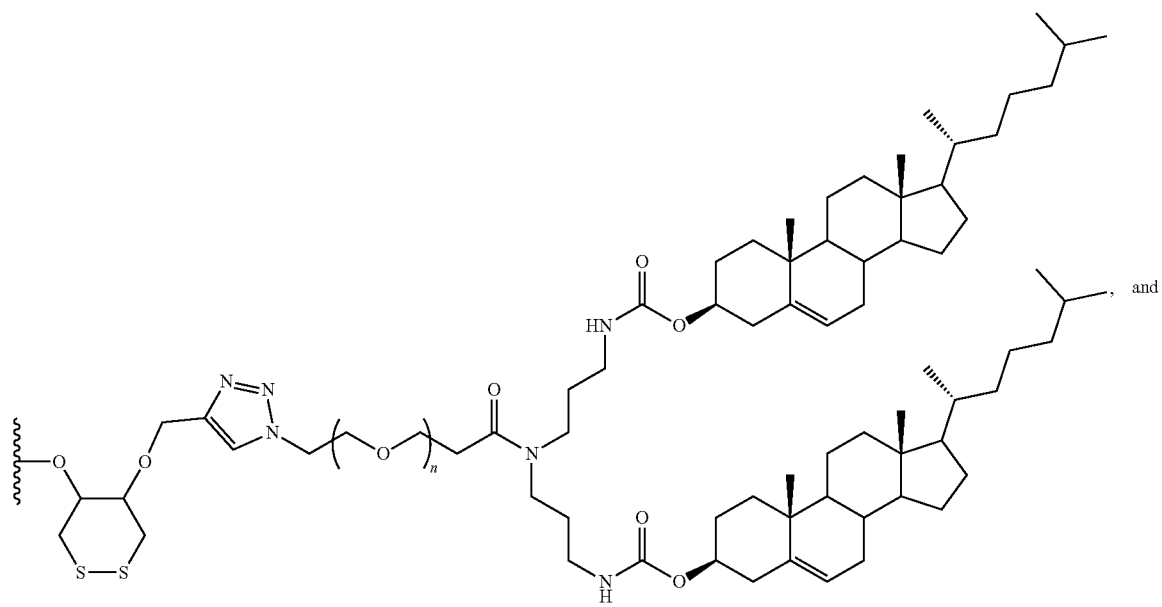

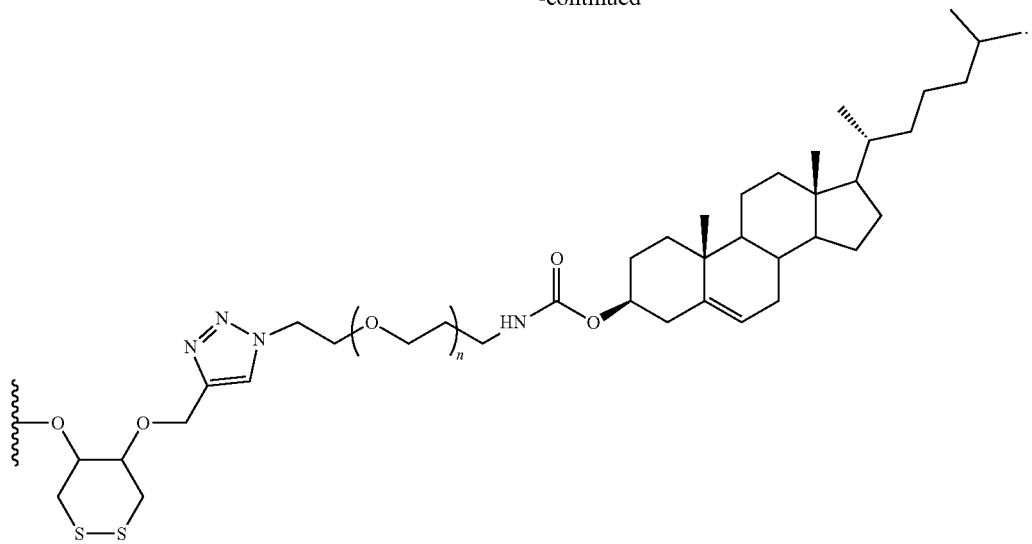

Another embodiment of the invention of Formula Ia and I is realized when V is O. Another subembodiment of the invention of Formula Ia and Formula I is realized when each V is S.

Still another embodiment of the invention of Formula Ia and Formula Ia and I is realized when K is H.

Another embodiment of the invention of Formula Ia and I is realized when K is

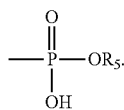

A subembodiment of this aspect of the invention is realized when $R_5$ is selected from the group consisting of H, $C_{1-6}$ alkyl and —$(CH_2CH_2O)_pCH_2CH_3$. Another subembodiment of this aspect of the invention is realized when $R_5$ is H. Another subembodiment of this aspect of the invention is realized when $R_5$ is $C_{1-6}$ alkyl. Still another subembodiment of this aspect of the invention is realized when $R_5$ is —$(CH_2CH_2O)_pCH_2CH_3$.

An embodiment of the invention of Formula Ia and I is realized when any W is independently selected from N and —CH—. Another embodiment of the invention of Formula Ia and I is realized when at least one W is N. Another embodiment of the invention of Formula Ia and I is realized when one to three W is N and the others are —CH—. Another embodiment of the invention of Formula Ia and I is realized when two or more W is —CH—. Another embodiment of the invention of Formula Ia and I is realized when one to three W is —CF—.

An embodiment of the invention of Formula Ia and I is realized when at least one Z is N. Still another embodiment of the invention of Formula Ia and I is realized when each Z is N. Another embodiment of the invention of Formula Ia and I is realized when each Z is —CH—. Another embodiment of the invention of Formula Ia and I is realized when at least one Z is —CH—. Another embodiment of the invention of Formula I is realized when any W and Z within a single nine membered bicycle is independently selected from W=N and Z=—CH—; W=—CH— and Z=N; W=N and Z=N; and W=—CH— and Z is —CH—. Another embodiment of the invention of Formula Ia and I is realized when each W is N and each Z is —CH—. Another embodiment of the invention of the Formula Ia and I is realized when each W is —CH— and each Z is —CH—. Another embodiment of the invention of the Formula Ia and I is realized when each W=—CH— and each Z=N. Another embodiment of the invention of the Formula Ia and I is realized when each W=N and each Z=N.

An embodiment of the invention of Formula Ia and I is realized when any $R_1$ of Formula Ia and I is selected from the group consisting of H, halogen, —OH, —OMe, Me, —$OCF_3$, —$O(CH_2)_2OCH_3$, —$OCH_2C\equiv CH$, —$NH_2$,

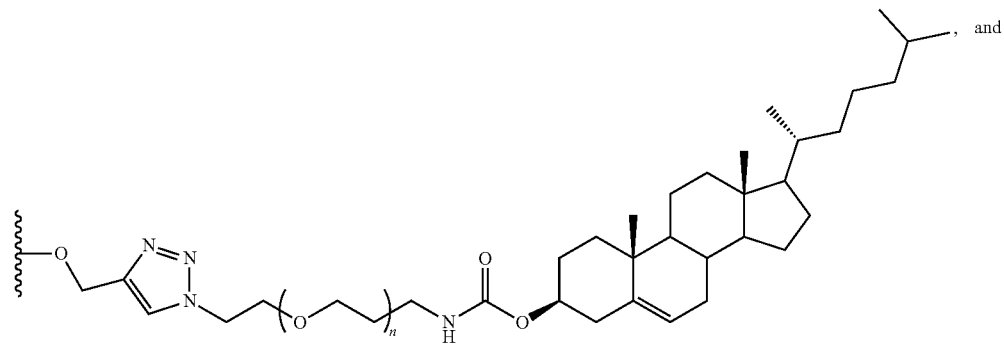

-continued

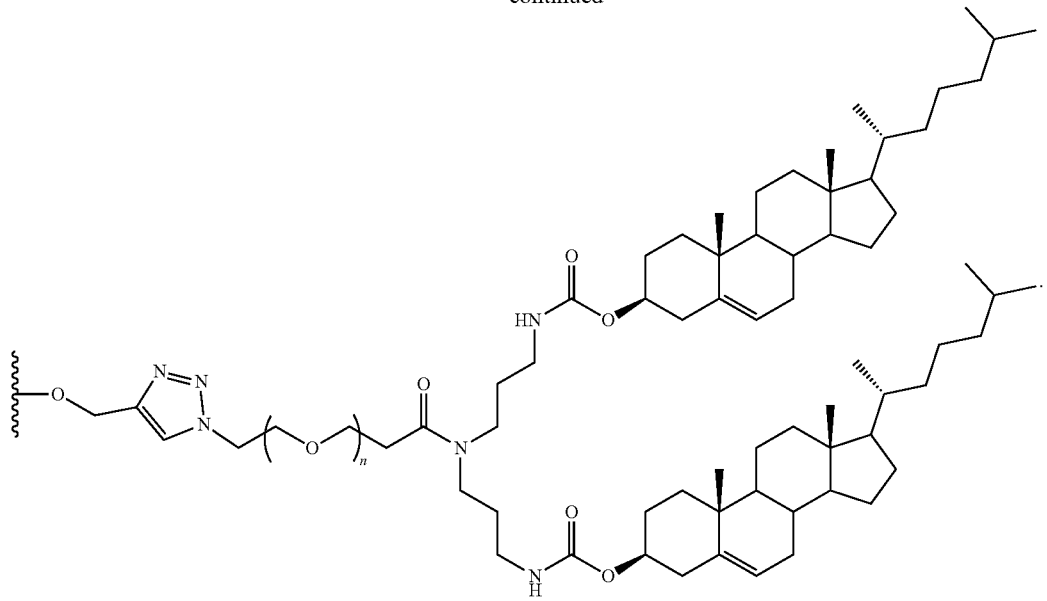

Another embodiment of the invention of Formula Ia and I is realized when any $R_1$ is independently selected from the group consisting of H, halogen, —OH, —OMe, -Me, —OCF$_3$, —O(CH$_2$)$_2$OCH$_3$, —OCH$_2$C≡CH, and —NH$_2$. Another embodiment of the invention of Formula Ia and I is realized when any $R_1$ is independently selected from H, halogen, —OH, —OMe, -Me, —OCF$_3$, —O(CH$_2$)$_2$OCH$_3$, and —NH$_2$.

An embodiment of the invention of Formula Ia and I is realized when any $R_2$ is independently selected from the group consisting of H, halogen, —OH, —OMe, -Me, and —OCF$_3$. A subembodiment of this invention of Formula Ia and I is realized when any $R_2$ is independently selected from the group consisting of H and -Me.

An embodiment of the invention of Formula Ia and I is realized when one to three adjacent $R_1$ and $R_2$ may combine to form =CH$_2$.

Another embodiment of the invention of Formula Ia and I is realized when any $R_3$ is independently H, halogen, C$_{1-6}$ alkyl, —C≡CH. A sub-embodiment of the invention Formula 1 is realized when any $R_3$ is independently selected from H, F, Cl, methyl, ethyl, propyl, butyl hexyl and —C≡CH. A subembodiment of the invention of Formula Ia and I is realized when one to three $R_1$ and $R_3$ combine to form —CH$_2$O— and $R_2$ is hydrogen. A subembodiment of the invention of Formula I is realized when $R_3$ is hydrogen.

An embodiment of the invention of Formula Ia and I is realized when $R_4$ is —CH$_2$OH. Another embodiment of the invention of Formula Ia and I is realized when $R_4$ is

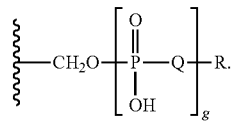

A subembodiment of this aspect of the invention is realized when R is H. Another subembodiment of the invention of Formula Ia and I is realized when R is —P(O)(OH)$_2$. A subembodiment of this aspect of the invention is realized when Q is O. Another subembodiment of this aspect of the invention is realized when Q is —NH—. Another subembodiment of this aspect of the invention is realized when Q is —CH$_2$—. Another subembodiment of this aspect of the invention is realized when g is 1, R is H and Q is O. Another subembodiment of the invention is realized when g is 2, R is H and Q is O. Still another subembodiment of the invention is realized when g is 3, R is H and Q is O. Yet another subembodiment of this aspect of the invention is realized when g is 1 and Q is —CH$_2$—, or —NH—. Another subembodiment of the invention is realized when g is 2, and Q is —NH— or —CH$_2$—. Still another subembodiment of the invention is realized when g is 3, and Q is —NH—, or —CH$_2$—.

Another embodiment of the invention of Formula Ia and I is realized when $R_4$ is

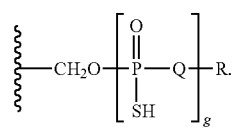

Another subembodiment of this aspect of the invention is realized when R is H. Another subembodiment of the invention of Formula Ia and I is realized when R is —P(O)(OH)$_2$. A subembodiment of this aspect of the invention is realized when Q is O. Another subembodiment of this aspect of the invention is realized when Q is NH. Another subembodiment of this aspect of the invention is realized when Q is CH$_2$. Another subembodiment of this aspect of the invention is realized when g is 1, R is H and Q is O. Another subembodiment of the invention is realized when g is 2, R is H and Q is O. Still another subembodiment of the invention is realized when g is 3, R is H and Q is O. Yet another subembodiment of this aspect of the invention is realized when g is 1 and Q is —CH$_2$—, or —NH—. Another subembodiment of the invention is realized when g is 2, and Q is —NH— or —CH$_2$—. Still another subembodiment of the invention is realized when g is 3, and Q is —NH—, or —CH$_2$—. Still another embodiment of the invention of Formula Ia and I is realized when R$_4$ is

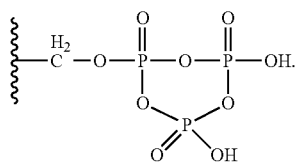 [SMILES: *COP1(=O)OP(=O)(O)OP(=O)(O)O1]

An embodiment of the invention of Formula Ia and I is realized when R$_4$ is

An embodiment of the invention of Formula Ia and I is realized when R is H. Another embodiment of the invention of Formula Ia and I is realized when R is —P(O)(OH)$_2$.

An embodiment of the invention of Formula Ia and I is realized when R$_4$ is —CH$_2$OH and K is H. A subembodiment of this aspect of the invention is realized when Q is O.

Another embodiment of the invention of Formula Ia and I is realized when R$_4$ is —CH$_2$OH and K is P(O)(OH)$_2$. A subembodiment of this aspect of the invention is realized when Q is O.

An embodiment of the invention of Formula Ia and I is realized when one or more adjacent R$_1$ and R$_2$ combine to form =CH$_2$, and R$_4$ is —CH$_2$OH. A subembodiment of this aspect of the invention is realized when K is H. Another subembodiment of this aspect of the invention is realized when K is —P(O)(OH)$_2$.

An embodiment of the invention of Formula Ia and I is realized when one or more adjacent R$_1$ and R$_2$ combine to form =CH$_2$; and R$_4$ is selected from the group consisting of

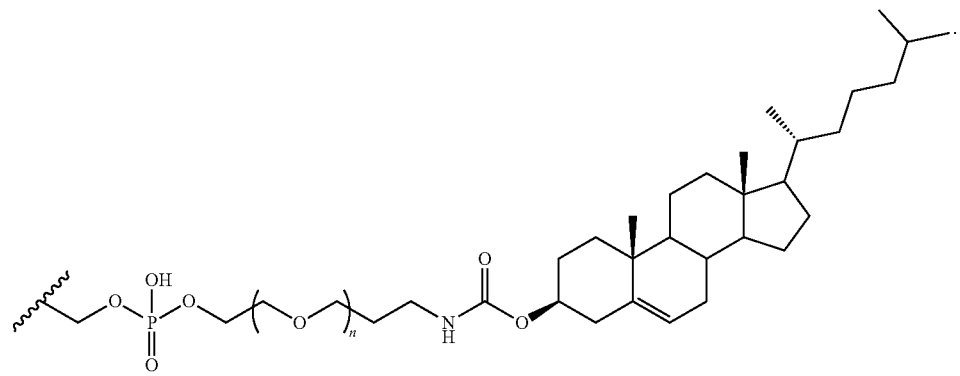

An embodiment of the invention of Formula Ia and I is realized when R$_5$ is H. Another embodiment of the invention of Formula Ia and I is realized when R$_5$ is C$_{1-6}$ alkyl, wherein alkyl is selected from the group consisting of methyl, ethyl, propyl, butyl, pentyl and hexyl. Another embodiment of the invention of Formula Ia and I is realized when R$_5$ is —(CH$_2$CH$_2$O)$_p$CH$_2$CH$_3$. Yet another embodiment of the invention of Formula Ia and I is realized when R$_5$ is

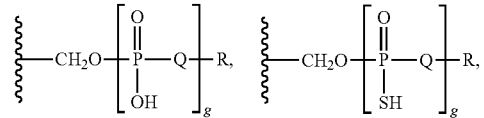

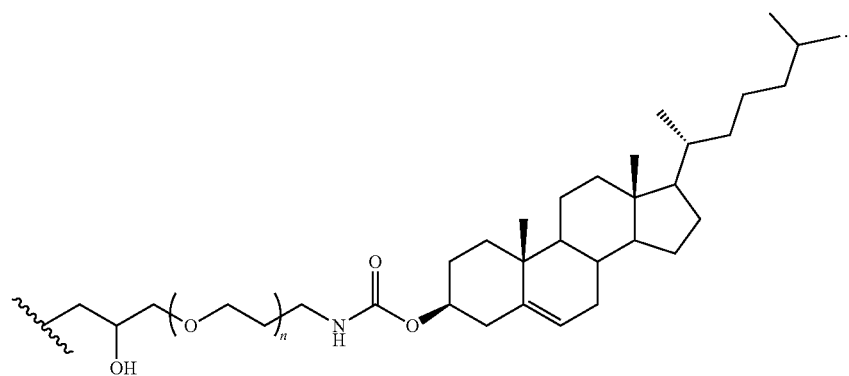

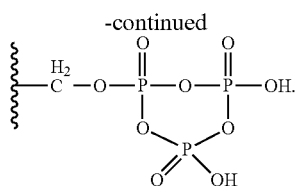

Still another subembodiment of this aspect of the invention is realized when Q is O. Yet another subembodiment of this aspect of the invention is realized when Q is —NH—, —CH$_2$—. A subembodiment of this aspect of the invention is realized when K is H. Another subembodiment of this aspect of the invention is realized when K is —P(O)(OH)$_2$. Another subembodiment of this aspect of the invention is realized when R is H. Another subembodiment of the invention of Formula Ia and I is realized when R is —P(O)(OH)$_2$.

An embodiment of the invention of Formula Ia and I is realized when $R_1$ and $R_3$ on a sugar moiety are linked to form —CH$_2$O— and $R_4$ is —CH$_2$OH. A subembodiment of this aspect of the invention is realized when K is H. Another subembodiment of this aspect of the invention is realized when K is —P(O)(OH)$_2$.

An embodiment of the invention of Formula Ia and I is realized when $R_1$ and $R_3$ on a sugar moiety are linked to form —CH$_2$O and $R_4$ is selected from the group consisting of

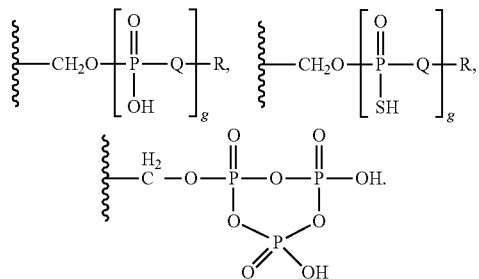

A subembodiment of this aspect of the invention is realized when K is H. Another subembodiment of this aspect of the invention is realized when K is —P(O)(OH)$_2$. Still another subembodiment of this aspect of the invention is realized when Q is O. Yet another subembodiment of this aspect of the invention is realized when Q is independently selected from O, —CH$_2$— or —NH—, —CH$_2$—. Another subembodiment of this aspect of the invention is realized when R is H. Another subembodiment of the invention of Formula Ia and I is realized when R is —P(O)(OH)$_2$.

Another aspect of the invention of Formula Ia is realized when $R_x$ is hydrogen. Still another aspect of the invention of Formula Ia is realized when $R_x$ is —C≡CH.

Another aspect of the invention of Formula Ia is realized when $R_s$ is NH$_2$. Still another aspect of the invention of Formula Ia is realized when $R_s$ is —C(O)—.

As described herein, unless otherwise indicated, the use of a compound in treatment means that an amount of the compound, generally presented as a component of a formulation that comprises other excipients, is administered in aliquots of an amount, and at time intervals, which provide and maintain at least a therapeutic serum level of at least one pharmaceutically active form of the compound over the time interval between dose administrations.

When any variable (e.g. aryl, heterocycle, R$^1$, R$^2$ etc.) occurs more than one time in any constituent, its definition on each occurrence is independent of every other occurrence. Also, combinations of substituents/or variables are permissible only if such combinations result in stable compounds, is chemically feasible and/or valency permits.

As used herein, unless otherwise specified, the terms in the paragraphs immediately below have the indicated meaning.

"Alkyl" refers to both branched- and straight-chain saturated aliphatic hydrocarbon groups of 1 to 18 carbon atoms, or more specifically, 1 to 12 carbon atoms. Examples of such groups include, but are not limited to, methyl (Me), ethyl (Et), n-propyl (Pr), n-butyl (Bu), n-pentyl, n-hexyl, and the isomers thereof such as isopropyl (i-Pr), isobutyl (i-Bu), sec-butyl (s-Bu), tert-butyl (t-Bu), isopentyl, and isohexyl. Alkyl groups may be optionally substituted with one or more substituents as defined herein. "C$_{1-6}$alkyl" refers to an alkyl group as defined herein having 1 to 6 carbon atoms.

"Carboxyl" refers to a monovalent functional group or radical (e.g., COOH) typical of organic acids.

"Halo" or "halogen" refers to fluoro, chloro, bromo or iodo, unless otherwise noted.

The term "haloalkyl" refers to an alkyl in which one or more hydrogen atoms are replaced by halo, and includes alkyl moieties in which all hydrogens have been replaced by halo (e.g., perfluoroalkyl). Alkyl and haloalkyl groups may be optionally inserted with O, N, or S. The terms "aralkyl" refers to an alkyl moiety in which an alkyl hydrogen atom is replaced by an aryl group. Aralkyl includes groups in which more than one hydrogen atom has been replaced by an aryl group. Examples of "aralkyl" include benzyl, 9-fluorenyl, benzhydryl, and trityl groups.

The term "alkenyl" refers to a straight or branched hydrocarbon chain containing 2-8 carbon atoms and characterized in having one or more double bonds. Examples of a typical alkenyl include, but not limited to, allyl, propenyl, 2-butenyl, 3-hexenyl and 3-octenyl groups.

The term "alkynyl" refers to a straight or branched hydrocarbon chain containing 2-8 carbon atoms and characterized in having one or more triple bonds. Some examples of a typical alkynyl are ethynyl, 2-propynyl, and 3-methylbutynyl, and propargyl.

The term "alkoxy" refers to an alky group singularly bonded to oxygen, and the terms "cycloalkoxy" and "arylkoxy" refer to an cyclo alky and aryl alkyl groups singularly bonded to oxygen respectively.

The term "alkylene" refers to a divalent alkyl, e.g., —CH$_2$—, —CH$_2$CH$_2$—, and —CH$_2$CH$_2$CH$_2$—.

The term "cycloalkyl" as employed herein includes saturated cyclic, bicyclic, tricyclic, or polycyclic hydrocarbon groups having 3 to 12 carbons. The cycloalkyl groups herein described may also contain fused rings. Fused rings are rings that share a common carbon-carbon bond or a common carbon atom (e.g., spiro-fused rings). Examples of cycloalkyl moieties include, but are not limited to, cycylopropyl, cyclobutyl, cyclopentyl, cyclohexyl, adamantyl, norbornyl, and decalin.

The term "heterocyclyl" refers to a nonaromatic 3-10 membered monocyclic, 8-12 membered bicyclic, or 11-14 membered tricyclic ring system having 1-3 heteroatoms of monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). The heterocyclyl groups herein described may also contain fused rings. Fused rings are rings that share a common carbon-carbon bond or a common carbon atom (e.g., spiro-fused rings). Examples of heterocyclyl include, but are not limited to tetrahydrofuranyl, tetrahydropyranyl, piperidinyl, morpholino, pyrrolinyl and pyrrolidinyl.

The term "cycloalkenyl" as employed herein includes partially unsaturated, nonaromatic, cyclic, bicyclic, tricyclic, or polycyclic hydrocarbon groups having 5 to 12 carbons, preferably 5 to 8 carbons. The cycloalkenyl groups herein described may also contain fused rings. Fused rings are rings that share a common carbon-carbon bond or a common carbon atom (e.g., spiro-fused rings). Examples of cycloalkenyl moieties include, but are not limited to, cyclohexenyl, and cyclohexadienyl.

The term "heteroaryl" refers to an aromatic 5-8 membered monocyclic, 8-12 membered bicyclic, or 11-14 membered tricyclic ring system having 1-3 heteroatoms for monocyclic, 1-6heteroatoms for bicyclic, or 1-9 heteroatoms for tricyclic, said heteroatoms selected from O, N, or S (e.g., carbon atoms and 1-3, 1-6, or 1-9 heteroatoms of N, O, or S for monocyclic, bicyclic, or tricyclic, respectively). The heteroaryl groups herein described may also contain fused rings that share a common carbon-carbon bond.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent.

The term "nucleobase" refers to a nitrogen-containing heterocyclic moiety, which are the parts of the nucleic acids that are involved in the hydrogen-bonding and bind one nucleic acid strand to another complementary strand in a sequence specific manner. The most common naturally-occurring nucleobases are: adenine (A), cyctosine (C), guanine (G), thymine (T), and uracil (U).

The term "modified nucleobase" refers to a moiety that can replace a nucleobase. The modified nucleobase mimics the spatial arrangement, electronic properties, or some other physiochemical property of the nucleobase and retains the property of the hydrogen-bonding that binds one nucleic acid strand to another in a sequence specific manner. A modified nucleobase can pair with at least one of the five naturally occurring bases (uracil, thymine, adenine, cytosine, and guanine) without substantially affecting the melting behavior, recognition by intracellular enzymes, or activity of the oligonucleotide duplex. The term "modified nucleoside" or "modified nucleotide" refers to a nucleoside or nucleotide that contains a modified nucleobase and/or other chemical modification disclosed herein, such as modified sugar, modified phosphorus atom bridges or modified internucleoside linkages. Non-limiting examples of nucleobases include uracil, thymine, adenine, cytosine, and guanine optionally having their respective amino groups protected by, e.g., acyl protecting groups, 5-propynyl-uracil, 2-thio-5-propynyl-uracil, 5-methylcytosine, 2-fluorouracil, 2-fluorocytosine, 5-bromouracil, 5-iodouracil, 2,6-diaminopurine, azacytosine, 2-thiouracil, 2-thiothymine, 2-aminopurine, N9-(2-amino-6-chloropurine, N9-(2,6-diaminopurine), hypoxanthine, N9-(7-deaza-guanine), N9-(7-deaza-8-aza-guanine), N8-(8-aza-7-deazaadenine), pyrimidine analogs such as pseudoisocytosine and pseudouracil and other modified nucleobases such as 8-substituted purines, xanthine, or hypoxanthine.

The terms "adeninyl, cytosinyl, guaninyl, thyminyl, and uracilyl" and the like refer to radicals of adenine, cytosine, guanine, thymine, and uracil.

The term cholesterol is presented by

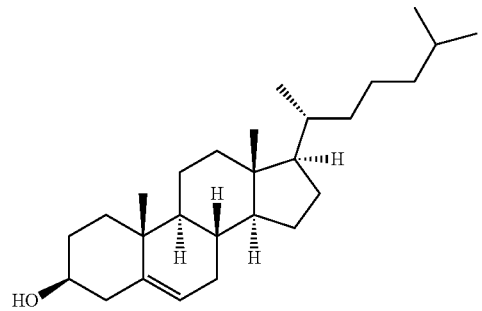

and when used as a radical, it is linked to the core structure through bond having the "OH" group.

A "protected" moiety refers to a reactive functional group, e.g., a hydroxyl group or an amino group, or a class of molecules, e.g., sugars, having one or more functional groups, in which the reactivity of the functional group is temporarily blocked by the presence of an attached protecting group. Protecting groups useful for the monomers and methods described herein can be found, e.g., in Greene, T. W., *Protective Groups in Organic Synthesis* (John Wiley and Sons: New York), 1981, which is hereby incorporated by reference.

A further aspect of the present invention relates to a pharmaceutical composition comprising a modified oligonucleotide as defined herein.

The pharmaceutical composition according to the invention may further comprise pharmaceutically acceptable carriers, diluents, and/or adjuvants. The term "carrier" when used herein includes carriers, excipients and/or stabilisers that are non-toxic to the cell or mammal being exposed thereto at the dosages and concentrations employed. Often the physiologically acceptable carriers are aqueous pH buffered solutions or liposomes. Examples of physiologically acceptable carriers include buffers such as phosphate, citrate and other organic acids (however, with regard to the formulation of the present invention, a phosphate buffer is preferred); anti-oxidants including ascorbic acid; low molecular weight (less than about 10 residues) polypeptides; proteins such as serum albumin, gelatin or immunoglobulins; hydrophilic polymers such as polyvinyl pyrrolidone; amino acids such as glycine, glutamine, asparagine, arginine or lysine; monosaccharides, disaccharides, and other carbohydrates including glucose, mannose or dextrins, gelating agents such as EDTA, sugar, alcohols such as mannitol or sorbitol; salt-forming counterions such as sodium; and/or non-ionic surfactants such as TWEEN, polyethylene or polyethylene glycol. According to an embodiment the compound of the invention is dissolved in sterile deionized water.

Such a composition and/or formulation according to the invention can be administered to a subject in need thereof, particularly a human patient, in a sufficient dose for the treatment of the specific conditions by suitable means. For example, the composition and/or formulation according to the invention may be formulated as a pharmaceutical composition together with pharmaceutically acceptable carriers, diluents and/or adjuvants. Therapeutic efficiency and toxicity may be determined according to standard protocols. The pharmaceutical composition may be administered intratumorally, and systemically, e.g., intraperitoneally, intramuscularly, intravenously, locally, such as intranasally, subcutaneously, intradermally or intrathecally. The dose of the composition and/or formulation administered will, of course, be dependent on the subject to be treated and on the condition of the subject, such as the subject's weight, the subject's age and the type and severity of the disease or injury to be treated, the manner of administration and the judgement of the prescribing physician.

In an embodiment, the pharmaceutical composition is administered intradermally. In another embodiment, the composition is administered intradermally via tattooing, microneedling and/or microneedle patches.

Methods of Use

Compounds described herein having therapeutic applications, such as the compounds of general Formula Ia and Formula I, and the compounds of Examples 1 through 838, can be administered to a patient for the purpose of inducing an immune response, inducing a RIG-I-dependent IFN production and/or inducing anti-tumor activity. In one embodiment, the present invention provides for both prophylactic and therapeutic methods of inducing an IFN response in a patient. The term "administration" and variants thereof (e.g., "administering" a compound) means providing the compound to the individual in need of treatment. When a compound is provided in combination with one or more other active agents (e.g., antiviral agents useful for treating HCV infection or anti-tumor agents for treating cancers), "administration" and its variants are each understood to include concurrent and sequential provision of the compound or salt and other agents.

The present invention encompasses the use of the short oligonucleotide hairpin molecule of the invention to prevent and/or treat any disease, disorder, or condition in which inducing IFN production would be beneficial. For example, increased IFN production, by way of the nucleic acid molecule of the invention, may be beneficial to prevent or treat a wide variety of disorders, including, but not limited to, bacterial infection, viral infection, parasitic infection, immune disorders, respiratory disorders, cancer and the like.

Infections include, but are not limited to, viral infections, bacterial infections, anthrax, parasitic infections, fungal infections and prion infection.

Viral infections include, but are not limited to, infections by hepatitis C, hepatitis B, influenza virus, herpes simplex virus (HSV), human immunodeficiency virus (HIV), respiratory syncytial virus (RSV), vesicular stomatitis virus (VSV), cytomegalovirus (CMV), poliovirus, encephalomyocarditis virus (EMCV), human papillomavirus (HPV) and smallpox virus. In one embodiment, the infection is an upper respiratory tract infection caused by viruses and/or bacteria, in particular, flu, more specifically, bird flu.

Bacterial infections include, but are not limited to, infections by streptococci, staphylococci, *E. coli*, and *Pseudomonas*. In one embodiment, the bacterial infection is an intracellular bacterial infection which is an infection by an intracellular bacterium such as mycobacteria (tuberculosis), *chlamydia, mycoplasma, listeria*, and an facultative intracellular bacterium such as *Staphylococcus aureus*.

Parasitic infections include, but are not limited to, worm infections, in particular, intestinal worm infection, microeukaryotes, and vector-borne diseases, including for example Leishmaniasis.

In a preferred embodiment, the infection is a viral infection or an intracellular bacterial infection. In a more preferred embodiment, the infection is a viral infection by hepatitis C, hepatitis B, influenza virus, RSV, HPV, HSV1, HSV2, and CMV.

Immune disorders include, but are not limited to, allergies, autoimmune disorders, and immunodeficiencies.

Allergies include, but are not limited to, respiratory allergies, contact allergies and food allergies.

Autoimmune diseases or disorders include, but are not limited to, multiple sclerosis, diabetes mellitus, arthritis (including rheumatoid arthritis, juvenile rheumatoid arthritis, osteoarthritis, psoriatic arthritis), encephalomyelitis, myasthenia gravis, systemic lupus erythematosis, autoimmune thyroiditis, dermatisis (including atopic dermatitis and eczematous dermatitis), psoriasis, Siogren's Syndrome, Crohn's Disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis.

Immunodeficiencies include, but are not limited to, spontaneous immunodeficiency, acquired immunodeficiency (including AIDS), drug-induced immunodeficiency or immunosuppression (such as that induced by immunosuppressants used in transplantation and chemotherapeutic agents used for treating cancer), and immunosuppression caused by chronic hemodialysis, trauma or surgical procedures.

Respiratory disorders include, but are not limited to, acute lung injury (ALI), acute respiratory distress syndrome (ARDS), asthma, chronic obstructive pulmonary disease (COPD), obstructive sleep apnea (OSA), idiopathic pulmonary fibrosis (IPF), tuberculosis, pulmonary hypertension, pleural effusion, and lung cancer.

Examples of cancers include, but are not limited to, Acute Lymphoblastic Leukemia; Acute Myeloid Leukemia; Adrenocortical Carcinoma; AIDS-Related Lymphoma; AIDS-Related Malignancies; Anal Cancer; Astrocytoma; Bile Duct Cancer; Bladder Cancer; Bone Cancer, Osteosarcoma/Malignant Fibrous Histiocytoma; Brain Stem Glioma; Brain Tumor, Cerebellar Astrocytoma; Brain Tumor, Cerebral Astrocytoma/Malignant Glioma; Brain Tumor, Ependymoma; Brain Tumor, Medulloblastoma; Brain Tumor, Supratentorial Primitive Neuroectodermal Tumors; Brain Tumor, Visual Pathway and Hypothalamic Glioma; Breast Cancer; Bronchial Adenomas/Carcinoids; Carcinoid Tumor; Carcinoid Tumor, Gastrointestinal; Carcinoma, Adrenocortical; Carcinoma, Islet Cell; Central Nervous System Lymphoma, Primary; Cerebral Astrocytoma/Malignant Glioma; Cervical Cancer; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer; Cutaneous T-Cell Lymphoma; Endometrial Cancer; Ependymoma; Epithelial Cancer, Ovarian; Esophageal Cancer; Esophageal Cancer; Ewing's Family of Tumors; Extracranial Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer; Hodgkin's Lymphoma; Hypopharyngeal Cancer; Hypothalamic and Visual Pathway Glioma;

Intraocular Melanoma; Islet Cell Carcinoma (Endocrine Pancreas); Kaposi's Sarcoma; Kidney Cancer; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoblastic Leukemia; Lymphoma, AIDS-Related; Lymphoma, Central Nervous System (Primary); Lymphoma, Cutaneous T-Cell; Lymphoma, Hodgkin's; Lymphoma, Hodgkin's During Pregnancy; Lymphoma, Non-Hodgkin's; Lymphoma, Primary Central Nervous System; Macroglobulinemia, Waldenstrom's; Male Breast Cancer; Malignant Mesothelioma; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia; Myeloma, Multiple; Myeloproliferative Disorders, Chronic; Nasal Cavity and Paranasal Sinus Cancer; Nasopharyngeal Cancer; Neuroblastoma; Non-Hodgkin's Lymphoma; Non-Small Cell Lung Cancer; Oral Cancer; Oral Cavity and Lip Cancer; Oropharyngeal Cancer; steosarcoma/Malignant Fibrous Histiocytoma of Bone; Ovarian Epithelial Cancer; Ovarian Germ Cell Tumor; Ovarian Low Malignant Potential Tumor; Pancreatic Cancer; Paranasal Sinus and Nasal Cavity Cancer; Parathyroid Cancer; Penile Cancer; Pheochromocytoma; Pineal and Supratentorial Primitive Neuroectodermal Tumors; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer; Prostate Cancer; Rectal Cancer; Renal Cell (Kidney) Cancer; Renal Pelvis and Ureter, Transitional Cell Cancer; Retinoblastoma; Rhabdomyosarcoma; Salivary Gland Cancer; Sarcoma, Ewing's Family of Tumors; Sarcoma, Kaposi's; Sarcoma (Osteosarcoma)/Malignant Fibrous Histiocytoma of Bone; Sarcoma, Soft Tissue; Sezary Syndrome; Skin Cancer; Skin Cancer (Melanoma); Skin Carcinoma, Merkel Cell; Small Cell Lung Cancer; Small Intestine Cancer; Soft Tissue Sarcoma; Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Thymoma, Malignant; Thyroid Cancer; Transitional Cell Cancer of the Renal Pelvis and Ureter; Trophoblastic Tumor, Gestational; Ureter and Renal Pelvis, Transitional Cell Cancer; Urethral Cancer; Uterine Sarcoma; Vaginal Cancer; Visual Pathway and Hypothalamic Glioma; Vulvar Cancer; Waldenstrom's Macro globulinemia; and Wilms' Tumor.

In one embodiment, the cancer is brain cancer, such as an astrocytic tumor (e.g., pilocytic astrocytoma, subependymal giant-cell astrocytoma, diffuse astrocytoma, pleomorphic xanthoastrocytoma, anaplastic astrocytoma, astrocytoma, giant cell glioblastoma, glioblastoma, secondary glioblastoma, primary adult glioblastoma, and primary pediatric glioblastoma); oligodendroglial tumor (e.g., oligodendroglioma, and anaplastic oligodendroglioma); oligoastrocytic tumor (e.g., oligoastrocytoma, and anaplastic oligoastrocytoma); ependymoma (e.g., myxopapillary ependymoma, and anaplastic ependymoma); medulloblastoma; primitive neuroectodermal tumor, schwannoma, meningioma, meatypical meningioma, anaplastic meningioma; and pituitary adenoma. In another embodiment, the brain cancer is glioma, glioblastoma multiforme, paraganglioma, or suprantentorial primordial neuroectodermal tumors (sPNET).

In another embodiment, the cancer is leukemia, such as acute myeloid leukemia (AML), myelodysplastic syndrome (MDS), chronic myelogenous leukemia (CML), myeloproliferative neoplasm (MPN), post-MPN AML, post-MDS AML, del(5q)-associated high risk MDS or AML, blastphase chronic myelogenous leukemia, angioimmunoblastic lymphoma, and acute lymphoblastic leukemia.

In one embodiment, the cancer is skin cancer, including melanoma. In another embodiment, the cancer is prostate cancer, breast cancer, thyroid cancer, colon cancer, or lung cancer. In another embodiment, the cancer is sarcoma, including central chondrosarcoma, central and periosteal chondroma, and fibrosarcoma. In another embodiment, the cancer is cholangiocarcinoma.

Administration and Dosing

As used herein, the terms "treatment" and "treating" refer to all processes wherein there may be a slowing, interrupting, arresting, controlling, or stopping of the progression of a disease or disorder described herein. The terms do not necessarily indicate a total elimination of all disease or disorder symptoms. The terms also include the potential prophylactic therapy of the mentioned conditions, particularly in a subject that is predisposed to such disease or disorder.

The terms "administration of" and or "administering" a compound should be understood to include providing a compound described herein, or a pharmaceutically acceptable salt thereof, and compositions of the foregoing to a subject.

The amount of a compound administered to a subject is an amount sufficient to induce an immune response and/or to induce RIG-I-dependent type I interferon production in the subject. In an embodiment, the amount of a compound can be an "effective amount" or "therapeutically effective amount," wherein the subject compound is administered in an amount that will elicit a biological or medical response of a tissue, system, animal or human that is being sought by a researcher, veterinarian, medical doctor or other clinician. An effective amount does not necessarily include considerations of toxicity and safety related to the administration of a compound.

An effective amount of a compound will vary with the particular compound chosen (e.g., considering the potency, efficacy, and/or half-life of the compound); the route of administration chosen; the condition being treated; the severity of the condition being treated; the age, size, weight, and physical condition of the subject being treated; the medical history of the subject being treated; the duration of the treatment; the nature of a concurrent therapy; the desired therapeutic effect; and like factors and can be routinely determined by the skilled artisan.

Biological methods for introducing a nucleic acid into a host cell include the use of DNA and RNA vectors. Viral vectors, and especially retroviral vectors, have become the most widely used method for inserting genes into mammalian, e.g., human cells.

The compounds disclosed herein may be administered by any suitable route including oral and parenteral administration. Parenteral administration is typically by injection or infusion and includes intravenous, intramuscular, and subcutaneous injection or infusion.

The compounds disclosed herein may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound disclosed herein depend on the pharmacokinetic properties of that compound, such as absorption, distribution and half-life which can be determined by a skilled artisan. In addition, suitable dosing regimens, including the duration such regimens are administered, for a compound disclosed herein depend on the disease or condition being treated, the severity of the disease or condition, the age and physical condition of the subject being treated, the medical history of the subject being treated, the nature of concurrent therapy, the desired therapeutic effect, and like factors within the knowledge and expertise of the skilled artisan. It will be further understood by such skilled artisans that suitable dosing regimens may require adjustment given an individual subject's response to the dosing regimen or over time as the individual subject needs change. Typical daily dosages may vary depending upon the particular route of administration chosen. Typical daily dosages for oral administration, to a human weighing approximately 70 kg would range from about 0.1 mg to about 2 g, or more specifically, 0.1 mg to 500 mg, or even more specifically, 0.2 mg to 100 mg, of a compound of general Formula Ia and Formula I.

One embodiment of the present disclosure provides for a method of treating a cell proliferation disorder comprising administration of an effective amount of a compound of general Formula Ia and Formula I to a subject in need of treatment thereof. In one embodiment, the cell proliferation disorder is cancer.

In one embodiment, the cancer is brain cancer, leukemia, skin cancer, prostate cancer, thyroid cancer, colon cancer, lung cancer or sarcoma. In another embodiment the cancer is glioma, glioblastoma multiforme, paraganglioma, suprantentorial primordial neuroectodermal tumors, acute myeloid leukemia, myelodysplastic syndrome, chronic myelogenous leukemia, melanoma, breast, prostate, thyroid, colon, lung, central chondrosarcoma, central and periosteal chondroma tumors, fibrosarcoma, and cholangiocarcinoma.

In one embodiment, disclosed herein is the use of a compound of general Formula Ia and Formula I in a therapy. The compound may be useful in a method of inducing an immune response and/or inducing RIG-I-dependent type I interferon production in a subject, such as a mammal in need of such inhibition, comprising administering an effective amount of the compound to the subject.

In one embodiment, disclosed herein is a pharmaceutical composition comprising at least one compound of general Formula Ia and Formula I, or a pharmaceutically acceptable salt thereof, for use in potential treatment to induce an immune response and/or to induce RIG-I-dependent type I interferon production.

In one embodiment, disclosed herein is the use of a compound of general Formula Ia and Formula I in the manufacture of a medicament for the treatment to induce an immune response and/or to induce RIG-I-dependent type I interferon production. In one embodiment, the disease or disorder to be treated is a cell proliferation disorder. In another embodiment, the cell proliferation disorder is cancer. In another embodiment, the cancer is brain cancer, leukemia, skin cancer, breast, prostate cancer, thyroid cancer, colon cancer, lung cancer, or sarcoma. In another embodiment, the cancer is glioma, glioblastoma multiforme, paraganglioma, suprantentorial primordial neuroectodermal tumors, acute myeloid leukemia, myelodysplastic syndrome, chronic myelogenous leukemia, melanoma, breast, prostate, thyroid, colon, lung, central chondrosarcoma, central and periosteal chondroma tumors, fibrosarcoma, and/or cholangiocarcinoma.

Compositions

The present invention provides a pharmaceutical composition comprising at least one nucleic acid molecule of the present invention and a pharmaceutically acceptable carrier. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

The term "composition" as used herein is intended to encompass a dosage form comprising a specified compound in a specified amount, as well as any dosage form which results, directly or indirectly, from combination of a specified compound in a specified amount. Such term is intended to encompass a dosage form comprising a compound of general Formula Ia and Formula I, or a pharmaceutically acceptable salt thereof, and one or more pharmaceutically acceptable carriers or excipients. Accordingly, the compositions of the present disclosure encompass any composition made by admixing a compound of the present disclosure and one or more pharmaceutically acceptable carrier or excipients. By "pharmaceutically acceptable", it is meant the carriers or excipients are compatible with the compound disclosed herein and with other ingredients of the composition.

For the purpose of inducing an immune response and/or inducing a RIG-I-dependent type I interferon production, the compounds, optionally in the form of a salt, can be administered by means that produce contact of the active agent with the agent's site of action. They can be administered by conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice.

An embodiment of the invention is realized by a composition comprising a nucleic acid capable of inducing interferon production, wherein the molecule comprises a single strand of 24 bases by 5' GCU-CAUUUACCAGCGUAAAUGAGC 3' (SEQ ID NO: 841), said single strand having a double-stranded section of less than 12 base pairs. A subembodiment of this aspect of the invention is realized when the single stranded nucleic acid forms a hairpin structure comprising the double-stranded section and a loop. Another subembodiment of this aspect of the invention is realized when the double-stranded nucleic acid comprises one or two blunt ends. Another subembodiment of this aspect of the invention is realized when the double-stranded nucleic acid comprises a 5' blunt end. Another subembodiment of this aspect of the invention is realized when the nucleic acid comprises at least one of the group consisting of a 5'-OH, 5'-triphosphate and a 5'-diphosphate. Another subembodiment of this aspect of the invention is realized when the molecule comprises a modified phosphodiester backbone. Still another subembodiment of this aspect of the invention is realized when the molecule comprises at least one 2'-modified nucleotide. A further aspect of this embodiment of the invention is realized when the 2'-modified nucleotide comprises a modification selected from the group consisting of: 2'-OH, 2'-methyl, 2'-OCF$_3$, 2'-OCH$_2$C≡CH, —NH$_2$, 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyl-oxyethyl (2'-O-DMAEOE), and 2'-O—N-methylacetamido (2'-O-NMA). Another subembodiment of this aspect of the invention is realized when the molecule comprises at least one modified phosphate group. Another subembodiment of this aspect of the invention is realized when the molecule comprises at least one modified base. Another subembodiment of this aspect of the invention is realized when the double stranded section comprises one or more mispaired bases.

The compositions of the disclosure are prepared using techniques and methods known to those skilled in the art. Some methods commonly used in the art are described in Remington's Pharmaceutical Sciences (Mack Publishing Company).

In one embodiment, disclosed herein is a composition comprising a compound of general Formula Ia and Formula I or a pharmaceutically acceptable salt thereof, and one or more pharmaceutically acceptable carriers or excipients. The composition may be prepared and packaged in bulk form wherein an effective amount of a compound of the disclosure can be extracted and then given to a subject, such as with powders or syrups. Alternatively, the composition may be prepared and packaged in unit dosage form wherein each physically discrete unit contains an effective amount of a compound of general Formula Ia and Formula I. When prepared in unit dosage form, the composition of the disclosure typically contains from about 0.1 mg to 2 g, or more specifically, 0.1 mg to 500 mg, or even more specifically, 0.2 mg to 100 mg, of a compound of general Formula Ia and Formula I, or a pharmaceutically acceptable salt thereof.

The pharmaceutical composition according to the invention may further comprise pharmaceutically acceptable carriers, diluents, and/or adjuvants. The term "carrier" when used herein includes excipients and/or stabilisers that are non-toxic to the cell or mammal being exposed thereto at the dosages and concentrations employed. Often the physiologically acceptable carriers are aqueous pH buffered solutions or liposomes. Suitable pharmaceutically acceptable carriers or excipients include the following non-limiting types: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. Particular examples of physiologically acceptable carriers include buffers such as phosphate, citrate and other organic acids; anti-oxidants including ascorbic acid, low molecular weight (less than about 10 residues) polypeptides; proteins such as serum albumin, gelatine or immunoglobulins; hydrophilic polymers such as polyvinyl pyrrolidone; amino acids such as glycine, glutamine, asparagine, arginine or lysine; monosaccharides, disaccharides, and other carbohydrates including glucose, mannose or dextrins; gelating agents such as EDTA, sugar, alcohols such as mannitol or sorbitol; salt-forming counterions such as sodium; and/or non-ionic surfactants such as TWEEN, polyethylene or polyethylene glycol. In another embodiment the compound of the invention is dissolved in sterile deionized water.

A skilled artisan possesses the knowledge and skill in the art to select suitable pharmaceutically acceptable carriers and excipients in appropriate amounts for the use in the disclosure. In addition, there are a number of resources available to the skilled artisan, which describe pharmaceutically acceptable carriers and excipients and may be useful in selecting suitable pharmaceutically acceptable carriers and excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The compounds disclosed herein and a pharmaceutically acceptable carrier or excipient(s) will typically be formulated into a dosage form adapted for administration to a subject by a desired route of administration. Many systems for administering active substances into cells are already known and include lipid nanoparticles (LNPs), emulsions, liposomes, exosomes, dendrimers, natural polymers, e.g., chitosan, polyethylenimines (PEIs), immuno- and ligand complexes, micelles, microparticles and/or polymeric nanoparticles and cyclodextrins (see, *Drug Transport in Antimicrobial and Anticancer Chemotherapy*. G. Papadakou Ed., CRC Press, 1995 and US2013/0037977). These systems may be adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients will vary depending upon the particular dosage form chosen. In addition, suitable pharmaceutically acceptable carriers or excipients may be chosen for a particular function that they may serve in the composition. For example, certain pharmaceutically acceptable carriers or excipients may be chosen for their ability to facilitate the production of uniform dosage forms. Certain pharmaceutically acceptable carriers or excipients may be chosen for their ability to facilitate the production of stable dosage forms. Certain pharmaceutically acceptable carriers or excipients may be chosen for their ability to facilitate the carrying or transporting of a compound disclosed herein, once administered to the subject, from one organ or portion of the body to another organ or another portion of the body. Certain pharmaceutically acceptable carriers or excipients may be chosen for their ability to enhance patient compliance.

In an embodiment, the disclosure is directed to a solid oral dosage form such as a tablet or capsule comprising an effective amount of a compound of the disclosure and a diluent or filler. Suitable diluents and fillers include lactose, sucrose, dextrose, mannitol, sorbitol, starch (e.g., corn starch, potato starch, and pre-gelatinized starch), cellulose and its derivatives, (e.g., microcrystalline cellulose), calcium sulfate, and dibasic calcium phosphate. The oral solid dosage form may further comprise a binder. Suitable binders include starch (e.g., corn starch, potato starch, and pre-gelatinized starch) gelatin, acacia, sodium alginate, alginic acid, tragacanth, guar gum, povidone, and cellulose and its derivatives (e.g., microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as, for example, by coating or embedding particulate material in polymers, wax, or the like.

The compounds disclosed herein may also be coupled with soluble polymers as targetable drug carriers. Such polymers can include polyvinylpyrrolidone, pyrancopolymer, polyhydroxypropylmethacrylamidephenol, polyhydroxyethylaspartamidephenol, or polyethyleneoxidepolylysine substituted with palmitoyl residues. Furthermore, the compounds of the disclosure may be coupled to a class of biodegradable polymers useful in achieving controlled release of a drug, for example polylactic acid, polepsilon caprolactone, polyhydroxy butyric acid, polyorthoesters, polyacetals, polydihydropyrans, polycyanacrylates and cross-linked or amphipathic block copolymers of hydrogels.

In one embodiment, the disclosure is directed to a liquid oral dosage form. Oral liquids such as solution, syrups and elixirs can be prepared in dosage unit form so that a given quantity contains a predetermined amount of a compound disclosed herein. Syrups can be prepared by dissolving the compound of the disclosure in a suitably flavored aqueous solution; while elixirs are prepared through the use of a non-toxic alcoholic vehicle. Suspensions can be formulated by dispersing a compound disclosed herein in a non-toxic vehicle. Solubilizers and emulsifiers such as ethoxylated isostearyl alcohols and polyoxy ethylene sorbitol ethers, preservatives, flavor additives such as peppermint oil or other natural sweeteners or saccharin or other artificial sweeteners and the like can also be added.

In another embodiment, the disclosure is directed to compositions for parenteral administration. Compositions adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions that may include suspending agents and thickening agents. The compositions may be presented in unit-dose or multi-dose containers, for example sealed ampoules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Combinations

The compounds of general Formula Ia and Formula I may be administered in combination with one or more additional therapeutic agents. In embodiments, one or more compound of general Formula Ia and Formula I may be co-administered. The additional therapeutic agent(s) may be administered in a single dosage form with the compound of general Formula Ia and Formula I, or the additional therapeutic agent(s) may be administered in separate dosage form(s) from the dosage form containing the compound of general Formula Ia and Formula I. The additional therapeutic agent(s) may be one or more agents selected from the group consisting of anti-viral compounds, antigens, adjuvants, anti-cancer agents, CTLA-4, LAG-3 and PD-1 pathway antagonists, lipids, peptides, chemotherapeutic agents, immunomodulatory cell lines, checkpoint inhibitors, vascular endothelial growth factor (VEGF) receptor inhibitors, topoisomerase II inhibitors, smoothen inhibitors, alkylating agents, anti-tumor antibiotics, anti-metabolites, retinoids, and immunomodulatory agents including but not limited to anti-cancer vaccines. It will be understood the descriptions of the above additional therapeutic agents may be overlapping. It will also be understood that the treatment combinations are subject to optimization, and it is understood that the best combination to use of the compounds of general Formula Ia and Formula I and one or more additional therapeutic agents will be determined based on the individual patient needs.

A compound disclosed herein may be used in combination with one or more other active agents, including but not limited to, other anti-cancer agents that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present disclosure.

When a compound disclosed herein is used contemporaneously with one or more other active agents, a composition containing such other active agents in addition to the compound disclosed herein is contemplated. Accordingly, the compositions of the present disclosure include those that also contain one or more other active ingredients, in addition to a compound disclosed herein. A compound disclosed herein may be administered either simultaneously with, or before or after, one or more other therapeutic agent(s). A compound disclosed herein may be administered separately, by the same or different route of administration, or together in the same pharmaceutical composition as the other agent(s).

Products provided as a combined preparation include a composition comprising a compound of general Formula Ia and Formula I and one or more other active agent(s) together in the same pharmaceutical composition, or a compound of general Formula Ia and Formula I and one or more other therapeutic agent(s) in separate form, e.g. in the form of a kit.

The weight ratio of a compound disclosed herein to a second active agent may be varied and will depend upon the effective dose of each agent. Generally, an effective dose of each will be used. Thus, for example, when a compound disclosed herein is combined with another agent, the weight ratio of the compound disclosed herein to the other agent will generally range from about 1000:1 to about 1:1000, such as about 200:1 to about 1:200. Combinations of a compound disclosed herein and other active agents will generally also be within the aforementioned range, but in each case, an effective dose of each active agent should be used. In such combinations, the compound disclosed herein and other active agents may be administered separately or in conjunction. In addition, the administration of one element may be prior to, concurrent to, or subsequent to the administration of other agent(s).

In one embodiment, this disclosure provides a composition comprising a compound of general Formula Ia and Formula I and at least one other therapeutic agent as a combined preparation for simultaneous, separate or sequential use in therapy. In one embodiment, the therapy is the treatment of a cell proliferation disorder, such as cancer.

In one embodiment, the disclosure provides a kit comprising two or more separate pharmaceutical compositions, at least one of which contains a compound of general Formula Ia and Formula I. In one embodiment, the kit comprises means for separately retaining said compositions, such as a container, divided bottle, or divided foil packet. An example of such a kit is a blister pack, as typically used for the packaging of tablets, capsules, and the like.

A kit of this disclosure may be used for administration of different dosage forms, for example, oral and parenteral, for administration of the separate compositions at different dosage intervals, or for titration of the separate compositions against one another. To assist with compliance, a kit of the disclosure typically comprises directions for administration.

Disclosed herein is a use of a compound of general Formula Ia and Formula I for treating a cell proliferation disorder, wherein the medicament is prepared for administration with another active agent. The disclosure also provides the use of another active agent for treating a cell proliferation disorder, wherein the medicament is administered with a compound of general Formula Ia and Formula I.

The disclosure also provides the use of a compound of general Formula Ia and Formula I for treating a cell proliferation disorder, wherein the patient has previously (e.g., within 24 hours) been treated with another active agent. The disclosure also provides the use of another therapeutic agent for treating a cell proliferation disorder, wherein the patient has previously (e.g., within 24 hours) been treated with a compound of general Formula Ia and Formula I. The second agent may be applied a week, several weeks, a month, or several months after the administration of a compound disclosed herein.

Anti-viral compounds that may be used in combination with the compounds of general Formula Ia and Formula I disclosed herein include hepatitis B virus (HBV) inhibitors, hepatitis C virus (HCV) protease inhibitors, HCV polymerase inhibitors, HCV NS4A inhibitors, HCV NS5A inhibitors, HCV NS5b inhibitors, and human immunodeficiency virus (HIV) inhibitors.

Antigens and adjuvants that may be used in combination with the compounds of general Formula Ia and Formula I disclosed herein include B7 costimulatory molecule, interleukin-2, interferon-γ, GM-CSF, CTLA-4 antagonists, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions. Adjuvants, such as aluminum hydroxide or aluminum phosphate, can be added to increase the ability of the compound to trigger, enhance, or prolong an immune response. Additional materials, such as cytokines, chemokines, and bacterial nucleic acid sequences, like CpG, a toll-like receptor (TLR) 9 agonist as well as additional agonists for TLR 2, TLR 4, TLR 5, TLR 7, TLR 8, TLR9, including lipoprotein, LPS, monophosphoryllipid A, lipoteichoic acid, imiquimod, resiquimod, stimulator of interferon genes (STING) agonists and in addition retinoic acid-inducible gene I (RIG-I) agonists such as poly I:C, used separately or in combination with the described compositions are also potential adjuvants.

CLTA-4 and PD-1 pathways are important negative regulators of immune response. Activated T-cells upregulate CTLA-4, which binds on antigen-presenting cells and inhibits T-cell stimulation, IL-2 gene expression, and T-cell proliferation; these anti-tumor effects have been observed in mouse models of colon carcinoma, metastatic prostate cancer, and metastatic melanoma. PD-1 binds to active T-cells and suppresses T-cell activation; PD-1 antagonists have demonstrated anti-tumor effects as well. CTLA-4 and PD-1 pathway antagonists that may be used in combination with the compounds of general Formula Ia and Formula I disclosed herein include ipilimumab, tremelimumab, nivolumab, pembrolizumab, CT-011, AMP-224, and MDX-1106.

"PD-1 antagonist" or "PD-1 pathway antagonist" means any chemical compound or biological molecule that blocks binding of PD-L1 expressed on a cancer cell to PD-1 expressed on an immune cell (T-cell, B-cell, or NKT-cell) and preferably also blocks binding of PD-L2 expressed on a cancer cell to the immune-cell expressed PD-1. Alternative names or synonyms for PD-1 and its ligands include: PDCD1, PD1, CD279, and SLEB2 for PD-1; PDCDIL1, PDL1, B7H1, B7-4, CD274, and B7-H for PD-L1; and PDCDIL2, PDL2, B7-DC, Btdc, and CD273 for PD-L2. In any of the treatment method, medicaments and uses of the present disclosure in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the treatment method, medicaments and uses of the present disclosure include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody, or a chimeric antibody and may include a human constant region. In some embodiments, the human constant region is selected from the group consisting of IgG1, IgG2, IgG3, and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv, and Fv fragments.

Examples of mAbs that bind to human PD-1, and useful in the treatment method, medicaments and uses of the present disclosure, are described in U.S. Pat. Nos. U.S. Pat. Nos. 7,488,802, 7,521,051, 8,008,449, 8,354,509, and 8,168,757, PCT International Patent Application Publication Nos. WO2004/004771, WO2004/072286, and WO2004/056875, and U.S. Patent Application Publication No. US2011/0271358.

Examples of mAbs that bind to human PD-L1, and useful in the treatment method, medicaments and uses of the present disclosure, are described in PCT International Patent Application Nos. WO2013/019906 and WO2010/077634 A1 and in U.S. Pat. No. 8,383,796. Specific anti-human PD-L1 mAbs useful as the PD-1 antagonist in the treatment method, medicaments and uses of the present disclosure include MPDL3280A, BMS-936559, MEDI4736, MSB0010718C, and an antibody that comprises the heavy chain and light chain variable regions of SEQ ID NO:24 and SEQ ID NO:21, respectively, of WO2013/019906.

Other PD-1 antagonists useful in any of the treatment method, medicaments, and uses of the present disclosure include an immune-adhesion that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immune-adhesion molecules that specifically bind to PD-1 are described in PCT International Patent Application Publication Nos. WO2010/027827 and WO2011/066342. Specific fusion proteins useful as the PD-1 antagonist in the treatment method, medicaments, and uses of the present disclosure include AMP-224 (also known as B7-DCIg), which is a PD-L2-FC fusion protein and binds to human PD-1.

Thus, the invention further relates to a method of treating cancer in a human patient comprising administration of a compound of Formula Ia and Formula I and a PD-1 antagonist to the patient. The compound of the invention and the PD-1 antagonist may be administered concurrently or sequentially.

In particular embodiments, the PD-1 antagonist is an anti-PD-1 antibody, or antigen binding fragment thereof. In alternative embodiments, the PD-1 antagonist is an anti-PD-L1 antibody, or antigen binding fragment thereof. In some embodiments, the PD-1 antagonist is pembrolizumab (KEYTRUDA™, Merck & Co., Inc., Kenilworth, N.J., USA), nivolumab (OPDIVO™, Bristol-Myers Squibb Company, Princeton, N.J., USA), cemiplimab (LIBTAYO™, Regeneron Pharmaceuticals, Inc., Tarrytown, N.Y., USA), atezolizumab (TECENTRIQ™, Genentech, San Francisco, Calif., USA), durvalumab (IMFINZI™, AstraZeneca Pharmaceuticals LP, Wilmington, Del.), or avelumab (BAVENCIO™, Merck KGaA, Darmstadt, Germany).

In some embodiments, the PD-1 antagonist is pembrolizumab. In particular sub-embodiments, the method comprises administering 200 mg of pembrolizumab to the patient about every three weeks. In other sub-embodiments, the method comprises administering 400 mg of pembrolizumab to the patient about every six weeks.

In further sub-embodiments, the method comprises administering 2 mg/kg of pembrolizumab to the patient about every three weeks. In particular sub-embodiments, the patient is a pediatric patient.

In some embodiments, the PD-1 antagonist is nivolumab. In particular sub-embodiments, the method comprises administering 240 mg of nivolumab to the patient about every two weeks.

In other sub-embodiments, the method comprises administering 480 mg of nivolumab to the patient about every four weeks.

In some embodiments, the PD-1 antagonist is cemiplimab. In particular embodiments, the method comprises administering 350 mg of cemiplimab to the patient about every 3 weeks.

In some embodiments, the PD-1 antagonist is atezolizumab. In particular sub-embodiments, the method comprises administering 1200 mg of atezolizumab to the patient about every three weeks.

In some embodiments, the PD-1 antagonist is durvalumab. In particular sub-embodiments, the method comprises administering 10 mg/kg of durvalumab to the patient about every two weeks.

In some embodiments, the PD-1 antagonist is avelumab. In particular sub-embodiments, the method comprises administering 800 mg of avelumab to the patient about every two weeks.

Examples of other cytotoxic agents include, but are not limited to, arsenic trioxide (sold under the tradename TRISENOX®), asparaginase (also known as L-asparaginase, and Erwinia L-asparaginase, sold under the tradenames ELSPAR® and KIDROLASE®).

Chemotherapeutic agents that may be used in combination with the compounds of general Formula Ia and Formula I disclosed herein include abiraterone acetate, altretamine, anhydrovinblastine, auristatin, bexarotene, bicalutamide, BMS 184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-L-proline-tbutylamide, cachectin, cemadotin, chlorambucil, cyclophosphamide, 3',4'-didehydro-4'deoxy-8'-norvincaleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, nivolumab, onapristone, paclitaxel, pembrolizumab, prednimustine, procarbazine, RPR109881, stramustine phosphate, tamoxifen, tasonermin, taxol, tretinoin, vinblastine, vincristine, vindesine sulfate, and vinflunine.

Examples of vascular endothelial growth factor (VEGF) receptor inhibitors include, but are not limited to, bevacizumab (sold under the trademark AVASTIN by Genentech/Roche), axitinib (described in PCT International Patent Publication No. WO01/002369), Brivanib Alaninate ((S)—((R)-1-(4-(4-fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-TH-indol-6-yl)-2-[(4-pyridinylmethyl)amino]-3-pyridinecarboxamide. and described in PCT International Patent Application Publication No. WO02/068470), pasireotide (also known as SO 230, and described in PCT International Patent Publication No. WO02/010192), and sorafenib (sold under the tradename NEXAVAR).

Examples of topoisomerase II inhibitors, include but are not limited to, etoposide (also known as VP-16 and Etoposide phosphate, sold under the tradenames TOPOSAR, VEPESID, and ETOPOPHOS), and teniposide (also known as VM-26, sold under the tradename VUMON).

Examples of alkylating agents, include but are not limited to, 5-azacytidine (sold under the trade name VIDAZA), decitabine (sold under the trade name of DECOGEN), temozolomide (sold under the trade names TEMODAR and TEMODAL by Schering-Plough/Merck), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames BUSULFEX® and MYLERAN®), carboplatin (sold under the tradename PARAPLATIN®), lomustine (also known as CCNU, sold under the tradename CEENU®), cisplatin (also known as CDDP, sold under the tradenames PLATINOL® and PLATINOL®-AQ), chlorambucil (sold under the tradename LEUKERAN®), cyclophosphamide (sold under the tradenames CYTOXAN® and NEOSAR®), dacarbazine (also known as DTIC, DIC and imidazole carboxamide, sold under the tradename DTIC-DOME®), altretamine (also known as hexamethylmelamine (HMM) sold under the tradename HEXALEN®), ifosfamide (sold under the tradename IFEX®), procarbazine (sold under the tradename MATULANE®), mechlorethamine (also known as nitrogen mustard, mustine and mechloroethamine hydrochloride, sold under the tradename MUSTARGEN®), streptozocin (sold under the tradename ZANOSAR®), thiotepa (also known as thiophosphoamide, TESPA and TSPA, and sold under the tradename THIOPLEX®.

Examples of anti-tumor antibiotics include, but are not limited to, doxorubicin (sold under the tradenames ADRIAMYCIN® and RUBEX®), bleomycin (sold under the tradename LENOXANE®), daunorubicin (also known as dauorubicin hydrochloride, daunomycin, and rubidomycin hydrochloride, sold under the tradename CERUBIDINE®), daunorubicin liposomal (daunorubicin citrate liposome, sold under the tradename DAUNOXOME®), mitoxantrone (also known as DHAD, sold under the tradename NOVANTRONE®), epirubicin (sold under the tradename ELLENCE™) idarubicin (sold under the tradenames IDAMYCIN®, IDAMYCIN PFS®), and mitomycin C (sold under the tradename MUTAMYCIN®).

Examples of anti-metabolites include, but are not limited to, claribine (2-chlorodeoxyadenosine, sold under the tradename LEUSTATIN®), 5-fluorouracil (sold under the tradename ADRUCIL®), 6-thioguanine (sold under the tradename PURINETHOL®), pemetrexed (sold under the tradename ALINMTA®), cytarabine (also known as arabinosylcytosine (Ara-C), sold under the tradename CYTOSAR-U®), cytarabine liposomal (also known as Liposomal Ara-C, sold under the tradename DEPOCYT™), decitabine (sold under the tradename DACOGEN®), hydroxyurea (sold under the tradenames HYDREA®, DROXIA™ and MYLOCEL™), fludarabine (sold under the tradename FLUDARA®), floxuridine (sold under the tradename FUDR®), cladribine (also known as 2-chlorodeoxyadenosine (2-CdA) sold under the tradename LEUSTATIN™), methotrexate (also known as amethopterin, methotrexate sodium (MTX), sold under the tradenames RHEUMATREX® and TREXALL™), and pentostatin (sold under the tradename NIPENT®).

Examples of retinoids include, but are not limited to, alitretinoin (sold under the tradename PANRETIN®), tretinoin (all-trans retinoic acid, also known as ATRA, sold under the tradename VESANOID®), isotretinoin (13-c/s-retinoic acid, sold under the tradenames ACCUTANE®, AMNESTEEM®, CLARAVIS®, CLARUS®, DECUTAN®, ISOTANE®, IZOTECH®, ORATANE®, ISOTRET®, and SOTRET®), and bexarotene (sold under the tradename TARGRETIN®).

Further disclosed herein is a compound disclosed herein, or a pharmaceutically acceptable salt thereof, for use in therapy. In one embodiment, disclosed herein is the use of a compound disclosed herein, or a pharmaceutically acceptable salt, solvate or hydrate thereof, for the preparation of a medicament for use in therapy.

Intermediates

Intermediates were either purchased from the following vendors or synthesized using the cited literature references as shown or further modified through additional synthetic manipulations analogous to phosphoramidites described in intermediates I-1 to I-21.

TABLE 1

Intermediates used in the synthesis of Examples of the instant invention.

| | Structure | Bases | Source |
|---|---|---|---|
| I-1 | OMe (structure) | B = nucleobase A, C, G, U | ChemGenes Vendor |
| I-2 | OMe (structure) | B = nucleobase A, C, G, U | ChemGenes Vendor |

TABLE 1-continued

Intermediates used in the synthesis of Examples of the instant invention.

| | Structure | Bases | Source |
|---|---|---|---|
| I-3 | 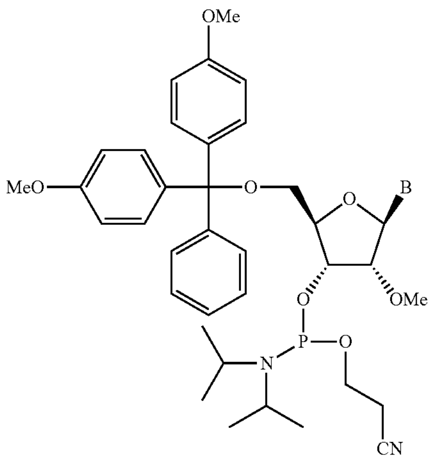 | B = nucleobase A, C, G, U | ChemGenes Vendor |
| I-4 | 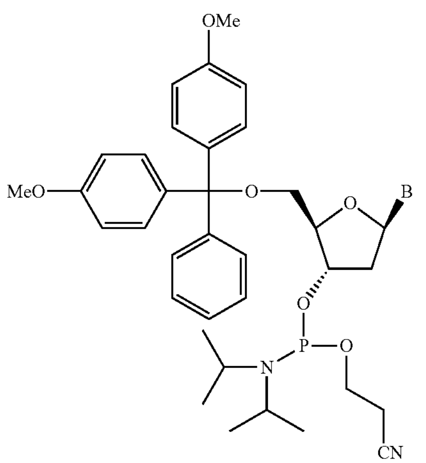 | B = nucleobase A, C, G, U | ChemGenes Vendor |
| I-5 | 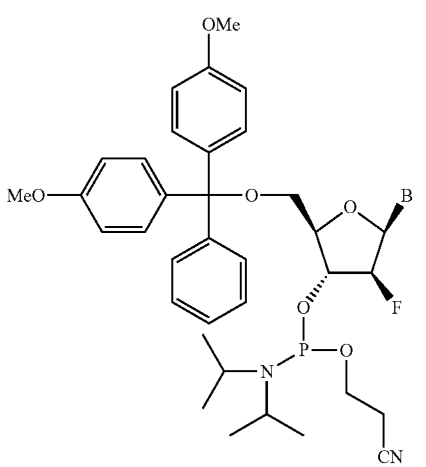 | B = nucleobase A, C, G, U | Glen Research Vendor |

TABLE 1-continued

Intermediates used in the synthesis of Examples of the instant invention.

| | Structure | Bases | Source |
|---|---|---|---|
| I-6 | 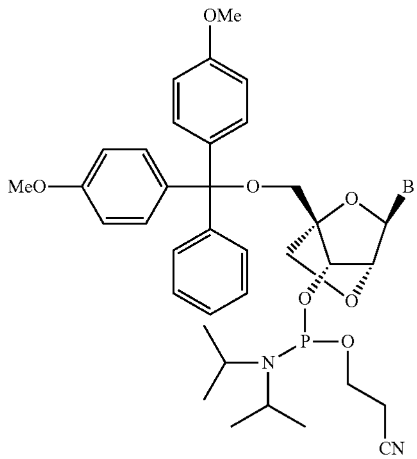 | B = nucleobase<br>A, 5-Me-C, G, T | Exiqon<br>Vendor |
| I-7 | 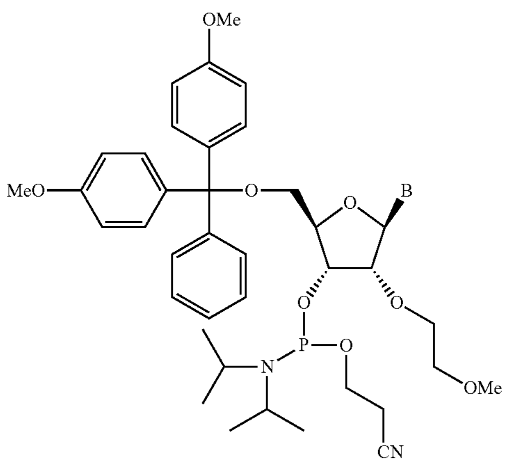 | B = nucleobase<br>A, 5-Me-C, G, T | ChemGenes<br>Vendor |
| I-8 | 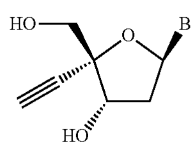 | B = nucleobase<br>A, C, G, U | J. Med. Chem. 2000,<br>43, 4516-4525 |
| I-9 | 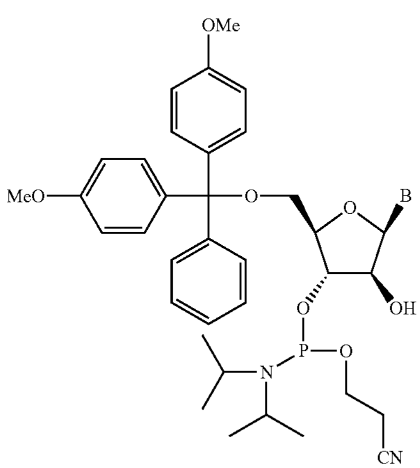 | B = nucleobase<br>A, C, G, U | Canadian Journal of<br>Chemistry 1989, 67,<br>831-9 |

TABLE 1-continued

Intermediates used in the synthesis of Examples of the instant invention.

| | Structure | Bases | Source |
|---|---|---|---|
| I-11 | 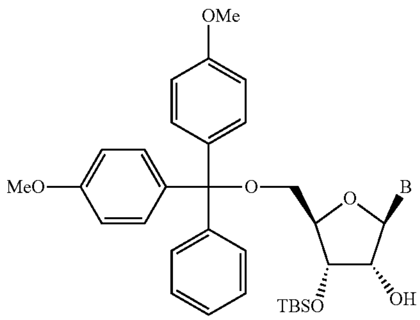 | B = nucleobase A, C, G, U | ChemGenes Vendor |
| I-12 | 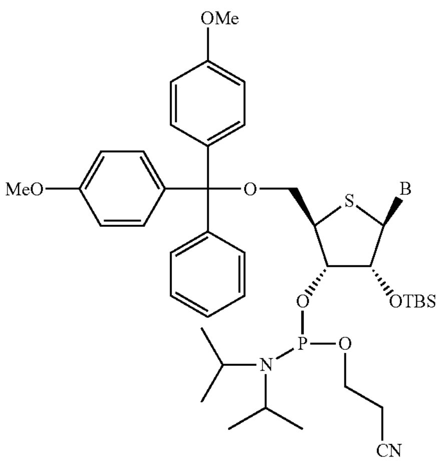 | B = nucleobase A, C, G, U | J. Med. Chem. 2006, 49, 1624-1634 |
| I-13 | 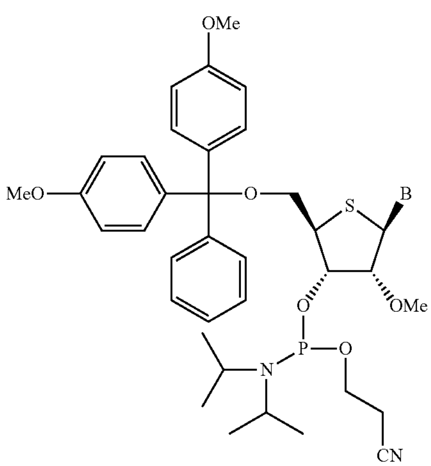 | B = nucleobase A, C, G, U | Nucleic Acids Research, 2009, Vol. 37, No. 4 1353-1362 |
| I-14 | 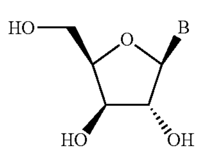 | B = nucleobase A, C, G, U | Nuc. Acids Res. 2015, 43, 7189-7200. |
| I-15 | 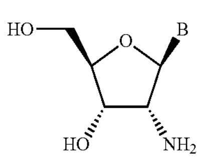 | B = nucleobase A, C, G, U | U.S., 4,849,513, 18 Jul. 1989; Nucleosides & Nucleotides 1992, 11, 1333-51 |

TABLE 1-continued

Intermediates used in the synthesis of Examples of the instant invention.

| | Structure | Bases | Source |
|---|---|---|---|
| I-17 | 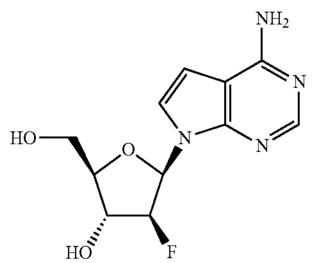 [SMILES: Nc1ncnc2c1ccn2[C@@H]1O[C@H](CO)[C@@H](O)[C@@H]1F] | | Journal of the Chemical Society, Perkin Transactions 1: Organic and Bio-Organic Chemistry 1995 (12), 1543-50 |
| I-18 | 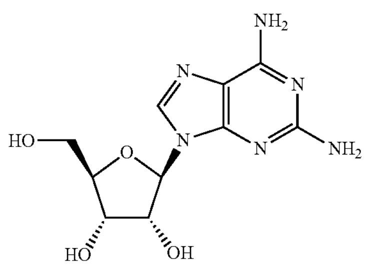 [SMILES: Nc1nc(N)c2ncn([C@@H]3O[C@H](CO)[C@@H](O)[C@H]3O)c2n1] | | Carbosynth Vendor |
| I-19 | 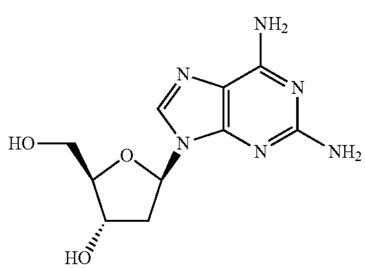 [SMILES: Nc1nc(N)c2ncn([C@H]3C[C@H](O)[C@@H](CO)O3)c2n1] | | Carbosynth Vendor |
| I-20 | 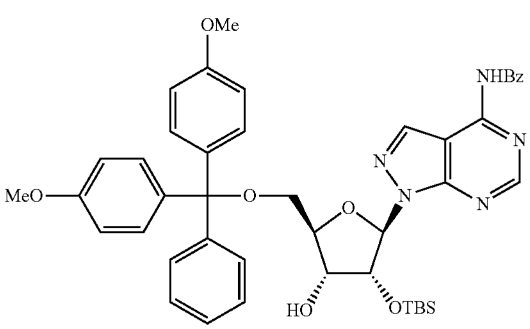 | | Barry and Associates Vendor |
| I-21 | 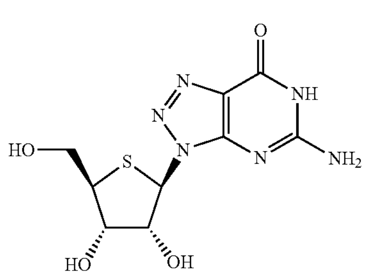 [SMILES: Nc1nc2c(nnn2[C@@H]2S[C@H](CO)[C@@H](O)[C@H]2O)c(=O)[nH]1] | | WO/2017/027646 |

TABLE 1-continued
Intermediates used in the synthesis of Examples of the instant invention.
| | Structure | Bases | Source |
|---|---|---|---|
| I-22 | 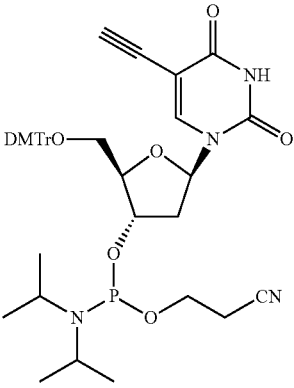 | | Carbosynth Vendor |
| I-23 | 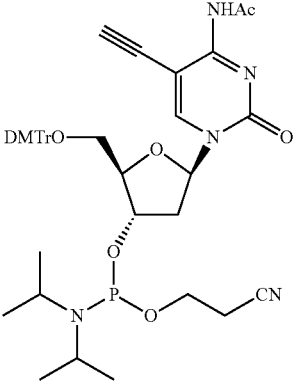 | | Journal of Organic Chemistry, 2013, 78, 11271-11282. |
| I-24 | 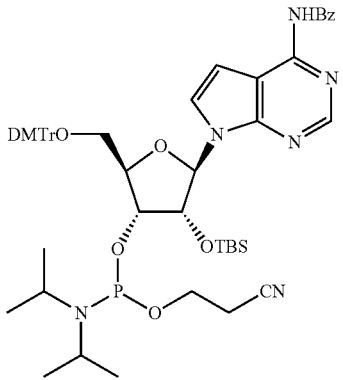 | | Barry and Associates Vendor |
| I-25 | 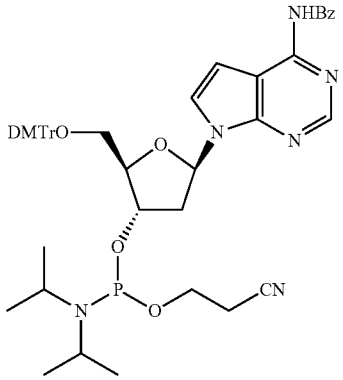 | | Barry and Associates Vendor |

The following experimental procedures detail the preparation of intermediates used in the synthesis of the Examples of the instant invention. The exemplified procedures are for illustrative purposes only, and are not intended to limit the scope of the instant invention in any way.
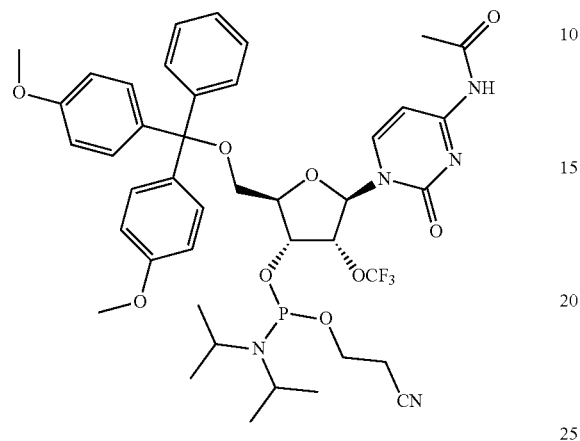
Intermediate I-23
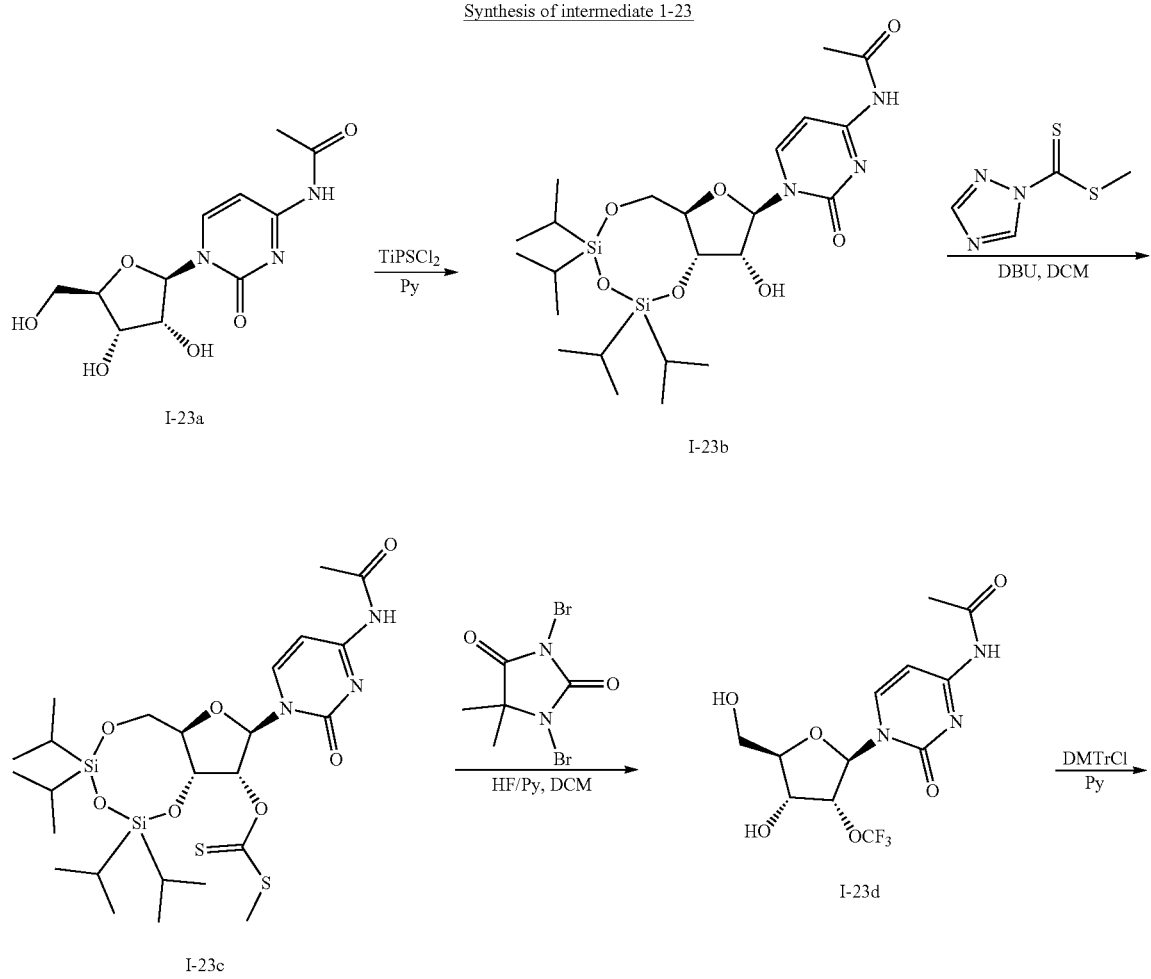
Scheme 1
Synthesis of intermediate I-23

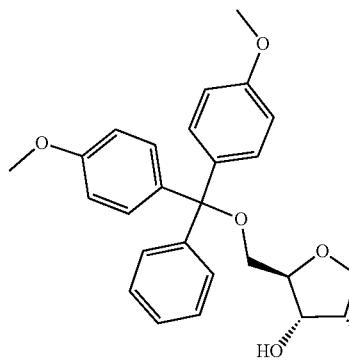

I-23e

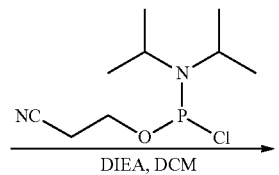

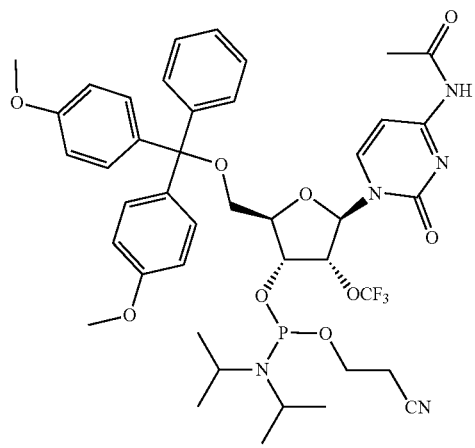

I-23

Step 1: To a solution of N-(1-((2R,3R,4S,5R)-3,4-dihydroxy-5-(hydroxymethyl)-tetrahydrofuran-2-yl)-2-oxo-1,2-dihydropyrimidin-4-yl)acetamide (200 g, 701.13 mmol, 1.00 equiv) in pyridine (3000 mL) was added the solution of 1,3-dichloro-1,1,3,3-teraisopropyldisiloxane (TIPSCl$_2$) (240 g, 762 mmol, 1.1 equiv) in pyridine dropwise. The resulting solution was allowed to react overnight with stirring at room temperature. The reaction mixture was concentrated under vacuum and the residue was extracted with EtOAc three times. The combined organic layer was washed with brine twice and dried over anhydrous Na$_2$SO$_4$ The filtrate was concentrated under vacuum and the residue was purified by a silica gel column, eluting with dichloromethane/methanol (100:1) to afford of N-(1-(((6aR,8R,9R,9aS)-9-hydroxy-2,2,4,4-tetraisopropyl-tetrahydro-6H-furo[3,2-f][1,3,5,2,4]trioxadisilicon-8-yl)-2-oxo-1,2-dihydropyrimidin-4-yl)acetamide. LCMS-(ES, m/z) found: 528[M+H]$^+$. $^1$H NMR (300 MHz, Chloroform-d) δ 9.99 (s, 1H), 8.19 (d, J=7.5 Hz, 1H), 7.43 (d, J=7.4 Hz, 1H), 5.80 (s, 1H), 4.32-4.15 (m, 4H), 4.00 (dd, J=13.4, 2.3 Hz, 1H), 3.34 (s, 1H), 2.28 (s, 3H), 1.14-0.86 (m, 28H).

Step 2: To a solution of N-(1-(((6aR,8R,9R,9aS)-9-hydroxy-2,2,4,4-tetraisopropyltetrahydro-6H-furo[3,2-f][1,3,5,2,4]trioxadisilicon-8-yl)-2-oxo-1,2-dihydropyrimidin-4-yl)acetamide (350 g, 663 mmol, 1.00 equiv) in dichloromethane (1500 mL) was added methyl 1H-1,2,4-triazole-1-carbodithioate (126 g, 794 mmol, 1.20 equiv) in several batches. To the above was added 1,8-diazabicyclo[5.4.0]-undec-7-ene (DBU) (152 g, 996 mmol, 1.50 equiv) dropwise with stirring at 0° C., and stirred overnight at room temperature. The resulting mixture was neutralized with hydrochloric acid (2 M) and the organic layer was washed with sodium bicarbonate solution (sat.), then dried over anhydrous sodium sulfate and concentrated under vacuum. The residue was purified by a silica gel column and eluted with dichloromethane/methanol (100:1) to afford 0-((6aR,8R,9R,9aR)-8-(4-acetamido-2-oxopyrimidin-1(2H)-yl)-2,2,4,4-tetraisopropyltetrahydro-6H-furo[3,2-f][1,3,5,2,4]trioxadisilicon-9-yl) S-methyl carbonodithioate.

LCMS (ES, m/z) found: 618 [M+H]$^+$. $^1$H NMR (300 MHz, DMSO-d$_6$) δ 10.91 (s, 1H), 8.05 (d, J=7.5 Hz, 1H), 7.20 (d, J=7.5 Hz, 1H), 6.34 (dd, J=5.3, 1.1 Hz, 1H), 5.80 (d, J=1.1 Hz, 1H), 4.70 (dd, J=8.5, 5.4 Hz, 1H), 4.07-3.91 (m, 3H), 2.58 (s, 3H), 2.09 (s, 3H), 1.07-0.77 (m, 28H).

Step 3: To a solution of 1,3-dibromo-5,5-dimethylimidazolidine-2,4-dione (23 g, 80.44 mmol, 5.00 equiv) in dichloromethane (230 mL) was added HF/Py (105 mL, 70% HF in Py) dropwise with stirring at −78° C. The mixture was stirred for 10 minutes at −78° C. To this was added a solution of N-[1-[((6aR,8R,9R,9aR)-9-[[(methylsulfanyl)methanethioyl]oxy]-2,2,4,4-tetrakis(propan-2-yl)-hexahydro-2H-furo[3,2-f][1,3,5,2,4]trioxadisilicon-8-yl]-2-oxo-1,2-dihydropyrimidin-4-yl]acetamide (10 g, 16.18 mmol, 1.00 equiv) in dichloromethane (70 mL) dropwise with stirring at −78° C. The resulting solution was stirred for 3 h at 0° C. in an ice/salt bath. The reaction was then quenched by the addition of 100 mL of NaHSO$_3$ (1M). The pH value of the solution was adjusted to 8 with sodium bicarbonate (solid). The solids were filtered out. The resulting solution was extracted with 4×300 mL of ethyl acetate and the combined organic layers were dried over anhydrous sodium sulfate and concentrated under vacuum. The residue was purified by a silica gel column with dichloromethane/methanol/TEA (95:5:0.3) as eluent to furnish 800 mg (13%) of N-[1-[(2R,3R,4R,5R)-4-hydroxy-5-(hydroxymethyl)-3-(trifluoromethoxy)oxolan-2-yl]-2-oxo-1,2-dihydropyrimidin-4-yl]acetamide as a white solid. The above procedure was repeated for ten batches (20 g×10), and the crude was purified together to give N-(1-((2R,3R,4R,5R)-4-hydroxy-5-(hydroxymethyl)-3-(trifluoromethoxy)tetrahydrofuran-2-yl)-2-oxo-1,2-dihydropyrimidin-4-yl)acetamide.

LCMS (ES, m/z) found: 354 [M+H]$^+$. $^1$H NMR (300 MHz, DMSO-d6) δ 10.92 (s, 1H), 8.38 (d, J=7.5 Hz, 1H), 7.18 (d, J=7.5 Hz, 1H), 6.00 (d, J=3.4 Hz, 1H), 5.76 (d, J=6.0 Hz, 1H), 5.28 (t, J=4.9 Hz, 1H), 4.97-4.81 (m, 1H), 4.21 (p, J=5.4 Hz, 1H), 3.92 (dt, J=6.1, 2.9 Hz, 1H), 3.81-3.68 (m, 1H), 3.65-3.52 (m, 1H), 2.07 (s, 3H).

Step 4: To a solution of N-[1-[(2R,3R,4R,5R)-4-hydroxy-5-(hydroxymethyl)-3-(trifluoromethoxy)oxolan-2-yl]-2-oxo-1,2-dihydropyrimidin-4-yl]acetamide (9 g, 25.48 mmol, 1.00 equiv, co-evaporated with anhydrous pyridine three times) in pyridine (100 mL) was added a solution of 1-[chloro(4-methoxyphenyl)benzyl]-4-methoxybenzene (17.1 g, 50.47 mmol, 2.00 equiv, co-evaporated with anhydrous pyridine three times) in pyridine (200 mL) dropwise with stirring at 30° C. After the resulting solution was stirred for 3 h at 30° C., then concentrated under vacuum. The resulting solution was diluted with 400 mL of DCM, then was washed with 1×300 mL of sodium bicarbonate (sat.) and 1×300 mL of brine. The organic layer was dried over anhydrous sodium sulfate and concentrated under vacuum. The residue was purified by a silica gel column with ethyl acetate/petroleum ether/Et$_3$N (60:40:0.3) as eluent to furnish N-[1-[(2R,3R,4R,5R)-5-[[bis(4-methoxyphenyl)(phenyl)methyl]methyl]-4-hydroxy-3-(trifluoromethoxy)oxolan-2-yl]-2-oxo-1,2-dihydropyrimidin-4-yl]acetamide. LCMS (ES, m/z) found: 656 [M+H]$^+$. $^1$H NMR (400 MHz, Chloroform-d) δ 9.49 (s, 1H), 8.35 (d, J=7.5 Hz, 1H), 7.43 (d, J=7.7 Hz, 2H), 7.39-7.26 (m, 6H), 7.25-7.07 (m, 2H), 6.88 (d, J=8.5 Hz, 4H), 6.16 (s, 1H), 5.16-5.10 (m, 1H), 4.60 (t, J=6.0 Hz, 1H), 4.24 (d, J=7.5 Hz, 1H), 3.83 (s, 6H), 3.65 (d, J=11.3 Hz, 1H), 3.58 (d, J=11.2 Hz, 1H), 3.34 (s, 1H), 2.22 (s, 3H).

Step 5: To a solution of N-[1-[(2R,3R,4R,5R)-5-[[bis(4-methoxyphenyl)(phenyl)methoxy]methyl]-4-hydroxy-3-(trifluoromethoxy)oxolan-2-yl]-2-oxo-1,2-dihydropyrimidin-4-yl]acetamide (13.0 g, 19.83 mmol, 1.00 equiv, which dried by co-evaporation with pyridine twice) in dichloromethane (200 mL) was added DIPEA (12.8 g, 99.04 mmol, 5.00 equiv) dropwise with stirring at 0° C. To the mixture was added 3-([bis(propan-2-yl)amino](chloro)phosphanyloxy)propanenitrile (7.0 g, 29.58 mmol, 1.50 equiv) dropwise with stirring at 0° C. After the resulting solution was stirred for 2 h at room temperature, it then was diluted with 500 mL of CH$_2$Cl$_2$. The resulting mixture was washed with 2×300 mL of saturated sodium bicarbonate and 300 mL of brine. The organic layer was dried over anhydrous sodium sulfate and concentrated under vacuum. The residue was purified by a silica gel column with petroleum ether (PE):ethyl acetate (EA):TEA (38:62:0.5) as eluent to obtain the crude. The crude product (13 g) was purified by Flash-Prep-HPLC with the following conditions (IntelFlash-1): Column, C18 silica gel; mobile phase, 50% CH$_3$CN/H$_2$O (0.5% NH$_4$HCO$_3$) increasing to 80% CH$_3$CN/H$_2$O (0.5% NH$_4$HCO$_3$) over 30 min; Detector, UV 254 nm. This resulted in N-[1-[(2R,3R,4R,5R)-5-[[bis(4-methoxyphenyl)(phenyl)methoxy]methyl]-4-([[bis(propan-2-yl)amino](2-cyanoethoxy)phosphanyl]oxy)-3-(trifluoromethoxy)oxolan-2-yl]-2-oxo-1,2-dihydropyrimidin-4-yl]acetamide. L-MS (ES, m/z) found: 856 [M+H]$^+$. $^1$H-NMR (300 MHz, Chloroform-d,ppm): δ 10.69-10.57 (m, 1H), 8.30 (m, 1H), 7.43 (m, 2H), 7.39-7.23 (m, 7H), 7.11 (m, 1H), 6.89 (m, 4H), 6.23 (d, J=2.8 Hz, 1H), 4.98 (m, 1H), 4.66 (m, 1H), 4.40-4.23 (m, 1H), 3.98-3.45 (m, 12H), 2.62 (t, J=6.2 Hz, 1H), 2.43 (m, 1H), 2.28 (d, J=1.8 Hz, 3H), 1.24-1.11 (m, 9H), 1.08 (d, J=6.8 Hz, 3H). F-NMR: (300 MHz, Chloroform-d, ppm): δ 58.148, −58.222. P-NMR: (300 MHz, Chloroform-d, ppm): δ 15.8, 150.9.

Intermediate I-24

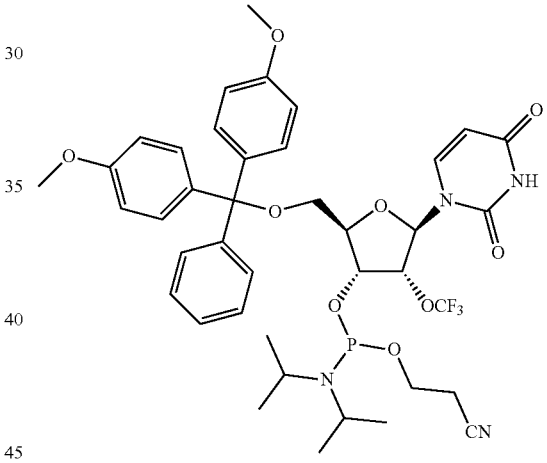

I-24

Scheme 2
Synthesis of intermediate I-24

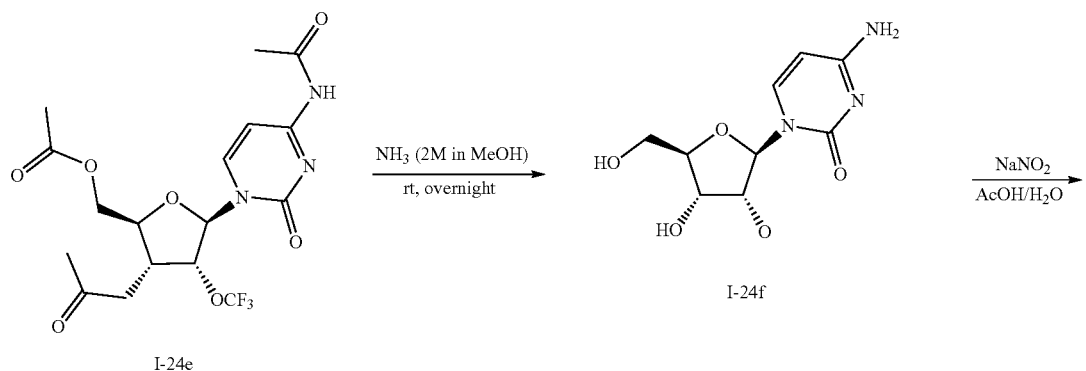

I-24e → I-24f

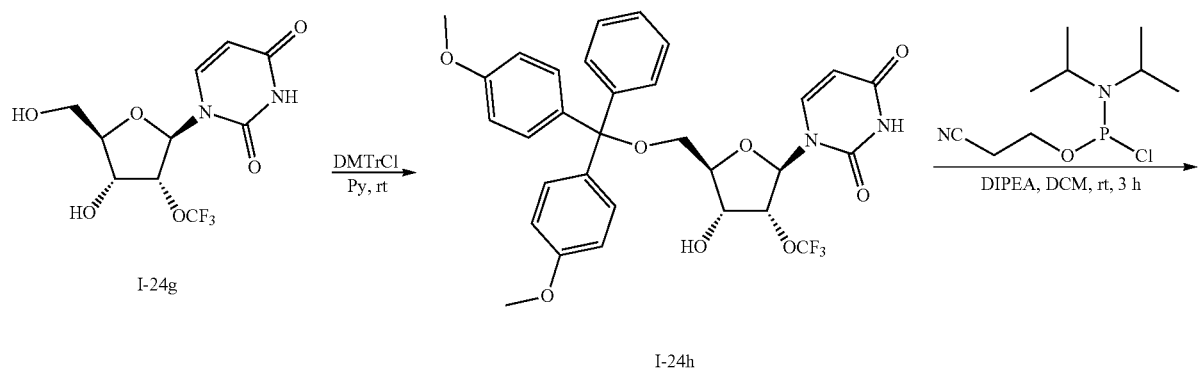

I-24g → I-24h

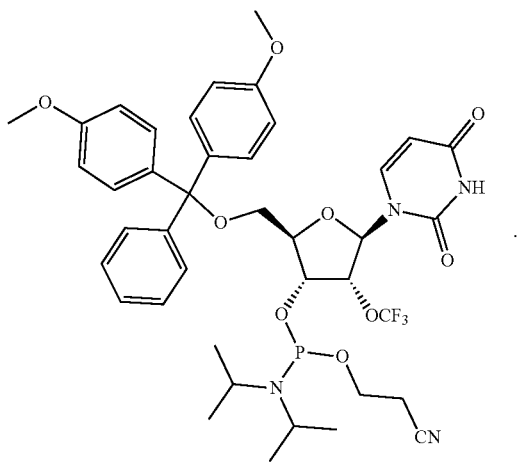

Step 1: I-23C was made in accordance to the procedure described in the procedure for making Intermediate I-23. To a solution of O-(6aR,8R,9aR)-8-(4-acetamido-2-oxopyrimidin-1(2H)-yl)-2,2,4,4-tetraisopropyl-tetrahydro-6H-furo[3,2-f][1,3,5,2,4]trioxadisilicon-9-yl S-methyl carbonodithioate (270 g, 425 mmol, 1.00 equiv) in acetic anhydride (1000 mL) and AcOH (1000 mL) was added sulfuric acid (10 mL) dropwise with stirring at 0° C. under inert atmosphere. The resulting solution was allowed to stir overnight at room temperature. The solvent was concentrated under vacuum and the residue was extracted with EtOAc three times. The combined organic phase was washed with NaHCO₃(sat.) twice and brine once, dried over anhydrous sodium sulfate and concentrated under vacuum. The residue was purified by a silica gel column, eluting with dichloromethane/methanol (100:1) and further purification by recrystallization from acetonitrile:ether=1:10 to afford (2R,3R,4R,5R)-5-(4-acetamido-2-oxopyrimidin-1(2H)-yl)-2-(acetoxymethyl)-4(((methylthio)carbonothioyl)oxy)tetrahydrofuran-3-yl acetate.

LCMS:(ES, m/z) found:460 [M+H]$^+$. $^1$H NMR (400 MHz, Chloroform-d) δ 10.47 (s, 1H), 7.80 (d, J=7.5 Hz, 1H), 7.50 (d, J=7.6 Hz, 1H), 6.30 (dd, J=5.9, 3.7 Hz, 1H), 6.03 (d, J=3.7 Hz, 1H), 5.53 (t, J=6.1 Hz, 1H), 4.51-4.38 (m, 3H), 2.58 (s, 3H), 2.28 (s, 3H), 2.15 (s, 3H), 2.10 (s, 3H).

Step 2: To a solution of 1,3-dibromo-5-isopropylimidazolidine-2,4-dione (47 g, 165 mmol, 5 equiv) in dichloromethane (300 mL) was added HF/Py (150 mL, 70% HF in Py) dropwise with stirring at −78° C. under inert atmosphere and kept stirring for 10 min. This was followed by the addition of a solution of (2R,3R,4R,5R)-5-(4-acetamido-2-oxopyrimidin-1(2H)-yl)-2-(acetoxymethyl)-4-(((methylthio)carbonothi-oyl)oxy)tetrahydrofuran-3-yl acetate (15 g, 32.68 mmol, 1.00 equiv) in dichloromethane (200 mL) dropwise with stirring at −78° C., and then kept stirring for 2 h at −20° C. The resulting mixture was quenched by the addition of NaHSO$_3$ (sat.) and extracted with dichloromethane four times. The combined organic layers was washed with sodium bicarbonate (sat.) twice and brine once, and dried over anhydrous sodium sulfate. The filtrate was concentrated and residue was purified by recrystallization from ether to afford (2R,3R,4R,5R)-5-(4-acetamido-2-oxopyrimidin-1(2H)-yl)-2-(acetoxymethyl)-4-(trifluoromethoxy)tetrahydrofuran-3-yl acetate. LCMS (ES, m/z) found: 438 [M+H]$^+$. $^1$H NMR (300 MHz, Chloroform-d) δ 10.13 (s, 1H), 7.91 (d, J=7.6 Hz, 1H), 7.46 (d, J=7.6 Hz, 1H), 5.91 (d, J=1.5 Hz, 1H), 5.16 (d, J=5.9 Hz, 2H), 4.57-4.17 (m, 3H), 2.24 (s, 3H), 2.16-1.97 (m, 6H).

Step 3: To a solution of 2R,3R,4R,5R)-5-(4-acetamido-2-oxopyrimidin-1(2H)-yl)-2-(acetoxymethyl)-4-(trifluoromethoxy)tetrahydrofuran-3-yl acetate (38 g, 87 mmol, 1.00 equiv) in MeOH (260 mL) was added NH$_3$ (130 mL, 7 M in MeOH) dropwise at 0° C. The resulting solution was stirred overnight at room temperature and then concentrated under vacuum to give 4-amino-1-((2R, 3R, 4R, 5R)-4-hydroxy-5-(hydro-xylmethyl)-3-(trifluoromethoxy)-tetrahydrofuran-2-yl) pyrimidin-2(1H)-one. LCMS: (ES, m/z): 312 [M+H]$^+$.

Step 4: To a solution of crude 4-amino-1-((2R,3R,4R,5R)-4-hydroxy-5-(hydroxymethyl)-3-(trifluorometh-oxy)-tetrahydrofuran-2-yl)pyrimidin-2(1H)-one (15 g, 48 mmol, 1.00 equiv) in water (100 mL) was added NaNO$_2$ (67 g, 971 mmol, 20 equiv) in several batches, and followed added acetic acid (50 mL) dropwise at 0° C. The resulting solution was stirred overnight at room temperature and concentrated under vacuum. The residue was triturated with EtOH and the filtrate was concentrated under vacuum after filtration to afford 1-((2R, 3R, 4R, 5R)-4-hydroxy-5-(hydroxymethyl)-3-(trifluoromethoxy)-tetrahydrofuran-2-yl) pyrimidine-2,4 (1H, 3H)-dione. LCMS (ES, m/z): 313[M+H]$^+$.

Step 5: To a solution of 1-((2R, 3R, 4R, 5R)-4-hydroxy-5-(hydroxymethyl)-3-(trifluoromethoxy)-tetrahydrofuran-2-yl) pyrimidine-2, 4(1H, 3H)-dione (14 g, 45 mmol, 1.00 equiv, coevaporate with pyridine twice previously) in pyridine (250 mL) was added a solution of 1-(chlorobis(4-methoxyphenyl) methyl)benzene (23 g, 67 mmol, 1.50 equiv) in pyridine (50 mL) dropwise with stirring at room temperature under inert atmosphere. The resulting solution was stirred overnight at room temperature and then concentrated under vacuum. The residue was extracted with EtOAc twice and the combined organic layer was washed with brine, dried over anhydrous sodium sulfate and concentrated under vacuum. The residue was purified by a silica gel column, eluting with dichloromethane/methanol/Et$_3$N (100:1:0.5) to afford 1-((2R, 3R, 4R, 5R)-5-((bis(4-methoxyphenyl)(phenyl)methoxy)methyl)-4-hydroxy-3-(trifluoromethoxy)-tetrahydrofuran-2-yl) pyrimidine-2, 4(1H, 3H)-dione. $^1$H NMR (300 MHz, Chloroform-d) δ 8.75 (d, J=2.0 Hz, 1H), 7.68 (d, J=8.2 Hz, 1H), 7.36-7.17 (m, 9H), 6.90-6.77 (m, 4H), 6.21 (d, J=5.2 Hz, 1H), 5.30 (dd, J=8.2, 2.2 Hz, 1H), 4.91 (t, J=5.0 Hz, 1H), 4.53 (q, J=4.5 Hz, 1H), 4.18-4.11 (m, 2H), 3.77 (s, 6H), 3.54-3.50 (m, 1H), 2.50 (d, J=5.0 Hz, 1H).

Step 6: 1-((2R, 3R, 4R, 5R)-5-((bis(4-methoxyphenyl) (phenyl)methoxy)methyl)-4-hydroxy-3-(trifluoromethoxy)-tetrahydrofuran-2-yl) pyrimidine-2, 4(1H, 3H)-dione (20 g, 33 mmol, 1.00 equiv) was co-evaporated with dry pyridine three times and then diluted with dry dichloromethane (200 mL), To the above solution was added N-ethyl-N-isopropylpropan-2-amine (13 g, 99 mmol, 3.00 equiv), followed by addition of 3-chloro-3-(diisopropylamino) phosphinooxypropanenitrile (12 g, 50 mmol, 1.50 equiv) dropwise with stirring at room temperature under inert atmosphere. The resulting solution was stirred for 2 h at room temperature and then quenched with sodium bicarbonate (sat.) and extracted with dichloromethane twice. The combined organic layer was washed with brine, dried over anhydrous sodium sulfate and concentrated under vacuum. The residue was purified by a silica gel column, eluting with ethyl acetate/hexane/EtN$_3$ (50:100:0.75) and then further purified by a reverse column, eluting with acetonitrile: water (containing 0.1% NH$_4$HCO$_3$) from 20:80 to 80:20 over 1.5 h to afford (2R,3R,4R,5R)-2-((bis(4-methoxyphenyl)(phenyl)methoxy)methyl)-5-(2,4-dioxo-3,4-dihydropyrimidin-1(2H)-yl)-4-(trifluoromethoxy)tetrahydrofuran-3-yl (2-cyanoethyl) diisopropylphosphoramidite. LCMS (ES, m/z) found: 815 [M+H]$^+$. $^1$H-NMR (400 MHz, CDCl$_3$, ppm): 8.82 (s, 1H), 7.76 (dd, J=11.9, 8.1 Hz, 1H), 7.42-7.25 (m, 7H), 6.88 (dd, J=8.6, 3.8 Hz, 4H), 6.23 (dd, J=9.3, 4.9 Hz, 1H), 5.33 (dd, J=8.3, 4.2 Hz, 1H), 5.01 (q, J=5.7 Hz, 1H), 4.69 (ddt, J=14.7, 9.4, 4.7 Hz, 1H), 4.34 (d, J=3.5 Hz, 1H), 4.23 (d, J=4.5 Hz, 0H), 3.93 (dt, J=13.4, 6.4 Hz, 0H), 3.86-3.72 (m, 6H), 3.65 (dq, J=12.3, 6.3, 5.8 Hz, 3H), 3.61-3.44 (m, 2H), 2.66 (t, J=6.2 Hz, 1H), 2.48 (s, 1H), 1.21 (t, J=5.5 Hz, 10H), 1.10 (d, J=6.7 Hz, 2H). $^{31}$P NMR-(400 MHz, CDCl$_3$, ppm): 151.5, 152.0. $^{19}$F NMR: (400 MHz, CDCl$_3$, ppm): δ−58.6, −59.1.

Intermediate I-25

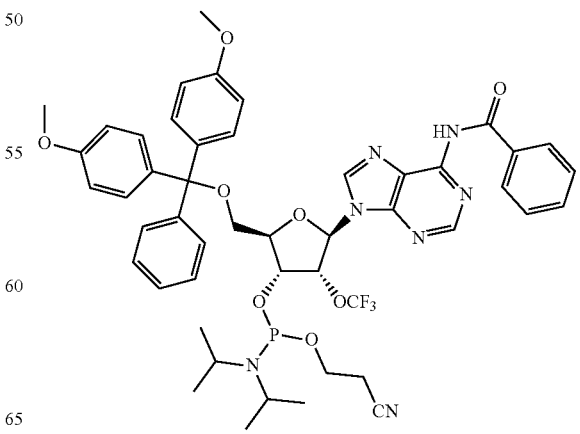

Scheme 3
Synthesis of intermediate I-25
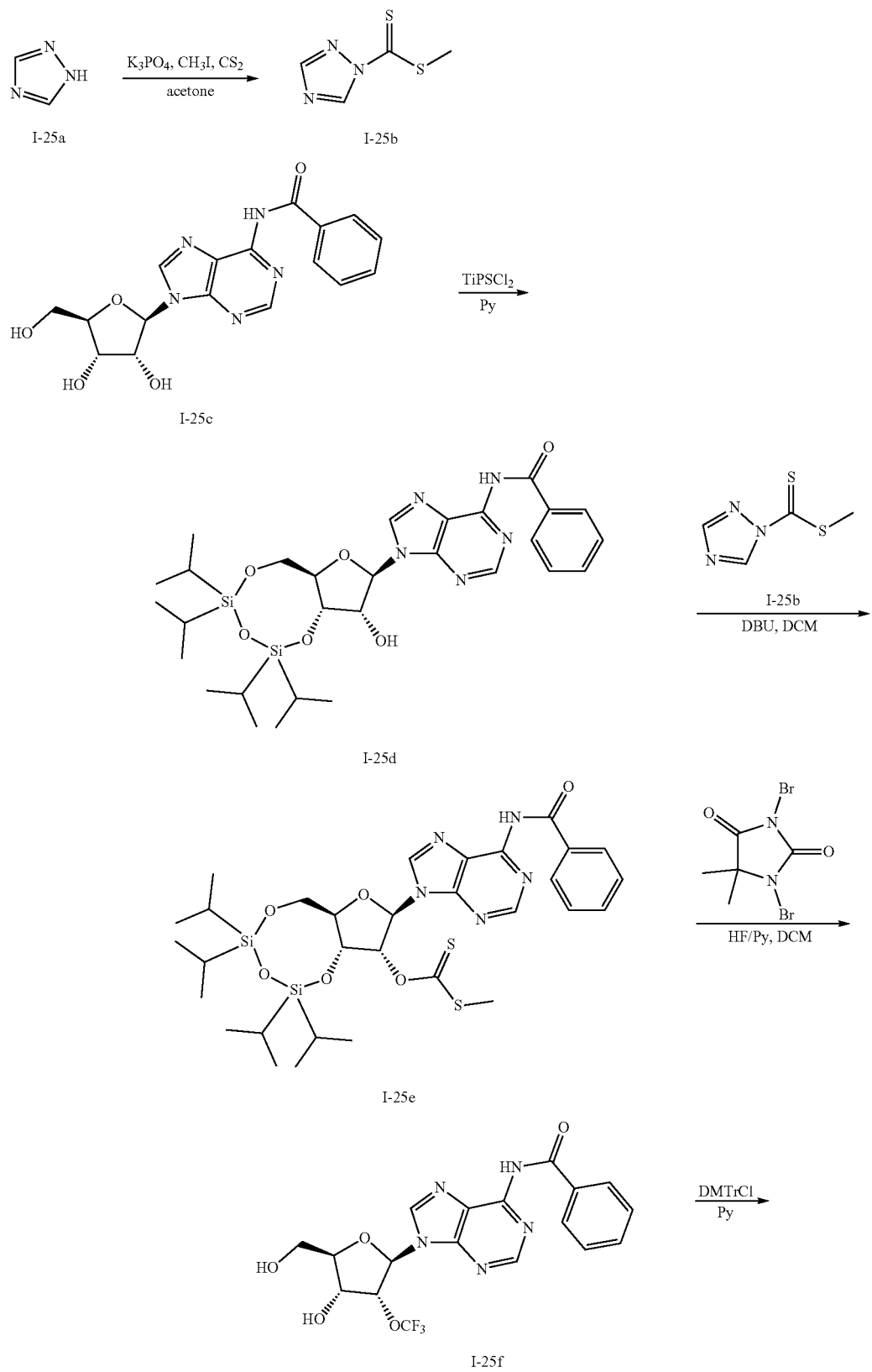

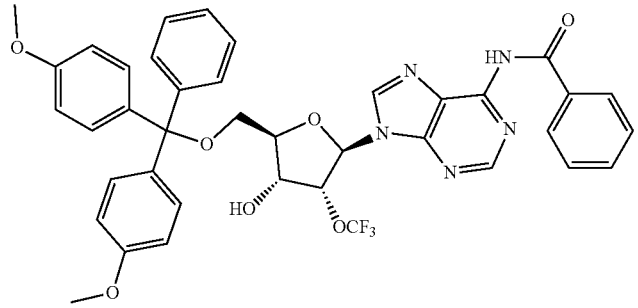

I-25g

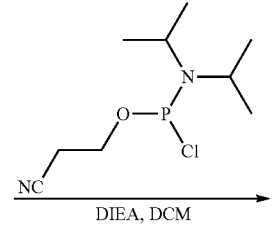

DIEA, DCM

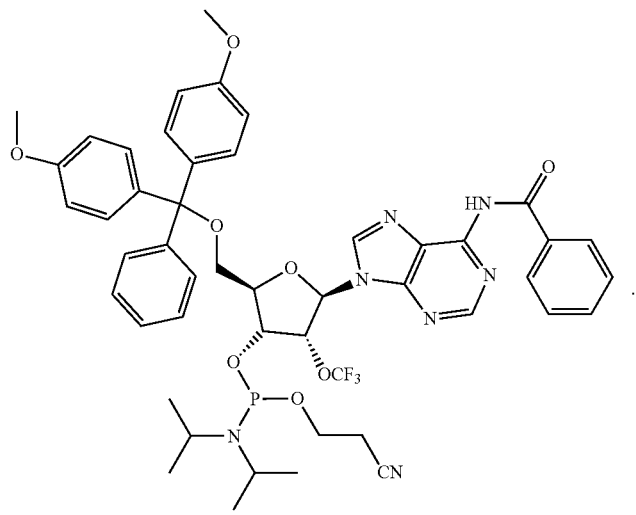

I-25

Step 1: To a solution of 1H-1,2,4-triazole (250 g, 3.62 mol, 1.00 equiv) in acetone (7000 mL) was added $K_3PO_4$ (768 g, 3.62 mol, 1.00 equiv). After the mixture was stirred for 20 minutes at 25° C., then was added $CS_2$ (826 g, 3.00 equiv) dropwise with stirring at 25° C. After the mixture was stirred for 20 minutes at 25° C., then was added $CH_3I$ (515 g, 3.63 mol, 1.00 equiv) dropwise with stirring at 25° C. After the resulting solution was stirred overnight at 25° C., the solids were filtered out. The filtrate was concentrated under vacuum, then was dissolved in 5 L of ethyl acetate. The insoluble solids were filtered out. The filtrate was concentrated under vacuum to get the crude. The crude product was re-crystallized from EA:Et₂O:PE with the ratio of 1:1:1 to afford 1-(methylsulfanyl)carbothioyl-1H-1,2,4-triazole. LCMS (ES, m/z) found: 160[M+H]⁺. ¹H NMR (300 MHz, Chloroform-d) δ 9.14 (s, 1H), 8.06 (s, 1H), 2.72 (s, 3H).

Step 2: To a solution of N-[9-[(2R,3R,4S,5R)-3,4-dihydroxy-5-(hydroxymethyl)oxolan-2-yl]-9H-purin-6-yl]benzamide (200 g, 538.58 mmol, 1.00 equiv) in anhydrous pyridine (2500 mL) was added (dichloro-4-sulfanylidene)(titanio)phosphane (186 g, 1.02 mol, 1.11 equiv) dropwise with stirring at room temperature. After the resulting solution was stirred overnight at room temperature, the crude mixture was concentrated under vacuum. The residue was dissolved in 1000 mL of dichloromethane, then was washed with 2×400 mL of sodium bicarbonate (sat.), dried over anhydrous sodium sulfate. The residue was purified by a silica gel column with ethyl acetate/petroleum ether (2:1) as eluent to N-[9-[(6aR,8R,9R,9aS)-9-hydroxy-2,2,4,4-tetrakis(propan-2-yl)-hexahydro-2H-furo[3,2-f][1,3,5,2,4]trioxadisilicon-8-yl]-9H-purin-6-yl]benzamide. LCMS (ES, m/z) found: 614 [M+H]⁺. ¹H NMR (300 MHz, DMSO-d₆) δ 11.17 (s, 1H), 8.63 (s, 1H), 8.50 (s, 1H), 8.05-7.96 (m, 2H), 7.61 (t, J=7.3 Hz, 1H), 7.52 (dd, J=8.3, 6.7 Hz, 2H), 5.97 (d, J=1.4 Hz, 1H), 5.64 (d, J=4.7 Hz, 1H), 4.79 (dd, J=8.3, 5.1 Hz, 1H), 4.62 (t, J=5.3 Hz, 1H), 4.10-3.94 (m, 2H), 3.97-3.86 (m, 1H), 1.07-0.88 (m, 28H).

Step 3: To a solution of N-[9-[(6aR,8R,9R,9aS)-9-hydroxy-2,2,4,4-tetrakis(propan-2-yl)-hexahydro-2H-furo[3,2-f][1,3,5,2,4]trioxadisilicon-8-yl]-9H-purin-6-yl]benzamide (246 g, 400.75 mmol, 1.00 equiv) in dichloromethane (600 mL) was added 1-(methylsulfanyl)carbothioyl-1H-1,2,4-triazole (115 g, 722.21 mmol, 1.80 equiv). This was followed by the addition of DBU (80 g, 525.49 mmol, 1.30 equiv) dropwise with stirring at 25° C. After the resulting solution was stirred for overnight at 25° C., then was washed with 2×300 mL of hydrogen chloride (1 M) and 1×300 mL of sodium bicarbonate (sat.), dried over anhydrous sodium sulfate and concentrated under vacuum. The residue was purified by a silica gel column with ethyl acetate/petroleum ether (1:1) as eluent to furnish N-[9-[(6aR,8R,9R,9aR)-9-[[(methylsulfanyl)methanethioyl]oxy]-2,2,4,4-tetrakis(propan-2-yl)-hexahydro-2H-furo[3,2-f][1,3,5,2,4]trioxadisilicon-8-yl]-9H-purin-6-yl]benzamide. LCMS (ES, m/z) found: 704[M+H]$^+$.

$^1$H NMR (400 MHz, DMSO-d$_6$) δ 11.28 (s, 1H), 8.64 (d, J=18.1 Hz, 2H), 8.09-8.02 (m, 2H), 7.67 (t, J=7.4 Hz, 1H), 7.57 (t, J=7.6 Hz, 1H), 6.77 (dd, J=5.7, 1.4 Hz, 1H), 6.41 (d, J=1.4 Hz, 1H), 5.45 (dd, J=8.4, 5.8 Hz, 1H), 4.05 (ddd, J=14.2, 11.1, 6.9 Hz, 3H), 2.65 (s, 3H), 1.28-0.74 (m, 28H).

Step 4: To a solution of 1,3-dibromo-5,5-dimethylimidazolidine-2,4-dione (20.5 g, 71.70 mmol, 5.00 equiv) in dichloromethane (150 mL) was added a solution of 70% HF in Py (60 mL) dropwise with stirring at −78° C. The mixture was stirred for 10 minutes at −78° C., then added a solution of N-[9-[(6aR,8R,9R,9aR)-9-[[(methylsulfanyl)methanethioyl]oxy]-2,2,4,4-tetrakis(propan-2-yl)-hexahydro-2H-furo[3,2-f][1,3,5,2,4]trioxadisilicon-8-yl]-9H-purin-6-yl]benzamide (10 g, 14.20 mmol, 1.00 equiv) in dichloromethane (50 mL) dropwise with stirring at −78° C. The mixture was stirred for 10 minutes at −78° C. followed by stirring for 3 h at −5° C. The reaction was then quenched by the addition of 10 g of NaHSO$_3$. The pH value of the solution was adjusted to 7-8 with sodium bicarbonate (sat.). The solids were filtered out. The filtrate was extracted with 2×200 mL of dichloromethane and the combined organic layers were dried over anhydrous sodium sulfate. The residue was purified by a silica gel column with dichloromethane/methanol (25:1) as eluent to furnish N-[9-[(2R,3R,4R,5R)-4-hydroxy-5-(hydroxymethyl)-3-(trifluoromethoxy)oxolan-2-yl]-9H-purin-6-yl]benzamide. LCMS (ES, m/z) found: 440 [M+H]$^+$. $^1$H-NMR: (300 MHz, CDCl$_3$, ppm): δ 8.81 (s, 1H), 8.14-7.98 (m, 3H), 7.70-7.48 (m, 3H), 6.14 (d, J=7.4 Hz, 1H), 5.62 (dd, J=7.5, 4.4 Hz, 1H), 4.72 (d, J=4.4 Hz, 1H), 4.40 (s, 1H), 3.99 (dd, J=13.2, 1.6 Hz, 1H), 3.84-3.68 (m, 1H), 3.48 (s, 2H).

Step 5: N-[9-[(2R,3R,4R,5R)-4-hydroxy-5-(hydroxymethyl)-3-(trifluoromethoxy)oxolan-2-yl]-9H-purin-6-yl]benzamide (11 g, 25.04 mmol, 1.00 equiv) was co-evaporated with anhydrous pyridine three times before added into a 500-mL 3-necked round-bottom flask purged and maintained with an inert atmosphere of nitrogen. This was followed by the addition of anhydrous pyridine (110 mL) and a solution of 1-[chloro(4-methoxyphenyl)benzyl]-4-methoxybenzene (17 g, 50.17 mmol, 2.00 equiv, was dried by co-evaporation with anhydrous pyridine three times) in anhydrous pyridine (170 mL) dropwise with stirring at 30° C. The resulting solution was stirred for 3 h at 30° C., then was concentrated under vacuum. The resulting solution was diluted with 500 mL of dichloromethane, then was washed with 2×200 mL of sodium bicarbonate (sat.) and 1×200 mL of brine (sat.), dried over anhydrous sodium sulfate and concentrated under vacuum. The residue was purified by a silica gel column with PE:EA:TEA (50:50:0.3) as eluent to furnish N-[9-[(2R,3R,4R,5R)-5-[[bis(4-methoxyphenyl)(phenyl)methoxy]methyl]-4-hydroxy-3-(trifluoromethoxy)oxolan-2-yl]-9H-purin-6-yl]benzamide. LCMS (ES, m/z) found: 742 [M+H]$^+$.

$^1$H NMR (400 MHz, Chloroform-d) δ 9.06 (s, 1H), 8.69 (s, 1H), 8.13 (s, 1H), 8.04 (d, J=8.0 Hz, 2H), 7.63 (t, J=7.3 Hz, 1H), 7.54 (t, J=7.7 Hz, 2H), 7.46-7.39 (m, 2H), 7.35-7.19 (m, 5H), 7.19 (d, J=8.6 Hz, 1H), 6.84 (t, J=9.1 Hz, 4H), 6.33 (d, J=5.9 Hz, 1H), 5.83 (t, J=5.4 Hz, 1H), 4.75 (dd, J=10.1, 4.9 Hz, 1H), 4.32 (q, J=3.6 Hz, 1H), 3.81 (d, J=8.2 Hz, 6H), 3.58 (dd, J=10.7, 3.6 Hz, 1H), 3.44 (dd, J=10.8, 3.8 Hz, 1H), 3.13-3.03 (m, 1H).

Step 6: N-[9-[(2R,3R,4R,5R)-5-[[bis(4-methoxyphenyl)(phenyl)methoxy]methyl]-4-hydroxy-3-(trifluoromethoxy)oxolan-2-yl]-9H-purin-6-yl]benzamide (13.5 g, 18.20 mmol, 1.00 equiv) was co-evaporated with anhydrous pyridine three times before added into a 250-mL 3-necked round-bottom flask purged and maintained with an inert atmosphere of nitrogen. This was followed by the addition of dichloromethane (140 mL) and DIPEA (12 g, 92.85 mmol, 5.00 equiv). This was followed by the addition of 3-([bis(propan-2-yl)amino](chloro)phosphanyloxy)-propanenitrile (6.5 g, 27.5 mmol, 1.50 equiv) dropwise with stirring at 20° C. The resulting solution was stirred for 1 h at 20° C., then quenched by 5 mL of methanol. The resulting solution was diluted with 500 mL of EA, then was washed with 1×200 mL of sodium bicarbonate (sat.) and 1×200 mL of brine (sat.), dried over anhydrous sodium sulfate and concentrated under vacuum. The residue was purified by a silica gel column with PE:EA:TEA (50:50:0.3) as eluent to furnish a crude. The crude was purified by a C18 silica gel column with H$_2$O(0.5% NH$_4$HCO$_3$):ACN(1:99). This resulted in N-[9-[(2R,3R,4R,5R)-5-[[bis(4-methoxyphenyl)(phenyl)methoxy]methyl]-4-([[bis(propan-2-yl)amino](2-cyanoethoxy)phosphanyl]oxy)-3-(trifluoromethoxy)oxolan-2-yl]-9H-purin-6-yl]benzamide. LCMS (ES, m/z) found: 942 [M+H]$^+$. $^1$H-NMR: (300 MHz, CDCl$_3$, ppm): δ 8.97 (d, J=4.9 Hz, 1H), 8.65 (d, J=1.6 Hz, 1H), 8.12 (d, J=4.3 Hz, 1H), 8.04-7.94 (m, 2H), 7.67-7.44 (m, 3H), 7.39 (dt, J=8.0, 1.7 Hz, 2H), 7.32-7.10 (m, 7H), 6.84-6.71 (m, 4H), 6.26 (dd, J=16.3, 6.1 Hz, 1H), 5.90-5.78 (m, 1H), 4.79 (dddd, J=17.7, 12.7, 7.2, 3.7 Hz, 1H), 4.34 (q, J=3.5 Hz, 1H), 3.86 (ddd, J=12.3, 6.0, 1.4 Hz, 1H), 3.75 (d, J=2.4 Hz, 6H), 3.60 (dddd, J=20.4, 13.7, 8.5, 3.9 Hz, 4H), 3.34 (ddd, J=10.7, 6.9, 3.8 Hz, 1H), 2.60 (t, J=6.3 Hz, 1H), 2.39 (td, J=6.4, 2.1 Hz, 1H), 1.19 (dd, J=7.0, 5.7 Hz, 8H), 1.06 (d, J=6.7 Hz, 4H). $^{31}$PNMR (400 MHz, CDCl$_3$, ppm): 152.1, 151.9. $^{19}$FNMR (400 MHz, CDCl$_3$, ppm): δ−59.0, 59.2.

Intermediate I-26

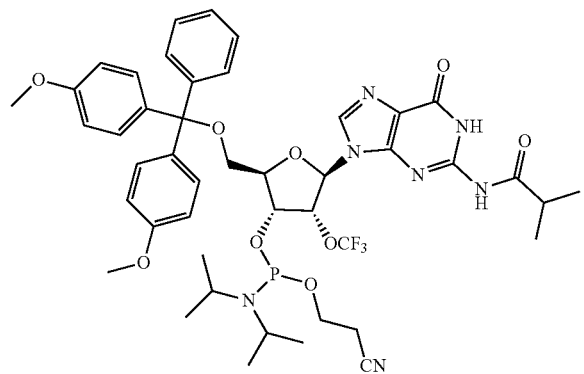

Scheme 4
Synthesis of intermediate I-26
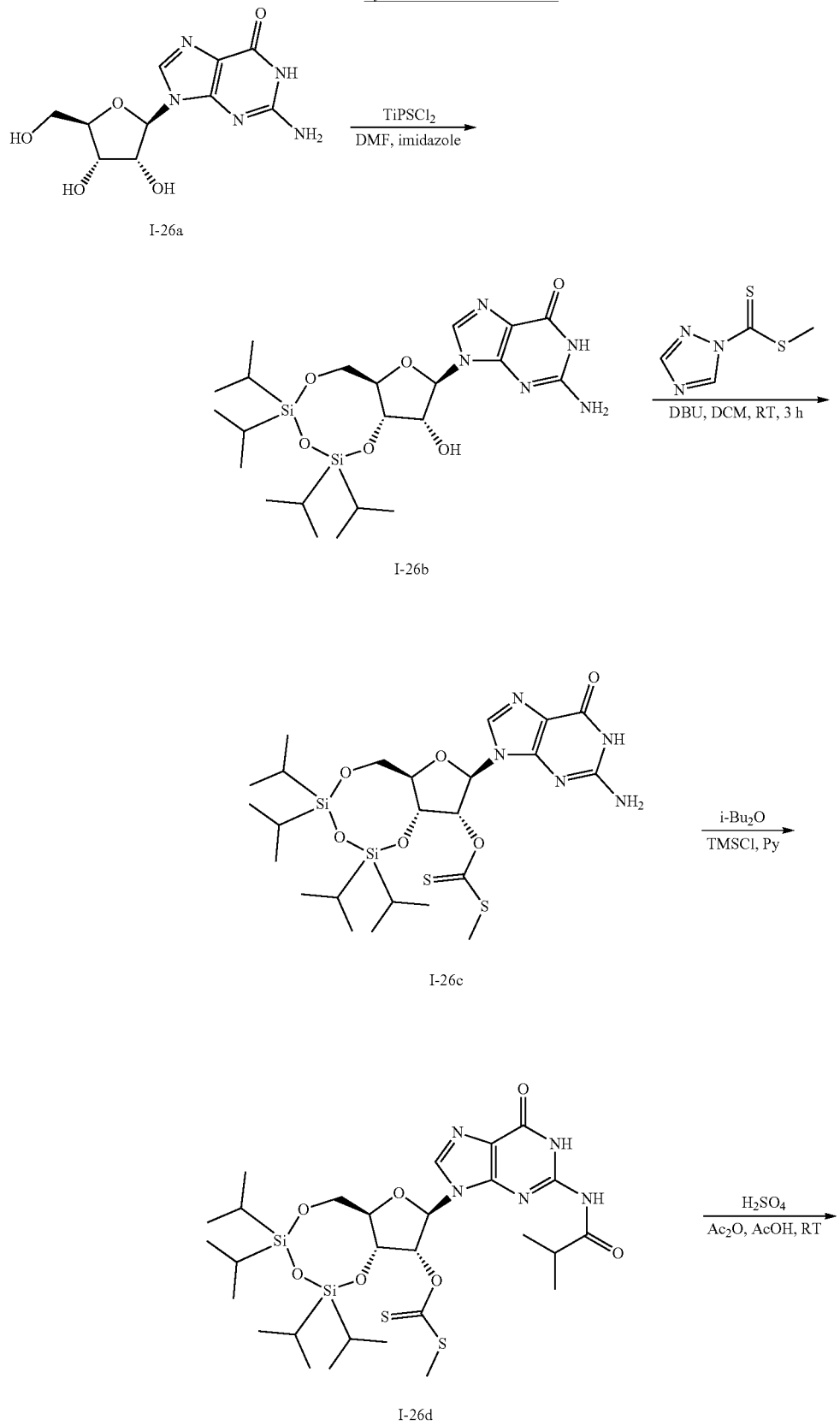

-continued
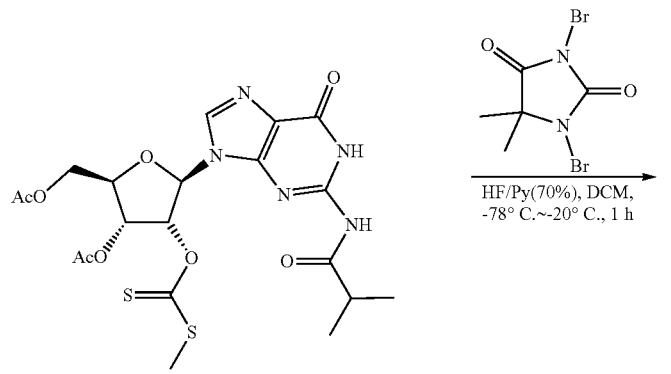
I-26e
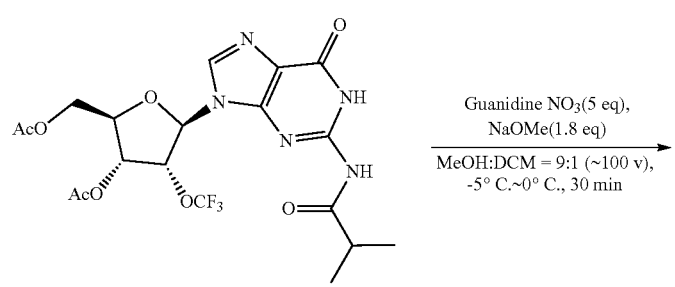
I-26f
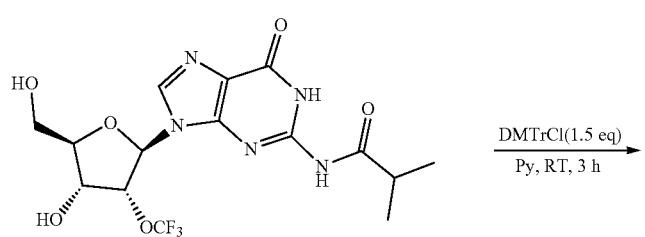
I-26g
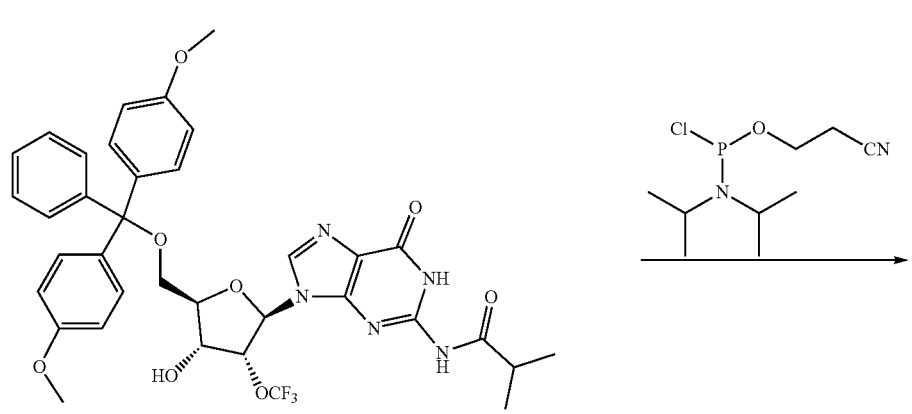
I-26h

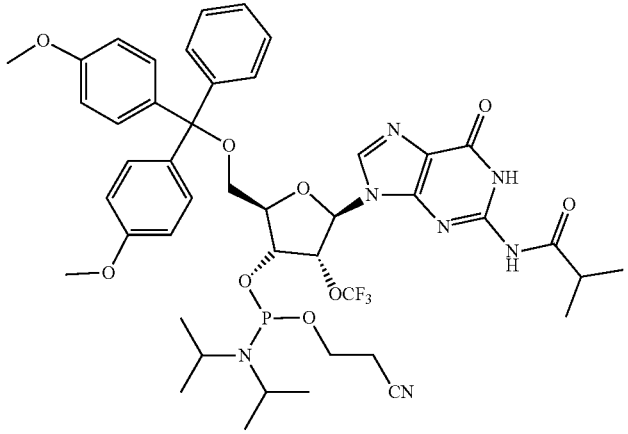

I-26

Step 1: To a solution of 2-amino-9-[(2R,3R,4S,5R)-3,4-dihydroxy-5-(hydroxymethyl)oxolan-2-yl]-6,9-dihydro-1H-purin-6-one (100 g, 353.06 mmol, 1.00 equiv) in N,N-dimethylformamide (1000 mL) was added imidazole (88.8 g, 1.31 mol, 3.70 equiv). This was followed by the addition of TiPSCl$_2$ (166.9 g, 529.84 mmol, 1.50 equiv) dropwise with stirring at room temperature. After the resulting solution was stirred for 2.5 h at room temperature, then quenched by the addition of 1500 mL of water/ice. The solids were collected by filtration and washed with water, then dried in an oven at 50° C. This resulted in (crude) of 9-[(6aR,8R,9R,9aS)-9-hydroxy-2,2,4,4-tetrakis(propan-2-yl)-hexahydro-2H-furo[3,2-f] [1,3, 5,2,4] trioxadisilicon-8-yl]-2-amino-6,9-dihydro-1H-purin-6-one. LC-MS (ES, m/z) found: 526 [M+H]$^+$ $^1$H NMR (300 MHz, DMSO-d6, ppm) δ 10.61 (s, 1H), 7.73 (s, 1H), 6.45 (s, 2H), 5.64 (d, J=1.8 Hz, 1H), 5.56 (s, 1H), 4.37-4.18 (m, 2H), 4.11-3.83 (m, 3H), 1.05-0.86 (m, 28H).

Step 2: To a solution of 9-[(6aR,8R,9R,9aS)-9-hydroxy-2,2,4,4-tetrakis(propan-2-yl)-hexahydro-2H-furo [3,2-f][1,3,5,2,4]trioxadisilicon-8-yl]-2-amino-6,9-dihydro-1H-purin-6-one (182 g, crude, 346.17 mmol, 1.00 equiv) in dichloromethane (1500 mL), was added 1-(methylsulfanyl) carbothioyl-1H-1,2,4-triazole (71.5 g, 449.03 mmol, 1.20 equiv) under atmosphere of argon. To this was added DBU (79 g, 518.92 mmol, 1.50 equiv) dropwise with stirring at room temperature. After the resulting solution was stirred for 3 h at room temperature, then washed with 2×1000 mL of brine (sat.) and concentrated under vacuum. The residue was purified by a silica gel column with dichloromethane/methanol (30:1) as eluent to furnish 9-[(6aR,8R,9R,9aR)-9-[[(methylsulfanyl)methanethioyl]oxy]-2,2,4,4-tetrakis(propan-2-yl)-hexahydro-2H-furo[3,2-f][1,3,5,2,4]trioxadisilicon-8-yl]-2-amino-6,9-dihydro-TH-purin-6-one. LC-MS (ES, m/z) found: 616 [M+H]$^+$. $^1$H NMR (300 MHz, DMSO-d6) δ 10.69 (s, 1H), 7.88 (s, 1H), 6.38 (dd, J=5.9, 2.7 Hz, 1H), 6.36 (s, 2H), 5.98 (d, J=2.6 Hz, 1H), 4.85-4.74 (m, 1H), 3.99 (tdt, J=12.3, 8.7, 4.1 Hz, 3H), 2.56 (s, 3H), 1.14-0.73 (m, 28H).

Step 3: To a solution of 9-[(6aR,8R,9R,9aR)-9-[[(methylsulfanyl)methanethioyl]oxy]-2,2,4,4-tetrakis (propan-2-yl)-hexahydro-2H-furo[3,2-f][1,3,5,2,4]trioxadisilicon-8-yl]-2-amino-6,9-dihydro-1H-purin-6-one (113 g, 183.47 mmol, 1.00 equiv) in pyridine (1200 mL), was added TMSCl (100 g, 920.47 mmol, 5.00 equiv) dropwise with stirring at 0° C. and stirred for 2 hours at room temperature. To this was added i-Bu$_2$O (49.3 g, 312.03 mmol, 1.70 equiv) dropwise with stirring at 0° C. After the resulting solution was stirred for 1 h at room temperature, it then was quenched by the addition of 150 mL saturated aqueous of sodium bicarbonate. The pyridine was evaporated out under vacuum, then diluted with 700 mL of brine (sat.), and extracted with 2 x 800 mL of ethyl acetate. The combined organic layers were concentrated and purified by a silica gel column with dichloromethane/methanol (100% DCM) as eluent to furnish N-[9-[(6aR,8R,9R,9aR)-9-[[(methylsulfanyl)methanethioyl]oxy]-2,2,4,4-tetrakis (propan-2-yl)-hexahydro-2H-furo[3,2-f][1,3,5,2,4]trioxadisilicon-8-yl]-6-oxo-6,9-dihydro-1H-purin-2-yl]-2-methylpropanamide. LCMS (ES, m/z) found: 686 [M+H]$^+$ Step 4: To a solution of N-[9-[(6aR,8R,9R,9aR)-9-[[(methylsulfanyl)methanethioyl]oxy]-2,2,4,4-tetrakis (propan-2-yl)-hexahydro-2H-furo[3,2-f][1,3,5,2,4]trioxadisilicon-8-yl]-6-oxo-6,9-dihydro-TH-purin-2-yl]-2-methylpropanamide (90 g, 131.19 mmol, 1.00 equiv) in acetic anhydride (420 mL) and HOAc (210 mL), was added sulfuric acid (conc.) (25.2 g, 256.93 mmol, 1.96 equiv) dropwise with stirring at 0° C. After the resulting solution was stirred overnight at room temperature, then diluted with 700 mL of brine (sat.). The pH value of the solution was adjusted to 7 with a solution of sodium carbonate (4 M), then extracted with dichloromethane 4×1000 ml and the combined organic layer were concentrated under vacuum. The residue was purified by a silica gel column with ethyl acetate/petroleum ether (up to 100% EA) as eluent to furnish [(2R,3R,4R,5R)-3-(acetyloxy)-5-[2-(2-methylpropanamido)-6-oxo-6,9-dihydro-1H-purin-9-yl]-4-[[(methylsulfanyl) methane thioyl]oxy] oxolan-2-yl]methyl acetate. LCMS (ES, m/z) found: 528 [M+H]$^+$ Step 5: To a solution of 1,3-dibromo-5,5-dimethylimidazolidine-2,4-dione (27.1 g, 94.78 mmol, 5.00 equiv) in dichloromethane (140 mL), was added a solution of 70% HF in Py (100 mL) dropwise with stirring at −78° C. To this was added [(2R,3R,4R,5R)-3-(acetyloxy)-5-[2-(2-methylpropanamido)-6-oxo-6,9-dihydro-1H-purin-9-yl]-4-[[(methylsulfanyl)methanethioyl]oxy]oxolan-2-yl]methyl acetate (10 g, 18.95 mmol, 1.00 equiv) with stirring at −78° C. After the resulting solution was stirred for 1 h at −78° C., then quenched by the addition of 100 mL saturated aqueous of NaHSO₃. The resulting solution was extracted with 3×200 mL of ethyl acetate and the organic layers combined. The pH value of the organic layers was adjusted to 8 with a saturated solution of sodium bicarbonate. Then the aqueous phase was extracted with ethyl acetate, and the combined organic layers were concentrated under vacuum. The residue was purified by a silica gel column with ethyl acetate/petroleum ether (up to 100% EA) as eluent to furnish [(2R,3R,4R,5R)-3-(acetyloxy)-5-[2-(2-methylpropanamido)-6-oxo-6,9-dihydro-1H-purin-9-yl]-4-(trifluoromethoxy)oxolan-2-yl] methyl acetate. LCMS (ES, m/z) found: 506 [M+H]⁺.

Step 6: To a solution of guanidine nitrate (11.81 g, 96.84 mmol, 5 equiv), MeONa (1.88 g, 34.86 mmol, 1.80 equiv) in dichloromethane (100 mL) and methanol (900 mL), was added [(2R,3R,4R,5R)-3-(acetyloxy)-5-[2-(2-methylpropanamido)-6-oxo-6,9-dihydro-1H-purin-9-yl]-4-(trifluoromethoxy)oxolan-2-yl]methyl acetate (9.8 g, 19.39 mmol, 1.00 equiv) with stirring at −5° C. After the resulting solution was stirred for 30 min at −5° C., the pH was adjusted 7 with citric acid (1 M) and concentrated under vacuum. The residue was purified by a silica gel column with dichloromethane/methanol (10:1) as eluent to furnish N-[9-[(2R,3R,4R,5R)-4-hydroxy-5-(hydroxymethyl)-3-(trifluoromethoxy)oxolan-2-yl]-6-oxo-6,9-dihydro-1H-purin-2-yl]-2-methylpropanamide. LCMS (ES, m/z) found: 422 [M+H]⁺.

Step 7: To a solution of N-[9-[(2R,3R,4R,5R)-4-hydroxy-5-(hydroxymethyl)-3-(trifluoromethoxy)oxolan-2-yl]-6-oxo-6,9-dihydro-1H-purin-2-yl]-2-methylpropanamide (7.15 g, 16.97 mmol, 1.00 equiv) in pyridine (70 mL), was added 1-methoxy-4-[1-(4-methoxyphenyl)-1-phenylethyl] benzene (8.63 g, 27.10 mmol, 1.50 equiv) at room temperature. After the resulting solution was stirred for 1.5 h at room temperature, it was concentrated under vacuum. The residue was purified by a silica gel column with EA/PE (up to 80% EA) as eluent to furnish N-[9-[(2R,3R,4R,5R)-5-[[bis(4-methoxyphenyl)(phenyl) methoxy] methyl]-4-hydroxy-3-(trifluoromethoxy)oxolan-2-yl]-6-oxo-6,9-dihydro-1H-purin-2-yl]-2-methylprop anamide. LCMS: (ES, m/z) found: 724 [M+H]⁺.

Step 8: To a solution of N-[9-[(2R,3R,4R,5R)-5-[[bis(4-methoxyphenyl)(phenyl)methoxy]methyl]-4-hydroxy-3-(trifluoromethoxy)oxolan-2-yl]-6-oxo-6,9-dihydro-1H-purin-2-yl]-2-methylpropanamide (11.1 g, 15.34 mmol, 1.00 equiv) in dichloromethane (110 mL), was added DIPEA (9.9 g, 76.74 mmol, 5.00 equiv) with stirring at room temperature. To this was added 3-([[bis(propan-2-yl)amino](chloro)phosphanyl]oxy)propanenitrile (7.25 g, 30.63 mmol, 2.00 equiv) dropwise with stirring at room temperature. After the solution was stirred for 1.5 h at room temperature, it was then quenched by the addition of 20 mL of methanol. The resulting mixture was washed with 2×150 mL saturated solution of sodium bicarbonate, and the organic layers concentrated under vacuum. The crude product was purified by Flash-Prep-HPLC with the following conditions (CombiFlash-1): C18 column; mobile phase, 5% ACN/NH₄CO₃ 0.05% in H₂O increasing to 80% ACN/NH₄CO₃ 0.05% in H₂O within 35 min; Detector, UV 254 nm. This resulted in N-[9-[(2R,3R,4R,5R)-5-[[bis(4-methoxyphenyl) (phenyl) methoxy]methyl]-4-([[bis(propan-2-yl)amino](2-cyanoethoxy)phosphanyl]oxy)-3-(trifluoro meth oxy) oxolan-2-yl]-6-oxo-6,9-dihydro-1H-purin-2-yl]-2-methylpropanamide as a white solid. LCMS: (ES, m/z): 924 [M+H]⁺. ¹H-NMR: (300 MHz, DMSO, ppm): δ 12.15 (s, 1H), 11.52 (s, 1H), 8.24 (d, J=1.4 Hz, 1H), 7.42-7.16 (m, 9H), 6.84 (m, 4H), 6.17 (dd, J=18.6, 6.2 Hz, 1H), 5.78 (m, 1H), 4.62-4.45 (m, 1H), 4.26 (m, 1H), 3.74 (d, J=2.0 Hz, 7H), 3.69-3.39 (m, 3H), 3.41 (m, 1H), 3.25 (dd, J=10.7, 3.0 Hz, 1H), 2.83-2.68 (m, 2H), 2.59 (t, J=5.9 Hz, 1H), 1.14 (m, 14H), 1.01 (d, J=6.7 Hz, 4H). ¹⁹FNMR: (300 MHz, DMSO, ppm): δ−57.612, −57.740. ³¹PNMR: (300 MHz, DMSO, ppm):150.775, 150.450.

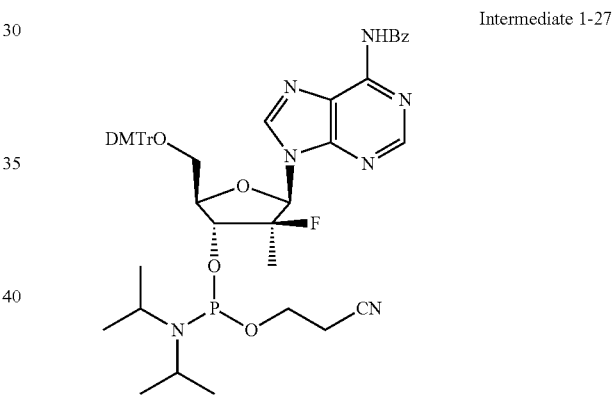

Intermediate I-27

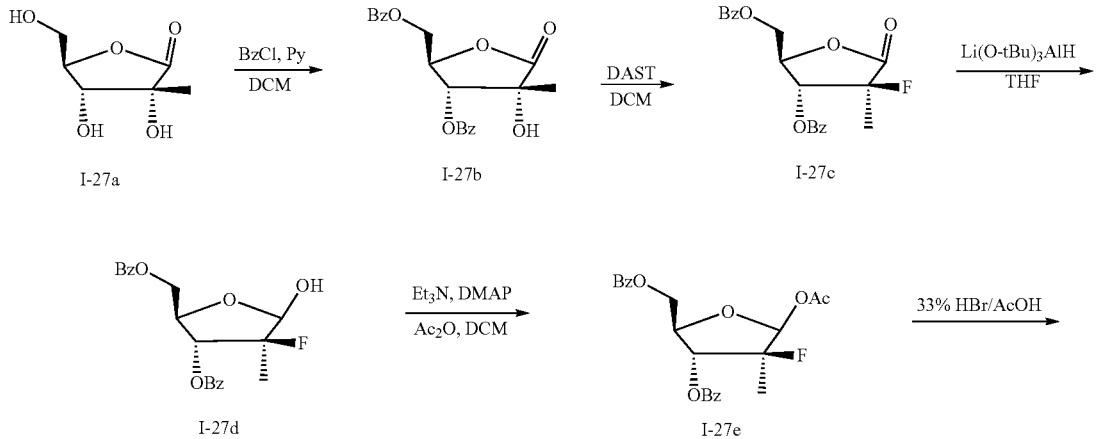

Scheme 5
Synthesis of Intermediate I-27

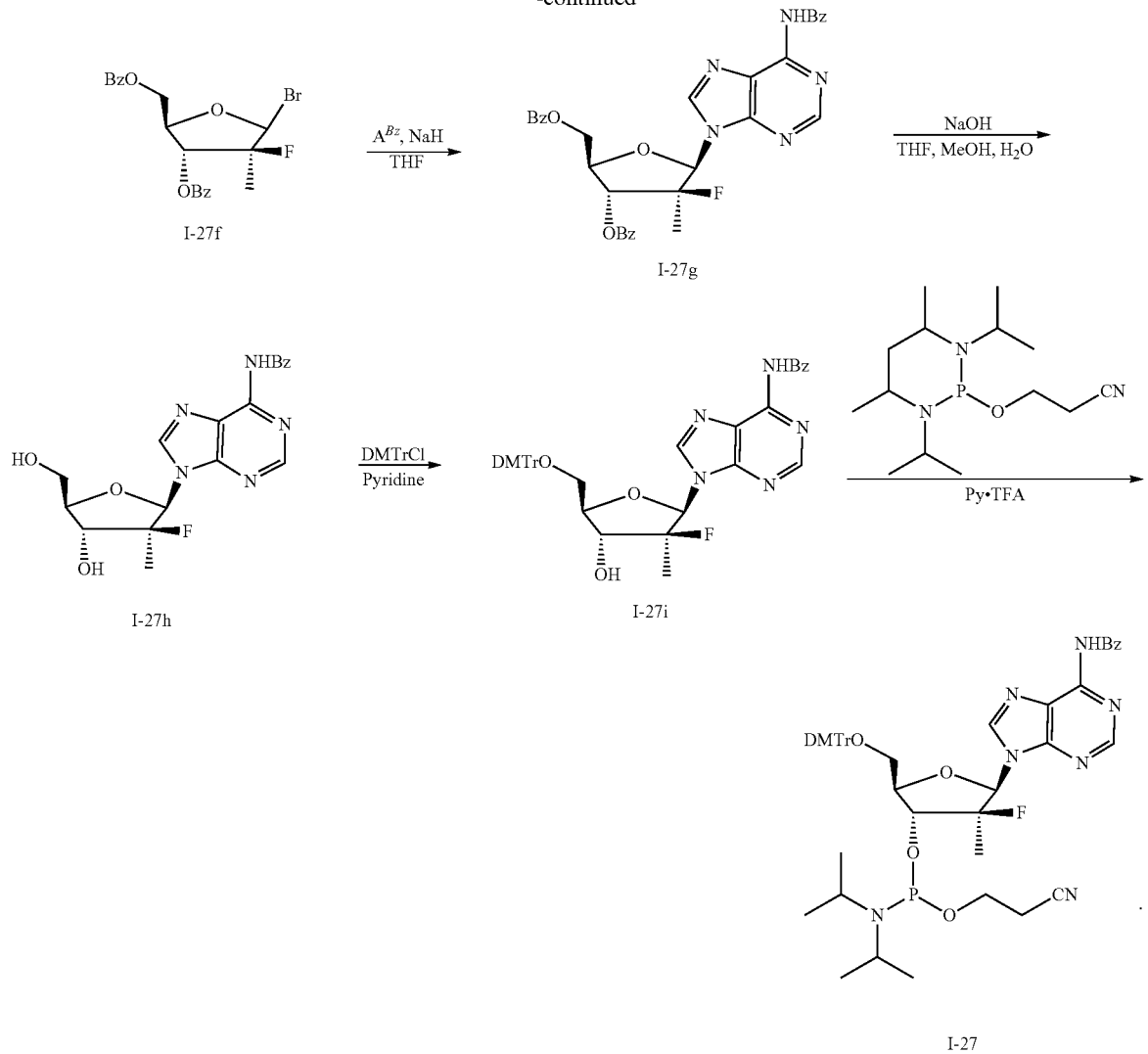

Step 1: To a slurry of (3R,4R,5R)-3,4-dihydroxy-5-(hydroxymethyl)-3-methyldihydrofuran-2(3H)-one (WO2013/188480, 2013, A1) (50 g, 308 mmol) in DCM (500 mL) was added pyridine (64.8 mL). The mixture was stirred in an ice bath and then benzoyl chloride (95 g, 678 mmol) was added dropwise over 65 minutes at −5° C. The reaction mixture was then warmed to room temperature and stirred for 1.5 h. The reaction mixture was then cooled with an ice bath and water (215 mL) was added. The reaction mixture was warmed to room temperature and stirred for 2 h at this temperature. The organic layer was washed with aqueous hydrogen chloride (1 N, 170 mL), water (170 mL), saturated aqueous sodium carbonate (170 mL), water (3×170 mL) and brine (170 mL), dried over anhydrous sodium sulfate, filtered and the filtrate was concentrated under reduced pressure. The residue was treated with toluene (100 mL) and it began to solidify. The solid was filtered and washed with toluene (100 mL) to give ((2R,3R,4R)-3-(benzoyloxy)-4-hydroxy-4-methyl-5-oxotetrahydrofuran-2-yl)methyl benzoate. MS ESI calculated for $C_{20}H_{18}O_7$ [M+H]$^+$ 371.11, found 371.10. $^1$H-NMR: (300 MHz, DMSO-$d_6$) δ 8.10-7.97 (m, 2H), 7.96-7.84 (m, 2H), 7.72-7.59 (m, 2H), 7.58-7.41 (m, 4H), 6.40 (s, 1H), 5.42 (d, J=7.1 Hz, 1H), 4.98 (td, J=6.4, 3.7 Hz, 1H), 4.67 (dd, J=12.3, 3.7 Hz, 1H), 4.59 (dd, J=12.4, 6.0 Hz, 1H), 1.45 (s, 3H).

Step 2: To a solution of ((2R,3R,4R)-3-(benzoyloxy)-4-hydroxy-4-methyl-5-oxotetrahydrofuran-2-yl)methyl benzoate (49 g, 132 mmol) in DCM (353 mL) was added dropwise diethylaminosulfurtrifluoride (34.1 g, 212 mmol) over 1 h at −78° C. The reaction was slowly warmed to room temperature and stirred for 16 h. The reaction was then quenched with saturated aqueous sodium carbonate (150 mL). The organic layer was washed with brine (150 mL), dried over anhydrous sodium sulfate, filtered and the filtrate was concentrated to give ((2R,3R,4S)-3-(benzoyloxy)-4-fluoro-4-methyl-5-oxotetrahydrofuran-2-yl)methyl benzoate. MS ESI calculated for $C_{20}H_{17}FO_6$ [M+H]$^+$ 373.10, found 373.10. $^1$H-NMR: (400 MHz, CDCl$_3$) δ 8.10-8.02 (m, 4H), 7.69-7.63 (m, 1H), 7.63-7.56 (m, 1H), 7.54-7.48 (m, 2H), 7.47-7.41 (m, 2H), 5.87 (dd, J=18.8, 5.3 Hz, 1H), 4.83-4.72 (m, 2H), 4.73-4.62 (m, 1H), 1.79 (d, J=23.2 Hz, 3H). $^{19}$F-NMR: (400 MHz, CDCl$_3$) δ−153.28 (s, 1F).

Step 3: To a solution of ((2R,3R,4S)-3-(benzoyloxy)-4-fluoro-4-methyl-5-oxotetrahydrofuran-2-yl)methyl benzoate (62 g, 167 mmol) in dry THF (500 mL) was added dropwise lithium tri-tert-butoxyaluminum hydride (1M in THF, 200 mL, 200 mmol) at −78° C. within 30 min. The reaction was warmed to room temperature and stirred for 2 h at this temperature. The mixture was cooled to 0° C. and quenched by saturated aqueous ammonium chloride (800 mL), diluted with ethyl acetate (1000 mL). The resulting mixture was then filtered and the organic layer was washed with brine (800 mL), dried over anhydrous sodium sulfate, filtered and the filtrate was concentrated under reduced pressure to give ((2R,3R,4S)-3-(benzoyloxy)-4-fluoro-5-hydroxy-4-methyltetrahydrofuran-2-yl)methyl benzoate which was used directly in next step. MS ESI calculated for $C_{20}H_{19}FO_6$ [M+H]$^+$ 375.12, found 357.10. $^{19}$F-NMR: (282 MHz, CDCl$_3$) δ−149.67, −167.30.

Step 4: To a solution of ((2R,3R,4S)-3-(benzoyloxy)-4-fluoro-5-hydroxy-4-methyltetrahydrofuran-2-yl)methyl benzoate (67.3 g, 180 mmol) (co-evaporated with dry toluene (100 mL×3) before being used) in dry DCM (565 mL) were added triethylamine (32.5 mL, 234 mmol), N,N-dimethylpyridin-4-amine (4.39 g, 36.0 mmol) and acetic anhydride (25.5 mL, 270 mmol) at 0° C. The reaction mixture was then warmed to room temperature and stirred for 2 h at this temperature. The solvent was removed under reduced pressure and the residue was purified by column chromatography on silica gel using a stepwise gradient of ethyl acetate (0-20%) in petroleum ether to give (2R,3R,4S)-5-acetoxy-2-((benzoyloxy)methyl)-4-fluoro-4-methyltetrahydrofuran-3-yl benzoate. MS ESI calculated for $C_{22}H_{21}FO_7$ [M+NH$_4$]$^+$ 434.13, found 434.20.

Step 5: To a solution of (2R,3R,4S)-5-acetoxy-2-((benzoyloxy)methyl)-4-fluoro-4-methyltetrahydrofuran-3-yl benzoate (80 g, 192 mmol) in DCM (720 mL) was added hydrogen bromide (33% in acetic acid, 95 mL, 576 mmol) at 0° C. The reaction was stirred at ambient temperature for 16 h. The reaction mixture was quenched by sodium bicarbonate until no carbon dioxide was observed and diluted with DCM (800 mL). The organic layer was then washed with saturated aqueous sodium bicarbonate (3×700 mL), water (700 mL), brine (700 mL), dried over anhydrous sodium sulfate, filtered and the filtrate was concentrated under reduced pressure to give ((2R,3R,4S)-3-(benzoyloxy)-5-bromo-4-fluoro-4-methyltetrahydrofuran-2-yl)methyl benzoate which was used directly in next step. MS ESI calculated for $C_{20}H_{18}BrFO_5$ [M+H]$^+$ 437.03, 439.03, found 437.15, 439.05.

Step 6: To a solution of N-(9H-purin-6-yl)benzamide (45.2 g, 189 mmol) in anhydrous dioxane (700 mL) was added sodium hydride (60% in mineral oil, 9.35 g, 234 mmol) at room temperature under argon atmosphere and the mixture was stirred for 5 min at this temperature. Then a solution of ((2R,3R,4S)-3-(benzoyloxy)-5-bromo-4-fluoro-4-methyltetrahydrofuran-2-yl)methyl benzoate (78.6 g, 180 mmol) in anhydrous dioxane (700 mL) was added at room temperature. The reaction mixture was stirred at 100° C. for 5 h. The reaction mixture was quenched by saturated aqueous ammonium chloride (800 mL) and diluted with ethyl acetate (1000 mL). The organic layer was then washed with water (800 mL), brine (800 mL), dried over anhydrous sodium sulfate, filtered and the filtrate was concentrated under reduced pressure. The residue was purified by column chromatography on silica gel using a stepwise gradient of 0-60% ethyl acetate in petroleum ether to give a crude product. The crude product was further purified by Combi-Flash with the following conditions: Column: AQ-C18 gel column (330 g), 20-40 μm; Mobile Phase: MeCN and water (Gradient: 45-100% within 35 min); Flow rate: 100 mL/min; Detector: UV 254 & 280 nm. The product-containing fractions were collected and evaporated under reduced pressure to give (2R,3R,4S,5R)-5-(6-benzamido-9H-purin-9-yl)-2-((benzoyloxy)methyl)-4-fluoro-4-methyltetrahydrofuran-3-yl benzoate.

MS ESI calculated for $C_{32}H_{26}FN_5O_6$ [M+H]$^+$ 596.19, found 596.20. $^1$H-NMR: (400 MHz, CDCl$_3$) δ 9.12 (s, 1H), 8.84 (s, 1H), 8.37 (d, J=3.3 Hz, 1H), 8.18-8.09 (m, 4H), 8.09-8.01 (m, 2H), 7.74-7.42 (m, 9H), 6.52 (d, J=20.4 Hz, 1H), 5.68 (dd, J=16.8, 2.6 Hz, 1H), 4.90 (dd, J=12.0, 5.9 Hz, 1H), 4.84 (dd, J=12.0, 4.1 Hz, 1H), 4.60-4.57 (m, 1H), 1.61 (d, J=22.6 Hz, 3H). $^{19}$F-NMR: (376 MHz, CDCl$_3$) δ−160.17 (s, 1F).

Step 7: To a solution of (2R,3R,4S,5R)-5-(6-benzamido-9H-purin-9-yl)-2-((benzoyloxy)methyl)-4-fluoro-4-methyltetrahydrofuran-3-yl benzoate (10 g, 16.79 mmol) in methanol (70 mL), THF (56 mL) and water (14 mL) was added dropwise aqueous sodium hydroxide solution (4 N, 12.59 mL, 50.4 mmol) at 0° C. The reaction mixture was stirred at 0° C. for 25 min. The reaction mixture was quenched by formic acid (1.89 mL). Then the solvent was removed under reduced pressure. The crude product was purified by column chromatography on silica gel using a stepwise gradient of MeOH (0-10%) in DCM to give N-(9-((2R,3S,4R,5R)-3-fluoro-4-hydroxy-5-(hydroxymethyl)-3-methyltetrahydrofuran-2-yl)-9H-purin-6-yl)benzamide. MS ESI calculated for $C_{18}H_{18}FN_5O_4$ [M+H]$^+$ 388.13, found 388.15. $^1$H-NMR: (400 MHz, CD$_3$OD): δ 8.76 (s, 1H), 8.64 (d, J=2.7 Hz, 1H), 8.13-8.06 (m, 2H), 7.71-7.62 (m, 1H), 7.62-7.53 (m, 2H), 6.37 (d, J=16.3 Hz, 1H), 4.33 (dd, J=19.1, 4.5 Hz, 1H), 4.03 (q, J=4.8 Hz, 1H), 3.92 (dd, J=12.1, 4.2 Hz, 1H), 3.87 (dd, J=12.1, 5.5 Hz, 1H), 1.51 (d, J=23.0 Hz, 3H). $^{19}$F-NMR: (376 MHz, CD$_3$OD): δ−159.16 (s, 1F).

Step 8: To a solution of N-(9-((2R,3S,4R,5R)-3-fluoro-4-hydroxy-5-(hydroxymethyl)-3-methyltetrahydrofuran-2-yl)-9H-purin-6-yl)benzamide (8.8 g, 22.72 mmol) in dry pyridine (45 mL) was added 4,4'-(chloro(phenyl)methylene)bis(methoxybenzene) (8.47 g, 24.99 mmol) at room temperature. The reaction mixture was stirred at room temperature for 2 h. The solvent was removed under reduced pressure. The residue was co-evaporated with toluene (3×40 mL) and then purified by column chromatography on silica gel using a stepwise gradient of ethyl acetate (0-100%) in petroleum ether to give a yellow crude product. The crude product was further purified by Combi-Flash with the following conditions: Column: AQ-C18 gel column (330 g), 20-40 μm; Mobile Phase: MeCN and water (Gradient: 45-100% within 35 min); Flow rate: 100 mL/min; Detector: UV 254 & 280 nm. The product-containing fractions were collected and roto-evaporated in vacuo to give N-(9-((2R,3S,4R,5R)-5-((bis(4-methoxyphenyl)(phenyl)methoxy)methyl)-3-fluoro-4-hydroxy-3-methyltetrahydrofuran-2-yl)-9H-purin-6-yl)benzamide. MS ESI calculated for $C_{39}H_{36}FN_5O_6$ [M+H]$^+$ 690.26, found 690.25.

$^1$H-NMR: (300 MHz, CD$_3$OD) δ 8.69 (s, 1H), 8.33 (d, J=2.9 Hz, 1H), 8.10-8.01 (m, 2H), 7.65-7.43 (m, 5H), 7.36-7.15 (m, 7H), 6.82 (d, J=8.9 Hz, 4H), 6.33 (d, J=17.0 Hz, 1H), 4.29 (dd, J=18.8, 4.3 Hz, 1H), 4.14-4.10 (m, 1H), 3.74 (s, 6H), 3.46 (dd, J=10.1, 6.4 Hz, 1H), 3.39 (dd, J=10.1, 4.0 Hz, 1H), 1.43 (d, J=23.1 Hz, 3H).

Step 9: To a solution of 3-((bis(diisopropylamino)phosphino)oxy)propanenitrile (8.46 g, 28.1 mmol) (co-evaporated with dry acetonitrile (3×20 mL) before being used) in dry acetonitrile (20 mL) was added pyridin-1-ium 2,2,2-trifluoroacetate (5.42 g, 28.1 mmol) at room temperature. The solution was marked as solution A. To a solution of N-(9-((2R,3S,4R,5R)-5-((bis(4-methoxyphenyl)(phenyl)methoxy)methyl)-3-fluoro-4-hydroxy-3-methyltetrahydrofuran-2-yl)-9H-purin-6-yl)benzamide (12.9 g, 18.70 mmol) (co-evaporated with dry acetonitrile (3×50 mL) before being used) in dry acetonitrile (45 mL) was added to solution A at room temperature. The reaction was stirred at room temperature for 1 h. The reaction was quenched by water (300 mL) and diluted with ethyl acetate (400 mL). The organic layer was washed with saturated aqueous sodium bicarbonate (300 mL), water (300 mL) and brine (300 mL), dried over anhydrous sodium sulfate, filtered and the filtrate was concentrated under reduced pressure. The crude product was purified by Combi-Flash with the following conditions: Column: AQ-C18 gel column (330 g), 20-40 μm; Mobile Phase: MeCN and water (Gradient: 45-100% within 35 min); Flow rate: 100 m/min; Detector: UV 254 & 280 nm. The product-containing fractions were collected and the solvent was removed under reduced pressure to give (2R,3R,4S,5R)-5-(6-benzamido-9H-purin-9-yl)-2-((bis(4-methoxyphenyl)(phenyl)methoxy)methyl)-4-fluoro-4-methyltetrahydrofuran-3-yl (2-cyanoethyl) diisopropylphosphoramidite. MS ESI calculated for $C_{48}H_{53}FN_7O_7P$ [M+H]$^+$ 890.37, found 890.45. $^1$H-NMR: (400 MHz, DMSO-$d_6$) δ 11.30 (s, 1H), 8.76 (s, 0.6H), 8.75 (s, 0.4H), 8.44 (d, J=2.3 Hz, 0.4H), 8.40 (d, J=2.4 Hz, 0.6H), 8.11-8.04 (m, 2H), 7.71-7.62 (m, 1H), 7.61-7.53 (m, 2H), 7.52-7.40 (m, 2H), 7.35-7.20 (m, 7H), 6.90-6.85 (m, 4H), 6.39 (d, J=16.0 Hz, 0.4H), 6.38 (d, J=16.0 Hz, 0.6H), 4.76-4.61 (m, 1H), 4.31-4.19 (m, 1H), 3.82-3.70 (m, 1H), 3.74 (s, 6H), 3.66-3.43 (m, 5H), 2.75 (t, J=5.8 Hz, 1H), 2.59 (t, J=5.9 Hz, 1H), 1.59 (d, J=22.9 Hz, 1.5H), 1.53 (d, J=23.0 Hz, 1.5H), 1.23-0.96 (m, 12H). $^{19}$F-NMR: (376 MHz, DMSO-$d_6$) δ −154.29 (d, J=3.7 Hz, 0.5F), −154.91 (s, 0.5F). $^{31}$P-NMR: (162 MHz, DMSO-$d_6$) δ 150.40 (d, J=3.7 Hz, 0.5P), 150.14 (s, 0.5P).

Intermediate I-28

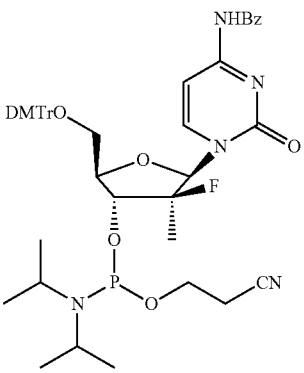

Scheme 6
Synthesis of Intermediate I-28

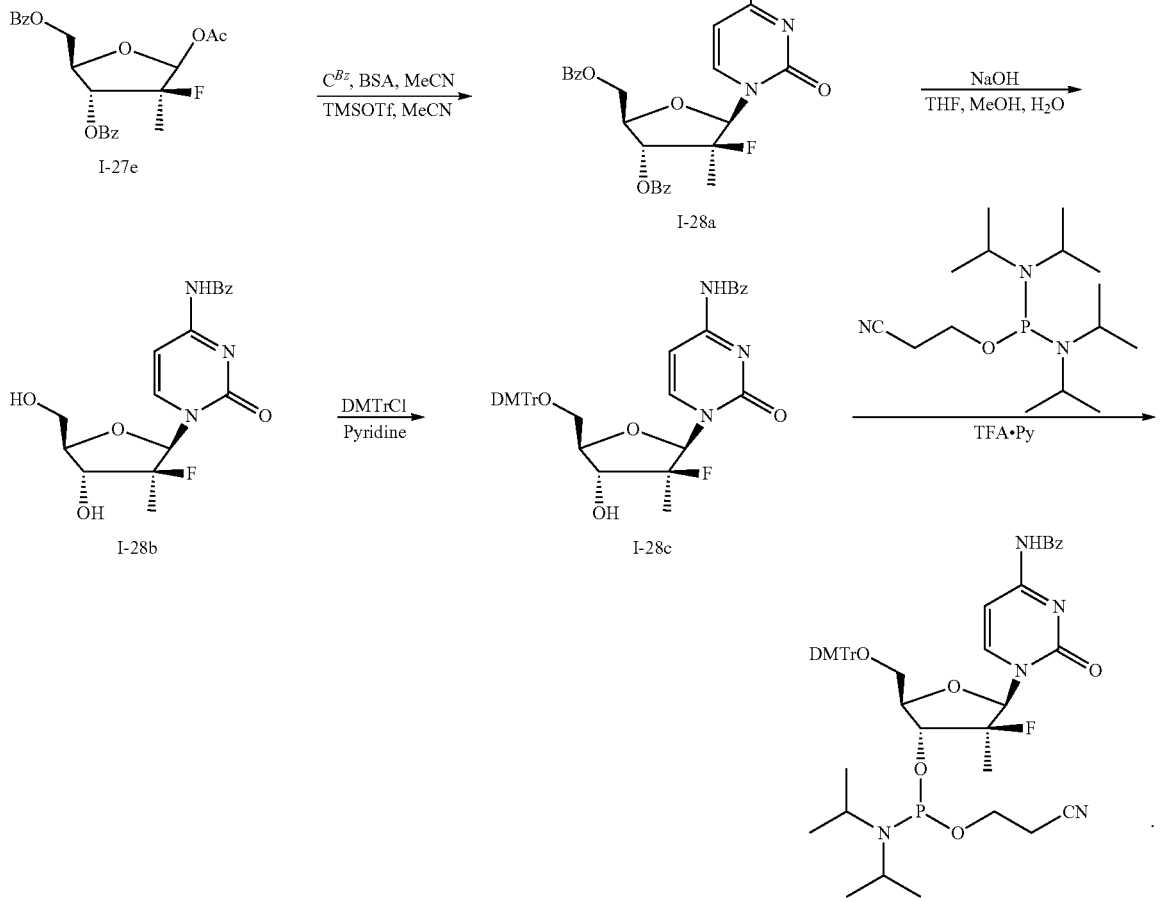

Step 1: To a suspension of N-(2-oxo-1,2-dihydropyrimidin-4-yl)benzamide (88 g, 408 mmol) in dry acetonitrile (200 mL) was added (E)-trimethylsilyl N-(trimethylsilyl)acetimidate (225 mL, 919 mmol) dropwise at room temperature under an argon atmosphere. The mixture was then heated to 70° C. and stirred for 2 h. The reaction was cooled to room temperature and a solution of (2R,3R,4S)-5-acetoxy-2-((benzoyloxy)methyl)-4-fluoro-4-methyltetrahydrofuran-3-yl benzoate (85 g, 204 mmol) (co-evaporated with dry acetonitrile (3×50 mL) before being used) in dry acetonitrile (225 mL) was added at room temperature. The mixture was heated to 70° C. and stirred for 10 h. The reaction was diluted with ethyl acetate (1500 mL) and quenched by saturated aqueous sodium bicarbonate (600 mL) at 0° C. and the mixture was filtered. The organic layer was washed with saturated sodium bicarbonate (3×600 mL), water (600 mL) and brine (800 mL). The organic layer was dried with anhydrous sodium sulfate, filtered and the filtrate was concentrated under reduced pressure. The residue was purified by column chromatography on silica gel using a stepwise gradient of ethyl acetate (0-50%) in petroleum ether to give (2R,3R,4S,5R)-5-(4-benzamido-2-oxopyrimidin-1(2H)-yl)-2-((benzoyloxy)methyl)-4-fluoro-4-methyltetrahydrofuran-3-yl benzoate. MS ESI calculated for $C_{31}H_{26}FN_3O_7$ [M+H]$^+$ 572.18, found 572.15. $^1$H-NMR: (400 MHz, DMSO-d$_6$) δ 11.36 (s, 1H), 8.18-7.99 (m, 7H), 7.81-7.48 (m, 9H), 7.41 (d, J=7.6 Hz, 1H), 6.42 (d, J=17.6 Hz, 1H), 5.60 (dd, J=19.7, 4.6 Hz, 1H), 4.80-4.74 (m, 2H), 4.68-4.61 (m, 1H), 1.60 (d, J=23.5 Hz, 3H). $^{19}$F-NMR: (376 MHz, DMSO) δ –158.48 (s, 1F).

Step 2: To a solution of (2R,3R,4S,5R)-5-(4-benzamido-2-oxopyrimidin-1(2H)-yl)-2-((benzoyloxy)methyl)-4-fluoro-4-methyltetrahydrofuran-3-yl benzoate (14.1 g, 24.67 mmol) in THF (99 mL), MeOH (79 mL) and water (19.7 mL) was added dropwise aqueous sodium hydroxide (4 N, 18.50 mL, 74.0 mmol) at 0° C. The reaction was then stirred at room temperature for 20 min. The reaction was quenched by formic acid (2.82 mL, 74.0 mmol) at 0° C. The solvent was then removed under reduced pressure and the residue was purified by column chromatography on silica gel using a stepwise gradient of MeOH (0-10%) in DCM to give N-(1-((2R,3S,4R,5R)-3-fluoro-4-hydroxy-5-(hydroxymethyl)-3-methyltetrahydrofuran-2-yl)-2-oxo-1,2-dihydropyrimidin-4-yl)benzamide. MS ESI calculated for C17H$_{18}$FN$_3$O$_5$ [M+H]$^+$ 364.12, found 364.15. $^1$H-NMR: (400 MHz, DMSO-d$_6$) δ 11.31 (s, 1H), 8.23 (d, J=7.6 Hz, 1H), 8.06-7.97 (m, 2H), 7.69-7.60 (m, 1H), 7.62-7.49 (m, 2H), 7.41-7.36 (m, 1H), 6.09 (d, J=13.8 Hz, 1H), 5.93 (d, J=5.7 Hz, 1H), 5.12 (t, J=5.6 Hz, 1H), 4.13-4.05 (m, 1H), 3.82-3.78 (m, 1H), 3.77-3.72 (m, 1H), 3.68-3.62 (m, 1H), 1.46 (d, J=23.6 Hz, 3H). $^{19}$F-NMR: (376 MHz, DMSO-d$_6$) δ –156.84 (s, 1F).

Step 3: To a solution of N-(1-((2R,3S,4R,5R)-3-fluoro-4-hydroxy-5-(hydroxymethyl)-3-methyltetrahydrofuran-2-yl)-2-oxo-1,2-dihydropyrimidin-4-yl)benzamide (7.2 g, 19.82 mmol) (co-evaporated with dry pyridine (3×20 mL) before being used) in dry pyridine (36 mL) was added 4,4'-(chloro(phenyl)methylene)bis(methoxybenzene) (7.39 g, 21.80 mmol) at room temperature. The reaction was stirred at room temperature for 2 h. The solvent was removed under reduced pressure and the residue was co-evaporated with toluene (2×15 mL). The residue was purified by column chromatography on silica gel using a stepwise gradient of ethyl acetate (0-100%) in petroleum ether to give a crude product. The crude product was further purified by Combi-Flash with the following conditions: Column: AQ C18 gel column (330 g), 20-40 μm; Mobile Phase: MeCN and water (Gradient: 45-100% within 35 min); Flow rate: 100 mL/min; Detector: UV 254 & 280 nm. The product-containing fractions were collected and the solvent was removed under reduced pressure to give N-(1-((2R,3S,4R,5R)-5-((bis(4-methoxyphenyl)(phenyl)methoxy)methyl)-3-fluoro-4-hydroxy-3-methyltetrahydrofuran-2-yl)-2-oxo-1,2-dihydropyrimidin-4-yl)benzamide. MS ESI calculated for $C_{38}H_{36}FN_3O_7$ [M+H]$^+$ 666.25, found 666.25. $^1$H-NMR: (400 MHz, DMSO-d$_6$) δ 11.32 (s, 1H), 8.05-8.01 (m, 3H), 7.69-7.60 (m, 1H), 7.58-7.49 (m, 2H), 7.44 (d, J=7.8 Hz, 2H), 7.38-7.26 (m, 8H), 6.97-6.90 (m, 4H), 6.13 (d, J=13.2 Hz, 1H), 6.03 (d, J=5.7 Hz, 1H), 4.16 (dt, J=21.4, 6.0 Hz, 1H), 4.01-3.97 (m, 1H), 3.77 (s, 6H), 3.42-3.33 (m, 2H), 1.46 (d, J=23.6 Hz, 3H). $^{19}$F-NMR: (376 MHz, DMSO-d$_6$) δ –156.48 (s, 1F).

Step 4: To a solution of 3-(((diisopropylamino)(2,4-dimethylpentan-3-yl)phosphino)oxy)propanenitrile (6.50 g, 21.63 mmol) (co-evaporated with dry acetonitrile (3×20 mL) before being used) in dry acetonitrile (20 mL) was added pyridine 2,2,2-trifluoroacetate (4.18 g, 21.63 mmol) at room temperature. After 5 min, a solution of N-(1-((2R,3S,4R,5R)-5-((bis(4-methoxyphenyl)(phenyl)methoxy)methyl)-3-fluoro-4-hydroxy-3-methyltetrahydrofuran-2-yl)-2-oxo-1,2-dihydropyrimidin-4-yl)benzamide (9.6 g, 14.42 mmol) (co-evaporated with dry acetonitrile (3×20 mL) before being used) in dry acetonitrile (30 mL) was added at room temperature. The reaction was stirred at room temperature for 1.5 h. The reaction was diluted with ethyl acetate (500 mL) and quenched by saturated aqueous sodium bicarbonate (300 mL). The organic layer was then washed with water (300 mL) and brine (300 mL), dried over anhydrous sodium sulfate, filtered and the filtrate was concentrated under reduced pressure. The residue was further purified by Combi-Flash with the following conditions: Column: AQ C18 gel column (330 g), 20-40 μm; Mobile Phase: MeCN and water (Gradient: 45-100% within 35 min); Flow rate: 100 mL/min; Detector: UV 254 & 280 nm. The product-containing fractions were collected and roto-evaporated in vacuo to give (2R,3R,4S,5R)-5-(4-benzamido-2-oxopyrimidin-1(2H)-yl)-2-((bis(4-methoxyphenyl)(phenyl)methoxy)methyl)-4-fluoro-4-methyltetrahydrofuran-3-yl (2-cyanoethyl) diisopropylphosphoramidite. MS ESI calculated for $C_{47}H_{53}FN_5O_8P$ [M+H]$^+$ 866.36, found 866.45. $^1$H-NMR: (400 MHz, DMSO-d$_6$) δ 11.35 (s, 1H), 8.12 (d, J=7.9 Hz, 0.5H), 8.10 (d, J=8.0 Hz, 0.5H), 8.05-7.98 (m, 2H), 7.69-7.60 (m, 1H), 7.58-7.49 (m, 2H), 7.49-7.39 (m, 2H), 7.38-7.26 (m, 8H), 6.97-6.88 (m, 4H), 6.23-6.12 (m, 1H), 4.51-4.41 (m, 1H), 4.16-4.11 (m, 1H), 3.77 (s, 6H), 3.59-3.40 (m, 6H), 2.75 (t, J=5.9 Hz, 1H), 2.59 (t, J=6.0 Hz, 1H), 1.58 (d, J=14.1 Hz, 1.4H), 1.52 (d, J=14.0 Hz, 1.6H), 1.22-0.93 (m, 12H). $^{19}$F-NMR: (376 MHz, DMSO-d$_6$) δ –155.59 (s, 0.5F), –155.99 (s, 0.5F). $^{31}$P-NMR: (162 MHz, DMSO-d$_6$) δ 150.64 (s, 0.5P), 150.46 (s, 0.5P).

Intermediate I-29

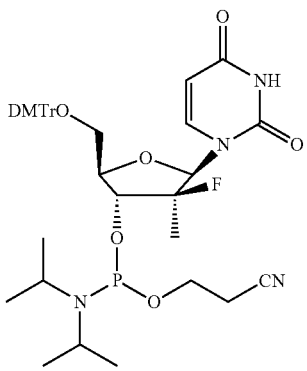

acetamide (84 mL, 324 mmol) at 85° C. The solution was stirred at 85° C. for 2 h and then cooled to room temperature. A solution of (2R,3R,4S)-5-acetoxy-2-((benzoyloxy) methyl)-4-fluoro-4-methyltetrahydrofuran-3-yl benzoate (30.0 g, 72 mmol) in acetonitrile (150 mL) was added followed by dropwise addition of trimethylsilyl trifluoromethanesulfonate (84 g, 360 mmol) at room temperature. The reaction mixture was slowly warmed to 85° C. and stirred for 16 h. The mixture was then cooled to 0° C., quenched with saturated sodium bicarbonate solution (500 mL). The mixture was diluted with ethyl acetate (500 mL). The separated organic layer was washed with brine (3×100 mL), dried over anhydrous sodium sulfate and filtered. The filtrate was concentrated under reduced pressure. The residue was purified by silica gel column chromatography, eluted with 10%-50% ethyl acetate in petroleum ether to afford ((2R,3R,4S)-3-(benzoyloxy)-5-(2,4-dioxo-3,4-dihy- Scheme 7
Synthesis of Intermediate I-29

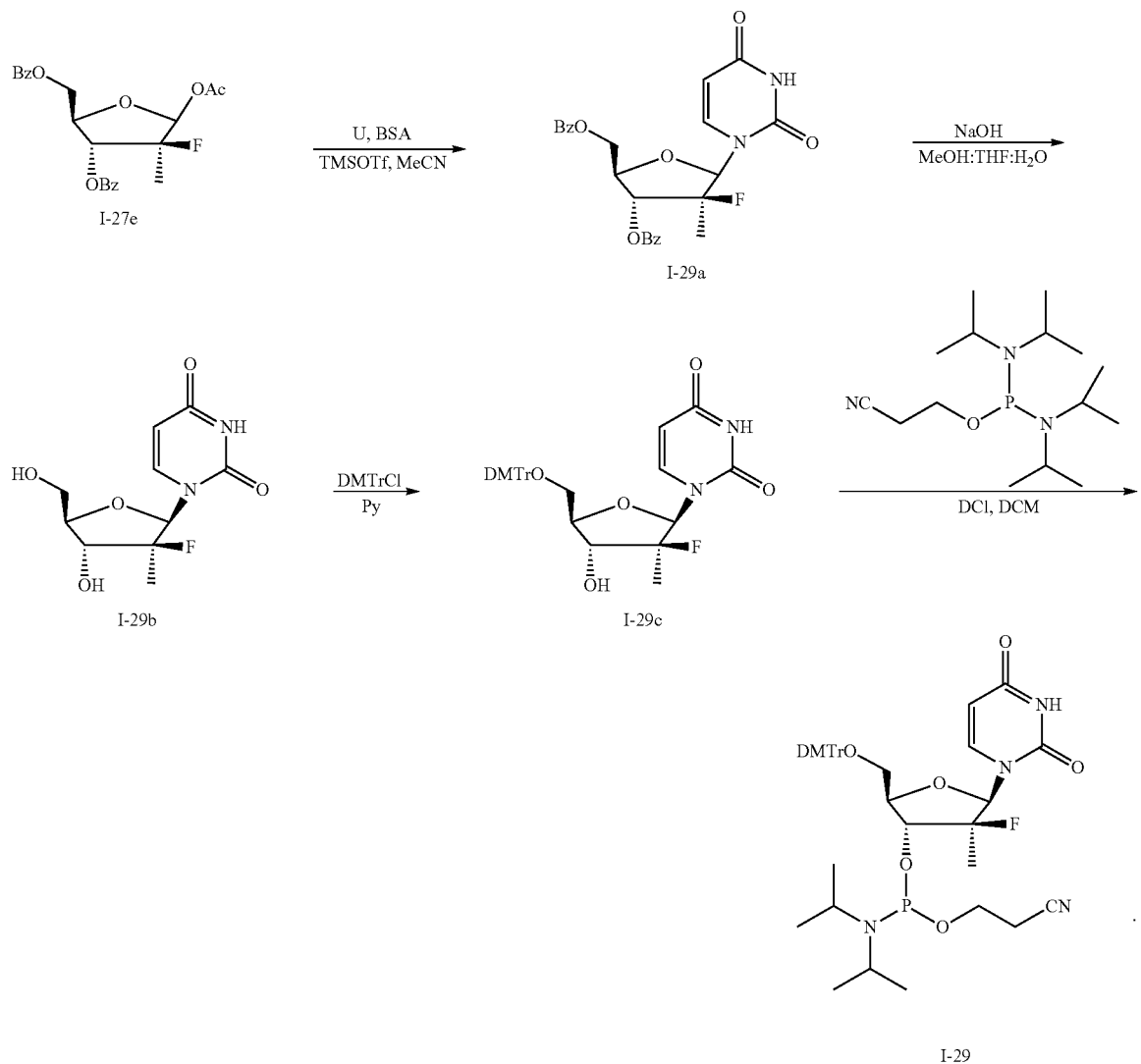

Step 1: To a solution of uracil (16.9 g, 144 mmol) in acetonitrile (150 mL) was added N,O-bis(trimethylsilyl) dropyrimidin-1(2H)-yl)-4-fluoro-4-methyltetrahydrofuran-2-yl)methyl benzoate. MS ESI calculated for $C_{24}H_{21}FN_2O_7$

[M+H]⁺ 469.13, found 469.15. ¹H-NMR (300 MHz, CDCl₃) δ 9.48 (brs, 0.5H), 9.40 (brs, 0.5H), 8.21-7.87 (m, 5H), 7.76-7.36 (m, 6H), 6.56 (d, J=15.5 Hz, 0.5H), 6.30 (d, J=20.3 Hz, 0.5H), 5.86-5.70 (m, 1H), 5.62-5.45 (m, 1H), 5.00-4.57 (m, 3H), 1.66 (d, J=11.4, 1.5H), 1.56 (d, J=11.4 Hz, 1.5H).

Step 2: To a solution of ((2R,3R,4S)-3-(benzoyloxy)-5-(2,4-dioxo-3,4-dihydropyrimidin-1(2H)-yl)-4-fluoro-4-methyltetrahydrofuran-2-yl)methyl benzoate (48 g, 103 mmol) in MeOH (125 mL), THF (100 mL) and H₂O (25 mL) was added aqueous sodium hydroxide solution (77.8 mL, 4 M, 309 mmol) at 0° C. The mixture was stirred at room temperature for 30 min. The pH of the mixture was adjusted to 7 with formic acid and the mixture was concentrated under reduced pressure. The residue was purified by silica gel column chromatography, eluted with 0%-20% MeOH in DCM to afford 1-((3S, 4R, 5R)-3-fluoro-4-hydroxy-5-(hydroxymethyl)-3-methyltetrahydrofuran-2-yl)pyrimidine-2,4 (1H, 3H)-dione as a white solid. The product (containing α and β isomers) was separated by Prep-SFC with the following conditions: (Column: ChiralPak IA-SFC, 5 cm×25 cm, 5 um; Mobile Phase A: CO₂: 50, Mobile Phase B: MeOH: 50; Flow rate:180 mL/min; 220 nm; RT1: 2.51 min (β isomer); RT2: 3.46 min (a isomer)) to give 1-((2R,3S,4R,5R)-3-fluoro-4-hydroxy-5-(hydroxymethyl)-3-methyltetrahydrofuran-2-yl)pyrimidine-2,4(1H,3H)-dione. MS ESI calculated for C₁₀H₁₃FN₂O₅ [M+H]⁺ 261.08, found 261.10. ¹H-NMR (300 MHz, CD₃OD) δ 7.82 (dd, J=8.2, 2.4 Hz, 1H), 6.03 (d, J=15.9 Hz, 1H), 5.70 (d, J=8.2 Hz, 1H), 4.13 (dd, J=20.7, 4.7 Hz, 1H), 3.92-3.79 (m, 2H), 3.84-3.68 (m, 1H), 1.48 (d, J=23.3 Hz, 3H).

Step 3: To a solution of 1-((2R,3S,4R,5R)-3-fluoro-4-hydroxy-5-(hydroxymethyl)-3-methyltetrahydrofuran-2-yl)pyrimidine-2,4(1H,3H)-dione (9.5 g, 365.0 mmol) in pyridine (60 mL) was added 4,4'-(chloro(phenyl)methylene)bis(methoxybenzene) (13.6 g, 402.0 mmol) at 0° C. The mixture was stirred at room temperature for 2 h. The mixture was concentrated under reduced pressure. The residue was purified by Combi Flash Column Chromatography as the following conditions: (Column: AQ-C¹⁸, 19×250 mm, 10 um; Mobile Phase A: Water, Mobile Phase B: MeCN; Flow rate: 100 mL/min; Gradient: 30% B hold 5 min, 30% B to 100% B in 35 min; 100% B hold 8 min, 254/280 nm). The product-containing fractions were pooled and concentrated under reduced pressure to afford 1-((2R,3S,4R,5R)-5-((bis(4-methoxyphenyl)(phenyl)methoxy)methyl)-3-fluoro-4-hydroxy-3-methyltetrahydrofuran-2-yl)pyrimidine-2,4(1H, 3H)-dione. MS ESI calculated for C₃₁H₃₁FN₂O₇ [M−H]⁻ 561.21, found 561.21. ¹H-NMR (400 MHz, CD₃OD) δ 7.78-7.70 (m, 1H), 7.50-7.43 (m, 2H), 7.39-7.19 (m, 7H), 6.93-6.82 (m, 4H), 6.03 (d, J=14.1 Hz, 1H), 5.47 (dd, J=8.0, 2.1 Hz, 1H), 4.27 (dd, J=20.7, 5.6 Hz, 1H), 3.96 (q, J=4.7 Hz, 1H), 3.83-3.74 (m, 6H), 3.44 (d, J=4.2 Hz, 2H), 1.48 (d, J=23.3 Hz, 3H).

Step 4: 1-((2R,3S,4R,5R)-5-((bis(4-methoxyphenyl)(phenyl)methoxy)methyl)-3-fluoro-4-hydroxy-3-methyltetrahydrofuran-2-yl)pyrimidine-2,4(1H,3H)-dione (15.0 g, 26.6 mmol) was co-evaporated with dry acetonitrile (3×10 mL) and then re-dissolved in DCM (40 mL), marked as solution A which was kept under an argon atmosphere before being used. 3-(Bis(diisopropylamino)phosphinooxy)propanenitrile (12.0 g, 39.9 mmol) was also co-evaporated with dry acetonitrile (3×10 mL) and then re-dissolved in DCM (35 mL), marked as solution B. 4,5-Dicyanoimidazole (2.6 g, 22.0 mmol) was added into the solution B, followed by the addition of solution A at ambient temperature. The resulting mixture was stirred at ambient temperature for 2 h. The reaction mixture was diluted with DCM (300 mL) and washed with saturated aqueous sodium bicarbonate solution (300 mL) and the organic layer was concentrated under reduced pressure. The residue was purified by Combi Flash Column Chromatography as the following conditions: (Column: AQ-C¹⁸, 19×250 mm, 10 um; Mobile Phase A: Water, Mobile Phase B: MeCN; Flow rate: 100 mL/min; Gradient: 30% B hold 5 min, 30% B to 100% B in 30 min; 100% B hold 8 min, 254/280 nm). The product-containing fractions were pooled and concentrated under reduced pressure to afford (2R,3R,4S,5R)-2-((bis(4-methoxyphenyl)(phenyl)methoxy)methyl)-5-(2,4-dioxo-3,4-dihydropyrimidin-1 (2H)-yl)-4-fluoro-4-methyltetrahydrofuran-3-yl (2-cyanoethyl) diisopropylphosphoramidite. MS ESI calculated for C₄₀H₄₈FN₄O₈P [M+H]⁺ 763.32, found 763.30. ¹H-NMR (300 MHz, DMSO-d₆) δ 11.55 (s, 1H), 7.63-7.60 (m, 1H), 7.46-7.42 (m, 2H), 7.37-7.24 (m, 7H), 6.94-6.85 (m, 4H), 6.05-5.95 (m, 1H), 5.60-5.46 (m, 1H), 4.47-4.33 (m, 1H), 4.15-4.03 (m, 1H), 3.85-3.65 (m, 1H), 3.76 (s, 6H), 3.65-3.29 (m, 5H), 2.75 (t, J=5.8 Hz, 1H), 2.58 (t, J=5.9 Hz, 1H), 1.55-1.43 (m, 3H), 1.14-0.98 (m, 12H). ¹⁹F-NMR (282 MHz, DMSO-d₆): δ−155.85 (s, 0.3F), −156.32 (s, 0.7F). ³¹P-NMR (121 MHz, DMSO-d₆): δ 150.57 (s, 0.4P), 150.23 (s, 0.6P).

Intermediate I-30

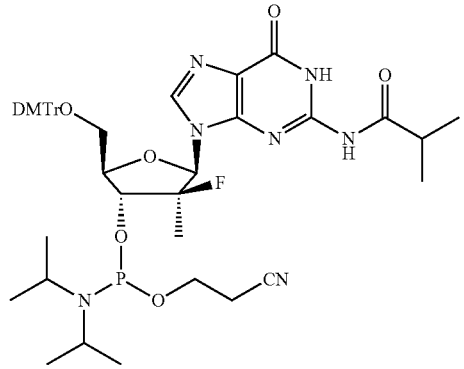

Scheme 8
Synthesis of Intermediate I-30

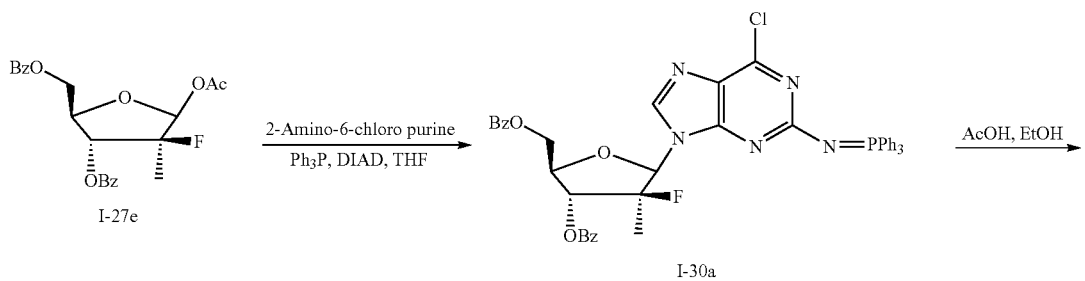

-continued

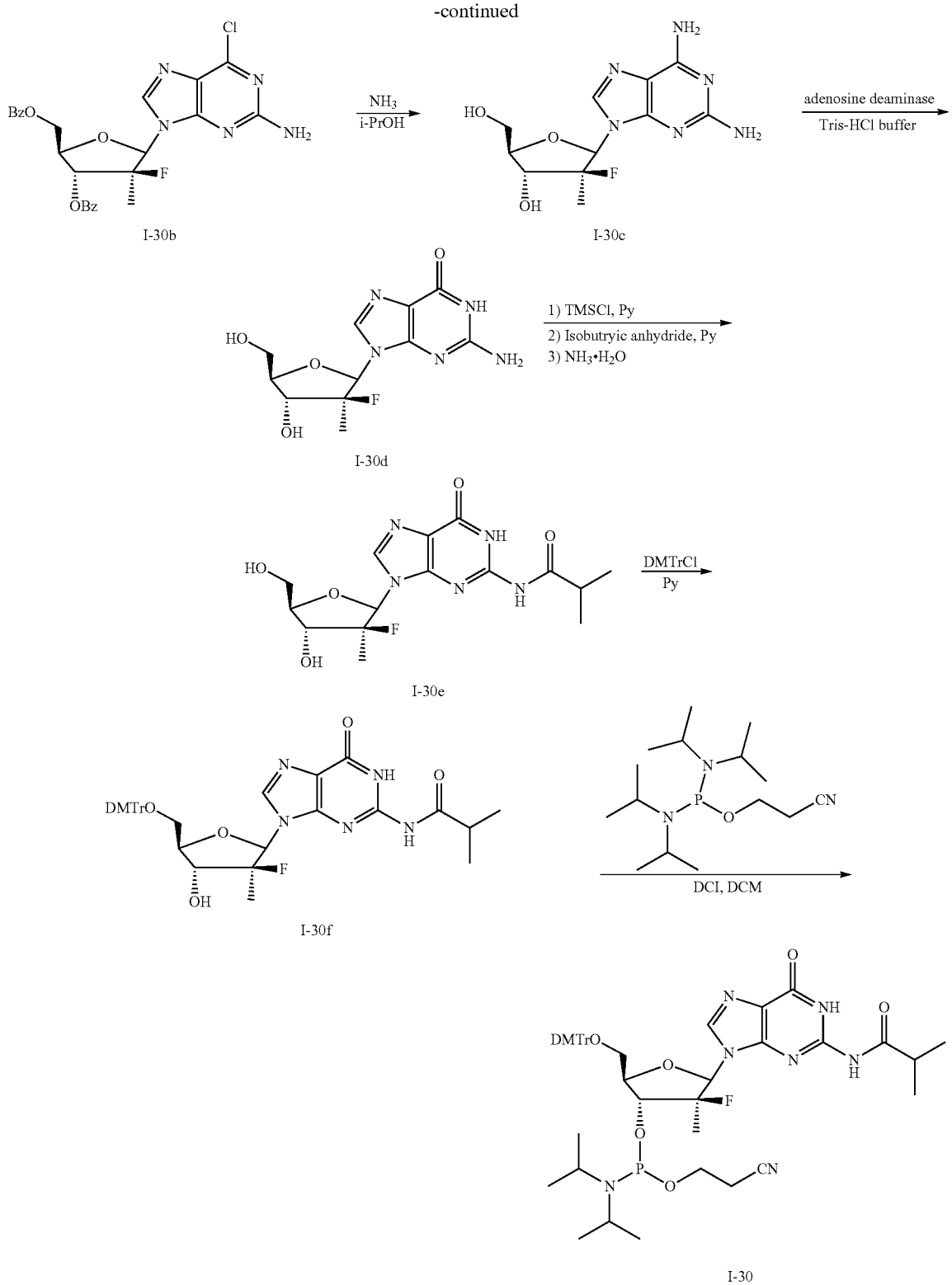

Step 1: To a suspension of ((2R,3R,4S)-3-(benzoyloxy)-4-fluoro-5-hydroxy-4-methyltetrahydrofuran-2-yl)methyl benzoate (74 g, 198 mmol), 6-chloro-9H-purin-2-amine (36.9 g, 217 mmol) and triphenylphosphine (156 g, 593 mmol) in dry THF (740 mL) was added (E)-diethyl diazene-1,2-dicarboxylate (93 mL, 593 mmol) at 0° C. The reaction was then stirred at ambient temperature for 3 h. After completion of the reaction, the solvent was removed and the residue was diluted with ethyl acetate (1000 mL). The organic layer was then washed with saturated aqueous sodium bicarbonate solution (2×500 mL), water (500 mL) and brine (500 mL), dried over anhydrous sodium sulfate, filtered and the filtrate was concentrated under reduced pressure. The residue was then purified by column chromatography on silica gel using a stepwise gradient of ethyl acetate (0-50%) in petroleum ether to give product which is a mixture of α and β isomers. The crude product was used as it. MS ESI calculated for $C_{43}H_{34}ClFN_5O_5P$ [M+H]$^+$ 786.20, 788.20, found 786.25, 788.25.

Step 2: To a suspension of ((2R,3R,4S,5R)-3-(benzoyloxy)-5-(6-chloro-2-((triphenylphosphoranylidene)amino)-9H-purin-9-yl)-4-fluoro-4-methyltetrahydrofuran-2-yl) methyl benzoate (133 g, 169 mmol) in EtOH (700 mL) was added acetic acid (700 mL, 1 M in water, 700 mmol) at ambient temperature. The reaction was then stirred at 80° C. for 2 h. After completion of the reaction, the solvent was removed and the residue was diluted with ethyl acetate (1000 mL) and neutralized with sodium bicarbonate (200 g). The organic layer was then washed with saturated aqueous sodium bicarbonate solution (6×500 mL), water (500 mL) and brine (500 mL), dried over anhydrous sodium sulfate, filtered and the filtrate was concentrated under reduced pressure. The residue was purified by column chromatography on silica gel using a stepwise gradient of ethyl acetate (0-50%) in petroleum ether to give a crude product. To the crude product was then added Et$_2$O (300 mL). The resulting solid, which contains triphenylphosphine oxide and most of the α isomer, was filtered off and the filtrate was concentrated under reduced pressure. The residue was then purified by column chromatography on silica gel using a stepwise gradient of ethyl acetate (0-50%) in petroleum ether to give (2R,3R,4S,5R)-5-(2-amino-6-chloro-9H-purin-9-yl)-2-((benzoyloxy)methyl)-4-fluoro-4-methyltetrahydrofuran-3-yl benzoate. MS ESI calculated for $C_{25}H_{21}ClFN_5O_5$ [M+H]$^+$ 526.12, 528.12, found 526.20, 528.20. $^1$H-NMR: (300 MHz, DMSO-d$_6$) δ 8.14 (d, J=3.2 Hz, 1H), 8.13 (m, 4H), 7.79-7.51 (m, 6H), 7.12 (brs, 2H), 6.25 (d, J=18.8 Hz, 1H), 5.71 (dd, J=18.9, 4.0 Hz, 1H), 4.83-4.69 (m, 2H), 4.69-4.65 (m, 1H), 1.55 (d, J=23.1 Hz, 3H). $^{19}$F-NMR: (282 MHz, DMSO-d$_6$) δ−157.00 (d, J=1.9 Hz, 1F).

Step 3: To (2R,3R,4S,5R)-5-(2-amino-6-chloro-9H-purin-9-yl)-2-((benzoyloxy)methyl)-4-fluoro-4-methyltetrahydrofuran-3-yl benzoate (22 g, 41.8 mmol) was added ammonia (200 mL, 7 M in 2-propanol, 1400 mmol) at −78° C. The reaction was then stirred at 90° C. for 2 d. After completion of the reaction, the solvent was removed and ethyl acetate (150 mL) was added. The suspension was filtered and the filter cake was washed with ethyl acetate (30 mL) to give (2R,3R,4S,5R)-5-(2,6-diamino-9H-purin-9-yl)-4-fluoro-2-(hydroxymethyl)-4-methyltetrahydrofuran-3-ol. MS ESI calculated for $C_{11}H_{15}FN_6O_3$ [M+H]$^+$ 299.12, found 299.10.

$^1$H-NMR: (300 MHz, DMSO-d$_6$): δ 7.77 (d, J=3.1 Hz, 1H), 6.80 (brs, 2H), 6.02 (s, 1H), 5.88 (brs, 2H), 5.86 (d, J=17.9 Hz, 1H), 5.07 (s, 1H), 4.15 (d, J=19.3 Hz, 1H), 3.84-3.73 (m, 1H), 3.73-3.55 (m, 2H), 1.36 (d, J=23.1 Hz, 3H). $^{19}$F-NMR: (282 MHz, DMSO-d$_6$): δ−157.21 (s, 1F).

Step 4: To a solution of (2R,3R,4S,5R)-5-(2,6-diamino-9H-purin-9-yl)-4-fluoro-2-(hydroxymethyl)-4-methyltetrahydrofuran-3-ol (11.5 g, 38.6 mmol) in Tris-buffer (193 mL, pH=7.5) was added adenosine deaminase (193 mg, 38.6 mmol) at ambient temperature. The mixture was then warmed to 40° C. and stirred for 16 h. The mixture was concentrated. The residue was purified by Combi-Flash Column Chromatography with the following conditions: Column: AQ C18gel column (330 g), 20-40 μm; Mobile Phase: MeCN and water (Gradient: 0-20% within 50 min); Flow rate: 100 mL/min; Detector: UV 254 & 280 nm. The product-containing fractions were collected and the solvent was removed under reduced pressure to give 2-amino-9-((2R,3S,4R,5R)-3-fluoro-4-hydroxy-5-(hydroxymethyl)-3-methyltetrahydrofuran-2-yl)-1H-purin-6(9H)-one. MS ESI calculated for $C_{11}H_{14}FN_5O_4$ [M+H]$^+$ 300.10, found 300.10. $^1$H-NMR: (300 MHz, DMSO-d$_6$): δ 7.58 (d, J=3.1 Hz, 1H), 7.01 (brs, 2H), 6.16 (brs, 1H), 5.77 (d, J=17.6 Hz, 1H), 5.16 (brs, 1H), 4.11 (dd, J=19.3, 4.5 Hz, 1H), 3.79-3.66 (m, 1H), 3.62-3.54 (m, 2H), 1.31 (d, J=23.0 Hz, 3H). $^{19}$F-NMR: (282 MHz, DMSO-d$_6$): δ−157.34 (s, 1F).

Step 5: To a suspension of 2-amino-9-((2R,3S,4R,5R)-3-fluoro-4-hydroxy-5-(hydroxymethyl)-3-methyltetrahydrofuran-2-yl)-1H-purin-6(9H)-one (6.2 g, 20.72 mmol) in dry pyridine (31 mL) was added trimethylsilyl chloride (9.6 mL, 103.7 mmol) at 0° C. The reaction was then warmed to room temperature and continued to stir for 2 h. Then isobutryic anhydride (3.2 mL, 31.1 mmol) was added at 0° C. The mixture was stirred at room temperature for 1.5 h. After completion of the reaction, ammonium hydroxide (100 mL) was added. The solvents were removed under reduced pressure and the residue was purified by chromatography on silica gel using a stepwise gradient of MeOH (0-20%) in DCM to give N-(9-((2R,3S,4R,5R)-3-fluoro-4-hydroxy-5-(hydroxymethyl)-3-methyltetrahydrofuran-2-yl)-6-oxo-6,9-dihydro-1H-purin-2-yl)isobutyramide. MS ESI calculated for $C_{15}H_{20}FN_5O_5$ [M+H]$^+$ 370.14, found 370.10.

$^1$H-NMR: (400 MHz, DMSO-d$_6$) δ 12.13 (s, 1H), 11.67 (s, 1H), 8.09 (d, J=2.7 Hz, 1H), 6.06 (d, J=5.1 Hz, 1H), 5.91 (d, J=15.8 Hz, 1H), 5.10 (t, J=5.7 Hz, 1H), 4.20 (dt, J=18.5, 4.9 Hz, 1H), 3.88-3.79 (m, 1H), 3.76-3.57 (m, 2H), 2.78 (h, J=6.8 Hz, 1H), 1.40 (d, J=23.2 Hz, 3H), 1.13 (d, J=6.8 Hz, 6H). $^{19}$F-NMR: (282 MHz, DMSO-d$_6$): δ−157.74 (s, 1F).

Step 6: To a solution of N-(9-((2R,3S,4R,5R)-3-fluoro-4-hydroxy-5-(hydroxymethyl)-3-methyltetrahydrofuran-2-yl)-6-oxo-6,9-dihydro-1H-purin-2-yl)isobutyramide (3 g, 8.12 mmol) in dry pyridine (15 mL) was added 4,4'-(chloro(phenyl)methylene)bis(methoxybenzene) (3.02 g, 8.9 mmol) at room temperature. The reaction was quenched by adding MeOH (5 mL). The solvent was removed and the residue was purified by Combi-Flash Colum Chromatography with the following conditions: Column: AQ C18gel column (330 g), 20-40 μm; Mobile Phase: MeCN and water (Gradient: 60-100% within 50 min); Flow rate: 100 mL/min; Detector: UV 254 & 280 nm. The product-containing fractions were collected and the solvent was removed under reduced pressure to give N-(9-((2R,3S,4R,5R)-5-((bis(4-methoxyphenyl)(phenyl)methoxy)methyl)-3-fluoro-4-hydroxy-3-methyltetrahydrofuran-2-yl)-6-oxo-6,9-dihydro-1H-purin-2-yl)isobutyramide. MS ESI calculated for $C_{36}H_{38}FN_5O_7$ [M+H]$^+$ 672.28, found 672.25. $^1$H-NMR: (400 MHz, DMSO-d$_6$) δ 12.15 (s, 1H), 11.68 (s, 1H), 7.86 (d, J=2.9 Hz, 1H), 7.48-7.38 (m, 2H), 7.35-7.18 (m, 7H), 6.93-6.81 (m, 4H), 6.09 (d, J=5.0 Hz, 1H), 5.97 (d, J=16.8 Hz, 1H), 4.20 (dt, J=18.8, 4.8 Hz, 1H), 4.08-3.98 (m, 1H), 3.74 (s, 6H), 3.44-3.29 (m, 1H), 3.23 (dd, J=10.3, 3.6 Hz, 1H), 2.78 (septet, J=6.8 Hz, 1H), 1.39 (d, J=23.2 Hz, 3H), 1.13 (dd, J=6.8, 1.7 Hz, 6H). $^{19}$F-NMR: (376 MHz, DMSO-d$_6$): δ−157.52 (s, 1F).

Step 7: To a solution of 3-((bis(diisopropylamino)phosphino)oxy)propanenitrile (11.30 g, 37.5 mmol)(co-evaporated with dry MeCN (3×60 mL) before being used) in dry DCM (24 mL) was added 4,5-dicyanoimidazole (4.4 g, 37.5 mmol) at room temperature. The solution was marked as solution A. To a solution of N-(9-((2R,3S,4R,5R)-5-((bis(4-methoxyphenyl)(phenyl)methoxy)methyl)-3-fluoro-4-hydroxy-3-methyltetrahydrofuran-2-yl)-6-oxo-6,9-dihydro-1H-purin-2-yl)isobutyramide (16.8 g, 25.01 mmol) (co-evaporated with dry MeCN (3×60 mL) before being used) in dry DCM (60 mL) was added solution A at room temperature under argon. The reaction was then stirred at room temperature for 1 h. After completion of the reaction, the reaction mixture was diluted with DCM (300 mL). The organic layer was then washed with saturated aqueous sodium bicarbonate solution (150 mL), water (150 mL) and brine (150 mL), dried over anhydrous sodium sulfate, filtered and the filtrate was concentrated under reduced pressure. The residue was then purified by Combi-Flash Column Chromatography with the following conditions: Column: AQ C18 gel column (330 g), 20-40 μm; Mobile Phase: MeCN and water (Gradient: 45-100% within 45 min); Flow rate: 100 mL/min; Detector: UV 254 & 280 nm. The product-containing fractions were collected and roto-evaporated in vacuo to give (2R,3R,4S,5R)-2-((bis(4-methoxyphenyl)(phenyl)methoxy)methyl)-4-fluoro-5-(2-isobutyramido-6-oxo-1H-purin-9(6H)-yl)-4-methyltetrahydrofuran-3-yl (2-cyanoethyl) diisopropylphosphoramidite. MS ESI calculated for $C_{45}H_{55}FN_7O_8P$ [M+H]$^+$ 872.38, found 872.40. $^1$H-NMR: (400 MHz, DMSO-d$_6$) δ 12.19 (s, 1H), 11.69 (s, 0.4H), 11.66 (s, 0.6H), 7.97-7.90 (m, 1H), 7.48-7.39 (m, 2H), 7.37-7.20 (m, 7H), 6.96-6.85 (m, 4H), 6.04-5.94 (m, 1H), 4.58-4.38 (m, 1H), 4.27-4.12 (m, 1H), 3.86-3.66 (m, 7H), 3.66-3.46 (m, 3H), 3.45-3.27 (m, 2H), 2.87-2.72 (m, 3H), 2.64-2.55 (m, 1H), 1.58-1.41 (m, 3H), 1.18-1.09 (m, 16H), 1.00 (d, J=6.7 Hz, 2H). $^{19}$F-NMR: (376 MHz, DMSO-d$_6$): δ −155.28 (s, 0.4F), −155.50 (s, 0.6F). $^{31}$P-NMR: (162 MHz, DMSO-d$_6$) δ 150.98 (s, 0.4P), 150.03 (s, 0.6P).

TABLE 2

Exemplary nomenclature for first position nucleotides starting at the 5' end include:

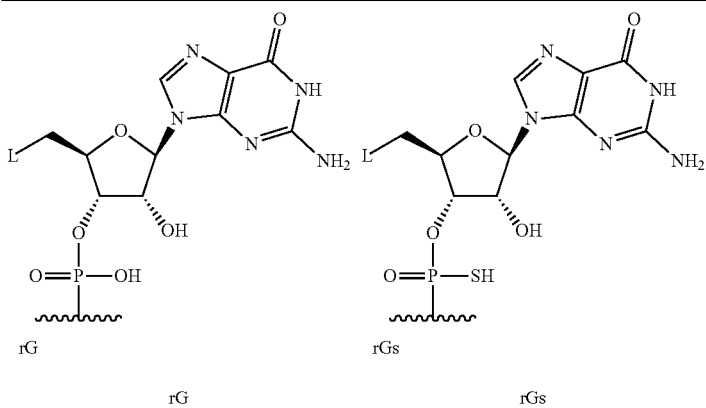

rG          rGs

Wherein L is selected from the Table 2a:

Also included within Table 2 above are first position nucleotides where "r" in "rG" or "rGs" represent groups comprising "ome", "flu," "thior," "d," "fara," "1na," "moe," "4alkd," "ara," "meF" "cf3," 25, rxylo, ami, ome4S, fara8az, and "me," as illustrated herein.

TABLE 2a

| 5' end substituents L | L Definition Structure |
|---|---|
| HO |  |

TABLE 2a-continued

| 5' end substituents L | L Definition Structure |
|---|---|
| pp | HO—P(=O)(OH)—O—P(=O)(OH)—O— |
| pcp | HO—P(=O)(OH)—CH$_2$—P(=O)(OH)—O— |
| ppp | HO—P(=O)(OH)—O—P(=O)(OH)—O—P(=O)(OH)—O— |
| p | HO—P(=O)(OH)—O— |

An embodiment of this invention is realized when the first position nucleotide starting at the 5' end of Formula Ia and Formula I is referred to as rG wherein V, Y, Z, W, and X are O, —OH, —CH—, N, and O, respectively. An embodiment of this invention is realized when the first position nucleotide starting at the 5' end of Formula Ia and Formula I is referred to as rGs wherein V, Y, Z, W, and X are O, —SH, —CH—, N, and O, respectively.

Table 3: Nomenclature for internally-located nucleotides (i.e., positions 2-23) contained within the single-stranded molecules exemplified in Table 5. For the purposes of this invention, in Table 3 the terms "r," "ome", "flu," "thior," "d," "fara," "1na," "moe," "4alkd," "ara," "meF" "cf3," 25, rxylo, ami, ome4S, fara8az, or "me," appearing before the "B" in the first and third column of Table 3 represents a sugar group as exemplified in columns two and four of Table 3, and "B" represents a nucleobase or derivative thereof selected from adenine, cytosine, guanine and uracil, which are designated "A", "C", "G", and "U", respectively.

TABLE 3

| Internal nucleotide nomenclature (positions 2-23) | Structure |
| --- | --- |
| rB B = nucleobase A, C, G, U, or I where "I" in "rI" is an "A" analog | 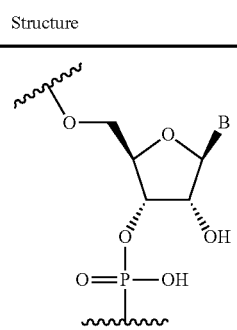 |
| omeB B = nucleobase A, C, G, U | 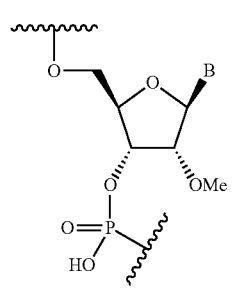 |
| fluB B = nucleobase A, C, G, U | 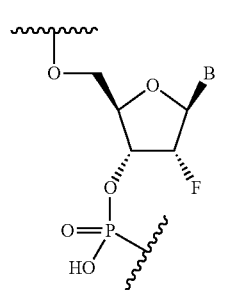 |
| thiorB B = nucleobase A, C, G, U | 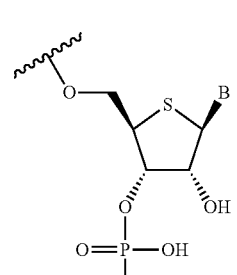 |
| dB B = nucleobase A, C, G, U | 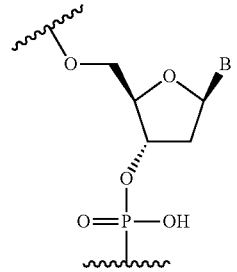 |

TABLE 3-continued

| Internal nucleotide nomenclature (positions 2-23) | Structure |
| --- | --- |
| faraB B = nucleobase A, C, G, U | 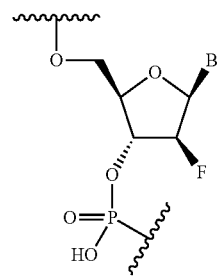 |
| lnaB B = nucleobase A, 5-Me-C, G, 5-Me-U | 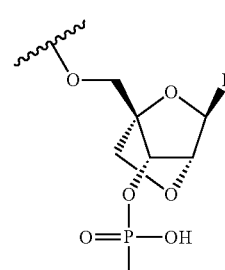 |
| moeB B = nucleobase A, 5-Me-C, G, 5-Me-U | 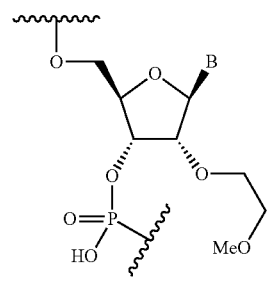 |
| 4alkdB B = nucleobase A, C, G, U | 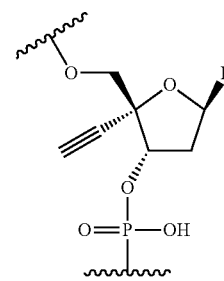 |
| araB B = nucleobase A, C, G, U | 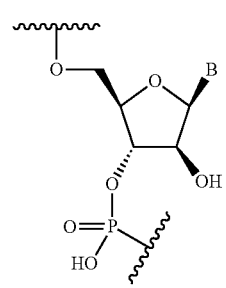 |

TABLE 3-continued
| Internal nucleotide nomenclature (positions 2-23) | Structure |
|---|---|
| meFB B = nucleobase A, C, G, U | 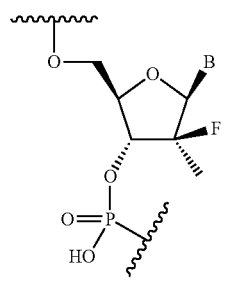 |
| cf3B B = nucleobase A, C, G, U | 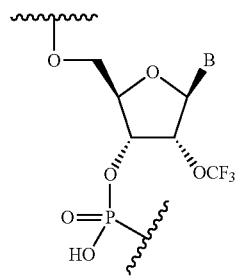 |
| 25B B = nucleobase A, C, G, U | 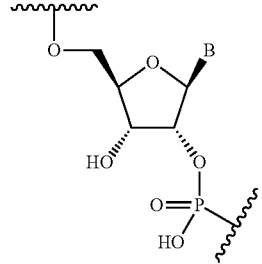 |
| rxyloB B = nucleobase A, C, G, U | 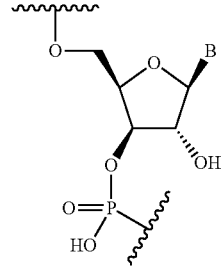 |
| amiB B = nucleobase A, C, G, U | 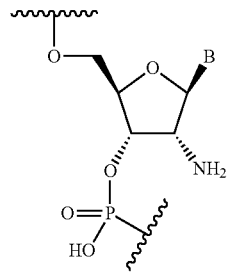 |
| ome4SB B = nucleobase A, C, G, U | 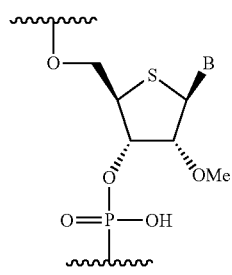 |
| rBs B = nucleobase A, C, G, U, or I where "I" in "rI" is an "A" analog | 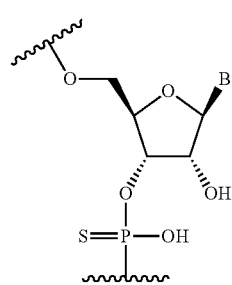 |
| omeBs B = nucleobase A, C, G, U | 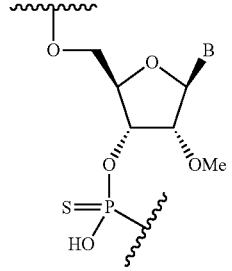 |
| fluBs B = nucleobase A, C, G, U | 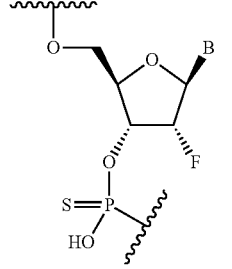 |
| thiorBs B = nucleobase A, C, G, U | 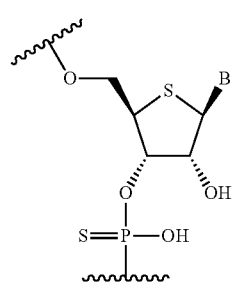 |

TABLE 3-continued
| Internal nucleotide nomenclature (positions 2-23) | Structure |
|---|---|
| dBs B = nucleobase A, C, G, U | 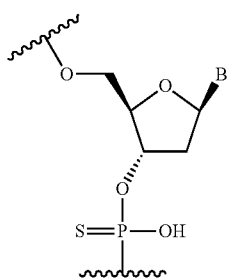 |
| faraBs B = nucleobase A, C, G, U | 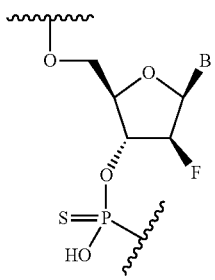 |
| lnaBs B = nucleobase A, 5-Me-C, G, 5-Me-U | 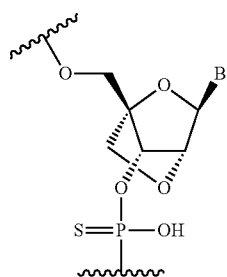 |
| moeBs B = nucleobase A, 5-Me-C, G, 5-Me-U | 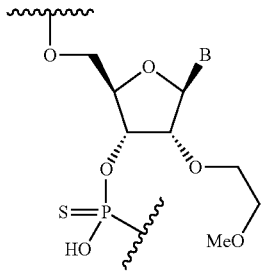 |
| 4alkdBs B = nucleobase A, C, G, U | 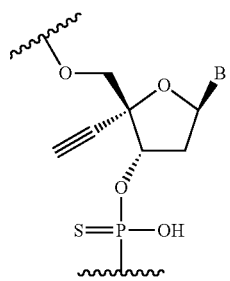 |
| araBs B = nucleobase A, C, G, U | 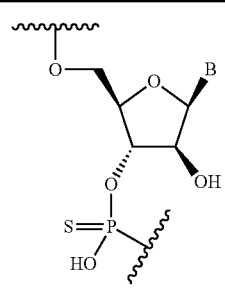 |
| meFBs B = nucleobase A, C, G, U | 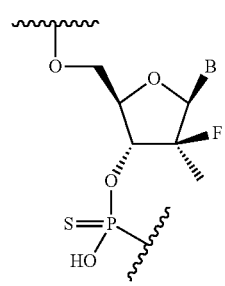 |
| cf3Bs B = nucleobase A, C, G, U | 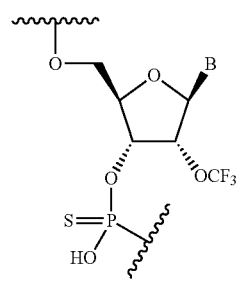 |
| 25Bs B = nucleobase A, C, G, U | 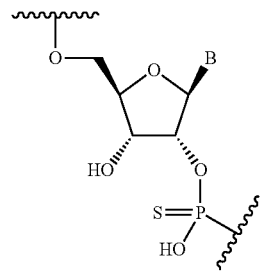 |
| rxyloBs B = nucleobase A, C, G, U | 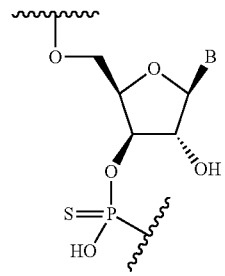 |

TABLE 3-continued
| Internal nucleotide nomenclature (positions 2-23) | Structure |
|---|---|
| amiBs B = nucleobase A, C, G, U | 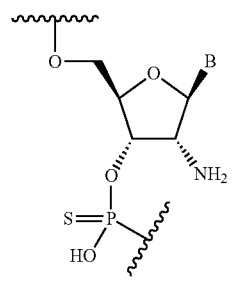 |
| ome4SBs B = nucleobase A, C, G, U | 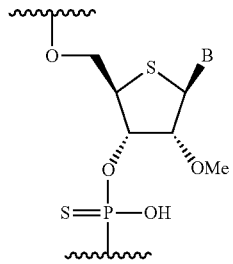 |
TABLE 3a
| Position 2-23 nucleotides or derivatives thereof |
|---|
| Nucleotide |
| fara8azA 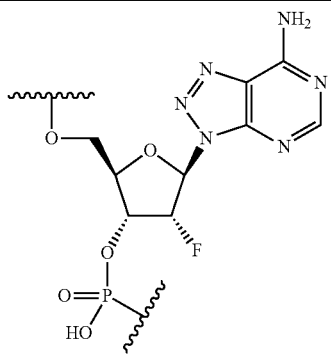 |
| fara7dzA 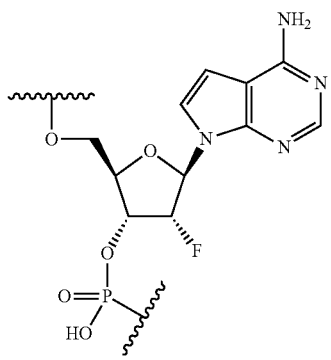 [SMILES: *OC[C@H]1O[C@@H](n2ccc3c(N)ncnc32)[C@H](F)[C@@H]1OP(*)(=O)O] |
-continued
TABLE 3a
| Position 2-23 nucleotides or derivatives thereof |
|---|
| Nucleotide |
| r2AP 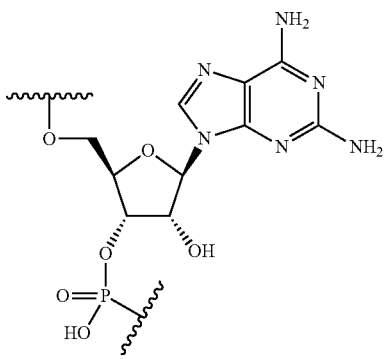 |
| d2aminoA 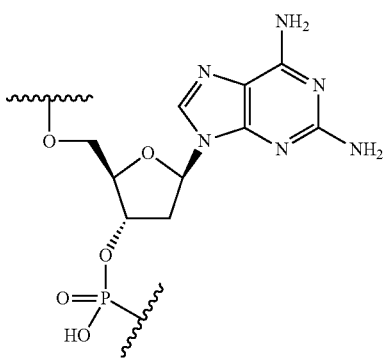 [SMILES: *OC[C@H]1O[C@@H](n2cnc3c(N)nc(N)nc32)C[C@@H]1OP(*)(=O)O] |
| r7dz8azA 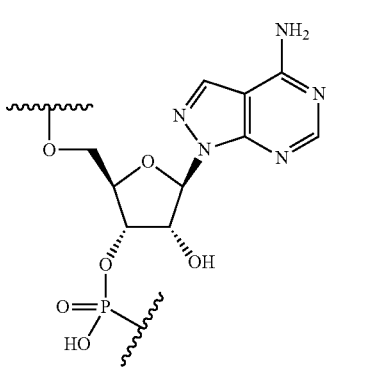 [SMILES: *OC[C@H]1O[C@@H](n2ncc3c(N)ncnc32)[C@H](O)[C@@H]1OP(*)(=O)O] |
| 4S8azG 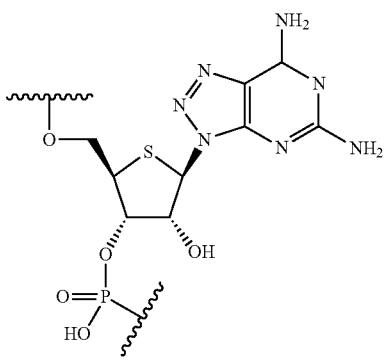 [SMILES: *OC[C@H]1S[C@@H](n2nnc3c2N=C(N)NC3N)[C@H](O)[C@@H]1OP(*)(=O)O] |

TABLE 3a-continued
Position 2-23 nucleotides or derivatives thereof
Nucleotide
d5propU
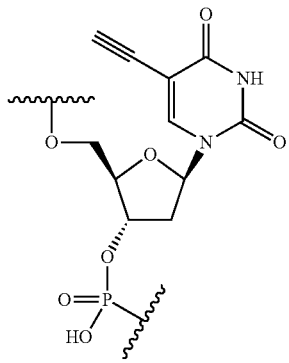 [SMILES: *OC[C@H]1O[C@@H](n2cc(C#C)c(=O)[nH]c2=O)C[C@@H]1OP(*)(=O)O]
d5propC
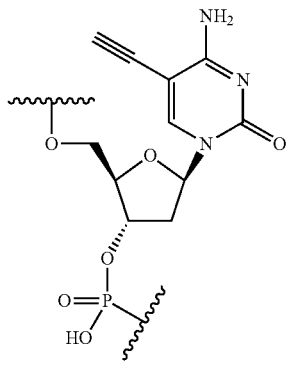 [SMILES: *OC[C@H]1O[C@@H](n2cc(C#C)c(N)nc2=O)C[C@@H]1OP(*)(=O)O]
r7dzA
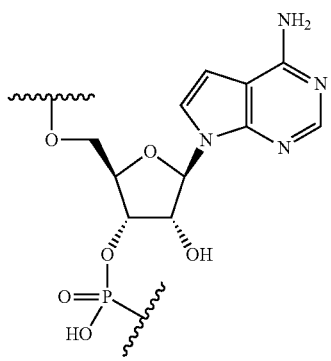 [SMILES: *OC[C@H]1O[C@@H](n2ccc3c(N)ncnc32)[C@H](O)[C@@H]1OP(*)(=O)O]
d7dzA
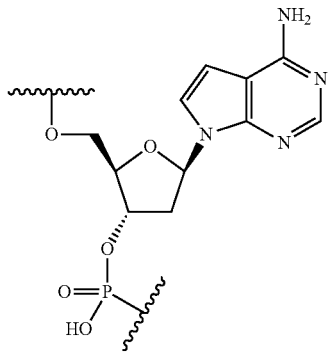 [SMILES: *OC[C@H]1O[C@@H](n2ccc3c(N)ncnc32)C[C@@H]1OP(*)(=O)O]
fara8azAs
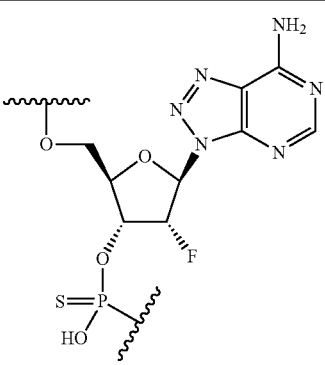
fara7dzAs
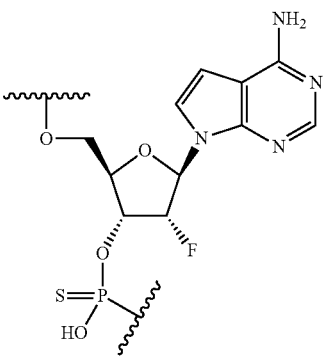 [SMILES: *OC[C@H]1O[C@@H](n2ccc3c(N)ncnc32)[C@H](F)[C@@H]1OP(*)(O)=S]
r2APs
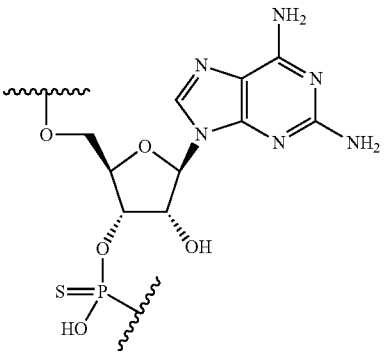
d2aminoAs
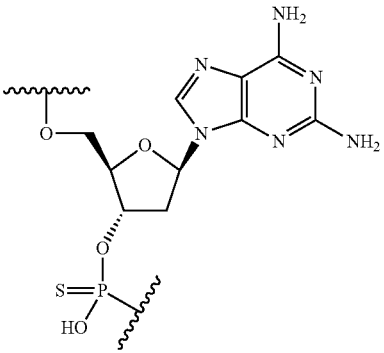 [SMILES: *OC[C@H]1O[C@@H](n2cnc3c(N)nc(N)nc32)C[C@@H]1OP(*)(O)=S]

TABLE 3a

Position 2-23 nucleotides or derivatives thereof

Nucleotide r7dz8azAs

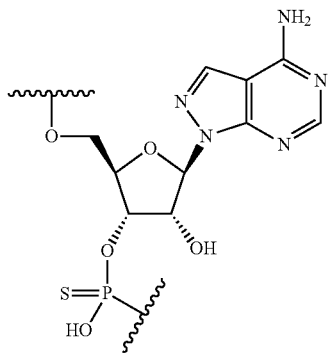

4S8azGs

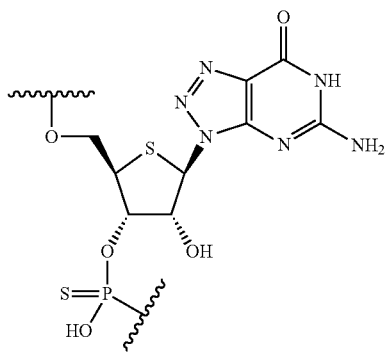 [SMILES: *OC[C@H]1S[C@@H](n2nnc3c(=O)[nH]c(N)nc32)[C@H](O)[C@@H]1OP(*)(O)=S]

d5propUs

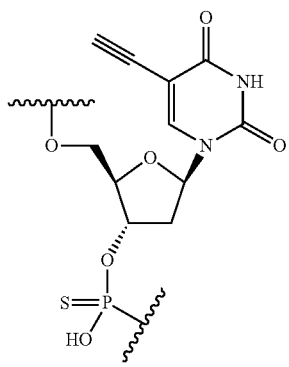 [SMILES: *OC[C@H]1O[C@@H](n2cc(C#C)c(=O)[nH]c2=O)C[C@@H]1OP(*)(O)=S]

TABLE 3a

Position 2-23 nucleotides or derivatives thereof

Nucleotide d5propCs

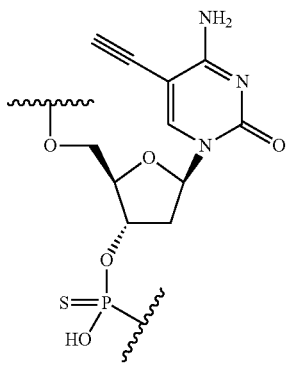

r7dzAs

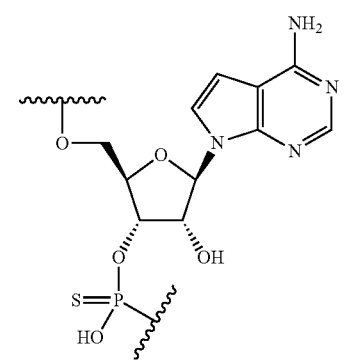 [SMILES: *OC[C@H]1O[C@@H](n2ccc3c(N)ncnc32)[C@H](O)[C@@H]1OP(*)(O)=S]

d7dzAs

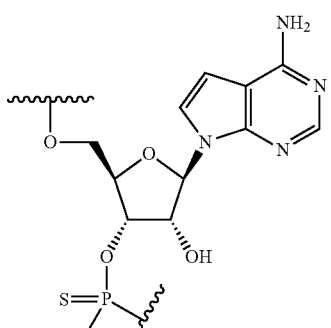

An embodiment of this invention is realized when nucleotide position 2 starting from the 5' end is selected from the group consisting of rC, rCs, fluC, fluCs, OMeC, and OMeCs. A subembodiment of this aspect of the invention is realized when nucleotide position 2 starting from the 5' end is rC or rCs. Another subembodiment of this aspect of the invention is realized when nucleotide position 2 starting from the 5' end is fluC or fluCs. Another subembodiment of this aspect of the invention is realized when nucleotide position 2 starting from the 5' end is OMeC or OMeCs.

TABLE 4

Nomenclature for nucleotide position 24 starting from 5' exemplified in Table 5

| Nucleotide position 24 | Structure | Nucleotide Position 24 | Structure |
| --- | --- | --- | --- |
| rCSup | 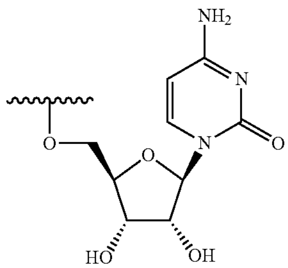 [SMILES: *OC[C@H]1O[C@@H](n2ccc(N)nc2=O)[C@H](O)[C@@H]1O] | rC;pSup | 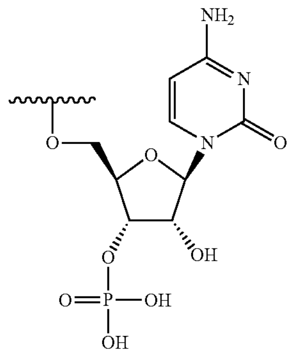 [SMILES: *OC[C@H]1O[C@@H](n2ccc(N)nc2=O)[C@H](O)[C@@H]1OP(=O)(O)O] |
| fluC Sup | 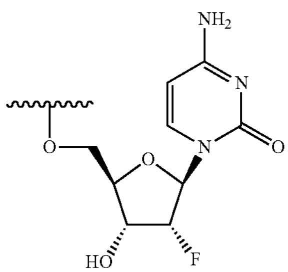 [SMILES: *OC[C@H]1O[C@@H](n2ccc(N)nc2=O)[C@H](F)[C@@H]1O] | fluC;pSup | 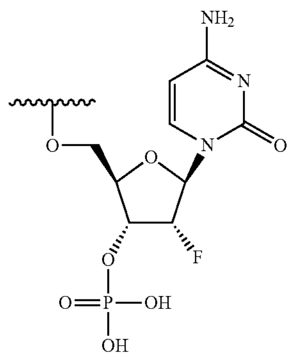 [SMILES: *OC[C@H]1O[C@@H](n2ccc(N)nc2=O)[C@H](F)[C@@H]1OP(=O)(O)O] |
| omeCSup | 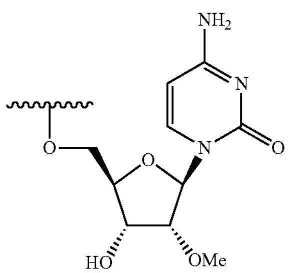 [SMILES: *OC[C@H]1O[C@@H](n2ccc(N)nc2=O)[C@H](OC)[C@@H]1O] | omeC;pSup | 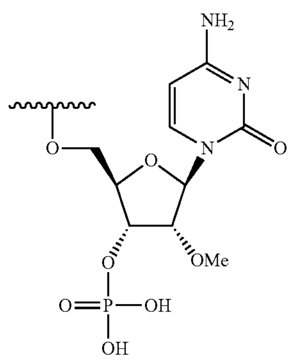 [SMILES: *OC[C@H]1O[C@@H](n2ccc(N)nc2=O)[C@H](OC)[C@@H]1OP(=O)(O)O] |

An embodiment of this invention is realized when $R_3$ of the position 24 nucleotide is hydrogen, K is hydrogen or $P(O)(OH)_2$, X is O, and one of $R_1$ and $R_2$ is hydrogen while the other is selected from F, OH, and OMe. An embodiment of this invention is realized when the position 24 nucleotide is selected from Table 4. A subembodiment of this aspect of the invention is realized when nucleotide position 24 is rCSup or rC;pSup. Another subembodiment of this aspect of the invention is realized when nucleotide position 24 starting from the 5' end is fluCSup or fluC;pSup. Another subembodiment of this aspect of the invention is realized when nucleotide position 24 starting from the 5' end is omeCSup or omeC;pSup.

An embodiment of this invention is realized when position 23 nucleotide starting from the 5' end of Formula Ia and Formula I is selected from rG, rGs, fluG, fluGs, omeG, and omeGs. A subembodiment of this aspect of the invention is realized when nucleotide position 23 is rG or rGs. Another subembodiment of this aspect of the invention is realized when nucleotide position 23 starting is fluG or fluGs. Another subembodiment of this aspect of the invention is realized when nucleotide position 23 is omeG or omeGs.

Another embodiment of this invention is realized when starting from the 5' end of Formula Ia and Formula I, position 1 nucleotide is rG or rGs, and position 24 nucleotide is selected from the group consisting of rCSup, rC;pSup, fluCSup, fluC;pSup, omeC;pSup, and omeCSup.

Another embodiment of this invention is realized when starting from the 5' end of Formula Ia and Formula I, position 1 nucleotide is rG or rGs, position 2 nucleotide is selected from the group consisting of rC, rCs, fluC, fluCs, omeCs, and omeC, position 23 is selected from the group consisting of rG, rGs, fluG, fluGs, omeG, and omeGs, and position 24 nucleotide is selected from the group consisting of rCSup, rC;pSup, fluCSup, fluC;pSup, omeC;pSup, and omeCSup.

General Synthetic Scheme

Scheme 1
General oligonucleotide synthesis cycle

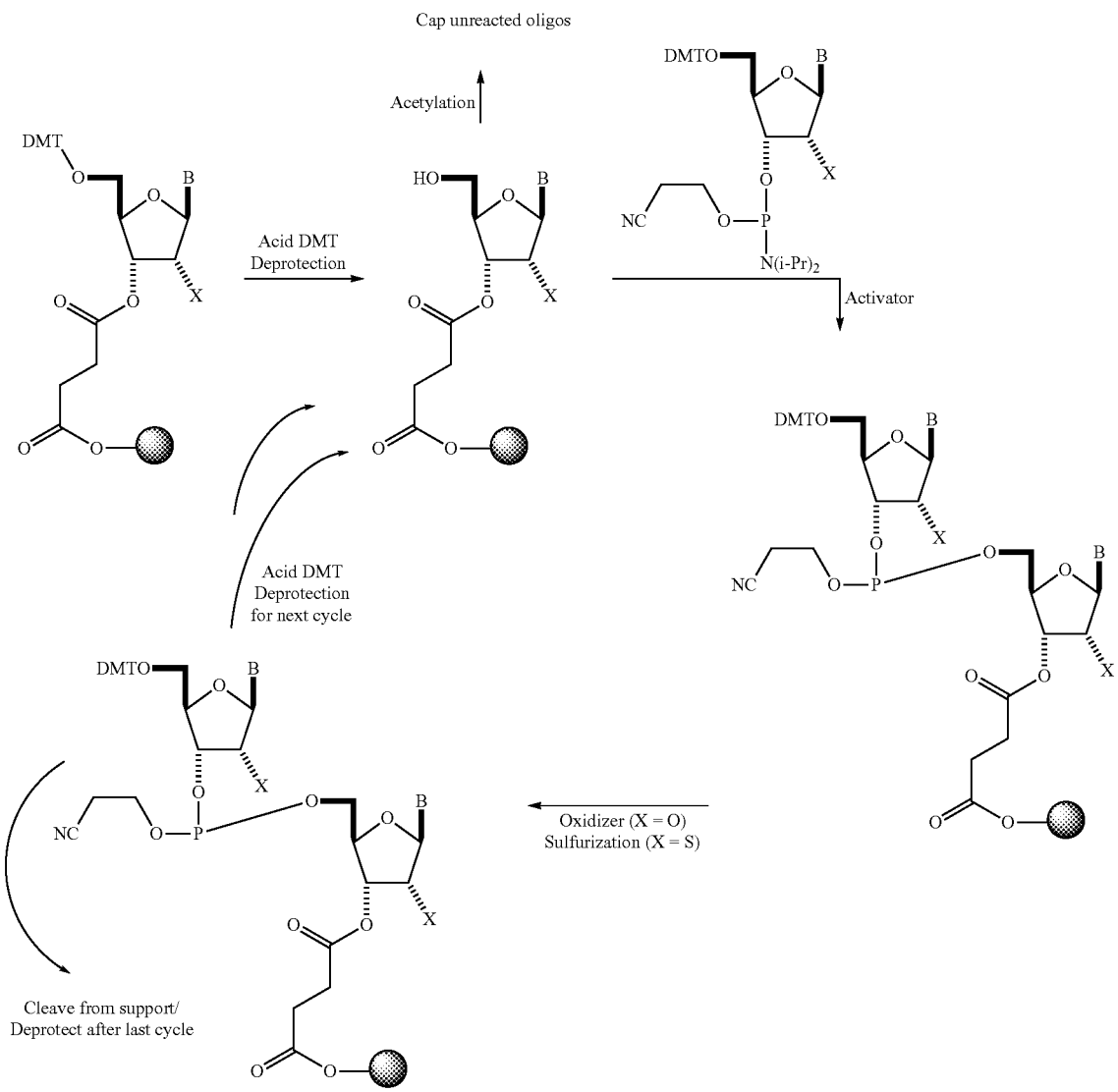

Oligonucleotides were prepared by chemical synthesis, as presented in Scheme 1. The oligonucleotide target sequence was synthesized on solid support, such as on controlled pore glass. After cleavage of the protected oligonucleotide from the solid support and deprotection of all protecting groups, each strand was purified chromatographically with a reversed phase (C18) or anion exchange (SAX) resin. After purification, each oligonucleotide product was lyophilized to dryness.

The synthesis of each oligonucleotide was accomplished on a solid support, such as controlled pore glass, using a commercially available automated oligosynthesizers. The solid support was obtained pre-loaded with the first (3') nucleoside unit of the desired sequence and placed in an appropriate column position for the oligosynthesizer. The first nucleoside was linked to the solid support via a succinate linkage and contained a suitable acid sensitive protecting group (e.g., trityl, dimethoxytrityl) on the 5'-hydroxyl group. The solid-phase oligosynthesis employed synthetic procedures that are generally known in the art. Elongation of the desired oligomeric sequence went through a cycle of four steps: 1) Acidic deprotection of the 5'-trityl protecting group; 2) Coupling of the next nucleotide unit as the 5'-trityl (or dimethoxytrityl) protected phosphoramidite in the presence of an activating agent, such as S-ethyl-tetrazole; 3) Oxidation of the P(III) phosphite triester to the P(V) phosphate triester by an oxidizing agent, such as iodine; and 4) Capping any remaining unreacted alcohol groups through esterification with an acylating agent, such as acetic anhydride. The phosphoramidites used were either derived from naturally occurring nucleotide units or from chemically modified versions of these nucleotides. Typically, all phosphoramidites were prepared in solutions of acetonitrile (or other suitable solvents or solvent mixtures, such as acetonitrile with some percentage of dimethyl formamide or some other appropriate organic solvent). The activator for phosphoramidite coupling was typically dissolved in acetonitrile. An oxidizing agent, such as iodine, was dissolved in a suitable solvent mixture, such as acetonitrile, pyridine and water. Acidic detritylation reagents, such as dichloroacetic acid or trichloroacetic acid, were dissolved in appropriate solvents, such as toluene or dichloromethane. Acylating capping reagents were, for example, a mixture of acetic anhydride, 2,6-lutidine and N-methyl-imidazole in acetonitrile. In place of the oxidation of the phosphite triester to the phosphate triester, the P(III) intermediate may be converted to the phosphorothioate analog with a sulfurizing reagent, such as phenyl-acetyl-disulfide, in a suitable solvent, such as a mixture of acetonitrile and pyridine. In between each step of the oligonucleotide elongation, acetonitrile (or another suitable solvent) was used to remove excess reagents and wash the solid support.

Oligonucleotide synthesis cycles were continued until the last (5') nucleotide unit was installed onto the extended oligomer. After the final cycle, the 5'-trityl protecting group may or may not be removed from the oligonucleotide while it remains on the solid support. In some instances, the 5'-terminal trityl group was first removed by treatment with an acidic solution. After this deprotection, the solid support was treated with an appropriate base, such as aqueous methyl amine or ammonia:methyl amine (1:1) (at either room temperature or with mild heating) in order to cleave the oligonucleotide from the support, remove the cyanoethyl protecting groups on the phosphate linkages and deprotect the acyl protecting groups on the nucleotide bases. Purification of these oligonucleotides would then be accomplished by SAX or reversed phase (C18 or C8) chromatography. Typically, the oligonucleotide was eluted from the SAX resin with a gradient of an inorganic salt, such as sodium chloride or sodium perchlorate. Salt was removed from the purified samples by dialysis or tangential flow filtration. The desalted material was then lyophilized or annealed. Alternatively, the purified oligonucleotides were annealed prior to removal of salt and then dialyzed.

In order to synthesize certain 5'-modified oligonucleotides, such as those containing 5'-ppp and 5'-pp, additional synthetic steps were performed on the oligonucleotide prior to cleavage from the solid support. After removal of the 5'-protecting group of the terminal nucleotide, a suitable phosphoramidite or comparable reagent was used to generate an activated monophosphate or phosphite intermediate. The intermediate was oxidized, followed by coupling with pyrophosphate or phosphate, or analogs thereof, to provide the desired 5'-ppp or 5'-pp oligonucleotide after cleavage and deprotection of the oligonucleotide under appropriate conditions. Alternatively, the intermediate was coupled to pyrophosphate or phosphate, or analogs thereof, followed by the oxidation step.

In other instances, the 5'-trityl protecting group was left on the oligonucleotide during basic cleavage from the solid support and deprotection of the oligonucleotide protecting groups. In this case, the oligonucleotide was purified with a reversed phase resin, such as C18. The presence of the trityl group allowed for the desired full length oligonucleotide to be retained on the resin, while undesired truncated products that were acylated during the capping reaction were removed from the resin. These undesired oligonucleotides were removed from the resin with a lower percentage of an organic solvent, such as acetonitrile. After this removal of failure products, the trityl group was removed by acidic treatment (with an acid such as aqueous trifluoroacetic acid) while still on the C18 resin. After salt exchange and extensive washing of the resin with water, the desired deprotected product was eluted with a higher percentage of organic solvent in water. These purified oligonucleotides were then either lyophilized or annealed as required.

If the desired oligonucleotide contained any ribose (2'-hydroxyl) nucleotides, a modified procedure was required to remove the silyl 2'-hydroxyl protecting groups. After cleaving the oligonucleotide from the solid support with aqueous base, the column was further washed with an appropriate solvent, such as DMSO, to remove any material remaining on the column. After basic deprotection of the oligonucleotide, the reaction mixture then was treated with an appropriate fluoride reagent, such as triethylamine-hydrogen fluoride or TBAF, to cleave all of the silyl ethers and expose the desired alcohols. After silyl deprotection was complete, an appropriate buffer was added to each sample in order to neutralize the solution prior to purification (either by SAX or C18). In certain cases, a 5'-vinyl phosphonate-3'-phosphoramidite was coupled to the 5'-terminus of an oligonucleotide. The oxidation reagent for this incorporation may be changed to t-butyl hydroperoxide rather than iodine. When an oligonucleotide contained a protected phosphonate moiety, the methyl or ethyl phosphate esters were deprotected with an appropriate reagent, such as iodotrimethylsilane or bromotrimethylsilane in pyridine/acetonitrile, while the oligonucleotide was still on the solid support. After washing the support with acetonitrile, the oligonucleotide was treated with (3-mercaptoethanol in triethylamine/acetonitrile. After further washing with acetonitrile, the oligonucleotide product was cleaved from the solid support and fully deprotected with aqueous methylamine. The 5'-phosphonate oligonucleotides were purified by either SAX or C18 chromatography.

Each purified oligonucleotide was analyzed for purity by appropriate methods, including reversed phase HPLC, SAX HPLC, and capillary gel electrophoresis. The identity of the oligonucleotide was confirmed by mass spectrometry, using an ionization technique such as ESI or MALDI. The yields of each oligonucleotide were assessed by UV (260 nm) with a theoretically derived extinction coefficient. The appropriate amounts of each strand were approximated by UV (260 nm) measurements and theoretical EC260 extinction coefficients. The final oligonucleotide material was lyophilized or dissolved in an appropriate aqueous buffer prior to biochemical or biological evaluation.

Example 1

5'-HO;rG;rC;rU;rC;rA;rU;rU;rU;rA;rC;rC;rA;rG;rC;rG;rU; rA;rA;rA;rU;rG;rA;rG;rC-3'(SEQ ID NO. 838)

Oligosynthesis was conducted on a MerMade12 oligosynthesizer at 10 μmol scale. Suitably protected ribonucleoside 3'-phosphoramidites (5'-ODMT, 2'-OTBS, N-acetyl-cytidine, N-benzoyl-adenosine, N-isobutyryl-guanosine) were dissolved in acetonitrile (0.1 M). Ethylthio-tetrazole (ETT) was used as activator (0.25 M in acetonitrile). A solution of iodine (0.025 M) in pyridine/acetonitrile/water (45/45/10) was used as oxidizer. Detritylation was accomplished with a solution of 3% trichloroacetic acid (TCA) in methylene chloride. The CPG solid support was preloaded with the 3'-terminal nucleoside, 5'-ODMT-2'-OTBS-N-acetyl-cytidine. The DMT protecting group was removed with three cycles of 3% TCA, followed by 3×2 mL washes of the support with acetonitrile. Equal volumes (0.5 mL each) of the required amidite solution (corresponding to the desired oligonucleotide sequence from the 3'-terminus) and activator was next added to the CPG. Nucleotide coupling was accomplished with three cycles of amidite/activator for 7.5 minutes each. After completion of the amidite coupling and washing of the CPG with acetonitrile (3×2 mL), the P(III) intermediate was oxidized to the P(V) phosphate ester with iodine (4×1 mL, 1 min each) and washed with acetonitrile (3×2 mL). Unreacted oligonucleotide 5'-hydroxyls were capped with an equal volume mixture (0.5 mL each) of 20% acetic anhydride/30% lutidine in acetonitrile and N-methylimidazole (20% in acetonitrile). The solid support was then washed with acetonitrile (4×2 mL), before the next coupling cycle was initiated with detritylation of the newly installed nucleotide unit.

After completion of the synthesis of the oligonucleotide sequence, the CPG support was washed with acetonitrile (4×2 mL). The protected oligonucleotide was removed from the solid support with 40% aqueous methylamine (3 mL, then 2 mL) and DMSO (2×3 mL). The combined solutions were heated at 35° C. for 45 minutes. The oligonucleotide was then treated with 3 mL of HF-triethylamine and heated to 40° C. for 60 minutes prior to the addition of 50 mM aqueous NaOAc (15 mL). The reaction mixture was directly loaded onto a C18 cartridge (5 g) that was prewashed with acetonitrile, water and 50 mM aqueous triethylammonium acetate (TEAA). After washing with water and 16% acetonitrile in 50 mM TEAA/50 mM NaCl (to remove shorter synthesis failures), the DMT group was deprotected on-column with 1% TFA. The column was washed with water, 1 M NaCl and additional water prior to elution of the desired oligonucleotide with 30% aqueous acetonitrile.

The desired oligonucleotide was further purified by preparative mass-directed HPLC with a Waters X-Bridge Phenyl column (19×150 mm, ambient temperature, 25 mL/min, buffer A: 200 mM aqueous TEAA, pH 7, buffer B: 200 mM TEAA, 20% aq. acetonitrile, pH 7) eluting with a gradient of 3% to 11% B over 9 minutes and 11% to 25% B over 3 minutes. The counterion of the oligonucleotide was exchanged to sodium via spin filtration (MWCO 3000) and the isolated product was lyophilized to a white solid.

LC-MS: (m/z)⁻ (z=4) 1908.1 (exp); 1908.1 (theor); (z=5) 1526.1 (exp); 1526.3 (theor)

Examples 2-336, 342-352, 360-404, 436-442, 475-477, 514-593, 595-605, 607, 609-613, 615, 617-633, 635-645, 647, 649-653, 655, and 657-838 noted as SEQ ID No. 1 as shown in Table 5 below were prepared according to the procedures analogous to those outlined in Example 1. Examples 337-341, 353-359, 405-435, 443-474, 478-513, 594, 606, 608, 614, 616, 634, 646, 648, 654, and 656 with modified nucleobases in Table 5 below were prepared using procedures known in the art in combination with the procedures analogous to those outlined in Example 1.

TABLE 5

| Ex | Sequence | MW | SEQ ID No. |
|---|---|---|---|
| 1 | 5'-HO;rG;rC;rU;rC;rA;rU;rU;rU;rA;rC;rC;rA;rG;rC;rG;rU;rA;rA;rA;rU;rG;rA;rG;rCSup-3' | 7636.72 | 1 |
| 2 | 5'-HO;rG;fluC;rU;fluC;fluA;fluU;rU;fluU;rA;rC;fluC;rA;fluG;rC;fluG;fluU;fluA;rA;rA;rU;omeG;rA;rG;fluCSup-3' | 7672.62 | 124 |
| 3 | 5'-HO;rG;fluC;rU;fluC;rA;fluU;omeU;rU;fluA;rC;rC;rA;fluG;rC;rG;rU;rA;omeA;fluA;fluU;rG;rA;fluG;omeCSup-3' | 7694.68 | 125 |
| 4 | 5'-HO;rG;rC;fluU;rC;fluA;rU;rU;omeU;fluA;fluC;rC;rA;fluG;fluC;fluG;rU;rA;omeA;omeA;rU;rG;rA;rG;omeCSup-3' | 7706.71 | 126 |
| 5 | 5'-HO;rG;rC;omeU;rC;rA;fluU;rU;omeU;fluA;rC;fluC;omeA;rG;rC;rG;fluU;rA;fluA;omeA;rU;fluG;fluA;fluG;fluCSup-3' | 7710.63 | 127 |
| 6 | 5'-HO;rG;omeC;rU;rC;rA;fluU;rU;rU;rA;fluC;rC;rA;fluG;omeC;rG;fluU;omeA;fluA;omeA;rU;rG;rA;rG;omeCSup-3' | 7716.81 | 128 |
| 7 | 5'-HO;rG;omeC;rU;fluC;rA;rU;fluU;omeU;fluA;omeC;fluC;fluA;rG;fluC;omeG;fluU;rA;fluA;fluA;fluU;fluG;fluA;fluG;fluCSup-3' | 7720.73 | 129 |
| 8 | 5'-HO;rG;rC;fluU;rC;fluA;omeU;fluU;rU;rA;fluC;omeC;omeA;rG;fluC;omeG;omeU;rA;rA;rA;rU;fluG;rA;fluG;rCSup-3' | 7720.73 | 130 |
| 9 | 5'-HO;rG;rC;rU;rC;fluA;omeU;omeU;fluU;rA;fluC;rC;fluA;rG;fluC;omeG;rU;rA;rA;fluA;fluU;omeG;fluA;rG;omeCSup-3' | 7722.70 | 131 |
| 10 | 5'-HO;rG;rC;fluU;rC;fluA;fluU;fluU;omeU;fluA;omeC;rC;rA;omeG;omeC;fluG;rU;rA;fluA;omeA;fluU;fluG;rA;rG;rCSup-3' | 7724.64 | 132 |
| 11 | 5'-HO;rG;rC;omeU;omeC;fluA;rU;rU;rU;fluA;fluC;fluC;rA;omeG;fluC;fluG;rU;omeA;rA;fluA;rU;fluG;fluA;omeG;rCSup-3' | 7724.71 | 133 |
| 12 | 5'-HO;rG;rC;omeU;fluC;rA;rU;rU;rU;fluA;fluC;rC;fluA;fluG;rC;fluG;rU;rA;fluA;fluA;omeU;omeG;omeA;omeG;fluCSup-3' | 7724.68 | 134 |
| 13 | 5'-HO;rG;omeC;fluU;rC;omeA;fluU;omeU;omeU;fluA;omeC;fluC;rA;fluG;fluC;rG;rU;fluA;rA;fluA;fluU;rG;fluA;rG;rCSup-3' | 7726.92 | 135 |
| 14 | 5'-HO;rG;rC;fluU;fluC;fluA;omeU;fluU;rU;fluA;omeC;fluC;fluA;rG;fluC;rG;omeU;rA;rA;fluA;fluU;rG;omeA;omeG;fluCSup-3' | 7728.71 | 136 |
| 15 | 5'-HO;rG;fluC;rU;omeC;rA;omeU;rU;omeU;omeA;fluC;rC;fluA;fluG;rC;fluG;omeU;fluA;rA;fluA;rU;fluG;fluA;fluG;fluCSup-3' | 7728.67 | 137 |
| 16 | 5'-HO;rG;fluC;rU;rC;fluA;rU;fluU;fluU;fluA;rC;rC;omeA;fluG;fluC;omeG;fluU;omeA;omeA;fluA;omeU;fluG;fluA;fluG;rCSup-3' | 7730.58 | 138 |
| 17 | 5'-HO;rG;omeC;fluU;omeC;rA;rU;rU;rU;rA;fluC;rC;rA;rG;rC;omeG;fluU;rA;fluA;fluA;omeU;omeG;omeA;rG;rCSup-3' | 7730.78 | 139 |
| 18 | 5'-HO;rG;rC;omeU;rC;omeA;rU;fluU;fluU;rA;rC;omeC;omeA;rG;fluC;omeG;rU;rA;rA;rA;fluU;fluG;rA;omeG;rCSup-3' | 7730.75 | 140 |
| 19 | 5'-HO;rG;rC;rU;rC;omeA;fluU;omeU;rU;rA;rC;fluC;omeA;omeA;rC;rG;fluU;rA;fluA;omeA;rU;rG;fluA;omeG;fluCSup-3' | 7732.73 | 141 |
| 20 | 5'-HO;rG;rC;rU;fluC;fluA;fluU;omeU;rU;rA;fluC;omeC;rA;rG;omeC;rG;omeU;fluA;omeA;rA;omeU;fluG;rA;fluG;rCSup-3' | 7734.77 | 142 |
| 21 | 5'-HO;rG;omeC;fluU;rC;fluA;fluU;fluU;rU;rA;fluC;rC;rA;rG;fluC;rG;omeU;omeA;omeA;fluA;rU;omeG;rA;omeG;fluCSup-3' | 7736.75 | 143 |
| 22 | 5'-HO;rG;rC;rU;rC;fluA;rU;fluU;rU;fluA;omeC;fluC;omeA;rG;fluC;omeG;fluU;fluA;rA;omeA;omeU;omeG;rA;fluG;rCSup-3' | 7736.71 | 144 |

TABLE 5-continued

| Ex | Sequence | MW | SEQ ID No. |
|---|---|---|---|
| 23 | 5'-HO;rG;omeC;fluU;rC;omeA;omeU;rU;fluU;omeA;rC;fluC;rA; fluG;rC;fluG;omeU;fluA;fluA;rA;omeC;fluG;rA;rG;rCSup-3' | 7736.68 | 145 |
| 24 | 5'-HO;rG;omeC;rU;rC;rA;rU;fluU;rU;omeA;rC;omeC;omeA;fluG; fluC;rG;fluU;rA;omeA;fluA;fluU;fluG;fluA;omeG;rCSup-3' | 7736.71 | 146 |
| 25 | 5'-HO;rG;omeC;omeU;rC;fluA;fluU;fluU;omeU;rA;omeC;omeC; rA;rG;rC;fluG;fluU;rA;fluA;fluA;omeU;rG;rA;rG;fluCSup-3' | 7736.75 | 147 |
| 26 | 5'-HO;rG;rC;fluU;omeC;omeA;fluU;rU;fluU;rA;omeC;fluC;rA; omeG;rC;rG;rU;rA;rA;fluA;fluU;omeG;omeA;fluG;fluCSup-3' | 7736.75 | 148 |
| 27 | 5'-HO;rG;omeC;fluU;rC;rA;omeU;fluU;fluU;fluA;omeC;rC;rA; rG;fluC;omeG;omeU;fluA;fluA;fluA;rU;fluG;rA;rG;omeCSup-3' | 7738.73 | 149 |
| 28 | 5'-HO;rG;omeC;omeU;fluC;fluA;rU;fluU;rU;rA;rC;rC;fluA;omeG; rC;rG;fluU;omeA;fluA;fluA;fluU;omeG;fluA;rG;omeCSup-3' | 7738.69 | 150 |
| 29 | 5'-HO;rG;fluC;fluU;rC;fluA;omeU;rU;rU;fluA;rC;rC;fluA;rG; omeC;omeG;omeU;fluA;fluA;omeA;rU;fluG;fluA;rG;omeCSup-3' | 7738.69 | 151 |
| 30 | 5'-HO;rG;fluC;omeU;rC;omeA;fluU;omeU;fluU;fluA;omeC;omeC; rA;fluG;rC;fluG;rU;omeA;fluA;fluA;rU;fluG;rA;fluG;rCSup-3' | 7740.67 | 152 |
| 31 | 5'-HO;rG;fluC;fluU;omeC;rA;fluU;fluU;rU;rA;fluC;fluC;omeA; omeC;omeC;fluG;fluU;rA;rA;fluA;omeU;fluG;fluA;rG;omeCSup-3' | 7742.75 | 153 |
| 32 | 5'-HO;rG;rC;rU;omeC;omeA;fluU;fluU;fluU;omeA;omeC;fluC; fluA;rG;rC;rG;omeU;rA;omeA;rA;omeU;rG;fluA;rG;rCSup-3' | 7746.77 | 154 |
| 33 | 5'-HO;rG;rC;omeU;omeC;rA;omeU;fluU;rU;omeA;rC;fluC;rA; omeC;fluC;omeG;rU;rA;fluA;rA;rU;fluG;rA;omeG;fluCSup-3' | 7746.81 | 155 |
| 34 | 5'-HO;rG;omeC;rU;omeC;omeA;omeU;omeU;fluU;fluA;fluC;rC; fluA;rG;fluC;rG;rU;rA;rA;omeA;rU;rG;fluA;omeG;fluCSup-3' | 7748.82 | 156 |
| 35 | 5'-HO;rG;fluC;rU;omeC;fluA;omeU;omeU;fluU;rA;fluC;fluC;rA; rG;fluC;omeG;fluU;omeA;rA;fluA;fluU;rG;omeA;omeG;rCSup-3' | 7750.76 | 157 |
| 36 | 5'-HO;rG;fluC;fluU;omeC;rA;rU;fluU;omeU;fluA;rC;rC;rA;fluG; fluC;omeG;rU;fluA;omeA;rA;rU;omeG;omeA;omeG;fluCSup-3' | 7750.76 | 158 |
| 37 | 5'-HO;rG;rC;fluU;omeC;omeA;rU;fluU;fluU;rA;omeC;fluC;fluA; fluG;rC;omeG;omeA;rA;fluA;omeU;rG;rA;fluG;omeCSup-3' | 7752.74 | 159 |
| 38 | 5'-HO;rG;omeC;omeU;fluC;omeA;rU;fluU;rU;fluA;omeC;rC;rA;rG; omeC;fluG;fluU;fluA;rA;fluA;rU;fluG;fluA;omeG;omeCSup-3' | 7752.77 | 160 |
| 39 | 5'-HO;rG;rC;rU;rC;rA;rU;omeU;omeU;rA;fluC;fluC;fluA;omeG; fluC;omeG;fluU;fluA;omeA;fluA;omeU;omeG;rA;omeG;rCSup-3' | 7752.74 | 161 |
| 40 | 5'-HO;rG;rC;fluU;rC;rA;rU;fluU;fluU;omeA;omeC;rC;omeA;fluG; rC;fluG;omeU;fluA;omeA;fluA;fluU;rG;omeA;fluG;omeCSup-3' | 7752.67 | 162 |
| 41 | 5'-HO;rG;fluC;omeU;omeC;omeA;rU;fluU;omeU;rA;fluC;rC;rA; omeG;fluC;rG;omeU;rA;fluA;omeA;omeU;fluG;fluA;fluG;fluCSup-3' | 7754.75 | 163 |
| 42 | 5'-HO;rG;rC;omeU;omeC;fluA;fluU;fluU;rU;rA;fluC;fluC;omeA; fluG;fluC;omeG;rU;fluA;fluA;rA;fluU;omeG;fluA;omeG;omeCSup-3' | 7756.73 | 164 |
| 43 | 5'-HO;rG;omeC;rU;rC;omeA;fluU;fluU;fluU;rA;omeC;fluC;omeA; rG;omeC;fluG;rU;omeA;fluA;fluA;fluU;fluG;omeA;fluG;fluCSup-3' | 7756.73 | 165 |
| 44 | 5'-HO;rG;rC;fluU;omeC;rA;omeU;rU;omeU;omeA;rC;omeC; rA;rG;rC;fluG;rU;omeA;omeA;omeA;rU;rG;rA;fluG;fluCSup-3' | 7756.83 | 166 |
| 45 | 5'-HO;rG;rC;rU;fluC;rA;rU;rU;omeU;omeA;omeC;omeC;rA; fluG;fluC;omeG;omeU;rA;rA;fluA;omeU;rG;rA;omeG;rCSup-3' | 7756.87 | 167 |
| 46 | 5'-HO;rG;omeC;fluU;fluC;omeA;fluU;rU;fluU;omeA;fluC;fluC; omeA;fluG;fluC;rG;omeU;omeA;rA;fluA;omeU;fluG;rA;fluG;fluCSup-3' | 7758.75 | 168 |
| 47 | 5'-HO;rG;rC;omeU;fluC;rA;rU;rU;rU;rA;rC;omeC;fluA;fluG;fluC; rG;omeU;fluA;omeA;omeA;omeU;fluG;omeA;rG;omeCSup-3' | 7760.82 | 169 |
| 48 | 5'-HO;rG;fluC;rU;rC;rA;omeU;omeU;fluU;fluA;rC;fluC;omeA; omeG;rC;fluG;omeU;rA;rA;omeA;rU;omeG;rA;fluG;omeCSup-3' | 7760.79 | 170 |
| 49 | 5'-HO;rG;rC;rU;fluC;omeA;omeU;fluU;rU;fluA;rC;rC;fluA;omeG; omeC;rG;rU;fluA;rA;omeA;omeU;fluG;omeA;omeG;fluCSup-3' | 7762.76 | 171 |
| 50 | 5'-HO;rG;fluC;rU;omeC;omeA;fluU;omeU;rU;omeA;rC;rC;rA;fluG; fluC;rG;omeU;fluA;fluA;omeA;omeU;omeG;fluA;rG;rCSup-3' | 7762.76 | 172 |
| 51 | 5'-HO;rG;omeC;rU;omeC;omeA;omeU;rU;omeU;fluA;omeC;fluC; rA;fluG;fluC;rG;fluU;fluA;rA;omeU;rG;rA;rG;omeCSup-3' | 7762.87 | 173 |
| 52 | 5'-HO;rG;fluC;fluU;omeC;omeA;rU;omeU;rU;rA;rC;fluC;fluA;rG; omeC;fluG;omeU;omeA;omeA;fluA;rU;omeG;fluA;omeG;fluCSup-3' | 7764.81 | 174 |
| 53 | 5'-HO;rG;fluC;omeU;fluC;fluA;rU;U;omeU;rA;fluC;fluC;omeA;rG; fluC;omeG;rU;omeA;rA;omeA;rU;rG;fluA;omeG;fluCSup-3' | 7764.85 | 175 |
| 54 | 5'-HO;rG;fluC;fluU;fluC;omeA;omeU;fluU;rU;rA;fluC;omeC;rA; fluU;rC;omeG;omeU;rA;fluA;omeA;fluU;rG;fluA;omeG;omeCSup-3' | 7766.79 | 176 |
| 55 | 5'-HO;rG;fluC;fluU;fluC;rA;fluU;fluU;rU;omeA;fluC;fluC;omeA; omeG;omeC;rG;fluU;omeA;fluA;rA;rU;omeG;omeA;fluG;omeCSup-3' | 7768.80 | 177 |
| 56 | 5'-HO;rG;omeC;rU;fluC;omeA;fluU;fluU;omeU;fluA;rC;omeC;fluA; rG;fluC;fluG;omeU;fluA;rA;omeA;omeU;omeA;fluG;fluCSup-3' | 7768.77 | 178 |
| 57 | 5'-HO;rG;omeC;fluU;rC;fluA;omeU;rU;fluU;fluA;rC;omeC;fluA; omeG;fluC;fluG;rU;omeA;fluA;fluA;fluU;omeG;rA;omeG;omeCSup-3' | 7768.73 | 179 |
| 58 | 5'-HO;rG;rC;fluU;fluC;omeA;fluU;omeU;omeU;omeA;fluC;rC;omeA; fluG;omeC;omeG;fluU;fluA;fluA;fluA;rU;rG;omeA;rG;fluCSup-3' | 7770.71 | 180 |
| 59 | 5'-HO;rG;omeC;fluU;rC;fluA;fluU;omeU;omeU;omeA;omeC;fluC; fluA;fluG;rC;omeG;fluU;fluA;fluA;rA;rU;omeG;fluA;omeG;fluCSup-3' | 7770.71 | 181 |
| 60 | 5'-HO;rG;fluC;omeU;omeC;fluA;omeU;fluU;fluU;fluA;fluC;omeC;fluA; fluG;omeC;omeG;fluU;rA;omeA;rA;omeU;fluG;fluA;rG;fluCSup-3' | 7772.76 | 182 |

TABLE 5-continued

| Ex | Sequence | MW | SEQ ID No. |
|---|---|---|---|
| 61 | 5'-HO;rG;fluC;omeU;rC;fluA;omeU;rU;omeU;rA;rC;omeC;fluA;rG; omeC;rG;fluU;omeA;omeA;rA;fluU;fluG;omeA;fluG;omeCSup-3' | 7776.81 | 183 |
| 62 | 5'-HO;rG;fluC;rU;rC;fluA;fluU;omeU;omeU;fluA;fluC;omeC;omeA; omeG;rC;omeG;omeU;rA;rA;fluA;rU;fluG;rA;omeG;omeCSup-3' | 7776.81 | 184 |
| 63 | 5'-HO;rG;omeC;omeU;omeC;rA;rU;fluU;fluU;fluA;rC;omeC;omeA; rG;omeC;rG;omeU;fluA;fluA;fluA;fluU;omeG;rA;omeG;fluCSup-3' | 7776.85 | 185 |
| 64 | 5'-HO;rG;omeC;fluU;omeC;rA;omeU;rU;omeU;fluA;omeC;fluC;fluA; fluG;rC;rG;omeU;rA;rA;omeA;fluU;omeG;fluA;omeG;rCSup-3' | 7776.81 | 186 |
| 65 | 5'-HO;rG;rC;rU;fluC;omeA;fluU;rU;rU;fluA;omeC;omeC;rA;omeG; omeC;omeG;omeU;rA;fluA;fluA;omeU;fluG;omeA;rG;fluCSup-3' | 7776.85 | 187 |
| 66 | 5'-HO;rG;fluC;omeU;fluC;rA;omeU;rU;fluU;rA;omeC;omeC;omeA; rG;rC;omeG;fluU;fluA;fluA;fluA;omeU;fluG;omeA;rG;omeCSup-3' | 7778.82 | 188 |
| 67 | 5'-HO;rG;fluC;omeU;fluC;fluA;fluU;fluU;rU;rA;rC;omeC;omeA;fluG; fluC;omeG;rU;rA;omeA;omeA;omeU;omeG;fluA;rG;omeCSup-3' | 7778.82 | 189 |
| 68 | 5'-HO;rG;omeC;fluU;fluC;fluA;omeU;omeU;rU;omeA;rC;omeC;omeA; omeG;fluC;omeG;rU;fluA;fluA;fluA;omeU;rG;fluA;rG;rCSup-3' | 7778.79 | 190 |
| 69 | 5'-HO;rG;rC;omeU;fluC;omeA;omeU;rU;rU;fluA;fluC;fluC;omeA; omeC;rC;rG;fluU;fluA;omeA;fluA;omeU;rG;omeA;omeG;fluCSup-3' | 7778.79 | 191 |
| 70 | 5'-HO;rG;omeC;rU;fluC;rA;omeU;fluU;rU;fluA;fluC;omeC;rA;omeG; rC;omeG;omeU;fluA;omeA;omeA;fluU;fluG;omeA;fluG;fluCSup-3' | 7780.80 | 192 |
| 71 | 5'-HO;rG;rC;omeU;fluC;rA;omeU;omeU;fluU;fluA;fluC;omeC;fluA; fluC;omeC;fluG;fluU;rA;fluA;omeA;rU;rG;omeA;omeG;omeCSup-3' | 7780.80 | 193 |
| 72 | 5'-HO;rG;omeC;omeU;fluC;rA;fluU;rU;rU;omeA;fluC;fluC;fluA;rG; omeC;fluG;omeU;omeA;omeA;fluA;omeU;fluG;fluA;omeG;rCSup-3' | 7780.80 | 194 |
| 73 | 5'-HO;rG;fluC;omeU;rC;omeA;omeU;rU;fluU;rA;omeC;omeC;omeA; fluC;fluG;rU;fluA;fluA;omeA;fluU;omeG;omeA;fluG;fluCSup-3' | 7782.78 | 195 |
| 74 | 5'-HO;rG;fluC;fluU;omeC;fluA;fluU;omeU;rU;fluA;omeC;rC;fluA;fluG; omeC;rG;fluU;omeA;omeA;omeU;fluG;omeA;omeG;fluCSup-3' | 7784.76 | 196 |
| 75 | 5'-HO;rG;omeC;fluU;fluC;fluA;omeU;fluU;fluU;omeA;fluC;omeC;fluA; omeC;rC;fluG;fluU;omeA;rA;omeA;rC;omeG;fluA;fluG;omeCSup-3' | 7784.75 | 197 |
| 76 | 5'-HO;rG;omeC;rU;omeC;rA;omeU;fluU;fluU;rA;rC;fluC;omeA; fluG;omeC;omeG;rU;omeA;rA;omeA;rU;omeG;omeA;rG;rCSup-3' | 7784.89 | 198 |
| 77 | 5'-HO;rG;rC;rU;omeC;omeA;fluU;rU;rU;omeA;omeC;omeC;fluA; rG;omeC;omeG;rU;fluA;rA;fluA;omeU;rG;omeA;fluG;omeCSup-3' | 7786.90 | 199 |
| 78 | 5'-HO;rG;fluC;omeU;fluC;fluA;fluU;omeU;omeU;omeC; omeC;fluA;omeC;fluC;rG;rU;rA;omeA;rA;rU;omeG;rA;rG;rCSup-3' | 7786.91 | 200 |
| 79 | 5'-HO;rG;rC;rU;fluC;omeA;omeU;fluU;omeU;fluA;omeC;rC;rA;fluG; omeC;omeG;rU;omeA;omeA;fluA;rU;omeG;rA;omeG;rCSup-3' | 7786.83 | 201 |
| 80 | 5'-HO;rG;fluC;omeU;fluC;omeA;fluU;omeU;omeU;omeU;rA;rC;rC;fluA;fluG; rC;omeU;omeA;fluA;fluA;rU;fluG;omeA;omeG;omeCSup-3' | 7792.77 | 202 |
| 81 | 5'-HO;rG;omeC;omeU;omeC;fluA;omeU;rU;rU;omeA;fluC;omeC;fluA; fluG;omeC;fluG;rU;fluA;omeA;omeA;fluU;fluG;rA;omeG;fluCSup-3' | 7794.85 | 203 |
| 82 | 5'-HO;rG;fluC;omeU;rC;omeA;omeU;fluU;rU;fluA;omeC;omeC;fluA; fluG;fluC;fluG;omeU;omeA;omeA;rA;fluU;omeG;omeA;rG;fluCSup-3' | 7794.82 | 204 |
| 83 | 5'-HO;rG;rC;fluU;omeC;fluA;omeU;rU;fluU;omeA;omeC;fluC;rA;omeG; fluC;fluG;omeU;fluA;fluA;rA;omeU;fluG;omeA;omeG;omeCSup-3' | 7794.81 | 205 |
| 84 | 5'-HO;rG;rC;omeU;rC;omeA;omeU;fluU;fluU;rA;rC;rC;omeA;omeG; rC;omeU;omeA;rA;fluA;omeU;omeG;fluA;rG;omeCSup-3' | 7798.80 | 206 |
| 85 | 5'-HO;rG;omeC;omeU;rC;rA;fluU;rU;rU;fluA;rC;fluC;omeA;omeG; omeC;omeG;omeU;omeA;rA;rA;fluU;rG;omeA;omeG;omeCSup-3' | 7798.90 | 207 |
| 86 | 5'-HO;rG;omeC;omeU;omeC;omeA;fluU;omeU;omeU;fluA;fluC;fluC; omeA;rG;omeC;omeG;fluU;fluA;omeA;omeA;rU;rG;rA;rG;rCSup-3' | 7802.90 | 208 |
| 87 | 5'-HO;rG;omeC;fluU;fluC;omeA;rU;omeU;fluU;fluA;omeC;fluC;omeA; fluG;omeC;rG;omeA;rA;omeA;rU;omeG;rA;rG;omeCSup-3' | 7802.93 | 209 |
| 88 | 5'-HO;rG;omeC;omeU;omeC;fluA;rU;omeU;fluU;rA;omeC;omeC;rA;omeG; fluC;omeG;omeU;omeA;omeA;omeA;fluU;fluG;rA;rG;fluCSup-3' | 7802.90 | 210 |
| 89 | 5'-HO;rG;rC;fluU;omeC;fluA;rU;fluU;omeU;fluA;omeC;omeC;omeA; rG;rC;omeG;fluU;omeA;omeA;rA;omeU;fluG;fluA;omeG;omeCSup-3' | 7816.87 | 211 |
| 90 | 5'-HO;rG;omeC;fluU;omeC;omeA;omeU;rU;rU;fluA;fluC;omeComeA; omeG;fluC;omeG;omeU;omeA;fluA;fluA;fluU;omeG;omeA;fluG;rCSup-3' | 7820.86 Exact 7817.20 | 212 |
| 91 | 5'-HO;rG;rC;omeU;omeC;rA;fluU;omeU;omeU;fluA;omeC;rC;omeA; omeG;omeC;omeG;omeU;omeA;omeA;omeA;omeU;omeG;fluA;fluG; fluCSup-3' | 7856.93 | 213 |
| 92 | 5'-HO;rG;fluC;fluU;fluC;fluA;fluU;fluU;fluU;fluA;fluC;fluC;fluA;fluG; fluC;fluG;fluU;fluA;fluA;fluA;fluU;fluG;fluA;fluG;fluCSup-3' | 7682.40 | 214 |
| 93 | 5'-HO;rG;rC;rU;fluU;rC;rA;fluU;rU;omeU;rA;rC;omeC;fluA; omeG;fluC;rG;fluU;fluA;rA;rA;rU;rG;fluA;rG;rCSup-3' | 7692.66 | 215 |
| 94 | 5'-HO;rG;rC;fluU;rC;rA;fluU;fluU;rU;omeA;rC;fluC;fluA; rG;rC;fluG;rU;fluA;omeA;rA;fluU;omeG;rA;rG;rCSup-3' | 7696.58 | 216 |
| 95 | 5'-HO;rG;rC;fluU;rC;rA;rU;omeU;rU;fluA;fluC;omeC;rA;rG; rC;rG;fluU;omeA;rA;rA;fluU;omeG;fluA;rG;fluCSup-3' | 7706.71 | 217 |
| 96 | 5'-HO;rG;fluC;omeU;fluC;rA;fluU;omeU;rU;rA;fluC;fluC;fluA; rG;rC;rG;rU;omeA;rA;fluA;fluU;omeG;rA;rG;fluCSup-3' | 7710.70 | 218 |
| 97 | 5'-HO;rG;fluC;rU;rC;fluA;rU;rU;rU;rA;fluC;fluC;omeA;omeG; fluC;fluG;omeU;fluA;omeA;rA;fluU;rG;fluA;rG;fluCSup-3' | 7712.72 | 219 |

TABLE 5-continued

| Ex | Sequence | MW | SEQ ID No. |
|---|---|---|---|
| 98 | 5'-HO;rG;rC;fluU;fluC;omeA;fluU;fluU;fluU;fluA;rC;fluC;fluA; rG;fluC;fluG;fluU;rA;omeA;omeA;fluG;omeA;rG;rCSup-3' | 7718.58 | 220 |
| 99 | 5'-HO;rG;rC;omeU;rC;rA;omeU;fluU;fluU;fluA;fluC;rC;rA;fluG; rC;omeG;rU;omeA;rA;rA;omeU;rG;fluA;rG;fluCSup-3' | 7720.69 | 221 |
| 100 | 5'-HO;rG;fluC;fluU;fluC;rA;fluU;fluU;rU;rA;omeC;omeC;rA; omeG;fluC;fluG;rU;rA;rA;rA;rU;omeG;omeA;fluG;fluCSup-3' | 7724.79 | 222 |
| 101 | 5'-HO;rG;omeC;rU;fluC;fluA;fluU;fluU;fluU;fluA;fluC;rC;omeA; fluG;rC;rG;omeU;rA;fluA;rA;omeU;rG;omeA;rG;rCSup-3' | 7724.68 | 223 |
| 102 | 5'-HO;rG;fluC;rU;omeC;fluA;fluU;rU;rU;omeA;rC;rC;omeA;rG; fluC;fluG;fluU;rA;fluA;fluA;fluU;fluG;fluA;omeG;omeCSup-3' | 7728.67 | 224 |
| 103 | 5'-HO;rG;rC;rU;omeC;fluA;fluU;fluU;rU;rA;fluC;rC;rA;rG; omeC;rG;fluU;fluA;rA;rA;rU;omeG;omeA;omeG;omeCSup-3' | 7732.79 | 225 |
| 104 | 5'-HO;rG;omeC;omeU;rC;rA;rU;omeU;rU;fluA;rC;rC;fluA; omeC;fluC;rG;omeU;fluA;fluA;rA;omeU;rG;rA;fluG;rCSup-3' | 7732.73 | 226 |
| 105 | 5'-HO;rG;omeC;fluU;rC;rA;rU;fluU;rU;rA;fluC;rC;omeA;rG; omeC;fluG;rU;fluA;omeA;rA;omeU;rG;omeA;fluG;fluCSup-3' | 7734.77 | 227 |
| 106 | 5'-HO;rG;fluC;rU;rC;fluA;rU;rU;omeU;fluA;rC;fluC;rA;fluG; omeC;rG;rU;rA;fluA;rA;omeU;omeG;omeA;fluG;omeCSup-3' | 7734.77 | 228 |
| 107 | 5'-HO;rG;fluC;fluU;fluC;fluA;rU;rU;omeU;omeA;rC;rC;omeA; rG;omeC;fluG;rU;omeA;rA;rA;rU;rG;fluA;omeG;fluCSup-3' | 7734.77 | 229 |
| 108 | 5'-HO;rG;fluC;fluU;omeC;rA;rU;fluU;rU;omeA;omeC;fluC;rA; fluC;fluC;omeG;fluU;omeA;omeA;rA;rU;rG;rA;fluG;fluCSup-3' | 7736.82 | 230 |
| 109 | 5'-HO;rG;rC;fluU;omeC;omeA;rU;fluU;omeU;rA;fluC;omeC; fluA;omeG;omeC;rG;rU;rA;fluA;fluA;rU;rG;fluA;fluG;rCSup-3' | 7736.75 | 231 |
| 110 | 5'-HO;rG;fluC;rU;rC;omeA;fluU;fluU;fluU;fluA;rC;omeC;rA;rG; omeC;rG;rU;fluA;fluA;rA;rU;fluA;rG;fluA;omeG;omeCSup-3' | 7736.75 | 232 |
| 111 | 5'-HO;rG;rC;rU;fluC;rA;rU;rU;omeU;fluA;fluC;fluC;fluA;rG; omeC;fluG;rU;omeA;fluA;fluA;omeU;omeG;rA;rG;omeCSup-3' | 7736.79 | 233 |
| 112 | 5'-HO;rG;fluC;rU;fluC;omeA;rA;rU;omeU;fluA;fluC;omeC; omeA;rG;rC;fluG;fluU;fluA;omeA;fluA;rU;omeG;rA;rG;rCSup-3' | 7736.75 | 234 |
| 113 | 5'-HO;rG;rC;rU;rC;omeA;rU;fluU;fluU;omeA;fluC;fluC;rA;fluG; omeC;rG;fluU;omeA;omeA;omeA;fluU;fluG;rA;rG;fluCSup-3' | 7738.73 | 235 |
| 114 | 5'-HO;rG;rC;rU;fluC;fluA;rU;omeU;fluU;rA;omeC;rC;fluA;omeG; rC;fluG;rU;fluA;omeA;omeA;rA;fluG;fluA;fluG;omeCSup-3' | 7738.69 | 236 |
| 115 | 5'-HO;rG;omeC;fluU;fluC;fluA;fluU;rU;fluU;omeA;rC;fluC;fluA; rG;rC;omeG;rU;rA;omeA;omeA;omeU;fluG;rA;rG;fluCSup-3' | 7738.73 | 237 |
| 116 | 5'-HO;rG;omeC;rU;rC;rA;omeU;rU;fluU;rA;fluC;rC;fluA;fluG; fluC;omeG;omeU;omeA;omeA;fluA;rU;fluG;fluA;fluG;rCSup-3' | 7738.69 | 238 |
| 117 | 5'-HO;rG;omeC;fluU;fluC;rA;rU;omeU;fluU;omeA;omeC;fluC;fluA; fluG;fluC;rG;rU;omeA;fluA;rA;rU;fluG;fluA;rG;omeCSup-3' | 7740.78 | 239 |
| 118 | 5'-HO;rG;rC;omeU;rC;fluA;rU;omeU;rU;rA;rC;omeC;rA;fluG; omeC;rG;omeU;omeA;fluA;fluA;rU;rG;omeA;rG;fluCSup-3' | 7744.80 | 240 |
| 119 | 5'-HO;rG;fluC;rU;fluC;rA;omeU;fluU;fluU;fluA;fluC;fluC;rA;omeG; omeC;fluG;omeU;fluA;omeA;fluA;fluU;rG;fluA;fluG;omeCSup-3' | 7746.71 | 241 |
| 120 | 5'-HO;rG;rC;fluU;omeC;rA;omeU;fluU;omeU;omeA;fluC;rC; omeA;fluG;rC;rG;omeU;rA;rA;rA;fluU;fluG;rA;rG;omeCSup-3' | 7746.77 | 242 |
| 121 | 5'-HO;rG;fluC;fluU;rC;omeA;rU;rU;rU;rA;omeC;omeC;fluA;fluG; omeC;omeG;omeU;fluA;rA;omeA;fluG;rA;fluG;rCSup-3' | 7750.76 | 243 |
| 122 | 5'-HO;rG;fluC;omeU;omeC;fluA;fluU;omeU;fluU;fluA;omeC;rC;fluA; rG;fluC;rG;omeU;omeA;fluA;rA;fluU;rG;rA;omeG;rCSup-3' | 7752.74 | 244 |
| 123 | 5'-HO;rG;rC;omeU;rC;fluA;omeU;fluU;omeU;omeA;rC;fluC;rA;fluG; omeC;fluG;fluU;fluA;rA;fluA;omeU;rG;fluA;omeG;rCSup-3' | 7752.67 | 245 |
| 124 | 5'-HO;rG;fluC;omeU;fluC;rA;rU;rU;fluU;omeA;omeC;rC;omeA;rG; fluC;fluG;omeU;fluA;fluA;omeA;fluU;rG;fluA;omeG;rCSup-3' | 7752.74 | 246 |
| 125 | 5'-HO;rG;fluC;omeU;omeC;omeA;rU;fluU;fluU;omeA;fluC;fluC;fluA; rG;omeC;rG;rU;fluA;fluA;omeA;fluU;rG;rA;rG;rCSup-3' | 7752.78 | 247 |
| 126 | 5'-HO;rG;omeC;rU;fluC;rA;rU;omeU;rU;omeA;fluC;omeC;rA;fluG; fluC;omeG;fluU;fluA;fluA;rA;omeU;omeG;fluA;fluG;fluCSup-3' | 7754.79 | 248 |
| 127 | 5'-HO;rG;omeC;omeU;omeC;fluA;fluU;rU;omeU;fluA;fluC;rC;omeA; fluC;rG;fluU;rA;fluA;rA;fluU;omeG;omeA;fluG;rCSup-3' | 7754.68 | 249 |
| 128 | 5'-HO;rG;fluC;rU;omeC;rA;omeU;rU;rU;omeA;rC;omeC;fluA; omeG;rC;rG;rU;omeA;omeA;rA;fluU;rG;omeA;rG;rCSup-3' | 7754.86 | 250 |
| 129 | 5'-HO;rG;omeC;fluU;fluC;rA;fluU;omeU;omeU;rA;rC;fluC;fluA;fluG; omeC;omeG;fluU;fluA;rA;rA;fluU;fluG;fluA;omeG;omeCSup-3' | 7756.73 | 251 |
| 130 | 5'-HO;rG;omeC;omeU;omeC;omeA;rU;rU;omeU;fluA;rC;rC; fluA;omeG;rC;omeG;fluA;rA;rA;rU;fluG;rA;rG;omeCSup-3' | 7756.83 | 252 |
| 131 | 5'-HO;rG;omeC;omeU;fluC;omeA;rU;rU;fluU;rA;rC;rC;omeA; omeC;rG;rG;fluU;rA;omeA;fluA;rU;rG;rA;omeG;omeCSup-3' | 7756.83 | 253 |
| 132 | 5'-HO;rG;rC;rU;rC;omeA;rU;rU;fluU;omeA;fluC;fluC;omeA;rG; fluC;rG;omeU;rA;omeA;fluA;rU;omeG;omeA;rG;omeCSup-3' | 7758.85 | 254 |
| 133 | 5'-HO;rG;fluU;rC;rA;omeU;omeU;omeU;rA;omeC;rC;omeA; rG;omeC;rG;rU;fluA;omeA;fluA;omeU;rG;rA;fluG;fluCSup-3' | 7758.81 | 255 |
| 134 | 5'-HO;rG;fluC;omeU;fluC;omeA;omeU;rU;omeU;rA;rC;omeC;rA; rG;fluC;fluG;rU;omeA;rA;rA;omeU;fluG;fluA;rG;omeCSup-3' | 7760.86 | 256 |
| 135 | 5'-HO;rG;fluC;rU;rC;rA;omeU;omeU;omeU;rA;omeC;fluC;omeA;rG; rC;omeG;rU;fluA;fluA;fluA;rU;fluG;omeA;omeG;rCSup-3' | 7760.79 | 257 |

TABLE 5-continued

| Ex | Sequence | MW | SEQ ID No. |
|---|---|---|---|
| 136 | 5'-HO;rG;fluC;fluU;rC;omeA;rU;omeU;fluU;omeA;fluC;rC;rA;omeG; rC;rG;rU;fluA;rA;omeA;omeU;fluG;omeA;omeG;rCSup-3' | 7760.75 | 258 |
| 137 | 5'-HO;rG;fluC;omeU;rC;rA;omeU;rU;fluU;fluA;fluC;fluC;rA;fluG;omeC; omeC;fluU;rA;rA;omeA;omeU;rG;omeA;omeG;rCSup-3' | 7762.80 | 259 |
| 138 | 5'-HO;rG;fluC;omeU;rC;omeA;rU;omeU;rU;omeA;omeC;fluC;fluA; omeG;fluC;fluG;fluU;rA;rA;rU;rG;omeA;fluG;omeCSup-3' | 7762.84 | 260 |
| 139 | 5'-HO;rG;rC;fluU;omeC;fluA;rU;omeU;rU;fluA;rC;omeC;rA;fluG;rC; fluG;omeU;omeA;rA;omeA;fluU;omeG;fluA;omeG;rCSup-3' | 7762.73 | 261 |
| 140 | 5'-HO;rG;fluC;fluU;rC;rA;rU;rU;fluU;omeA;rC;omeC;fluA;omeC;omeC; omeG;fluU;rA;rA;omeA;omeU;fluG;rA;omeG;fluCSup-3' | 7763.80 | 262 |
| 141 | 5'-HO;rG;rC;fluU;omeC;rA;omeU;fluU;fluU;omeA;omeC;omeC;rA; rG;omeC;rG;fluU;fluA;fluA;omeA;rU;omeG;fluA;fluG;rCSup-3' | 7764.77 | 263 |
| 142 | 5'-HO;rG;rC;rU;rC;omeA;omeU;omeU;rU;omeA;fluC;rC;omeA;omeG; fluC;fluG;fluU;omeA;fluA;fluA;rU;fluG;omeA;rG;fluCSup-3' | 7764.74 | 264 |
| 143 | 5'-HO;rG;rC;omeU;fluC;rA;fluU;omeU;fluU;omeA;rC;rC;rA;omeG; fluC;fluG;fluU;fluA;omeA;fluA;fluU;omeG;omeA;omeG;rCSup-3' | 7766.68 | 265 |
| 144 | 5'-HO;rG;fluC;fluU;omeC;omeA;omeU;fluU;rU;rA;rC;rC;rA;omeG; fluC;fluG;fluU;omeA;omeA;omeA;omeU;rG;fluA;fluG;fluCSup-3' | 7766.75 | 266 |
| 145 | 5'-HO;rG;omeC;rU;omeC;fluA;omeU;omeU;fluU;rA;omeC;fluC;fluA; omeC;omeC;fluG;omeU;rA;fluA;rA;fluU;fluG;rA;rG;fluCSup-3' | 7766.82 | 267 |
| 146 | 5'-HO;rG;omeC;rU;omeC;fluA;fluU;fluU;fluU;omeA;fluC;omeC;omeA; fluC;fluC;rG;rU;fluA;rA;omeA;rU;fluG;omeA;fluG;omeCSup-3' | 7768.80 | 268 |
| 147 | 5'-HO;rG;omeC;omeU;fluC;omeA;fluU;rU;fluU;fluA;omeC;omeC;rA; omeC;omeC;omeG;fluU;fluA;fluA;rA;fluU;rG;fluA;fluG;fluCSup-3' | 7770.78 | 269 |
| 148 | 5'-HO;rG;fluC;fluU;fluC;omeA;omeU;omeU;omeU;fluA;fluC;omeC; fluA;fluC;fluG;omeU;omeA;fluA;rA;omeU;omeG;rA;fluG;fluCSup-3' | 7770.78 | 270 |
| 149 | 5'-HO;rG;omeC;fluU;rC;fluA;fluU;rU;rU;omeA;omeC;omeC;omeA; omeC;omeC;omeG;rU;omeA;rA;fluA;rU;rG;rA;rG;rCSup-3' | 7770.88 | 271 |
| 150 | 5'-HO;rG;rC;rU;fluC;rA;omeU;fluU;omeU;rA;rC;rC;omeA;omeG;fluC; omeU;fluU;omeA;rA;rA;omeU;omeG;rA;omeG;rCSup-3' | 7770.81 | 272 |
| 151 | 5'-HO;rG;omeC;omeU;omeC;rA;rU;omeU;omeU;rA;rC;fluC;omeA; omeC;rC;fluG;rU;fluA;fluA;omeA;rU;fluG;omeA;rG;rCSup-3' | 7772.82 | 273 |
| 152 | 5'-HO;rG;omeC;fluU;fluC;omeA;omeU;rU;omeU;rA;omeC;rC;omeA; fluG;rC;fluG;fluU;omeA;omeA;rA;rU;rG;omeA;rG;rCSup-3' | 7772.82 | 274 |
| 153 | 5'-HO;rG;fluC;rU;fluC;fluA;rU;rU;omeU;omeA;omeC;rC;omeA;rG; omeC;omeG;omeU;rA;rA;omeA;fluU;omeG;fluA;rG;fluCSup-3' | 7774.87 | 275 |
| 154 | 5'-HO;rG;rC;rU;omeC;omeA;rU;omeU;rU;fluA;rC;fluC;omeA;rG;rC; omeG;fluU;omeA;fluA;omeA;fluU;omeG;rA;fluG;omeCSup-3' | 7774.80 | 276 |
| 155 | 5'-HO;rG;fluC;rU;rC;rA;rU;fluU;omeU;rA;omeC;fluC;fluA;fluG;rC; rG;omeU;omeA;fluA;omeA;omeC;omeA;omeG;fluCSup-3' | 7776.81 | 277 |
| 156 | 5'-HO;rG;fluC;fluU;omeC;rA;rU;rU;fluU;fluA;omeC;omeC;omeA;omeG; rC;rG;fluU;omeA;omeA;rA;omeU;fluG;fluA;omeG;rCSup-3' | 7776.81 | 278 |
| 157 | 5'-HO;rG;fluC;omeU;fluC;rA;omeU;fluU;omeU;omeA;fluC;fluC;omeA; omeC;omeC;rG;rU;rA;fluA;omeA;fluU;fluG;rA;omeG;rCSup-3' | 7778.83 | 279 |
| 158 | 5'-HO;rG;rC;fluU;omeC;fluA;omeU;omeU;omeU;fluA;rC;omeC;omeA; fluG;omeC;fluG;fluU;rA;omeA;rA;fluU;rG;omeA;fluG;rCSup-3' | 7778.75 | 280 |
| 159 | 5'-HO;rG;rC;omeU;fluC;fluA;omeU;fluU;fluU;fluA;omeC;fluC;omeA; omeC;omeC;rG;omeU;fluA;fluA;rA;rU;omeG;omeA;omeG;fluCSup-3' | 7780.80 | 281 |
| 160 | 5'-HO;rG;omeC;omeU;omeC;rA;fluU;fluU;omeU;fluA;fluC;rC;fluA; rG;fluC;fluG;fluU;omeA;rA;omeA;fluU;omeG;omeA;rG;omeCSup-3' | 7780.80 | 282 |
| 161 | 5'-HO;rG;omeC;rU;fluC;rA;rU;omeU;fluU;rA;omeC;omeC;rA;omeG; omeC;fluG;rU;rA;omeA;rA;omeU;omeG;fluA;omeG;rCSup-3' | 7784.93 | 283 |
| 162 | 5'-HO;rG;rC;rU;omeComeA;rU;omeU;omeU;omeA;fluC;omeC;omeA; fluG;rC;fluG;omeU;omeA;rA;rA;fluU;fluG;fluA;rG;omeCSup-3' | 7788.85 | 284 |
| 163 | 5'-HO;rG;omeC;rU;omeC;omeA;fluU;fluU;omeU;omeA;fluC;omeC; fluA;omeG;rC;fluG;omeU;fluA;rA;rA;omeU;rG;rA;omeG;fluCSup-3' | 7790.86 | 285 |
| 164 | 5'-HO;rG;omeC;fluU;omeC;fluA;omeU;omeU;fluU;fluA;rC;omeC;omeA; rG;fluC;rG;omeU;fluA;omeA;fluA;rU;omeG;omeA;rG;fluCSup-3' | 7792.84 | 286 |
| 165 | 5'-HO;rG;omeC;omeU;omeC;fluA;omeU;omeU;omeU;rA;omeC;fluC; rA;omeG;fluC;rG;fluU;omeA;omeA;fluA;fluU;fluG;fluA;rG;omeCSup-3' | 7794.81 | 287 |
| 166 | 5'-HO;rG;omeC;fluU;omeC;rA;fluU;omeU;fluU;fluA;fluC;omeC; omeA;omeG;fluC;omeG;rU;omeA;rA;fluA;fluU;omeG;omeA;rG; omeCSup-3' | 7794.85 found | 288 |
| 167 | 5'-HO;rG;omeC;omeU;fluC;fluA;omeU;fluU;omeU;omeA;fluC;fluC; omeA;fluG;rC;omeG;rU;fluA;omeA;omeA;fluU;rG;fluA;fluG;omeCSup-3' | 7796.79 | 289 |
| 168 | 5'-HO;rG;omeC;omeU;rC;fluA;omeU;omeU;rU;omeA;omeC;omeC; rA;rG;rC;rG;fluU;rA;rA;rA;omeU;omeG;omeA;fluG;omeCSup-3' | 7796.93 | 290 |
| 169 | 5'-HO;rG;omeC;omeU;fluC;fluA;rU;omeU;omeU;omeA;omeC;rC; rA;rG;rC;omeG;omeU;omeA;rA;omeA;fluU;fluG;omeA;rG;fluCSup-3' | 7800.88 | 291 |
| 170 | 5'-HO;rG;rC;omeU;fluC;rA;omeU;omeU;omeU;omeA;fluC;fluC;rA; rG;omeC;fluG;omeU;omeA;omeA;rA;fluU;rG;omeA;fluG;omeCSup-3' | Calculated 7802.90 | 292 |
| 171 | 5'-HO;rG;omeC;omeU;rC;omeA;fluU;fluU;fluU;omeA;fluC;omeC;fluA; rG;rC;omeG;omeU;rA;omeA;rU;omeG;fluA;omeG;rCSup-3' | 7802.82 | 293 |
| 172 | 5'-HO;rG;fluC;fluU;rC;omeA;fluU;omeU;rA;fluC;fluC;rA;omeG; omeC;omeG;rU;fluA;omeA;omeA;omeG;omeA;rG;rCSup-3' | 7802.86 | 294 |
| 173 | 5'-HO;rG;omeC;rU;omeC;fluA;fluU;fluU;omeU;rA;fluC;fluC;omeA;omeG; fluC;fluG;omeU;omeA;fluA;omeA;omeU;omeG;rA;fluG;omeCSup-3' | 7808.86 | 295 |

TABLE 5-continued

| Ex | Sequence | MW | SEQ ID No. |
|---|---|---|---|
| 174 | 5'-HO;rG;omeC;rU;omeU;rA;omeU;omeU;rU;rA;omeC;rC;omeA;rG; omeC;fluG;rU;omeA;fluA;omeA;omeU;rG;rA;omeG;omeCSup-3' | 7809.00 | 296 |
| 175 | 5'-HO;rG;rC;rU;fluC;omeA;omeU;rU;rU;omeA;omeC;rC;omeA;omeG; omeC;rG;rU;fluA;omeA;omeA;fluU;omeG;rA;omeG;omeCSup-3' | 7810.94 | 297 |
| 176 | 5'-HO;rG;omeC;omeU;rC;omeA;omeU;omeU;rU;omeA;omeC;rC;omeA; omeG;omeC;fluG;fluU;rA;rA;rA;omeU;omeG;fluA;fluG;rCSup-3' | 7812.88 | 298 |
| 177 | 5'-HO;rG;fluC;omeU;omeC;fluA;rU;rU;omeU;omeA;rC;omeC;rA;omeG; omeC;omeG;omeU;rA;fluA;fluA;omeU;rG;omeA;fluG;omeCSup-3' | 7814.93 | 299 |
| 178 | 5'-HO;rG;omeC;omeU;omeC;fluA;rU;fluU;omeU;omeA;omeC;omeC; omeA;omeG;omeC;rG;fluU;fluA;rA;fluA;rU;omeG;omeA;rG;fluCSup-3' | 7816.94 | 300 |
| 179 | 5'-HO;rG;dC;rU;rC;rA;fluU;rU;rU;rA;fluC;rC;rA;fluG;omeC; rG;fluU;omeA;fluA;omeA;rU;rG;rA;rG;omeCSup-3' | 7686.65 | 301 |
| 180 | 5'-HO;rG;omeC;dU;rC;rA;fluU;rU;rU;rA;fluC;rC;rA;fluG; omeC;rG;fluU;omeA;fluA;omeA;rU;rG;rA;rG;omeCSup-3' | 7700.68 | 302 |
| 181 | 5'-HO;rG;omeC;rU;dC;rA;fluU;rU;rU;rA;fluC;rC;rA;fluG; omeC;rG;fluU;omeA;fluA;omeA;rU;rG;rA;rG;omeCSup-3' | 7700.68 | 303 |
| 182 | 5'-HO;rG;omeC;rU;rC;rA;dU;rU;rU;rA;fluC;rC;rA;fluG; omeC;rG;fluU;omeA;fluA;omeA;rU;rG;rA;rG;omeCSup-3' | 7698.68 | 304 |
| 183 | 5'-HO;rG;omeC;rU;rC;rA;fluU;dU;rU;rA;fluC;rC;rA;fluG; omeC;rG;fluU;omeA;fluA;omeA;rU;rG;rA;rG;omeCSup-3' | 7700.68 | 305 |
| 184 | 5'-HO;rG;omeC;rU;rC;rA;fluU;rU;dU;rA;fluC;rC;rA;fluG; omeC;rG;fluU;omeA;fluA;omeA;rU;rG;rA;rG;omeCSup-3' | 7700.68 | 306 |
| 185 | 5'-HO;rG;omeC;rU;rC;rA;fluU;rU;rU;rA;dC;rC;rA;fluG; omeC;rG;fluU;omeA;fluA;omeA;rU;rG;rA;rG;omeCSup-3' | 7698.68 | 307 |
| 186 | 5'-HO;rG;omeC;rU;rC;rA;fluU;rU;rU;rA;fluC;dC;rA;fluG; omeC;rG;fluU;omeA;fluA;omeA;rU;rG;rA;rG;omeCSup-3' | 7700.68 | 308 |
| 187 | 5'-HO;rG;omeC;rU;rC;rA;fluU;rU;rU;rA;fluC;rC;dA;fluG; omeC;rG;fluU;omeA;fluA;omeA;rU;rG;rA;rG;omeCSup-3' | 7700.68 | 309 |
| 188 | 5'-HO;rG;omeC;rU;rC;rA;fluU;rU;rU;rA;fluC;rC;rA;dG; omeC;rG;fluU;omeA;fluA;omeA;rU;rG;rA;rG;omeCSup-3' | 7698.68 | 310 |
| 189 | 5'-HO;rG;omeC;rU;rC;rA;fluU;rU;rU;rA;fluC;rC;rA;fluG; dC;rG;fluU;omeA;fluA;omeA;rU;rG;rA;rG;omeCSup-3' | 7686.65 | 311 |
| 190 | 5'-HO;rG;omeC;rU;rC;rA;fluU;rU;rU;rA;fluC;rC;rA;fluG; omeC;dG;fluU;omeA;fluA;omeA;rU;rG;rA;rG;omeCSup-3' | 7700.68 | 312 |
| 191 | 5'-HO;rG;omeC;rU;rC;rA;fluU;rU;rU;rA;fluC;rC;rA;fluG; omeC;rG;dU;omeA;fluA;omeA;rU;rG;rA;rG;omeCSup-3' | 7698.68 | 313 |
| 192 | 5'-HO;rG;omeC;rU;rC;rA;fluU;rU;rU;rA;fluC;rC;rA;fluG; omeC;rG;fluU;dA;fluA;omeA;rU;rG;rA;rG;omeCSup-3' | 7686.65 | 314 |
| 193 | 5'-HO;rG;omeC;rU;rC;rA;fluU;rU;rU;rA;fluC;rC;rA;fluG; omeC;rG;fluU;omeA;dA;omeA;rU;rG;rA;rG;omeCSup-3' | 7698.68 | 315 |
| 194 | 5'-HO;rG;omeC;rU;rC;rA;fluU;rU;rU;rA;fluC;rC;rA;fluG; omeC;rG;fluU;omeA;fluA;dA;rU;rG;rA;rG;omeCSup-3' | 7686.65 | 316 |
| 195 | 5'-HO;rG;omeC;rU;rC;rA;fluU;rU;rU;rA;fluC;rC;rA;fluG; omeC;rG;fluU;omeA;fluA;omeA;dU;rG;rA;rG;omeCSup-3' | 7700.68 | 317 |
| 196 | 5'-HO;rG;omeC;rU;rC;rA;fluU;rU;rU;rA;fluC;rC;rA;fluG; omeC;rG;fluU;omeA;fluA;omeA;rU;dG;rA;rG;omeCSup-3' | 7700.68 | 318 |
| 197 | 5'-HO;rG;omeC;rU;rC;rA;fluU;rU;rU;rA;fluC;rC;rA;fluG;omeC;rG; fluU;omeA;fluA;omeA;rU;rG;dA;rG;omeCSup-3' | 7700.68 | 319 |
| 198 | 5'-HO;rG;omeC;rU;rC;rA;fluU;rU;rU;rA;fluC;rC;rA;fluG; omeC;rG;fluU;omeA;fluA;omeA;rU;rG;rA;dG;omeCSup-3' | 7700.68 | 320 |
| 199 | 5'-HO;rG;omeC;rU;rC;rA;fluU;rU;rU;rA;fluC;rC;rA;fluG; omeC;rG;fluU;omeA;fluA;omeA;rU;rG;rA;dCSup-3' | 7686.65 | 321 |
| 200 | 5'-HO;rG;faraC;rU;rC;rA;fluU;rU;rU;rA;fluC;rC;rA;fluG; omeC;rG;fluU;omeA;fluA;omeA;rU;rG;rA;rG;omeCSup-3' | 7704.64 | 322 |
| 201 | 5'-HO;rG;omeC;faraU;rC;rA;fluU;rU;rU;rA;fluC;rC;rA;fluG; omeC;rG;fluU;omeA;fluA;omeA;rU;rG;rA;rG;omeCSup-3' | 7718.67 | 323 |
| 202 | 5'-HO;rG;omeC;rU;faraC;rA;fluU;rU;rU;rA;fluC;rC;rA;fluG; omeC;rG;fluU;omeA;fluA;omeA;rU;rG;rA;rG;omeCSup-3' | 7718.67 | 324 |
| 203 | 5'-HO;rG;omeC;rU;rC;rA;faraU;rU;rU;rA;fluC;rC;rA;fluG; omeC;rG;fluU;omeA;fluA;omeA;rU;rG;rA;rG;omeCSup-3' | 7716.67 | 325 |
| 204 | 5'-HO;rG;omeC;rU;rC;rA;fluU;faraU;rU;rA;fluC;rC;rA;fluG; omeC;rG;fluU;omeA;fluA;omeA;rU;rG;rA;rG;omeCSup-3' | 7718.67 | 326 |
| 205 | 5'-HO;rG;omeC;rU;rC;rA;fluU;rU;faraU;rA;fluC;rC;rA;fluG; omeC;rG;fluU;omeA;fluA;omeA;rU;rG;rA;rG;omeCSup-3' | 7718.67 | 327 |
| 206 | 5'-HO;rG;omeC;rU;rC;rA;fluU;rU;rU;rA;faraC;rC;rA;fluG; omeC;rG;fluU;omeA;fluA;omeA;rU;rG;rA;rG;omeCSup-3' | 7716.68 | 328 |
| 207 | 5'-HO;rG;omeC;rU;rC;rA;fluU;rU;rU;rA;fluC;faraC;rA;fluG; omeC;rG;fluU;omeA;fluA;omeA;rU;rG;rA;rG;omeCSup-3' | 7718.67 | 329 |
| 208 | 5'-HO;rG;omeC;rU;rC;rA;fluU;rU;rU;rA;fluC;rC;rA;fluG; faraC;rG;fluU;omeA;fluA;omeA;rU;rG;rA;rG;omeCSup-3' | 7704.64 | 330 |
| 209 | 5'-HO;rG;omeC;rU;rC;rA;fluU;rU;rU;rA;fluC;rC;rA;fluG; omeC;rG;faraU;omeA;fluA;omeA;rU;rG;rA;rG;omeCSup-3' | 7716.67 | 331 |
| 210 | 5'-HO;rG;omeC;rU;rC;rA;fluU;rU;rU;rA;fluC;rC;rA;fluG; omeC;rG;fluU;omeA;fluA;omeA;faraU;rG;rA;rG;omeCSup-3' | 7718.67 | 332 |
| 211 | 5'-HO;rG;dC;omeU;rC;fluA;rU;omeU;rU;rA;rC;omeC;rA;fluG; omeC;rG;omeU;omeA;fluA;fluA;rU;rG;omeA;rG;fluCSup-3' | 7728.73 | 333 |

TABLE 5-continued

| Ex | Sequence | MW | SEQ ID No. |
|---|---|---|---|
| 212 | 5'-HO;rG;rC;dU;rC;fluA;rU;omeU;rU;rA;rC;omeC;rA;fluG; omeC;rG;omeU;omeA;fluA;fluA;rU;rG;omeA;rG;fluCSup-3' | 7714.70 | 334 |
| 213 | 5'-HO;rG;rC;omeU;dC;fluA;rU;omeU;rU;rA;rC;omeC;rA;fluG; omeC;rG;omeU;omeA;fluA;fluA;rU;rG;omeA;rG;fluCSup-3' | 7728.73 | 335 |
| 214 | 5'-HO;rG;rC;omeU;rC;fluA;dU;omeU;rU;rA;rC;omeC;rA;fluG; omeC;rG;omeU;omeA;fluA;fluA;rU;rG;omeA;rG;fluCSup-3' | 7728.73 | 336 |
| 215 | 5'-HO;rG;rC;omeU;rC;fluA;rU;dU;rU;rA;rC;omeC;rA;fluG; omeC;rG;omeU;omeA;fluA;fluA;rU;rG;omeA;rG;fluCSup-3' | 7714.70 | 337 |
| 216 | 5'-HO;rG;rC;omeU;rC;fluA;rU;omeU;dU;rA;rC;omeC;rA;fluG; omeC;rG;omeU;omeA;fluA;fluA;rU;rG;omeA;rG;fluCSup-3' | 7728.73 | 338 |
| 217 | 5'-HO;rG;rC;omeU;rC;fluA;rU;omeU;rU;rA;dC;omeC;rA;fluG; omeC;rG;omeU;omeA;fluA;fluA;rU;rG;omeA;rG;fluCSup-3' | 7728.73 | 339 |
| 218 | 5'-HO;rG;rC;omeU;rC;fluA;rU;omeU;rU;rA;rC;dC;rA;fluG; omeC;rG;omeU;omeA;fluA;fluA;rU;rG;omeA;rG;fluCSup-3' | 7714.70 | 340 |
| 219 | 5'-HO;rG;rC;omeU;rC;fluA;rU;omeU;rU;rA;rC;omeC;dA;fluG; omeC;rG;omeU;omeA;fluA;fluA;rU;rG;omeA;rG;fluCSup-3' | 7728.73 | 341 |
| 220 | 5'-HO;rG;rC;omeU;rC;fluA;rU;omeU;rU;rA;rC;omeC;rA;dG; omeC;rG;omeU;omeA;fluA;fluA;rU;rG;omeA;rG;fluCSup-3' | 7726.74 | 342 |
| 221 | 5'-HO;rG;rC;omeU;rC;fluA;rU;omeU;rU;rA;rC;omeC;rA;fluG; dC;rG;omeU;omeA;fluA;fluA;rU;rG;omeA;rG;fluCSup-3' | 7714.70 | 343 |
| 222 | 5'-HO;rG;rC;omeU;rC;fluA;rU;omeU;rU;rA;rC;omeC;rA;fluG; omeC;dG;omeU;omeA;fluA;fluA;rU;rG;omeA;rG;fluCSup-3' | 7728.73 | 344 |
| 223 | 5'-HO;rG;rC;omeU;rC;fluA;rU;omeU;rU;rA;rC;omeC;rA;fluG; omeC;rG;dU;omeA;fluA;fluA;rU;rG;omeA;rG;fluCSup-3' | 7714.70 | 345 |
| 224 | 5'-HO;rG;rC;omeU;rC;fluA;rU;omeU;rU;rA;rC;omeC;rA;fluG; omeC;rG;omeU;dA;fluA;fluA;rU;rG;omeA;rG;fluCSup-3' | 7714.70 | 346 |
| 225 | 5'-HO;rG;rC;omeU;rC;fluA;rU;omeU;rU;rA;rC;omeC;rA;fluG; omeC;rG;omeU;omeA;dA;fluA;rU;rG;omeA;rG;fluCSup-3' | 7726.74 | 347 |
| 226 | 5'-HO;rG;rC;omeU;rC;fluA;rU;omeU;rU;rA;rC;omeC;rA;fluG; omeC;rG;omeU;omeA;fluA;dA;rU;rG;omeA;rG;fluCSup-3' | 7726.74 | 348 |
| 227 | 5'-HO;rG;rC;omeU;rC;fluA;rU;omeU;rU;rA;rC;omeC;rA;fluG; omeC;rG;omeU;omeA;fluA;dU;rG;omeA;rG;fluCSup-3' | 7728.73 | 349 |
| 228 | 5'-HO;rG;rC;omeU;rC;fluA;rU;omeU;rU;rA;rC;omeC;rA;fluG; omeC;rG;omeU;omeA;fluA;rU;dG;omeA;rG;fluCSup-3' | 7728.73 | 350 |
| 229 | 5'-HO;rG;rC;omeU;rC;fluA;rU;omeU;rU;rA;rC;omeC;rA;fluG; omeC;rG;omeU;omeA;fluA;fluA;rU;dA;rG;fluCSup-3' | 7714.70 | 351 |
| 230 | 5'-HO;rG;rC;omeU;rC;fluA;rU;omeU;rU;rA;rC;omeC;rA;fluG; omeC;rG;omeU;omeA;fluA;fluA;rU;rG;omeA;dG;fluCSup-3' | 7728.73 | 352 |
| 231 | 5'-HO;rG;rC;omeU;rC;fluA;rU;omeU;rU;rA;rC;omeC;rA;fluG; omeC;rG;omeU;omeA;fluA;fluA;rU;rG;omeA;rG;dCSup-3' | 7726.74 | 353 |
| 232 | 5'-HO;rG;faraC;omeU;rC;fluA;rU;omeU;rU;rA;rC;omeC;rA;fluG; omeC;rG;omeU;omeA;fluA;fluA;rU;rG;omeA;rG;fluCSup-3' | 7746.72 | 354 |
| 233 | 5'-HO;rG;rC;faraU;rC;fluA;rU;omeU;rU;rA;rC;omeC;rA;fluG; omeC;rG;omeU;omeA;fluA;fluA;rU;rG;omeA;rG;fluCSup-3' | 7732.69 | 355 |
| 234 | 5'-HO;rG;rC;omeU;faraC;fluA;rU;omeU;rU;rA;rC;omeC;rA;fluG; omeC;rG;omeU;omeA;fluA;fluA;rU;rG;omeA;rG;fluCSup-3' | 7746.72 | 356 |
| 235 | 5'-HO;rG;rC;omeU;rC;fluA;faraU;omeU;rU;rA;rC;omeC;rA;fluG; omeC;rG;omeU;omeA;fluA;fluA;rU;rG;omeA;rG;fluCSup-3' | 7746.72 | 357 |
| 236 | 5'-HO;rG;rC;omeU;rC;fluA;rU;faraU;rU;rA;rC;omeC;rA;fluG; omeC;rG;omeU;omeA;fluA;fluA;rU;rG;omeA;rG;fluCSup-3' | 7732.69 | 358 |
| 237 | 5'-HO;rG;rC;omeU;rC;fluA;rU;omeU;faraU;rA;rC;omeC;rA;fluG; omeC;rG;omeU;omeA;fluA;fluA;rU;rG;omeA;rG;fluCSup-3' | 7746.72 | 359 |
| 238 | 5'-HO;rG;rC;omeU;rC;fluA;rU;omeU;rU;rA;faraC;omeC;rA;fluG; omeC;rG;omeU;omeA;fluA;fluA;rU;rG;omeA;rG;fluCSup-3' | 7746.72 | 360 |
| 239 | 5'-HO;rG;rC;omeU;rC;fluA;rU;omeU;rU;rA;rC;faraC;rA;fluG; omeC;rG;omeU;omeA;fluA;fluA;rU;rG;omeA;rG;fluCSup-3' | 7732.69 | 361 |
| 240 | 5'-HO;rG;rC;omeU;rC;fluA;rU;omeU;rU;rA;rC;omeC;faraA;fluG; omeC;rG;omeU;omeA;fluA;fluA;rU;rG;omeA;rG;fluCSup-3' | 7746.72 | 362 |
| 241 | 5'-HO;rG;rC;omeU;rC;fluA;rU;omeU;rU;rA;rC;omeC;rA;fluG; faraC;rG;omeU;omeA;fluA;fluA;rU;rG;omeA;rG;fluCSup-3' | 7732.69 | 363 |
| 242 | 5'-HO;rG;rC;omeU;rC;fluA;rU;omeU;rU;rA;rC;omeC;rA;fluG; omeC;rG;faraU;omeA;fluA;fluA;rU;rG;omeA;rG;fluCSup-3' | 7732.69 | 364 |
| 243 | 5'-HO;rG;rC;omeU;rC;fluA;rU;omeU;rU;rA;rC;omeC;rA;fluG; omeC;rG;omeU;omeA;fluA;fluA;faraU;rG;omeA;rG;fluCSup-3' | 7746.72 | 365 |
| 244 | 5'-HO;rG;omeC;fluU;rC;rA;fluU;rU;rU;rA;fluC;rC;rA;fluG; omeC;rG;fluU;omeA;rA;fluA;rU;rG;rA;rG;omeCSup-3' | 7704.64 | 366 |
| 245 | 5'-HO;rG;omeC;rU;rC;rA;fluU;rU;rU;rA;fluC;fluC;rA;fluG; omeC;rG;fluU;omeA;rA;fluA;rU;rG;rA;rG;omeCSup-3' | 7704.64 | 367 |
| 246 | 5'-HO;rG;omeC;fluU;rC;rA;fluU;fluU;rU;rA;fluC;fluC;rA;fluG; omeC;rG;fluU;omeA;rA;fluA;rU;rG;rA;rG;omeCSup-3' | 7706.63 | 368 |
| 247 | 5'-HO;rG;omeC;rU;rC;rA;fluU;fluU;rU;rA;fluC;rC;rA;fluG; omeC;rG;fluU;omeA;rA;fluA;rU;rG;rA;rG;omeCSup-3' | 7704.64 | 369 |
| 248 | 5'-HO;rG;omeC;fluU;rC;rA;fluU;fluU;rU;rA;fluC;rC;rA;fluG; omeC;rG;fluU;omeA;rA;fluA;rU;rG;rA;rG;omeCSup-3' | 7706.63 | 370 |
| 249 | 5'-HO;rG;omeC;rU;rC;rA;fluU;fluU;rU;rA;fluC;fluC;rA;fluG; omeC;rG;fluU;omeA;rA;fluA;rU;rG;rA;rG;omeCSup-3' | 7706.63 | 371 |

TABLE 5-continued

| Ex | Sequence | MW | SEQ ID No. |
|---|---|---|---|
| 250 | 5'-HO;rG;omeC;fluU;rC;rA;fluU;fluU;rU;rA;fluC;fluC;rA;fluG; omeC;rG;fluU;omeA;rA;fluA;rU;rG;rA;rG;omeCSup-3' | 7708.62 | 372 |
| 251 | 5'-HO;rG;omeC;rU;rC;rA;fluU;rU;rU;rA;fluC;rC;rA;fluG;omeC; omeG;fluU;omeA;rA;fluA;rU;rG;rA;rG;omeCSup-3' | 7716.67 | 373 |
| 252 | 5'-HO;rG;omeC;fluU;rC;rA;fluU;rU;rU;rA;fluC;rC;rA;fluG; omeC;omeG;fluU;omeA;rA;fluA;rU;rG;rA;rG;omeCSup-3' | 7718.67 | 374 |
| 253 | 5'-HO;rG;lna5meC;rU;rC;rA;fluU;rU;rU;rA;fluC;rC;rA;fluG; omeC;rG;fluU;omeA;fluA;omeA;rU;rG;rA;rG;omeCSup-3' | 7728.69 | 375 |
| 254 | 5'-HO;rG;omeC;lna5MeU;rC;rA;fluU;rU;rU;rA;fluC;rC;rA;fluG; omeC;rG;fluU;omeA;fluA;omeA;rU;rG;rA;rG;omeCSup-3' | 7742.71 | 376 |
| 255 | 5'-HO;rG;omeC;rU;rC;lnaA;fluU;rU;rU;rA;fluC;rC;rA;fluG; omeC;rG;fluU;omeA;fluA;omeA;rU;rG;rA;rG;omeCSup-3' | 7728.69 | 377 |
| 256 | 5'-HO;rG;omeC;rU;rC;rA;lna5MeU;rU;rU;rA;fluC;rC;rA;fluG; omeC;rG;fluU;omeA;fluA;omeA;rU;rG;rA;rG;omeCSup-3' | 7740.72 | 378 |
| 257 | 5'-HO;rG;omeC;rU;rC;rA;fluU;lna5MeU;rU;rA;fluC;rC;rA;fluG; omeC;rG;fluU;omeA;fluA;omeA;rU;rG;rA;rG;omeCSup-3' | 7742.71 | 379 |
| 258 | 5'-HO;rG;omeC;rU;rC;rA;fluU;rU;lna5MeU;rA;fluC;rC;rA;fluG; omeC;rG;fluU;omeA;fluA;omeA;rU;rG;rA;rG;omeCSup-3' | 7742.71 | 380 |
| 259 | 5'-HO;rG;omeC;rU;rC;rA;fluU;rU;rU;lnaA;fluC;rC;rA;fluG; omeC;rG;fluU;omeA;fluA;omeA;rU;rG;rA;rG;omeCSup-3' | 7728.69 | 381 |
| 260 | 5'-HO;rG;omeC;rU;rC;rA;fluU;rU;rU;rA;lna5meC;rC;rA;fluG; omeC;rG;fluU;omeA;fluA;omeA;rU;rG;rA;rG;omeCSup-3' | 7740.72 | 382 |
| 261 | 5'-HO;rG;omeC;rU;rC;rA;fluU;rU;rU;rA;fluC;lna5meC;rA;fluG; omeC;rG;fluU;omeA;fluA;omeA;rU;rG;rA;rG;omeCSup-3' | 7742.71 | 383 |
| 262 | 5'-HO;rG;omeC;rU;rC;rA;fluU;rU;rU;rA;fluC;rC;lnaA;fluG; omeC;rG;fluU;omeA;fluA;omeA;rU;rG;rA;rG;omeCSup-3' | 7728.69 | 384 |
| 263 | 5'-HO;rG;omeC;rU;rC;rA;fluU;rU;rU;rA;fluC;rC;rA;lnaG; omeC;rG;fluU;omeA;fluA;omeA;rU;rG;rA;rG;omeCSup-3' | 7726.69 | 385 |
| 264 | 5'-HO;rG;omeC;rU;rC;rA;fluU;rU;rU;rA;fluC;rC;rA;fluG; lna5meC;rG;fluU;omeA;fluA;omeA;rU;rG;rA;rG;omeCSup-3' | 7728.69 | 386 |
| 265 | 5'-HO;rG;omeC;rU;rC;rA;fluU;rU;rU;rA;fluC;rC;rA;fluG; omeC;lnaG;fluU;omeA;fluA;omeA;rU;rG;rA;rG;omeCSup-3' | 7728.69 | 387 |
| 266 | 5'-HO;rG;omeC;rU;rC;rA;fluU;rU;rU;rA;fluC;rC;rA;fluG; omeC;rG;lna5MeU;omeA;fluA;omeA;rU;rG;rA;rG;omeCSup-3' | 7740.72 | 388 |
| 267 | 5'-HO;rG;omeC;rU;rC;rA;fluU;rU;rU;rA;fluC;rC;rA;fluG; omeC;rG;fluU;lnaA;fluA;omeA;rU;rG;rA;rG;omeCSup-3' | 7714.66 | 389 |
| 268 | 5'-HO;rG;omeC;rU;rC;rA;fluU;rU;rU;rA;fluC;rC;rA;fluG; omeC;rG;fluU;omeA;lnaA;omeA;rU;rG;rA;rG;omeCSup-3' | 7726.69 | 390 |
| 269 | 5'-HO;rG;omeC;rU;rC;rA;fluU;rU;rU;rA;fluC;rC;rA;fluG; omeC;rG;fluU;omeA;fluA;lnaA;rU;rG;rA;rG;omeCSup-3' | 7714.66 | 391 |
| 270 | 5'-HO;rG;omeC;rU;rC;rA;fluU;rU;rU;rA;fluC;rC;rA;fluG; omeC;rG;fluU;omeA;fluA;omeA;lna5MeU;rG;rA;rG;omeCSup-3' | 7742.71 | 392 |
| 271 | 5'-HO;rG;omeC;rU;rC;rA;fluU;rU;rU;rA;fluC;rC;rA;fluG; omeC;rG;fluU;omeA;fluA;omeA;rU;lnaG;rA;rG;omeCSup-3' | 7728.69 | 393 |
| 272 | 5'-HO;rG;omeC;rU;rC;rA;fluU;rU;rU;rA;fluC;rC;rA;fluG; omeC;rG;fluU;omeA;fluA;omeA;rU;rG;lnaA;rG;omeCSup-3' | 7728.69 | 394 |
| 273 | 5'-HO;rG;omeC;rU;rC;rA;fluU;rU;rU;rA;fluC;rC;rA;fluG; omeC;rG;fluU;omeA;fluA;omeA;rU;rG;rA;lnaG;omeCSup-3' | 7728.69 | 395 |
| 274 | 5'-HO;rG;25C;rU;rC;rA;fluU;rU;rU;rA;fluC;rC;rA;fluG; omeC;rG;fluU;omeA;fluA;omeA;rU;rG;rA;rG;omeCSup-3' | 7702.65 | 396 |
| 275 | 5'-HO;rG;omeC;25U;rC;rA;fluU;rU;rU;rA;fluC;rC;rA;fluG; omeC;rG;fluU;omeA;fluA;omeA;rU;rG;rA;rG;omeCSup-3' | 7716.67 | 397 |
| 276 | 5'-HO;rG;omeC;rU;25C;rA;fluU;rU;rU;rA;fluC;rC;rA;fluG; omeC;rG;fluU;omeA;fluA;omeA;rU;rG;rA;rG;omeCSup-3' | 7716.68 | 398 |
| 277 | 5'-HO;rG;omeC;rU;rC;25A;fluU;rU;rU;rA;fluC;rC;rA;fluG; omeC;rG;fluU;omeA;fluA;omeA;rU;rG;rA;rG;omeCSup-3' | 7716.67 | 399 |
| 278 | 5'-HO;rG;omeC;rU;rC;rA;25U;rU;rU;rA;fluC;rC;rA;fluG;omeC; rG;fluU;omeA;fluA;omeA;rU;rG;rA;rG;omeCSup-3' | 7714.68 | 400 |
| 279 | 5'-HO;rG;omeC;rU;rC;rA;fluU;25U;rU;rA;fluC;rC;rA;fluG; omeC;rG;fluU;omeA;fluA;omeA;rU;rG;rA;rG;omeCSup-3' | 7716.67 | 401 |
| 280 | 5'-HO;rG;omeC;rU;rC;rA;fluU;rU;25U;rA;fluC;rC;rA;fluG; omeC;rG;fluU;omeA;fluA;omeA;rU;rG;rA;rG;omeCSup-3' | 7716.67 | 402 |
| 281 | 5'-HO;rG;omeC;rU;rC;rA;fluU;rU;rU;25A;fluC;rC;rA;fluG; omeC;rG;fluU;omeA;fluA;omeA;rU;rG;rA;rG;omeCSup-3' | 7716.67 | 403 |
| 282 | 5'-HO;rG;omeC;rU;rC;rA;fluU;rU;rU;rA;25C;rC;rA;fluG;omeC; rG;fluU;omeA;fluA;omeA;rU;rG;rA;rG;omeCSup-3' | 7714.69 | 404 |
| 283 | 5'-HO;rG;omeC;rU;rC;rA;fluU;rU;rU;rA;fluC;25C;rA;fluG; omeC;rG;fluU;omeA;fluA;omeA;rU;rG;rA;rG;omeCSup-3' | 7716.68 | 405 |
| 284 | 5'-HO;rG;omeC;rU;rC;rA;fluU;rU;rU;rA;fluC;rC;25A;fluG; omeC;rG;fluU;omeA;fluA;omeA;rU;rG;rA;rG;omeCSup-3' | 7716.67 | 406 |
| 285 | 5'-HO;rG;omeC;rU;rC;rA;fluU;rU;rU;rA;fluC;rC;rA;25G;omeC; rG;fluU;omeA;fluA;omeA;rU;rG;rA;rG;omeCSup-3' | 7714.68 | 407 |
| 286 | 5'-HO;rG;omeC;rU;rC;rA;fluU;rU;rU;rA;fluC;rC;rA;fluG;25C; rG;fluU;omeA;fluA;omeA;rU;rG;rA;rG;omeCSup-3' | 7702.65 | 408 |
| 287 | 5'-HO;rG;omeC;rU;rC;rA;fluU;rU;rU;rA;fluC;rC;rA;fluG; omeC;rG;25U;omeA;fluA;omeA;rU;rG;rA;rG;omeCSup-3' | 7714.68 | 409 |

TABLE 5-continued

| Ex | Sequence | MW | SEQ ID No. |
|---|---|---|---|
| 288 | 5'-HO;rG;omeC;rU;rC;rA;fluU;rU;rU;rA;fluC;rC;rA;fluG;<br>omeC;rG;fluU;25A;fluA;omeA;rU;rG;rA;rG;omeCSup-3' | 7702.65 | 410 |
| 289 | 5'-HO;rG;omeC;rU;rC;rA;fluU;rU;rU;rA;fluC;rC;rA;fluG;<br>omeC;rG;fluU;omeA;25A;omeA;rU;rG;rA;rG;omeCSup-3' | 7714.68 | 411 |
| 290 | 5'-HO;rG;omeC;rU;rC;rA;fluU;rU;rU;rA;fluC;rC;rA;fluG;<br>omeC;rG;fluU;omeA;fluA;25A;rU;rG;rA;rG;omeCSup-3' | 7702.65 | 412 |
| 291 | 5'-HO;rG;omeC;rU;rC;rA;fluU;rU;rU;rA;fluC;rC;rA;fluG;<br>omeC;rG;fluU;omeA;fluA;omeA;25U;rG;rA;rG;omeCSup-3' | 7716.67 | 413 |
| 292 | 5'-HO;rG;omeC;rU;rC;rA;fluU;rU;rU;rA;fluC;rC;rA;fluG;<br>omeC;rG;fluU;omeA;fluA;omeA;rU;rG;25A;rG;omeCSup-3' | 7716.67 | 414 |
| 293 | 5'-HO;rG;lna5meC;omeU;rC;fluA;rU;omeU;rU;rA;rC;omeC;rA;fluG;<br>omeC;rG;omeU;omeA;fluA;fluA;rU;rG;omeA;rG;fluCSup-3' | 7770.77 | 415 |
| 294 | 5'-HO;rG;rC;lna5MeU;rC;fluA;rU;omeU;rU;rA;rC;omeC;rA;fluG;<br>omeC;rG;omeU;omeA;fluA;fluA;rU;rG;omeA;rG;fluCSup-3' | 7756.74 | 416 |
| 295 | 5'-HO;rG;rC;omeU;lna5meC;fluA;rU;omeU;rU;rA;rC;omeC;rA;fluG;<br>omeC;rG;omeU;omeA;fluA;fluA;rU;rG;omeA;rG;fluCSup-3' | 7770.77 | 417 |
| 296 | 5'-HO;rG;rC;omeU;rC;lnaA;rU;omeU;rU;rA;rC;omeC;rA;fluG;<br>omeC;rG;omeU;omeA;fluA;fluA;rU;rG;omeA;rG;fluCSup-3' | 7754.75 | 418 |
| 297 | 5'-HO;rG;rC;omeU;rC;fluA;lna5MeU;omeU;rU;rA;rC;omeC;rA;fluG;<br>omeC;rG;omeU;omeA;fluA;fluA;rU;rG;omeA;rG;fluCSup-3' | 7770.77 | 419 |
| 298 | 5'-HO;rG;rC;omeU;rC;fluA;rU;lna5MeU;rU;rA;rC;omeC;rA;fluG;<br>omeC;rG;omeU;omeA;fluA;fluA;rU;rG;omeA;rG;fluCSup-3' | 7756.74 | 420 |
| 299 | 5'-HO;rG;rC;omeU;rC;fluA;rU;omeU;lna5MeU;rA;rC;omeC;rA;fluG;<br>omeC;rG;omeU;omeA;fluA;fluA;rU;rG;omeA;rG;fluCSup-3' | 7770.77 | 421 |
| 300 | 5'-HO;rG;rC;omeU;rC;fluA;rU;omeU;rU;lnaA;rC;omeC;rA;fluG;<br>omeC;rG;omeU;omeA;fluA;fluA;rU;rG;omeA;rG;fluCSup-3' | 7756.74 | 422 |
| 301 | 5'-HO;rG;rC;omeU;rC;fluA;rU;omeU;rU;rA;lna5meC;omeC;rA;fluG;<br>omeC;rG;omeU;omeA;fluA;fluA;rU;rG;omeA;rG;fluCSup-3' | 7770.77 | 423 |
| 302 | 5'-HO;rG;rC;omeU;rC;fluA;rU;omeU;rU;rA;rC;lna5meC;rA;fluG;<br>omeC;rG;omeU;omeA;fluA;fluA;rU;rG;omeA;rG;fluCSup-3' | 7756.74 | 424 |
| 303 | 5'-HO;rG;rC;omeU;rC;fluA;rU;omeU;rU;rA;rC;omeC;lnaA;fluG;<br>omeC;rG;omeU;omeA;fluA;fluA;rU;rG;omeA;rG;fluCSup-3' | 7756.74 | 425 |
| 304 | 5'-HO;rG;rC;omeU;rC;fluA;rU;omeU;rU;rA;rC;omeC;rA;lnaG;<br>omeC;rG;omeU;omeA;fluA;fluA;rU;rG;omeA;rG;fluCSup-3' | 7754.75 | 426 |
| 305 | 5'-HO;rG;rC;omeU;rC;fluA;rU;omeU;rU;rA;rC;omeC;rA;fluG;<br>omeC;lnaG;omeU;omeA;fluA;fluA;rU;rG;omeA;rG;fluCSup-3' | 7756.74 | 427 |
| 306 | 5'-HO;rG;rC;omeU;rC;fluA;rU;omeU;rU;rA;rC;omeC;rA;fluG;<br>omeC;lna5MeU;omeA;fluA;fluA;rU;rG;omeA;rG;fluCSup-3' | 7756.74 | 428 |
| 307 | 5'-HO;rG;rC;omeU;rC;fluA;rU;omeU;rU;rA;rC;omeC;rA;fluG;<br>omeC;rG;omeU;lnaA;fluA;fluA;rU;rG;omeA;rG;fluCSup-3' | 7742.71 | 429 |
| 308 | 5'-HO;rG;rC;omeU;rC;fluA;rU;omeU;rU;rA;rC;omeC;rA;fluG;<br>omeC;rG;omeU;omeA;lnaA;fluA;rU;rG;omeA;rG;fluCSup-3' | 7754.75 | 430 |
| 309 | 5'-HO;rG;rC;omeU;rC;fluA;rU;omeU;rU;rA;rC;omeC;rA;fluG;<br>omeC;rG;omeU;omeA;fluA;lnaA;rU;rG;omeA;rG;fluCSup-3' | 7754.75 | 431 |
| 310 | 5'-HO;rG;rC;omeU;rC;fluA;rU;omeU;rU;rA;rC;omeC;rA;fluG;<br>omeC;rG;omeU;omeA;fluA;fluA;lna5MeU;rG;omeA;rG;fluCSup-3' | 7770.77 | 432 |
| 311 | 5'-HO;rG;rC;omeU;rC;fluA;rU;omeU;rU;rA;rC;omeC;rA;fluG;<br>omeC;rG;omeU;omeA;fluA;fluA;rU;lnaG;omeA;rG;fluCSup-3' | 7756.74 | 433 |
| 312 | 5'-HO;rG;rC;omeU;rC;fluA;rU;omeU;rU;rA;rC;omeC;rA;fluG;<br>omeC;rG;omeU;omeA;fluA;fluA;rU;rG;lnaA;rG;fluCSup-3' | 7742.71 | 434 |
| 313 | 5'-HO;rG;rC;omeU;rC;fluA;rU;omeU;rU;rA;rC;omeC;rA;fluG;<br>omeC;rG;omeU;omeA;fluA;fluA;rU;rG;omeA;lnaG;fluCSup-3' | 7756.74 | 435 |
| 314 | 5'-HO;rG;25C;omeU;rC;fluA;rU;omeU;rU;rA;rC;omeC;rA;fluG;<br>omeC;rG;omeU;omeA;fluA;fluA;rU;rG;omeA;rG;fluCSup-3' | 7744.73 | 436 |
| 315 | 5'-HO;rG;rC;25U;rC;fluA;rU;omeU;rU;rA;rC;omeC;rA;fluG;<br>omeC;rG;omeU;omeA;fluA;fluA;rU;rG;omeA;rG;fluCSup-3' | 7730.70 | 437 |
| 316 | 5'-HO;rG;rC;omeU;25C;fluA;rU;omeU;rU;rA;rC;omeC;rA;fluG;<br>omeC;rG;omeU;omeA;fluA;fluA;rU;rG;omeA;rG;fluCSup-3' | 7744.73 | 438 |
| 317 | 5'-HO;rG;rC;omeU;rC;25A;rU;omeU;rU;rA;rC;omeC;rA;fluG;<br>omeC;rG;omeU;omeA;fluA;fluA;rU;rG;omeA;rG;fluCSup-3' | 7742.74 | 439 |
| 318 | 5'-HO;rG;rC;omeU;rC;fluA;25U;omeU;rU;rA;rC;omeC;rA;fluG;<br>omeC;rG;omeU;omeA;fluA;fluA;rU;rG;omeA;rG;fluCSup-3' | 7744.73 | 440 |
| 319 | 5'-HO;rG;rC;omeU;rC;fluA;rU;25U;rU;rA;rC;omeC;rA;fluG;<br>omeC;rG;omeU;omeA;fluA;fluA;rU;rG;omeA;rG;fluCSup-3' | 7730.70 | 441 |
| 320 | 5'-HO;rG;rC;omeU;rC;fluA;rU;omeU;25U;rA;rC;omeC;rA;fluG;<br>omeC;rG;omeU;omeA;fluA;fluA;rU;rG;omeA;rG;fluCSup-3' | 7744.73 | 442 |
| 321 | 5'-HO;rG;rC;omeU;rC;fluA;rU;omeU;rU;25A;rC;omeC;rA;fluG;<br>omeC;rG;omeU;omeA;fluA;fluA;rU;rG;omeA;rG;fluCSup-3' | 7744.73 | 443 |
| 322 | 5'-HO;rG;rC;omeU;rC;fluA;rU;omeU;rU;rA;25C;omeC;rA;fluG;<br>omeC;rG;omeU;omeA;fluA;fluA;rU;rG;omeA;rG;fluCSup-3' | 7744.73 | 444 |
| 323 | 5'-HO;rG;rC;omeU;rC;fluA;rU;omeU;rU;rA;rC;25C;rA;fluG;<br>omeC;rG;omeU;omeA;fluA;fluA;rU;rG;omeA;rG;fluCSup-3' | 7730.71 | 445 |
| 324 | 5'-HO;rG;rC;omeU;rC;fluA;rU;omeU;rU;rA;rC;omeC;25A;fluG;<br>omeC;rG;omeU;omeA;fluA;fluA;rU;rG;omeA;rG;fluCSup-3' | 7744.73 | 446 |
| 325 | 5'-HO;rG;rC;omeU;rC;fluA;rU;omeU;rU;rA;rC;omeC;rA;25G;<br>omeC;rG;omeU;omeA;fluA;fluA;rU;rG;omeA;rG;fluCSup-3' | 7742.74 | 447 |

TABLE 5-continued

| Ex | Sequence | MW | SEQ ID No. |
|---|---|---|---|
| 326 | 5'-HO;rG;rC;omeU;rC;fluA;rU;omeU;rU;rA;rC;omeC;rA;fluG; 25C;rG;omeU;omeA;fluA;fluA;rU;rG;omeA;rG;fluCSup-3' | 7730.71 | 448 |
| 327 | 5'-HO;rG;rC;omeU;rC;fluA;rU;omeU;rU;rA;rC;omeC;rA;fluG; omeC;25G;omeU;omeA;fluA;fluA;rU;rG;omeA;rG;fluCSup-3' | 7744.73 | 449 |
| 328 | 5'-HO;rG;rC;omeU;rC;fluA;rU;omeU;rU;rA;rC;omeC;rA;fluG; omeC;25U;omeU;omeA;fluA;fluA;rU;rG;omeA;rG;fluCSup-3' | 7730.70 | 450 |
| 329 | 5'-HO;rG;rC;omeU;rC;fluA;rU;omeU;rU;rA;rC;omeC;rA;fluG; omeC;rG;omeU;25A;fluA;fluA;rU;rG;omeA;rG;fluCSup-3' | 7730.70 | 451 |
| 330 | 5'-HO;rG;rC;omeU;rC;fluA;rU;omeU;rU;rA;rC;omeC;rA;fluG; omeC;rG;omeU;omeA;25A;fluA;rU;rG;omeA;rG;fluCSup-3' | 7742.74 | 452 |
| 331 | 5'-HO;rG;rC;omeU;rC;fluA;rU;omeU;rU;rA;rC;omeC;rA;fluG; omeC;rG;omeU;omeA;fluA;25A;rU;rG;omeA;rG;fluCSup-3' | 7742.74 | 453 |
| 332 | 5'-HO;rG;rC;omeU;rC;fluA;rU;omeU;rU;rA;rC;omeC;rA;fluG; omeC;rG;omeU;omeA;fluA;fluA;25U;rG;omeA;rG;fluCSup-3' | 7744.73 | 454 |
| 333 | 5'-HO;rG;rC;omeU;rC;fluA;rU;omeU;rU;rA;rC;omeC;rA;fluG; omeC;rG;omeU;omeA;fluA;fluA;rU;rG;25A;rG;fluCSup-3' | 7730.70 | 455 |
| 334 | 5'-HO;rG;rC;omeU;rC;fluA;fluU;omeU;rU;rA;rC;omeC;rA;fluG; omeC;rG;omeU;omeA;rA;fluA;rU;rG;omeA;rG;omeCSup-3' | 7756.76 | 456 |
| 335 | 5'-HO;rG;rC;omeU;rC;fluA;rU;omeU;rU;rA;fluC;omeC;rA;fluG; omeC;rG;omeU;omeA;rA;fluA;rU;rG;omeA;rG;omeCSup-3' | 7756.76 | 457 |
| 336 | 5'-HO;rG;rC;omeU;rC;fluA;fluU;omeU;rU;rA;fluC;omeC;rA;fluG; omeC;rG;omeU;omeA;rA;fluA;rU;rG;omeA;rG;omeCSup-3' | 7758.75 | 458 |
| 337 | 5'-HO;rG;omeC;rU;rC;r2AP;fluU;rU;rU;rA;fluC;rC;rA;fluG; omeC;rG;fluU;omeA;fluA;omeA;rU;rG;rA;rG;omeCSup-3' | 7716.68 | 2 |
| 338 | 5'-HO;rG;omeC;rU;rC;rA;fluU;rU;rU;rA;fluC;rC;r2AP;fluG; omeC;rG;fluU;omeA;fluA;omeA;rU;rG;rA;rG;omeCSup-3' | 7716.68 | 3 |
| 339 | 5'-HO;rG;omeC;rU;rC;rA;fluU;rU;rU;rA;fluC;rC;rA;fluG; omeC;rG;fluU;r2AP;fluA;omeA;rU;rG;rA;rG;omeCSup-3' | 7702.65 | 4 |
| 340 | 5'-HO;rG;omeC;rU;rC;rA;fluU;rU;rU;rA;fluC;rC;rA;fluG; omeC;rG;fluU;omeA;r2AP;omeA;rU;rG;rA;rG;omeCSup-3' | 7714.68 | 5 |
| 341 | 5'-HO;rG;omeC;rU;rC;rA;fluU;rU;rU;rA;fluC;rC;rA;fluG; omeC;rG;fluU;omeA;fluA;r2AP;rU;rG;rA;rG;omeCSup-3' | 7702.65 | 6 |
| 342 | 5'-HO;rG;omeC;rU;rC;moeA;fluU;rU;rU;rA;fluC;rC;rA;fluG; omeC;rG;fluU;omeA;fluA;omeA;rU;rG;rA;rG;omeCSup-3' | 7774.75 | 459 |
| 343 | 5'-HO;rG;omeC;rU;rC;rA;fluU;rU;rU;rA;moeC;fluC;rC;rA;fluG; omeC;rG;fluU;omeA;fluA;omeA;rU;rG;rA;rG;omeCSup-3' | 7774.75 | 460 |
| 344 | 5'-HO;rG;omeC;rU;rC;rA;fluU;rU;rU;rA;fluC;rC;moeA;fluG; omeC;rG;fluU;omeA;fluA;omeA;rU;rG;rA;rG;omeCSup-3' | 7774.75 | 461 |
| 345 | 5'-HO;rG;omeC;rU;rC;rA;fluU;rU;rU;rA;fluC;rC;rA;moeG; omeC;rG;fluU;omeA;fluA;omeA;rU;rG;rA;rG;omeCSup-3' | 7772.76 | 462 |
| 346 | 5'-HO;rG;omeC;rU;rC;rA;fluU;rU;rU;rA;fluC;rC;rA;fluG; omeC;moeG;fluU;omeA;fluA;omeA;rU;rG;rA;rG;omeCSup-3' | 7774.75 | 463 |
| 347 | 5'-HO;rG;omeC;rU;rC;rA;fluU;rU;rU;rA;fluC;rC;rA;fluG;omeC; rG;fluU;moeA;fluA;omeA;rU;rG;rA;rG;omeCSup-3' | 7760.73 | 464 |
| 348 | 5'-HO;rG;omeC;rU;rC;rA;fluU;rU;rU;rA;fluC;rC;rA;fluG; omeC;rG;fluU;omeA;moeA;omeA;rU;rG;rA;rG;omeCSup-3' | 7772.76 | 465 |
| 349 | 5'-HO;rG;omeC;rU;rC;rA;fluU;rU;rU;rA;fluC;rC;rA;fluG; omeC;rG;fluU;omeA;fluA;moeA;rU;rG;rA;rG;omeCSup-3' | 7760.73 | 466 |
| 350 | 5'-HO;rG;omeC;rU;rC;rA;fluU;rU;rU;rA;fluC;rC;rA;fluG; omeC;rG;fluU;omeA;fluA;omeA;rU;moeG;rA;rG;omeCSup-3' | 7774.75 | 467 |
| 351 | 5'-HO;rG;omeC;rU;rC;rA;fluU;rU;rU;rA;fluC;rC;rA;fluG; omeC;rG;fluU;omeA;fluA;omeA;rU;rG;moeA;rG;omeCSup-3' | 7774.75 | 468 |
| 352 | 5'-HO;rG;omeC;rU;rC;rA;fluU;rU;rU;rA;fluC;rC;rA;fluG; omeC;rG;fluU;omeA;fluA;omeA;rU;rG;rA;moeG;omeCSup-3' | 7774.75 | 469 |
| 353 | 5'-HO;rG;rC;omeU;rC;r2AP;rU;omeU;rU;rA;rC;omeC;rA;fluG; omeC;rG;omeU;omeA;fluA;fluA;rU;rG;omeA;rG;fluCSup-3' | 7742.74 | 7 |
| 354 | 5'-HO;rG;rC;omeU;rC;fluA;rU;omeU;rU;r2AP;rC;omeC;rA;fluG; omeC;rG;omeU;omeA;fluA;fluA;rU;rG;omeA;rG;fluCSup-3' | 7744.73 | 8 |
| 355 | 5'-HO;rG;rC;omeU;rC;fluA;rU;omeU;rU;rA;rC;omeC;r2AP;fluG; omeC;rG;omeU;omeA;fluA;fluA;rU;rG;omeA;rG;fluCSup-3' | 7744.73 | 9 |
| 356 | 5'-HO;rG;rC;omeU;rC;fluA;rU;omeU;rU;rA;rC;omeC;rA;fluG; omeC;rG;omeU;r2AP;fluA;fluA;rU;rG;omeA;rG;fluCSup-3' | 7730.70 | 10 |
| 357 | 5'-HO;rG;rC;omeU;rC;fluA;rU;omeU;rU;rA;rC;omeC;rA;fluG; omeC;rG;omeU;omeA;r2AP;fluA;rU;rG;omeA;rG;fluCSup-3' | 7742.74 | 11 |
| 358 | 5'-HO;rG;rC;omeU;rC;fluA;rU;omeU;rU;rA;rC;omeC;rA;fluG; omeC;rG;omeU;omeA;fluA;r2AP;rU;rG;omeA;rG;fluCSup-3' | 7742.74 | 12 |
| 359 | 5'-HO;rG;rC;omeU;rC;fluA;rU;omeU;rU;rA;rC;omeC;rA;fluG; omeC;rG;omeU;omeA;fluA;fluA;rU;rG;r2AP;rG;fluCSup-3' | 7730.70 | 13 |
| 360 | 5'-HO;rG;rC;omeU;rC;moeA;rU;omeU;rU;rA;rC;omeC;rA;fluG; omeC;rG;omeU;omeA;fluA;fluA;rU;rG;omeA;rG;fluCSup-3' | 7800.82 | 470 |
| 361 | 5'-HO;rG;rC;omeU;rC;fluA;rU;omeU;rU;moeA;rC;omeC;rA;fluG; omeC;rG;omeU;omeA;fluA;fluA;rU;rG;omeA;rG;fluCSup-3' | 7802.81 | 471 |
| 362 | 5'-HO;rG;rC;omeU;rC;fluA;rU;omeU;rU;rA;rC;omeC;moeA;fluG; omeC;rG;omeU;omeA;fluA;fluA;rU;rG;omeA;rG;fluCSup-3' | 7802.81 | 472 |
| 363 | 5'-HO;rG;rC;omeU;rC;fluA;rU;omeU;rU;rA;rC;omeC;rA;moeG; omeC;rG;omeU;omeA;fluA;fluA;rU;rG;omeA;rG;fluCSup-3' | 7800.82 | 473 |

TABLE 5-continued

| Ex | Sequence | MW | SEQ ID No. |
|---|---|---|---|
| 364 | 5'-HO;rG;rC;omeU;rC;fluA;rU;omeU;rU;rA;rC;omeC;rA;fluG; omeC;moeG;omeU;omeA;fluA;fluA;rU;rG;omeA;rG;fluCSup-3' | 7802.81 | 474 |
| 365 | 5'-HO;rG;rC;omeU;rC;fluA;rU;omeU;rU;rA;rC;omeC;rA;fluG; omeC;rG;omeU;moeA;fluA;fluA;rU;rG;omeA;rG;fluCSup-3' | 7788.78 | 475 |
| 366 | 5'-HO;rG;rC;omeU;rC;fluA;rU;omeU;rU;rA;rC;omeC;rA;fluG; omeC;rG;omeU;omeA;moeA;fluA;rU;rG;omeA;rG;fluCSup-3' | 7800.82 | 476 |
| 367 | 5'-HO;rG;rC;omeU;rC;fluA;rU;omeU;rU;rA;rC;omeC;rA;fluG; omeC;rG;omeU;omeA;fluA;moeA;rU;rG;omeA;rG;fluCSup-3' | 7800.82 | 477 |
| 368 | 5'-HO;rG;rC;omeU;rC;fluA;rU;omeU;rU;rA;rC;omeC;rA;fluG; omeC;rG;omeU;omeA;fluA;fluA;rU;moeG;omeA;rG;fluCSup-3' | 7802.81 | 478 |
| 369 | 5'-HO;rG;rC;omeU;rC;fluA;rU;omeU;rU;rA;rC;omeC;rA;fluG; omeC;rG;omeU;omeA;fluA;fluA;rU;rG;moeA;rG;fluCSup-3' | 7788.78 | 479 |
| 370 | 5'-HO;rG;rC;omeU;rC;fluA;rU;omeU;rU;rA;rC;omeC;rA;fluG; omeC;rG;omeU;omeA;fluA;fluA;rU;rG;omeA;moeG;fluCSup-3' | 7802.81 | 480 |
| 371 | 5'-HO;rG;omeC;fluU;rC;rA;fluU;fluU;rU;rA;fluC;rC;rA;fluG; omeC;omeG;fluU;omeA;rA;fluA;rU;rG;rA;rG;omeCSup-3' | 7720.66 | 481 |
| 372 | 5'-HO;rG;omeC;rU;rC;rA;fluU;fluU;rU;rA;fluC;fluC;rA;fluG; omeC;omeG;fluU;omeA;rA;fluA;rU;rG;rA;rG;omeCSup-3' | 7720.66 | 482 |
| 373 | 5'-HO;rG;omeC;fluU;rC;rA;fluU;fluU;rU;rA;fluC;fluC;rA;fluG; omeC;omeG;fluU;omeA;rA;fluA;rU;rG;rA;rG;omeCSup-3' | 7722.65 | 483 |
| 374 | 5'-HO;rG;moe5meC;rU;rC;rA;fluU;rU;rU;rA;fluC;rC;rA;fluG; omeC;rG;fluU;omeA;fluA;omeA;rU;rG;rA;rG;omeCSup-3' | 7774.75 | 484 |
| 375 | 5'-HO;rG;omeC;rU;rC;rA;fluU;rU;rU;rA;fluC;rC;rA;fluG;moe5meC rG;fluU;omeA;fluA;omeA;rU;rG;rA;rG;omeCSup-3'; | 7774.75 | 485 |
| 376 | 5'-HO;rG;omeC;rU;rC;rA;moe-5-MeU;rU;rU;rA;fluC;rC;rA;fluG; omeC;rG;fluU;omeA;fluA;omeA;rU;rG;rA;rG;omeCSup-3' | 7786.79 | 486 |
| 377 | 5'-HO;rG;omeC;rU;rC;rA;fluU;rU;rU;rA;moe5meC;rC;rA;fluG; omeC;rG;fluU;omeA;fluA;omeA;rU;rG;rA;rG;omeCSup-3' | 7786.79 | 487 |
| 378 | 5'-HO;rG;omeC;rU;rC;rA;fluU;rU;rU;rA;fluC;rC;rA;fluG; omeC;rG;moe5MeU;omeA;fluA;omeA;rU;rG;rA;rG;omeCSup-3' | 7786.79 | 488 |
| 379 | 5'-HO;rG;omeC;moe5MeU;rC;rA;fluU;rU;rU;rA;fluC;rC;rA;fluG; omeC;rG;fluU;omeA;fluA;omeA;rU;rG;rA;rG;omeCSup-3' | 7788.78 | 489 |
| 380 | 5'-HO;rG;omeC;rU;moe5meC;rA;fluU;rU;rU;rA;fluC;rC;rA; fluG;omeC;rG;fluU;omeA;fluA;omeA;rU;rG;rA;rG;omeCSup-3' | 7788.78 | 490 |
| 381 | 5'-HO;rG;omeC;rU;rC;rA;fluU;moe5MeU;rU;rA;fluC;rC;rA;fluG; omeC;rG;fluU;omeA;fluA;omeA;rU;rG;rA;rG;omeCSup-3' | 7788.78 | 491 |
| 382 | 5'-HO;rG;omeC;rU;rC;rA;fluU;rU;moe5MeU;rA;fluC;rC;rA;fluG; omeC;rG;fluU;omeA;fluA;omeA;rU;rG;rA;rG;omeCSup-3' | 7788.78 | 492 |
| 383 | 5'-HO;rG;omeC;rU;rC;rA;fluU;rU;rU;rA;fluC;moe5meC;rA; fluG;omeC;rG;fluU;omeA;fluA;omeA;rU;rG;rA;rG;omeCSup-3' | 7788.78 | 493 |
| 384 | 5'-HO;rG;omeC;rU;rC;rA;fluU;rU;rU;rA;fluC;rC;rA;fluG; omeC;rG;fluU;omeA;fluA;omeA;moe5MeU;rG;rA;rG;omeCSup-3' | 7788.78 | 494 |
| 385 | 5'-HO;rG;rC;moe5meC;rC;fluA;rU;omeU;rU;rA;rC;omeC;rA;fluG; omeC;rG;omeU;omeA;fluA;fluA;rU;rG;omeA;rG;fluCSup-3' | 7802.81 | 495 |
| 386 | 5'-HO;rG;rC;omeU;rC;fluA;rU;moe5MeU;rU;rA;rC;omeC;rA;fluG; omeC;rG;omeU;omeA;fluA;fluA;rU;rG;omeA;rG;fluCSup-3' | 7802.81 | 496 |
| 387 | 5'-HO;rG;rC;omeU;rC;fluA;rU;omeU;rU;rA;rC;moe5meC;rA; fluG;omeC;rG;omeU;omeA;fluA;fluA;rU;rG;omeA;rG;fluCSup-3' | 7802.81 | 497 |
| 388 | 5'-HO;rG;rC;omeU;rC;fluA;rU;omeU;rU;rA;rC;omeC;rA;fluG; moe5meC;rG;omeU;omeA;fluA;fluA;rU;rG;omeA;rG;fluCSup-3' | 7802.81 | 498 |
| 389 | 5'-HO;rG;rC;omeU;rC;fluA;rU;omeU;rU;rA;rC;omeC;rA;fluG; omeC;rG;moe5MeU;omeA;fluA;fluA;rU;rG;omeA;rG;fluCSup-3' | 7802.81 | 499 |
| 390 | 5'-HO;rG;moe5meC;omeU;rC;fluA;rU;omeU;rU;rA;rC;omeC;rA;fluG; omeC;rG;omeU;omeA;fluA;fluA;rU;rG;omeA;rG;fluCSup-3' | 7816.83 | 500 |
| 391 | 5'-HO;rG;rC;omeU;moe5meC;fluA;rU;omeU;rU;rA;rC;omeC;rA;fluG; omeC;rG;omeU;omeA;fluA;fluA;rU;rG;omeA;rG;fluCSup-3' | 7816.83 | 501 |
| 392 | 5'-HO;rG;rC;omeU;rC;fluA;moe5MeU;omeU;rU;rA;rC;omeC;rA;fluG; omeC;rG;omeU;omeA;fluA;fluA;rU;rG;omeA;rG;fluCSup-3' | 7816.83 | 502 |
| 393 | 5'-HO;rG;rC;omeU;rC;fluA;rU;omeU;moe5MeU;rA;rC;omeC;rA;fluG; omeC;rG;omeU;omeA;fluA;fluA;rU;rG;omeA;rG;fluCSup-3' | 7816.83 | 503 |
| 394 | 5'-HO;rG;rC;omeU;rC;fluA;rU;omeU;rU;rA;moe5meC;omeC;rA;fluG; omeC;rG;omeU;omeA;fluA;fluA;rU;rG;omeA;rG;fluCSup-3' | 7816.83 | 504 |
| 395 | 5'-HO;rG;rC;omeU;rC;fluA;rU;omeU;rU;rA;rC;omeC;rA;fluG; omeC;rG;omeU;omeA;fluA;fluA;moe5MeU;rG;omeA;rG;fluCSup-3' | 7816.83 | 505 |
| 396 | 5'-HO;rG;omeC;rU;rC;rA;fluU;rU;rUs;rA;fluC;rC;rAs;fluG; omeC;rG;fluU;omeA;fluA;omeA;rUs;rG;rAs;rGs;omeCSup-3' | 7797.00 | 506 |
| 397 | 5'-HO;rG;rC;rUs;fluC;omeA;fluU;rU;rUs;fluA;omeC;omeC;rAs;omeG; omeC;omeG;omeU;rA;fluA;rA;omeUs;fluG;omeAs;rGs;fluCSup-3' | 7873.16 | 507 |
| 398 | 5'-HO;rG;omeC;rU;rC;rI;fluU;rU;rUs;rA;fluC;rC;rAs;fluG; omeC;rG;fluU;omeA;fluA;omeA;rUs;rG;rAs;rGs;omeCSup-3' | 7797.99 | 508 |
| 399 | 5'-HO;rG;omeC;rU;rC;rA;fluU;rU;rUs;rI;fluC;rC;rAs;fluG; omeC;rG;fluU;omeA;fluA;omeA;rUs;rG;rAs;rGs;omeCSup-3' | 7797.99 | 509 |
| 400 | 5'-HO;rG;omeC;rU;rC;rA;fluU;rU;rUs;rA;fluC;rC;rIs;fluG; omeC;rG;fluU;omeA;fluA;omeA;rUs;rG;rAs;rGs;omeCSup-3' | 7797.99 | 510 |
| 401 | 5'-HO;rG;omeC;rU;rC;rA;fluU;rU;rUs;rA;fluC;rC;rAs;fluG; omeC;rG;fluU;rI;fluA;omeA;rUs;rG;rAs;rGs;omeCSup-3' | 7783.96 | 511 |

TABLE 5-continued

| Ex | Sequence | MW | SEQ ID No. |
|---|---|---|---|
| 402 | 5'-HO;rG;omeC;rU;rC;rA;fluU;rU;rUs;rA;fluC;rC;rAs;fluG; omeC;rG;fluU;omeA;rI;omeA;rUs;rG;rAs;rGs;omeCSup-3' | 7796.00 | 512 |
| 403 | 5'-HO;rG;omeC;rU;rC;rA;fluU;rU;rUs;rA;fluC;rC;rAs;fluG; omeC;rG;fluU;omeA;fluA;rI;rUs;rG;rAs;rGs;omeCSup-3' | 7783.96 | 513 |
| 404 | 5'-HO;rG;omeC;rU;rC;rA;fluU;rU;rUs;rA;fluC;rC;rAs;fluG; omeC;rG;fluU;omeA;fluA;omeA;rUs;rG;rIs;rGs;omeCSup-3' | 7797.99 | 514 |
| 405 | 5'-HO;rG;omeC;d5propC;rU;rC;rA;fluU;rU;rUs;rA;fluC;rC;rAs;fluG; omeC;rG;fluU;omeA;fluA;omeA;rUs;rG;rAs;rGs;omeCSup-3' | 7805.03 | 14 |
| 406 | 5'-HO;rG;omeC;d5propU;rC;rA;fluU;rU;rUs;rA;fluC;rC;rAs;fluG; omeC;rG;fluU;omeA;fluA;omeA;rUs;rG;rAs;rGs;omeCSup-3' | 7819.05 | 15 |
| 407 | 5'-HO;rG;omeC;rU;d5propC;rA;fluU;rU;rUs;rA;fluC;rC;rAs;fluG; omeC;rG;fluU;omeA;fluA;omeA;rUs;rG;rAs;rGs;omeCSup-3' | 7819.05 | 16 |
| 408 | 5'-HO;rG;omeC;rU;rC;rA;d5propU;rU;rUs;rA;fluC;rC;rAs;fluG; omeC;rG;fluU;omeA;fluA;omeA;rUs;rG;rAs;rGs;omeCSup-3' | 7817.06 | 17 |
| 409 | 5'-HO;rG;omeC;rU;rC;rA;fluU;d5propU;rUs;rA;fluC;rC;rAs;fluG; omeC;rG;fluU;omeA;fluA;omeA;rUs;rG;rAs;rGs;omeCSup-3' | 7819.05 | 18 |
| 410 | 5'-HO;rG;omeC;rU;rC;rA;fluU;rU;d5propUs;rA;fluC;rC;rAs;fluG; omeC;rG;fluU;omeA;fluA;omeA;rUs;rG;rAs;rGs;omeCSup-3' | 7819.05 | 19 |
| 411 | 5'-HO;rG;omeC;rU;rC;rA;fluU;rU;rUs;rA;d5propC;rC;rAs;fluG; omeC;rG;fluU;omeA;fluA;omeA;rUs;rG;rAs;rGs;omeCSup-3' | 7817.06 | 20 |
| 412 | 5'-HO;rG;omeC;rU;rC;rA;fluU;rU;rUs;rA;fluC;d5propC;rAs;fluG; omeC;rG;fluU;omeA;fluA;omeA;rUs;rG;rAs;rGs;omeCSup-3' | 7819.05 | 21 |
| 413 | 5'-HO;rG;omeC;rU;rC;rA;fluU;rU;rUs;rA;fluC;rC;rAs;fluG; d5propC;rG;fluU;omeA;fluA;omeA;rUs;rG;rAs;rGs;omeCSup-3' | 7805.03 | 22 |
| 414 | 5'-HO;rG;omeC;rU;rC;rA;fluU;rU;rUs;rA;fluC;rC;rAs;fluG;omeC; rG;d5propU;omeA;fluA;omeA;rUs;rG;rAs;rGs;omeCSup-3' | 7817.06 | 23 |
| 415 | 5'-HO;rG;omeC;rU;rC;rA;fluU;rU;rUs;rA;fluC;rC;rAs;fluG;omeC; rG;fluU;omeA;fluA;omeA;d5propUs;rG;rAs;rGs;omeCSup-3' | 7819.05 | 24 |
| 416 | 5'-HO;rG;omeC;rU;rC;r7dz8azA;fluU;rU;rUs;rA;fluC;rC;rAs;fluG; omeC;rG;fluU;omeA;fluA;omeA;rUs;rG;rAs;rGs;omeCSup-3' | 7797.01 | 25 |
| 417 | 5'-HO;rG;omeC;rU;rC;rA;fluU;rU;rUs;r7dz8azA;fluC;rC;rAs;fluG; omeC;rG;fluU;omeA;fluA;omeA;rUs;rG;rAs;rGs;omeCSup-3' | 7797.01 | 26 |
| 418 | 5'-HO;rG;omeC;rU;rC;rA;fluU;rU;rUs;rA;fluC;rC;r7dz8azAs;fluG; omeC;rG;fluU;omeA;fluA;omeA;rUs;rG;rAs;rGs;omeCSup-3' | 7797.00 | 27 |
| 419 | 5'-HO;rG;omeC;rU;rC;rA;fluU;rU;rUs;rA;fluC;rC;rAs;fluG;omeC; rG;fluU;r7dz8azA;fluA;omeA;rUs;rG;rAs;rGs;omeCSup-3' | 7782.98 | 28 |
| 420 | 5'-HO;rG;omeC;rU;rC;rA;fluU;rU;rUs;rA;fluC;rC;rAs;fluG;omeC; rG;fluU;omeA;r7dz8azA;omeA;rUs;rG;rAs;rGs;omeCSup-3' | 7795.01 | 29 |
| 421 | 5'-HO;rG;omeC;rU;rC;rA;fluU;rU;rUs;rA;fluC;rC;rAs;fluG;omeC; rG;fluU;omeA;fluA;r7dz8azA;rUs;rG;rAs;rGs;omeCSup-3' | 7782.98 | 30 |
| 422 | 5'-HO;rG;omeC;rU;rC;rA;fluU;rU;rUs;rA;fluC;rC;rAs;fluG;omeC; rG;fluU;omeA;fluA;omeA;rUs;rG;r7dz8azAs;rGs;omeCSup-3' | 7797.00 | 31 |
| 423 | 5'-HO;rG;omeC;rU;rC;d2aminoA;fluU;rU;rUs;rA;fluC;rC;rAs;fluG; omeC;rG;fluU;omeA;fluA;omeA;rUs;rG;rAs;rGs;omeCSup-3' | 7796.02 | 32 |
| 424 | 5'-HO;rG;omeC;rU;rC;rA;fluU;rU;rUs;d2aminoA;fluC;rC;rAs;fluG; omeC;rG;fluU;omeA;fluA;omeA;rUs;rG;rAs;rGs;omeCSup-3' | 7796.02 | 33 |
| 425 | 5'-HO;rG;omeC;rU;rC;rA;fluU;rU;rUs;rA;fluC;rC;d2aminoAs;fluG; omeC;rG;fluU;omeA;fluA;omeA;rUs;rG;rAs;rGs;omeCSup-3' | 7796.02 | 34 |
| 426 | 5'-HO;rG;omeC;rU;rC;rA;fluU;rU;rUs;rA;fluC;rC;rAs;fluG;omeC;rG; fluU;d2aminoA;fluA;omeA;rUs;rG;rAs;rGs;omeCSup-3' | 7781.99 | 35 |
| 427 | 5'-HO;rG;omeC;rU;rC;rA;fluU;rU;rUs;rA;fluC;rC;rAs;fluG;omeC;rG; fluU;omeA;d2aminoA;omeA;rUs;rG;rAs;rGs;omeCSup-3' | 7794.03 | 36 |
| 428 | 5'-HO;rG;omeC;rU;rC;rA;fluU;rU;rUs;rA;fluC;rC;rAs;fluG;omeC;rG; fluU;omeA;fluA;d2aminoA;rUs;rG;rAs;rGs;omeCSup-3' | 7781.99 | 37 |
| 429 | 5'-HO;rG;omeC;rU;rC;rA;fluU;rU;rUs;rA;fluC;rC;rAs;fluG;omeC;rG; fluU;omeA;fluA;omeA;rUs;rG;d2aminoAs;rGs;omeCSup-3' | 7796.02 | 38 |
| 430 | 5'-HO;rG;omeC;rU;rC;fara8azA;fluU;rU;rUs;rA;fluC;rC;rAs;fluG;omeC; rG;fluU;omeA;fluA;omeA;rUs;rG;rAs;rGs;omeCSup-3' | 7799.98 | 39 |
| 431 | 5'-HO;rG;omeC;rU;rC;rA;fluU;rU;rUs;fara8azA;fluC;rC;rAs;fluG; omeC;rG;fluU;omeA;fluA;omeA;rUs;rG;rAs;rGs;omeCSup-3' | 7799.98 | 40 |
| 432 | 5'-HO;rG;omeC;rU;rC;rA;fluU;rU;rUs;rA;fluC;rC;fara8azAs;fluG;omeC; rG;fluU;omeA;fluA;omeA;rUs;rG;rAs;rGs;omeCSup-3' | 7799.98 | 41 |
| 433 | 5'-HO;rG;omeC;rU;rC;rA;fluU;rU;rUs;rA;fluC;rC;rAs;fluG;omeC;rG; fluU;fara8azA;fluA;omeA;rUs;rG;rAs;rGs;omeCSup-3' | 7785.96 | 42 |
| 434 | 5'-HO;rG;omeC;rU;rC;rA;fluU;rU;rUs;rA;fluC;rC;rAs;fluG;omeC;rG; fluU;omeA;fara8azA;omeA;rUs;rG;rAs;rGs;omeCSup-3' | 7797.99 | 43 |
| 435 | 5'-HO;rG;omeC;rU;rC;rA;fluU;rU;rUs;rA;fluC;rC;rAs;fluG;omeC;rG; fluU;omeA;fluA;fara8azA;rUs;rG;rAs;rGs;omeCSup-3' | 7785.96 | 44 |
| 436 | 5'-HO;rG;rC;rUs;fluC;rI;fluU;rU;rUs;fluA;omeC;omeC;rAs;omeG;omeC; omeU;omeA;rA;fluA;fluA;omeUs;fluG;omeAs;rGs;fluCSup-3' | 7860.12 | 515 |
| 437 | 5'-HO;rG;rC;rUs;fluC;omeA;fluU;rU;rUs;rI;omeC;omeC;rAs;omeG; omeC;omeG;omeU;rA;fluA;fluA;omeUs;fluG;omeAs;rGs;fluCSup-3' | 7872.15 | 516 |
| 438 | 5'-HO;rG;rC;rUs;fluC;omeA;fluU;rU;rUs;fluA;omeC;omeC;rIs;omeG; omeC;omeG;omeU;rA;fluA;fluA;omeUs;fluG;omeAs;rGs;fluCSup-3' | 7874.14 | 517 |
| 439 | 5'-HO;rG;rC;rUs;fluC;omeA;fluU;rU;rUs;fluA;omeC;omeC;rAs;omeG; omeC;omeG;omeU;rI;fluA;fluA;omeUs;fluG;omeAs;rGs;fluCSup-3' | 7874.14 | 518 |

TABLE 5-continued

| Ex | Sequence | MW | SEQ ID No. |
|---|---|---|---|
| 440 | 5'-HO;rG;rC;rUs;fluC;omeA;fluU;rU;rUs;fluA;omeC;omeC;rAs;omeG; omeC;omeG;omeU;rA;rI;fluA;omeUs;fluG;omeAs;rGs;fluCSup-3' | 7872.15 | 519 |
| 441 | 5'-HO;rG;rC;rUs;fluC;omeA;fluU;rU;rUs;fluA;omeC;omeC;rAs;omeG; omeC;omeG;omeU;rA;fluA;rI;omeUs;fluG;omeAs;rGs;fluCSup-3' | 7872.15 | 520 |
| 442 | 5'-HO;rG;rC;rUs;fluC;omeA;fluU;rU;rUs;fluA;omeC;omeC;rAs;omeG; omeC;omeG;omeU;rA;fluA;fluA;omeUs;fluG;rIs;rGs;fluCSup-3' | 7860.12 | 521 |
| 443 | 5'-HO;rG;d5propC;rUs;fluC;omeA;fluU;rU;rUs;fluA;omeC;omeC;rAs; omeG;omeC;omeG;omeU;rA;fluA;fluA;omeUs;fluG;omeAs;rGs;fluCSup-3' | 7895.21 | 45 |
| 444 | 5'-HO;rG;rC;d5propUs;fluC;omeA;fluU;rU;rUs;fluA;omeC;omeC;rAs; omeC;omeC;omeG;omeU;rA;fluA;fluA;omeUs;fluG;omeAs;rGs;fluCSup-3' | 7895.20 | 46 |
| 445 | 5'-HO;rG;rC;rUs;d5propC;omeA;fluU;rU;rUs;fluA;omeC;omeC;rAs; omeC;omeC;omeG;omeU;rA;fluA;fluA;omeUs;fluG;omeAs;rGs;fluCSup-3' | 7893.22 | 47 |
| 446 | 5'-HO;rG;rC;rUs;fluC;omeA;d5propU;rU;rUs;fluA;omeC;omeC;rAs; omeC;omeC;omeG;omeU;rA;fluA;fluA;omeUs;fluG;omeAs;rGs;fluCSup-3' | 7893.22 | 48 |
| 447 | 5'-HO;rG;rC;rUs;fluC;omeA;fluU;d5propU;rUs;fluA;omeC;omeC;rAs; omeC;omeC;omeG;omeU;rA;fluA;fluA;omeUs;fluG;omeAs;rGs;fluCSup-3' | 7895.21 | 49 |
| 448 | 5'-HO;rG;rC;rUs;fluC;omeA;fluU;rU;d5propUs;fluA;omeC;omeC;rAs; omeC;omeC;omeG;omeU;rA;fluA;fluA;omeUs;fluG;omeAs;rGs;fluCSup-3' | 7895.20 | 50 |
| 449 | 5'-HO;rG;rC;rUs;fluC;omeA;fluU;rU;rUs;fluA;d5propC;omeC;rAs;omeG; omeC;omeG;omeU;rA;fluA;fluA;omeUs;fluG;omeAs;rGs;fluCSup-3' | 7881.18 | 51 |
| 450 | 5'-HO;rG;rC;rUs;fluC;omeA;fluU;rU;rUs;fluA;omeC;d5propC;rAs;omeG; omeC;omeG;omeU;rA;fluA;fluA;omeUs;fluG;omeAs;rGs;fluCSup-3' | 7881.18 | 52 |
| 451 | 5'-HO;rG;rC;rUs;fluC;omeA;fluU;rU;rUs;fluA;omeC;omeC;rAs;omeG; d5propC;omeG;omeU;rA;fluA;fluA;omeUs;fluG;omeAs;rGs;fluCSup-3' | 7881.18 | 53 |
| 452 | 5'-HO;rG;rC;rUs;fluC;omeA;fluU;rU;rUs;fluA;omeC;omeC;rAs;omeG; omeC;omeG;d5propU;rA;fluA;fluA;omeUs;fluG;omeAs;rGs;fluCSup-3' | 7881.18 | 54 |
| 453 | 5'-HO;rG;rC;rUs;fluC;omeA;fluU;rU;rUs;fluA;omeC;omeC;rAs;omeG; omeC;omeG;omeU;rA;fluA;d5propUs;fluG;omeAs;rGs;fluCSup-3' | 7881.18 | 55 |
| 454 | 5'-HO;rG;rC;rUs;fluC;r7dz8azA;fluU;rU;rUs;fluA;omeC;omeC;rAs; omeC;omeC;omeG;omeU;rA;fluA;fluA;omeUs;fluG;omeAs;rGs;fluCSup-3' | 7859.13 | 56 |
| 455 | 5'-HO;rG;rC;rUs;fluC;omeA;fluU;rU;rUs;r7dz8azA;omeC;omeC;rAs; omeC;omeC;omeG;omeU;rA;fluA;fluA;omeUs;fluG;omeAs;rGs;fluCSup-3' | 7871.17 | 57 |
| 456 | 5'-HO;rG;rC;rUs;fluC;omeA;fluU;rU;rUs;fluA;omeC;omeC;r7dz8azAs; omeC;omeC;omeG;omeU;rA;fluA;fluA;omeUs;fluG;omeAs;rGs;fluCSup-3' | 7873.16 | 58 |
| 457 | 5'-HO;rG;rC;rUs;fluC;omeA;fluU;rU;rUs;fluA;omeC;omeC;rAs;omeG; omeC;omeG;omeU;r7dz8azA;fluA;fluA;omeUs;fluG;omeAs;rGs;fluCSup-3' | 7873.16 | 59 |
| 458 | 5'-HO;rG;rC;rUs;fluC;omeA;fluU;rU;rUs;fluA;omeC;omeC;rAs;omeG; omeC;omeG;omeU;rA;r7dz8azA;fluA;omeUs;fluG;omeAs;rGs;fluCSup-3' | 7871.17 | 60 |
| 459 | 5'-HO;rG;rC;rUs;fluC;omeA;fluU;rU;rUs;fluA;omeC;omeC;rAs;omeG; omeC;omeG;omeU;rA;fluA;r7dz8azA;omeUs;fluG;omeAs;rGs;fluCSup-3' | 7871.17 | 61 |
| 460 | 5'-HO;rG;rC;rUs;fluC;omeA;fluU;rU;rUs;fluA;omeC;omeC;rAs;omeG; omeC;omeG;omeU;rA;fluA;fluA;omeUs;fluG;r7dz8azAs;rGs;fluCSup-3' | 7859.13 | 62 |
| 461 | 5'-HO;rG;rC;rUs;fluC;d2aminoA;fluU;rU;rUs;fluA;omeC;omeC;rAs; omeC;omeC;omeG;omeU;rA;fluA;fluA;omeUs;fluG;omeAs;rGs;fluCSup-3' | 7858.15 | 63 |
| 462 | 5'-HO;rG;rC;rUs;fluC;omeA;fluU;rU;rUs;d2aminoA;omeC;omeC;rAs; omeC;omeC;omeG;omeU;rA;fluA;fluA;omeUs;fluG;omeAs;rGs;fluCSup-3' | 7870.18 | 64 |
| 463 | 5'-HO;rG;rC;rUs;fluC;omeA;fluU;rU;rUs;fluA;omeC;omeC;d2aminoAs; omeC;omeC;omeG;omeU;rA;fluA;fluA;omeUs;fluG;omeAs;rGs;fluCSup-3' | 7872.17 | 65 |
| 464 | 5'-HO;rG;rC;rUs;fluC;omeA;fluU;rU;rUs;fluA;omeC;omeC;rAs;omeG; omeC;omeG;omeU;d2aminoA;fluA;fluA;omeUs;fluG;omeAs;rGs; fluCSup-3' | 7872.18 | 66 |
| 465 | 5'-HO;rG;rC;rUs;fluC;omeA;fluU;rU;rUs;fluA;omeC;omeC;rAs;omeG; omeC;omeG;omeU;rA;d2aminoA;fluA;omeUs;fluG;omeAs;rGs;fluCSup-3' | 7870.18 | 67 |
| 466 | 5'-HO;rG;rC;rUs;fluC;omeA;fluU;rU;rUs;fluA;omeC;omeC;rAs;omeG; omeC;omeG;omeU;rA;fluA;d2aminoA;omeUs;fluG;omeAs;rGs;fluCSup-3' | 7870.18 | 68 |
| 467 | 5'-HO;rG;rC;rUs;fluC;omeA;fluU;rU;rUs;fluA;omeC;omeC;rAs;omeG; omeC;omeG;omeU;rA;fluA;fluA;omeUs;fluG;d2aminoAs;rGs;fluCSup-3' | 7858.14 | 69 |
| 468 | 5'-HO;rG;rC;rUs;fluC;fara8azA;fluU;rU;rUs;fluA;omeC;omeC;rAs; omeC;omeC;omeG;omeU;rA;fluA;fluA;omeUs;fluG;omeAs;rGs;fluCSup-3' | 7862.11 | 70 |
| 469 | 5'-HO;rG;rC;rUs;fluC;omeA;fluU;rU;rUs;fara8azA;omeC;omeC;rAs; omeC;omeC;omeG;omeU;rA;fluA;fluA;omeUs;fluG;omeAs;rGs;fluCSup-3' | 7874.15 | 71 |
| 470 | 5'-HO;rG;rC;rUs;fluC;omeA;fluU;rU;rUs;fluA;omeC;omeC;fara8azAs; omeC;omeC;omeG;omeU;rA;fluA;fluA;omeUs;fluG;omeAs;rGs;fluCSup-3' | 7876.13 | 72 |
| 471 | 5'-HO;rG;rC;rUs;fluC;omeA;fluU;rU;rUs;fluA;omeC;omeC;rAs;omeG; omeC;omeG;omeU;fara8azA;fluA;fluA;omeUs;fluG;omeAs;rGs;fluCSup-3' | 7876.14 | 73 |
| 472 | 5'-HO;rG;rC;rUs;fluC;omeA;fluU;rU;rUs;fluA;omeC;omeC;rAs;omeG; omeC;omeG;omeU;rA;fara8azA;fluA;omeUs;fluG;omeAs;rGs;fluCSup-3' | 7874.15 | 74 |
| 473 | 5'-HO;rG;rC;rUs;fluC;omeA;fluU;rU;rUs;fluA;omeC;omeC;rAs;omeG; omeC;omeG;omeU;rA;fluA;fara8azA;omeUs;fluG;omeAs;rGs;fluCSup-3' | 7874.15 | 75 |
| 474 | 5'-HO;rG;rC;rUs;fluC;omeA;fluU;rU;rUs;fluA;omeC;omeC;rAs;omeG; omeC;omeG;omeU;rA;fluA;fluA;omeUs;fluG;fara8azAs;rGs;fluCSup-3' | 7862.11 | 76 |
| 475 | 5'-HO;rG;omeC;rU;rC;rA;fluU;rU;rUs;rA;fluC;fluC;rAs;fluG;omeC; omeG;fluU;omeA;rA;fluA;rUs;rG;rAs;rGs;omeCSup-3' | 7798.99 | 522 |
| 476 | 5'-HO;rG;omeC;fluU;rC;rA;fluU;rU;rUs;rA;fluC;fluC;rAs;fluG;omeC; omeG;fluU;omeA;rA;fluA;rUs;rG;rAs;rGs;omeCSup-3' | 7800.99 | 523 |
| 477 | 5'-HO;rG;omeC;rU;rC;rA;fluU;fluU;rUs;rA;fluC;rC;rAs;fluG; omeC;omeG;fluU;omeA;rA;fluA;rUs;rG;rAs;rGs;omeCSup-3' | 7798.99 | 524 |

TABLE 5-continued

| Ex | Sequence | MW | SEQ ID No. |
|---|---|---|---|
| 478 | 5'-HO;rG;omeC;rU;rC;fara7dzA;fluU;rU;rUs;rA;fluC;rC;rAs;fluG;omeC; rG;fluU;omeA;fluA;omeA;rUs;rG;rAs;rGs;omeCSup-3' | 7798.01 | 77 |
| 479 | 5'-HO;rG;omeC;rU;rC;rA;fluU;rU;rUs;fara7dzA;fluC;rC;rAs;fluG; omeC;rG;fluU;omeA;fluA;omeA;rUs;rG;rAs;rGs;omeCSup-3' | 7798.01 | 78 |
| 480 | 5'-HO;rG;omeC;rU;rC;rA;fluU;rU;rUs;rA;fluC;rC;fara7dzAs;fluG;omeC; rG;fluU;omeA;fluA;omeA;rUs;rG;rAs;rGs;omeCSup-3' | 7798.00 | 79 |
| 481 | 5'-HO;rG;omeC;rU;rC;rA;fluU;rU;rUs;rA;fluC;rC;rAs;fluG; omeC;rG;fluU;fara7dzA;fluA;omeA;rUs;rG;rAs;rGs;omeCSup-3' | 7783.98 | 80 |
| 482 | 5'-HO;rG;omeC;rU;rC;rA;fluU;rU;rUs;rA;fluC;rC;rAs;fluG;omeC;rG; fluU;omeA;fara7dzA;omeA;rUs;rG;rAs;rGs;omeCSup-3' | 7796.02 | 81 |
| 483 | 5'-HO;rG;omeC;rU;rC;rA;fluU;rU;rUs;rA;fluC;rC;rAs;fluG; omeC;rG;fluU;omeA;fluA;fara7dzA;rUs;rG;rAs;rGs;omeCSup-3' | 7783.98 | 82 |
| 484 | 5'-HO;rG;omeC;rU;rC;rA;fluU;rU;rUs;rA;fluC;rC;rAs;fluG;omeC;rG; fluU;omeA;fluA;omeA;rUs;rG;fara7dzAs;rGs;omeCSup-3' | 7798.00 | 83 |
| 485 | 5'-HO;rG;omeC;rU;rC;d7dzA;fluU;rU;rUs;rA;fluC;rC;rAs;fluG; omeC;rG;fluU;omeA;fluA;omeA;rUs;rG;rAs;rGs;omeCSup-3' | 7780.02 | 84 |
| 486 | 5'-HO;rG;omeC;rU;rC;rA;fluU;rU;rUs;d7dzA;fluC;rC;rAs;fluG; omeC;rG;fluU;omeA;fluA;omeA;rUs;rG;rAs;rGs;omeCSup-3' | 7780.02 | 85 |
| 487 | 5'-HO;rG;omeC;rU;rC;rA;fluU;rU;rUs;rA;fluC;rC;d7dzAs;fluG; omeC;rG;fluU;omeA;fluA;omeA;rUs;rG;rAs;rGs;omeCSup-3' | 7780.01 | 86 |
| 488 | 5'-HO;rG;omeC;rU;rC;rA;fluU;rU;rUs;rA;fluC;rC;rAs;fluG; omeC;rG;fluU;d7dzA;fluA;omeA;rUs;rG;rAs;rGs;omeCSup-3' | 7765.99 | 87 |
| 489 | 5'-HO;rG;omeC;rU;rC;rA;fluU;rU;rUs;rA;fluC;rC;rAs;fluG; omeC;rG;fluU;omeA;d7dzA;omeA;rUs;rG;rAs;rGs;omeCSup-3' | 7778.03 | 88 |
| 490 | 5'-HO;rG;omeC;rU;rC;rA;fluU;rU;rUs;rA;fluC;rC;rAs;fluG; omeC;rG;fluU;omeA;fluA;d7dzA;rUs;rG;rAs;rGs;omeCSup-3' | 7765.99 | 89 |
| 491 | 5'-HO;rG;omeC;rU;rC;rA;fluU;rU;rUs;rA;fluC;rC;rAs;fluG;omeC;rG; fluU;omeA;fluA;omeA;rUs;rG;d7dzAs;rGs;omeCSup-3' | 7780.01 | 90 |
| 492 | 5'-HO;rG;omeC;rU;rC;r7dzA;fluU;rU;rUs;rA;fluC;rC;rAs;fluG; omeC;rG;fluU;omeA;fluA;omeA;rUs;rG;rAs;rGs;omeCSup-3' | 7796.02 | 91 |
| 493 | 5'-HO;rG;omeC;rU;rC;rA;fluU;rU;rUs;r7dzA;fluC;rC;rAs;fluG; omeC;rG;fluU;omeA;fluA;omeA;rUs;rG;rAs;rGs;omeCSup-3' | 7796.02 | 92 |
| 494 | 5'-HO;rG;omeC;rU;rC;rA;fluU;rU;rUs;rA;fluC;rC;r7dzAs;fluG; omeC;rG;fluU;omeA;fluA;omeA;rUs;rG;rAs;rGs;omeCSup-3' | 7796.01 | 93 |
| 495 | 5'-HO;rG;omeC;rU;rC;rA;fluU;rU;rUs;rA;fluC;rC;rAs;fluG; omeC;rG;fluU;r7dzA;fluA;omeA;rUs;rG;rAs;rGs;omeCSup-3' | 7781.99 | 94 |
| 496 | 5'-HO;rG;omeC;rU;rC;rA;fluU;rU;rUs;rA;fluC;rC;rAs;fluG; omeC;rG;fluU;omeA;r7dzA;omeA;rUs;rG;rAs;rGs;omeCSup-3' | 7794.03 | 95 |
| 497 | 5'-HO;rG;omeC;rU;rC;rA;fluU;rU;rUs;rA;fluC;rC;rAs;fluG; omeC;rG;fluU;omeA;fluA;r7dzA;rUs;rG;rAs;rGs;omeCSup-3' | 7781.99 | 96 |
| 498 | 5'-HO;rG;omeC;rU;rC;rA;fluU;rU;rUs;rA;fluC;rC;rAs;fluG;omeC;rG; fluU;omeA;fluA;omeA;rUs;rG;r7dzAs;rGs;omeCSup-3' | 7796.01 | 97 |
| 499 | 5'-HO;rG;rC;rUs;fluC;fara7dzA;fluU;rU;rUs;fluA;omeC;omeC;rAs; omeG;omeC;omeG;omeU;rA;fluA;fluA;omeUs;fluG;omeAs;rGs;fluCSup-3' | 7860.14 | 98 |
| 500 | 5'-HO;rG;rC;rUs;fluC;omeA;fluU;rU;rUs;fara7dzA;omeC;omeC;rAs; omeG;omeC;omeG;omeU;rA;fluA;fluA;omeUs;fluG;omeAs;rGs;fluCSup-3' | 7872.17 | 99 |
| 501 | 5'-HO;rG;rC;rUs;fluC;omeA;fluU;rU;rUs;fluA;omeC;omeC;fara7dzAs; omeG;omeC;omeG;omeU;rA;fluA;fluA;omeUs;fluG;omeAs;rGs;fluCSup-3' | 7874.16 | 100 |
| 502 | 5'-HO;rG;rC;rUs;fluC;omeA;fluU;rU;rUs;fluA;omeC;omeC;rAs;omeG; omeC;omeG;omeU;fara7dzA;fluA;fluA;omeUs;fluG;omeAs;rGs;fluCSup-3' | 7874.16 | 101 |
| 503 | 5'-HO;rG;rC;rUs;fluC;omeA;fluU;rU;rUs;fluA;omeC;omeC;rAs;omeG; omeC;omeG;omeU;rA;fara7dzA;fluA;omeUs;fluG;omeAs;rGs;fluCSup-3' | 7872.17 | 102 |
| 504 | 5'-HO;rG;rC;rUs;fluC;omeA;fluU;rU;rUs;fluA;omeC;omeC;rAs;omeG; omeC;omeG;omeU;rA;fluA;fara7dzA;omeUs;fluG;omeAs;rGs;fluCSup-3' | 7872.17 | 103 |
| 505 | 5'-HO;rG;rC;rUs;fluC;omeA;fluU;rU;rUs;fluA;omeC;omeC;rAs;omeG; omeC;omeG;omeU;rA;fluA;fluA;omeUs;fluG;fara7dzAs;rGs;fluCSup-3' | 7860.13 | 104 |
| 506 | 5'-HO;rG;rC;rUs;fluC;d7dzA;fluU;rU;rUs;fluA;omeC;omeC;rAs;omeG; omeC;omeG;omeU;rA;fluA;fluA;omeUs;fluG;omeAs;rGs;fluCSup-3' | 7842.15 | 105 |
| 507 | 5'-HO;rG;rC;rUs;fluC;omeA;fluU;rU;rUs;d7dzA;omeC;omeC;rAs;omeG; omeC;omeG;omeU;rA;fluA;fluA;omeUs;fluG;omeAs;rGs;fluCSup-3' | 7854.18 | 106 |
| 508 | 5'-HO;rG;rC;rUs;fluC;omeA;fluU;rU;rUs;fluA;omeC;omeC;d7dzAs; omeG;omeC;omeG;omeU;rA;fluA;fluA;omeUs;fluG;omeAs;rGs;fluCSup-3' | 7856.17 | 107 |
| 509 | 5'-HO;rG;rC;rUs;fluC;omeA;fluU;rU;rUs;fluA;omeC;omeC;rAs;omeG; omeC;omeG;omeU;d7dzA;fluA;fluA;omeUs;fluG;omeAs;rGs;fluCSup-3' | 7856.17 | 108 |
| 510 | 5'-HO;rG;rC;rUs;fluC;omeA;fluU;rU;rUs;fluA;omeC;omeC;rAs;omeG; omeC;omeG;omeU;rA;d7dzA;fluA;omeUs;fluG;omeAs;rGs;fluCSup-3' | 7854.18 | 109 |
| 511 | 5'-HO;rG;rC;rUs;fluC;omeA;fluU;rU;rUs;fluA;omeC;omeC;rAs;omeG; omeC;omeG;omeU;rA;fluA;d7dzA;omeUs;fluG;omeAs;rGs;fluCSup-3' | 7854.18 | 110 |
| 512 | 5'-HO;rG;rC;rUs;fluC;omeA;fluU;rU;rUs;fluA;omeC;omeC;rAs;omeG; omeC;omeG;omeU;rA;fluA;fluA;omeUs;fluG;d7dzAs;rGs;fluCSup-3' | 7842.14 | 111 |
| 513 | 5'-HO;rG;rC;rUs;fluC;omeA;fluU;rU;rUs;r7dzA;omeC;omeC;rAs;omeG; omeC;omeG;omeU;rA;fluA;fluA;omeUs;fluG;omeAs;rGs;fluCSup-3' | 7870.18 | 112 |
| 514 | 5'-HO;rG;rC;rUs;fluC;omeA;fluU;rU;rUs;fluA;fluC;omeC;rAs;omeG; omeC;omeG;omeU;rA;rA;fluA;rUs;rG;omeAs;rGs;fluCSup-3' | 7843.11 | 525 |
| 515 | 5'-HO;rG;rC;rUs;fluC;omeA;fluU;rU;rUs;fluA;omeC;omeC;rAs;omeG; omeC;omeG;omeU;rA;rA;fluA;rUs;rG;omeAs;rGs;fluCSup-3' | 7855.15 | 526 |

TABLE 5-continued

| Ex | Sequence | MW | SEQ ID No. |
|---|---|---|---|
| 516 | 5'-HO;rG;rC;rUs;fluC;omeA;fluU;rU;rUs;fluA;fluC;omeC;rAs;omeG; omeC;omeG;omeU;rA;fluA;fluA;rUs;rG;omeAs;rGs;fluCSup-3' | 7845.10 | 527 |
| 517 | 5'-HO;rG;rC;rUs;fluC;omeA;fluU;rU;rUs;fluA;fluC;omeC;rAs;omeG; omeC;omeG;omeU;rA;rA;fluA;omeUs;rG;omeAs;rGs;fluCSup-3' | 7857.14 | 528 |
| 518 | 5'-HO;rG;rC;rUs;fluC;omeA;fluU;rU;rUs;fluA;fluC;omeC;rAs;omeG; omeC;omeG;omeU;rA;rA;fluA;rUs;fluG;omeAs;rGs;fluCSup-3' | 7845.10 | 529 |
| 519 | 5'-HO;thiorG;omeC;rU;rC;rA;fluU;rU;rUs;rA;fluC;rC;rAs;fluG;omeC; rG;fluU;omeA;fluA;omeA;rUs;rG;rAs;rGs;omeCSup-3' | 7813.07 | 530 |
| 520 | 5'-HO;rG;omeC;thiorU;rC;rA;fluU;rU;rUs;rA;fluC;rC;rAs;fluG;omeC; rG;fluU;omeA;fluA;omeA;rUs;rG;rAs;rGs;omeCSup-3' | 7813.06 | 531 |
| 521 | 5'-HO;rG;omeC;rU;thiorC;rA;fluU;rU;rUs;rA;fluC;rC;rAs;fluG;omeC; rG;fluU;omeA;fluA;omeA;rUs;rG;rAs;rGs;omeCSup-3' | 7813.07 | 532 |
| 522 | 5'-HO;rG;omeC;rU;rC;thiorA;fluU;rU;rUs;rA;fluC;rC;rAs;fluG;omeC; rG;fluU;omeA;fluA;omeA;rUs;rG;rAs;rGs;omeCSup-3' | 7813.07 | 533 |
| 523 | 5'-HO;rG;omeC;rU;rC;rA;thiorU;rU;rUs;rA;fluC;rC;rAs;fluG;omeC; rG;fluU;omeA;fluA;omeA;rUs;rG;rAs;rGs;omeCSup-3' | 7811.07 | 534 |
| 524 | 5'-HO;rG;omeC;rU;rC;rA;fluU;thiorU;rUs;rA;fluC;rC;rAs;fluG;omeC; rG;fluU;omeA;fluA;omeA;rUs;rG;rAs;rGs;omeCSup-3' | 7813.06 | 535 |
| 525 | 5'-HO;rG;omeC;rU;rC;rA;fluU;rU;thiorUs;rA;fluC;rC;rAs;fluG;omeC; rG;fluU;omeA;fluA;omeA;rUs;rG;rAs;rGs;omeCSup-3' | 7813.06 | 536 |
| 526 | 5'-HO;rG;omeC;rU;rC;rA;fluU;rU;rUs;thiorA;fluC;rC;rAs;fluG;omeC; rG;fluU;omeA;fluA;omeA;rUs;rG;rAs;rGs;omeCSup-3' | 7813.07 | 537 |
| 527 | 5'-HO;rG;omeC;rU;rC;rA;fluU;rU;rUs;rA;thiorC;rC;rAs;fluG;omeC; rG;fluU;omeA;fluA;omeA;rUs;rG;rAs;rGs;omeCSup-3' | 7811.07 | 538 |
| 528 | 5'-HO;rG;omeC;rU;rC;rA;fluU;rU;rUs;rA;fluC;thiorC;rAs;fluG;omeC; rG;fluU;omeA;fluA;omeA;rUs;rG;rAs;rGs;omeCSup-3' | 7813.07 | 539 |
| 529 | 5'-HO;rG;omeC;rU;rC;rA;fluU;rU;rUs;rA;fluC;rC;thiorAs;fluG;omeC; rG;fluU;omeA;fluA;omeA;rUs;rG;rAs;rGs;omeCSup-3' | 7813.06 | 540 |
| 530 | 5'-HO;rG;omeC;rU;rC;rA;fluU;rU;rUs;rA;fluC;rC;rAs;thiorG;omeC; rG;fluU;omeA;fluA;omeA;rUs;rG;rAs;rGs;omeCSup-3' | 7811.08 | 541 |
| 531 | 5'-HO;rG;omeC;rU;rC;rA;fluU;rU;rUs;rA;fluC;rC;rAs;fluG;thiorC;rG; fluU;omeA;fluA;omeA;rUs;rG;rAs;rGs;omeCSup-3' | 7799.04 | 542 |
| 532 | 5'-HO;rG;omeC;rU;rC;rA;fluU;rU;rUs;rA;fluC;rC;rAs;fluG;omeC; thiorG;fluU;omeA;fluA;omeA;rUs;rG;rAs;rGs;omeCSup-3' | 7813.07 | 543 |
| 533 | 5'-HO;rG;omeC;rU;rC;rA;fluU;rU;rUs;rA;fluC;rC;rAs;fluG;omeC;rG; thiorU;omeA;fluA;omeA;rUs;rG;rAs;rGs;omeCSup-3' | 7811.07 | 544 |
| 534 | 5'-HO;rG;omeC;rU;rC;rA;fluU;rU;rUs;rA;fluC;rC;rAs;fluG;omeC;rG; fluU;thiorA;fluA;omeA;rUs;rG;rAs;rGs;omeCSup-3' | 7799.04 | 545 |
| 535 | 5'-HO;rG;omeC;rU;rC;rA;fluU;rU;rUs;rA;fluC;rC;rAs;fluG;omeC;rG; fluU;omeA;thiorA;omeA;rUs;rG;rAs;rGs;omeCSup-3' | 7811.08 | 546 |
| 536 | 5'-HO;rG;omeC;rU;rC;rA;fluU;rU;rUs;rA;fluC;rC;rAs;fluG;omeC;rG; fluU;omeA;fluA;thiorA;rUs;rG;rAs;rGs;omeCSup-3' | 7799.04 | 547 |
| 537 | 5'-HO;rG;omeC;rU;rC;rA;fluU;rU;rUs;rA;fluC;rC;rAs;fluG;omeC;rG; fluU;omeA;fluA;omeA;thiorUs;rG;rAs;rGs;omeCSup-3' | 7813.06 | 548 |
| 538 | 5'-HO;rG;omeC;rU;rC;rA;fluU;rU;rUs;rA;fluC;rC;rAs;fluG;omeC;rG; fluU;omeA;fluA;omeA;rUs;thiorG;rAs;rGs;omeCSup-3' | 7813.07 | 549 |
| 539 | 5'-HO;rG;omeC;rU;rC;rA;fluU;rU;rUs;rA;fluC;rC;rAs;fluG;omeC;rG; fluU;omeA;fluA;omeA;rUs;rG;thiorAs;rGs;omeCSup-3' | 7813.06 | 550 |
| 540 | 5'-HO;rG;omeC;rU;rC;rA;fluU;rU;rUs;rA;fluC;rC;rAs;fluG;omeC;rG; fluU;omeA;fluA;omeA;rUs;rG;rAs;thiorGs;omeCSup-3' | 7813.06 | 551 |
| 541 | 5'-HO;rG;cf3C;rU;rC;rA;fluU;rU;rUs;rA;fluC;rC;rAs;fluG; omeC;rG;fluU;omeA;fluA;omeA;rUs;rG;rAs;rGs;omeCSup-3' | 7850.97 | 552 |
| 542 | 5'-HO;rG;omeC;cf3U;rC;rA;fluU;rU;rUs;rA;fluC;rC;rAs;fluG; omeC;rG;fluU;omeA;fluA;omeA;rUs;rG;rAs;rGs;omeCSup-3' | 7865.00 | 553 |
| 543 | 5'-HO;rG;omeC;rU;cf3C;rA;fluU;rU;rUs;rA;fluC;rC;rAs;fluG; omeC;rG;fluU;omeA;fluA;omeA;rUs;rG;rAs;rGs;omeCSup-3' | 7865.00 | 554 |
| 544 | 5'-HO;rG;omeC;rU;rC;cf3U;rU;rUs;rA;fluC;rC;rAs;fluG; omeC;rG;fluU;omeA;fluA;omeA;rUs;rG;rAs;rGs;omeCSup-3' | 7863.01 | 555 |
| 545 | 5'-HO;rG;omeC;rU;rC;rA;fluU;cf3U;rUs;rA;fluC;rC;rAs;fluG; omeC;rG;fluU;omeA;fluA;omeA;rUs;rG;rAs;rGs;omeCSup-3' | 7865.00 | 556 |
| 546 | 5'-HO;rG;omeC;rU;rC;rA;fluU;rU;cf3Us;rA;fluC;rC;rAs;fluG; omeC;rG;fluU;omeA;fluA;omeA;rUs;rG;rAs;rGs;omeCSup-3' | 7865.00 | 557 |
| 547 | 5'-HO;rG;omeC;rU;rC;rA;fluU;rU;rUs;rA;cf3C;rC;rAs;fluG; omeC;rG;fluU;omeA;fluA;omeA;rUs;rG;rAs;rGs;omeCSup-3' | 7863.01 | 558 |
| 548 | 5'-HO;rG;omeC;rU;rC;rA;fluU;rU;rUs;rA;fluC;cf3C;rAs;fluG; omeC;rG;fluU;omeA;fluA;omeA;rUs;rG;rAs;rGs;omeCSup-3' | 7865.00 | 559 |
| 549 | 5'-HO;rG;omeC;rU;rC;rA;fluU;rU;rUs;rA;fluC;rC;cf3As;fluG; omeC;rG;fluU;omeA;fluA;omeA;rUs;rG;rAs;rGs;omeCSup-3' | 7865.00 | 560 |
| 550 | 5'-HO;rG;omeC;rU;rC;rA;fluU;rU;rUs;rA;fluC;rC;rAs;fluG; cf3C;rG;fluU;omeA;fluA;omeA;rUs;rG;rAs;rGs;omeCSup-3' | 7850.97 | 561 |
| 551 | 5'-HO;rG;omeC;rU;rC;rA;fluU;rU;rUs;rA;fluC;rC;rAs;fluG; omeC;rG;cf3U;omeA;fluA;omeA;rUs;rG;rAs;rGs;omeCSup-3' | 7863.01 | 562 |
| 552 | 5'-HO;rG;omeC;rU;rC;rA;fluU;rU;rUs;rA;fluC;rC;rAs;fluG; omeC;rG;fluU;cf3A;fluA;omeA;rUs;rG;rAs;rGs;omeCSup-3' | 7850.97 | 563 |
| 553 | 5'-HO;rG;omeC;rU;rC;rA;fluU;rU;rUs;rA;fluC;rC;rAs;fluG; omeC;rG;fluU;omeA;cf3A;omeA;rUs;rG;rAs;rGs;omeCSup-3' | 7863.01 | 564 |

TABLE 5-continued

| Ex | Sequence | MW | SEQ ID No. |
|---|---|---|---|
| 554 | 5'-HO;rG;omeC;rU;rC;rA;fluU;rU;rUs;rA;fluC;rC;rAs;fluG; omeC;rG;fluU;omeA;fluA;omeA;cf3Us;rG;rAs;rGs;omeCSup-3' | 7865.00 | 565 |
| 555 | 5'-HO;rG;omeC;rU;rC;rA;fluU;rU;rUs;rA;fluC;rC;rAs;fluG; omeC;rG;fluU;omeA;fluA;omeA;rUs;rG;cf3As;rGs;omeCSup-3' | 7865.00 | 566 |
| 556 | 5'-HO;rG;omeC;rU;rC;rA;fluU;rU;rUs;rA;fluC;rC;rAs;fluG; omeC;rG;fluU;omeA;fluA;omeA;rUs;rAs;cf3Gs;omeCSup-3' | 7865.00 | 567 |
| 557 | 5'-HO;thiorG;rC;rUs;fluC;omeA;fluU;rU;rUs;fluA;omeC;omeC;rAs; omeG;omeC;omeG;omeU;rA;fluA;fluA;omeUs;fluG;omeAs;rGs;fluCSup-3' | 7889.22 | 568 |
| 558 | 5'-HO;rG;thiorC;rUs;fluC;omeA;fluU;rU;rUs;fluA;omeC;omeC;rAs; omeC;omeG;omeG;omeU;rA;fluA;fluA;omeUs;fluG;omeAs;rGs;fluCSup-3' | 7889.22 | 569 |
| 559 | 5'-HO;rG;rC;thiorUs;fluC;omeA;fluU;rU;rUs;fluA;omeC;omeC;rAs; omeC;omeC;omeG;omeU;rA;fluA;fluA;omeUs;fluG;omeAs;rGs;fluCSup-3' | 7889.21 | 570 |
| 560 | 5'-HO;rG;rC;rUs;fluC;omeA;thiorU;rU;rUs;fluA;omeC;omeC;rAs;omeG; omeC;omeG;omeU;rA;fluA;fluA;omeUs;fluG;omeAs;rGs;fluCSup-3' | 7887.23 | 571 |
| 561 | 5'-HO;rG;rC;rUs;fluC;omeA;fluU;thiorU;rUs;fluA;omeC;omeC;rAs; omeC;omeC;omeG;omeU;rA;fluA;fluA;omeUs;fluG;omeAs;rGs;fluCSup-3' | 7889.22 | 572 |
| 562 | 5'-HO;rG;rC;rUs;fluC;omeA;fluU;rU;thiorUs;fluA;omeC;omeC;rAs; omeC;omeC;omeG;omeU;rA;fluA;fluA;omeUs;fluG;omeAs;rGs;fluCSup-3' | 7889.21 | 573 |
| 563 | 5'-HO;rG;rC;rUs;fluC;omeA;fluU;rU;rUs;thiorA;omeC;omeC;rAs;omeG; omeC;omeG;omeU;rA;fluA;fluA;omeUs;fluG;omeAs;rGs;fluCSup-3' | 7887.23 | 574 |
| 564 | 5'-HO;rG;rC;rUs;fluC;omeA;fluU;rU;rUs;fluA;thiorC;omeC;rAs;omeG; omeC;omeG;omeU;rA;fluA;fluA;omeUs;fluG;omeAs;rGs;fluCSup-3' | 7875.19 | 575 |
| 565 | 5'-HO;rG;rC;rUs;fluC;omeA;fluU;rU;rUs;fluA;omeC;thiorC;rAs;omeG; omeC;omeG;omeU;rA;fluA;fluA;omeUs;fluG;omeAs;rGs;fluCSup-3' | 7875.19 | 576 |
| 566 | 5'-HO;rG;rC;rUs;fluC;omeA;fluU;rU;rUs;fluA;omeC;omeC;thiorAs; omeC;omeC;omeG;omeU;rA;fluA;fluA;omeUs;fluG;omeAs;rGs;fluCSup-3' | 7889.22 | 577 |
| 567 | 5'-HO;rG;rC;rUs;fluC;omeA;fluU;rU;rUs;fluA;omeC;omeC;rAs;thiorG; omeC;omeG;omeU;rA;fluA;fluA;omeUs;fluG;omeAs;rGs;fluCSup-3' | 7875.19 | 578 |
| 568 | 5'-HO;rG;rC;rUs;fluC;omeA;fluU;rU;rUs;fluA;omeC;omeC;rAs;omeG; thiorC;omeG;omeU;rA;fluA;fluA;omeUs;fluG;omeAs;rGs;fluCSup-3' | 7875.19 | 579 |
| 569 | 5'-HO;rG;rC;rUs;fluC;omeA;fluU;rU;rUs;fluA;omeC;omeC;rAs;omeG; omeC;thiorG;omeU;rA;fluA;fluA;omeUs;fluG;omeAs;rGs;fluCSup-3' | 7875.19 | 580 |
| 570 | 5'-HO;rG;rC;rUs;fluC;omeA;fluU;rU;rUs;fluA;omeC;omeC;rAs;omeG; omeC;omeG;thiorU;rA;fluA;fluA;omeUs;fluG;omeAs;rGs;fluCSup-3' | 7875.19 | 581 |
| 571 | 5'-HO;rG;rC;rUs;fluC;omeA;fluU;rU;rUs;fluA;omeC;omeC;rAs;omeG; omeC;omeG;omeU;thiorA;fluA;fluA;omeUs;fluG;omeAs;rGs;fluCSup-3' | 7889.22 | 582 |
| 572 | 5'-HO;rG;rC;rUs;fluC;omeA;fluU;rU;rUs;fluA;omeC;omeC;rAs;omeG; omeC;omeG;omeU;rA;thiorA;fluA;omeUs;fluG;omeAs;rGs;fluCSup-3' | 7887.23 | 583 |
| 573 | 5'-HO;rG;rC;rUs;fluC;omeA;fluU;rU;rUs;fluA;omeC;omeC;rAs;omeG; omeC;omeG;omeU;rA;fluA;thiorA;omeUs;fluG;omeAs;rGs;fluCSup-3' | 7887.23 | 584 |
| 574 | 5'-HO;rG;rC;rUs;fluC;omeA;fluU;rU;rUs;fluA;omeC;omeC;rAs;omeG; omeC;omeG;omeU;rA;fluA;fluA;thiorUs;fluG;omeAs;rGs;fluCSup-3' | 7875.19 | 585 |
| 575 | 5'-HO;rG;rC;rUs;fluC;omeA;fluU;rU;rUs;fluA;omeC;omeC;rAs;omeG; omeC;omeG;omeU;rA;fluA;fluA;omeUs;thiorG;omeAs;rGs;fluCSup-3' | 7887.23 | 586 |
| 576 | 5'-HO;rG;rC;rUs;fluC;omeA;fluU;rU;rUs;fluA;omeC;omeC;rAs;omeG; omeC;omeG;omeU;rA;fluA;fluA;omeUs;fluG;thiorAs;rGs;fluCSup-3' | 7875.19 | 587 |
| 577 | 5'-HO;rG;rC;rUs;fluC;omeA;fluU;rU;rUs;fluA;omeC;omeC;rAs;omeG; omeC;omeG;omeU;rA;fluA;fluA;omeUs;fluG;omeAs;thiorGs;fluCSup-3' | 7889.22 | 588 |
| 578 | 5'-HO;rG;cf3C;rUs;fluC;omeA;fluU;rU;rUs;fluA;omeC;omeC;rAs;omeG; omeC;omeG;omeU;rA;fluA;fluA;omeUs;fluG;omeAs;rGs;fluCSup-3' | 7941.16 | 589 |
| 579 | 5'-HO;rG;rC;cf3Us;fluC;omeA;fluU;rU;rUs;fluA;omeC;omeC;rAs;omeG; omeC;omeG;omeU;rA;fluA;fluA;omeUs;fluG;omeAs;rGs;fluCSup-3' | 7941.16 | 590 |
| 580 | 5'-HO;rG;rC;rUs;cf3C;omeA;fluU;rU;rUs;fluA;omeC;omeC;rAs;omeG; omeC;omeG;omeU;rA;fluA;fluA;omeUs;fluG;omeAs;rGs;fluCSup-3' | 7939.16 | 591 |
| 581 | 5'-HO;rG;rC;rUs;fluC;omeA;cf3U;rU;rUs;fluA;omeC;omeC;rAs;omeG; omeC;omeG;omeU;rA;fluA;fluA;omeUs;fluG;omeAs;rGs;fluCSup-3' | 7939.16 | 592 |
| 582 | 5'-HO;rG;rC;rUs;fluC;omeA;fluU;cf3U;rUs;fluA;omeC;omeC;rAs;omeG; omeC;omeG;omeU;rA;fluA;fluA;omeUs;fluG;omeAs;rGs;fluCSup-3' | 7941.16 | 593 |
| 583 | 5'-HO;rG;rC;rUs;fluC;omeA;fluU;rU;cf3Us;fluA;omeC;omeC;rAs;omeG; omeC;omeG;omeU;rA;fluA;fluA;omeUs;fluG;omeAs;rGs;fluCSup-3' | 7941.16 | 594 |
| 584 | 5'-HO;rG;rC;rUs;fluC;omeA;fluU;rU;rUs;cf3A;omeC;omeC;rAs;omeG; omeC;omeG;omeU;rA;fluA;fluA;omeUs;fluG;omeAs;rGs;fluCSup-3' | 7939.16 | 595 |
| 585 | 5'-HO;rG;rC;rUs;fluC;omeA;fluU;rU;rUs;fluA;cf3C;omeC;rAs;omeG; omeC;omeG;omeU;rA;fluA;fluA;omeUs;fluG;omeAs;rGs;fluCSup-3' | 7927.13 | 596 |
| 586 | 5'-HO;rG;rC;rUs;fluC;omeA;fluU;rU;rUs;fluA;omeC;cf3C;rAs;omeG; omeC;omeG;omeU;rA;fluA;fluA;omeUs;fluG;omeAs;rGs;fluCSup-3' | 7927.13 | 597 |
| 587 | 5'-HO;rG;rC;rUs;fluC;omeA;fluU;rU;rUs;fluA;omeC;omeC;cf3As;omeG; omeC;omeG;omeU;rA;fluA;fluA;omeUs;fluG;omeAs;rGs;fluCSup-3' | 7941.16 | 598 |
| 588 | 5'-HO;rG;rC;rUs;fluC;omeA;fluU;rU;rUs;fluA;omeC;omeC;rAs;omeG; cf3C;omeG;omeU;rA;fluA;fluA;omeUs;fluG;omeAs;rGs;fluCSup-3' | 7927.13 | 599 |
| 589 | 5'-HO;rG;rC;rUs;fluC;omeA;fluU;rU;rUs;fluA;omeC;omeC;rAs;omeG; omeC;cf3G;omeU;rA;fluA;fluA;omeUs;fluG;omeAs;rGs;fluCSup-3' | 7927.13 | 600 |
| 590 | 5'-HO;rG;rC;rUs;fluC;omeA;fluU;rU;rUs;fluA;omeC;omeC;rAs;omeG; omeC;omeG;cf3U;rA;fluA;fluA;omeUs;fluG;omeAs;rGs;fluCSup-3' | 7939.16 | 601 |
| 591 | 5'-HO;rG;rC;rUs;fluC;omeA;fluU;rU;rUs;fluA;omeC;omeC;rAs;omeG; omeC;omeG;omeU;rA;cf3A;fluA;omeUs;fluG;omeAs;rGs;fluCSup-3' | 7939.16 | 602 |

TABLE 5-continued

| Ex | Sequence | MW | SEQ ID No. |
|---|---|---|---|
| 592 | 5'-HO;rG;rC;rUs;fluC;omeA;fluU;rU;rUs;fluA;omeC;omeC;rAs;omeG; omeC;omeG;omeU;rA;fluA;fluA;cf3Us;fluG;omeAs;rGs;fluCSup-3' | 7927.13 | 603 |
| 593 | 5'-HO;rG;rC;rUs;fluC;omeA;fluU;rU;rUs;fluA;omeC;omeC;rAs;omeG; omeC;omeG;omeU;rA;fluA;fluA;omeUs;fluG;cf3As;rGs;fluCSup-3' | 7927.13 | 604 |
| 594 | 5'-HO;4S8azG;omeC;rU;rC;rA;fluU;rU;rUs;rA;fluC;rC;rAs;fluG;omeC; rG;fluU;omeA;fluA;omeA;rUs;rG;rAs;rGs;omeCSup-3' | 7814.05 | 113 |
| 595 | 5'-HO;rG;araC;rU;rC;rA;fluU;rU;rUs;rA;fluC;rC;rAs;fluG;omeC;rG; fluU;omeA;fluA;omeA;rUs;rG;rAs;rGs;omeCSup-3' | 7782.98 | 605 |
| 596 | 5'-HO;rG;omeC;araU;rC;rA;fluU;rU;rUs;rA;fluC;rC;rAs;fluG;omeC; rG;fluU;omeA;fluA;omeA;rUs;rG;rAs;rGs;omeCSup-3' | 7797.00 | 606 |
| 597 | 5'-HO;rG;omeC;rU;araC;rA;fluU;rU;rUs;rA;fluC;rC;rAs;fluG;omeC; rG;fluU;omeA;fluA;omeA;rUs;rG;rAs;rGs;omeCSup-3' | 7797.00 | 607 |
| 598 | 5'-HO;rG;omeC;rU;rC;araA;fluU;rU;rUs;rA;fluC;rC;rAs;fluG;omeC; rG;fluU;omeA;fluA;omeA;rUs;rG;rAs;rGs;omeCSup-3' | 7797.00 | 608 |
| 599 | 5'-HO;rG;omeC;rU;rC;rA;araU;rU;rUs;rA;fluC;rC;rAs;fluG;omeC;rG; fluU;omeA;fluA;omeA;rUs;rG;rAs;rGs;omeCSup-3' | 7795.01 | 609 |
| 600 | 5'-HO;rG;omeC;rU;rC;rA;fluU;araU;rUs;rA;fluC;rC;rAs;fluG;omeC; rG;fluU;omeA;fluA;omeA;rUs;rG;rAs;rGs;omeCSup-3' | 7797.00 | 610 |
| 601 | 5'-HO;rG;omeC;rU;rC;rA;fluU;rU;araUs;rA;fluC;rC;rAs;fluG;omeC; rG;fluU;omeA;fluA;omeA;rUs;rG;rAs;rGs;omeCSup-3' | 7797.00 | 611 |
| 602 | 5'-HO;rG;omeC;rU;rC;rA;fluU;rU;rUs;araA;fluC;rC;rAs;fluG;omeC; rG;fluU;omeA;fluA;omeA;rUs;rG;rAs;rGs;omeCSup-3' | 7797.00 | 612 |
| 603 | 5'-HO;rG;omeC;rU;rC;rA;fluU;rU;rUs;rA;araC;rC;rAs;fluG;omeC;rG; fluU;omeA;fluA;omeA;rUs;rG;rAs;rGs;omeCSup-3' | 7795.01 | 613 |
| 604 | 5'-HO;rG;omeC;rU;rC;rA;fluU;rU;rUs;rA;fluC;araC;rAs;fluG;omeC; rG;fluU;omeA;fluA;omeA;rUs;rG;rAs;rGs;omeCSup-3' | 7797.00 | 614 |
| 605 | 5'-HO;rG;omeC;rU;rC;rA;fluU;rU;rUs;rA;fluC;rC;araAs;fluG;omeC; rG;fluU;omeA;fluA;omeA;rUs;rG;rAs;rGs;omeCSup-3' | 7797.00 | 615 |
| 606 | 5'-HO;rG;omeC;rU;rC;rA;fluU;rU;rUs;rA;fluC;rC;rAs;4S8azG;omeC; rG;fluU;omeA;fluA;omeA;rUs;rG;rAs;rGs;omeCSup-3' | 7812.06 | 114 |
| 607 | 5'-HO;rG;omeC;rU;rC;rA;fluU;rU;rUs;rA;fluC;rC;rAs;fluG;araC;rG; fluU;omeA;fluA;omeA;rUs;rG;rAs;rGs;omeCSup-3' | 7782.98 | 616 |
| 608 | 5'-HO;rG;omeC;rU;rC;rA;fluU;rU;rUs;rA;fluC;rC;rAs;fluG;omeC; 4S8azG;fluU;omeA;fluA;omeA;rUs;rG;rAs;rGs;omeCSup-3' | 7814.05 | 115 |
| 609 | 5'-HO;rG;omeC;rU;rC;rA;fluU;rU;rUs;rA;fluC;rC;rAs;fluG;omeC;rG; araU;omeA;fluA;omeA;rUs;rG;rAs;rGs;omeCSup-3' | 7795.01 | 617 |
| 610 | 5'-HO;rG;omeC;rU;rC;rA;fluU;rU;rUs;rA;fluC;rC;rAs;fluG;omeC;rG; fluU;araA;fluA;omeA;rUs;rG;rAs;rGs;omeCSup-3' | 7782.98 | 618 |
| 611 | 5'-HO;rG;omeC;rU;rC;rA;fluU;rU;rUs;rA;fluC;rC;rAs;fluG;omeC;rG; fluU;omeA;araA;omeA;rUs;rG;rAs;rGs;omeCSup-3' | 7795.01 | 619 |
| 612 | 5'-HO;rG;omeC;rU;rC;rA;fluU;rU;rUs;rA;fluC;rC;rAs;fluG;omeC;rG; fluU;omeA;fluA;araA;rUs;rG;rAs;rGs;omeCSup-3' | 7782.98 | 620 |
| 613 | 5'-HO;rG;omeC;rU;rC;rA;fluU;rU;rUs;rA;fluC;rC;rAs;fluG;omeC;rG; fluU;omeA;fluA;omeA;araUs;rG;rAs;rGs;omeCSup-3' | 7797.00 | 621 |
| 614 | 5'-HO;rG;omeC;rU;rC;rA;fluU;rU;rUs;rA;fluC;rC;rAs;fluG;omeC;rG; fluU;omeA;fluA;omeA;rUs;4S8azG;rAs;rGs;omeCSup-3' | 7814.05 | 116 |
| 615 | 5'-HO;rG;omeC;rU;rC;rA;fluU;rU;rUs;rA;fluC;rC;rAs;fluG;omeC;rG; fluU;omeA;fluA;omeA;rUs;rG;araAs;rGs;omeCSup-3' | 7797.00 | 622 |
| 616 | 5'-HO;rG;omeC;rU;rC;rA;fluU;rU;rUs;rA;fluC;rC;rAs;fluG;omeC;rG; fluU;omeA;fluA;omeA;rUs;rG;rAs;4S8azGs;omeCSup-3' | 7814.05 | 117 |
| 617 | 5'-HO;rG;omeC;rU;rC;rA;rxyloU;rU;rUs;rA;fluC;rC;rAs;fluG;omeC; rG;fluU;omeA;fluA;omeA;rUs;rG;rAs;rGs;omeCSup-3' | 7795.01 | 623 |
| 618 | 5'-HO;rG;omeC;rU;rC;rA;fluU;rxyloU;rUs;rA;fluC;rC;rAs;fluG;omeC; rG;fluU;omeA;fluA;omeA;rUs;rG;rAs;rGs;omeCSup-3' | 7797.00 | 624 |
| 619 | 5'-HO;rG;omeC;rU;rC;rA;fluU;rU;rxyloUs;rA;fluC;rC;rAs;fluG;omeC; rG;fluU;omeA;fluA;omeA;rUs;rG;rAs;rGs;omeCSup-3' | 7797.00 | 625 |
| 620 | 5'-HO;rG;omeC;rU;rC;rA;fluU;rU;rUs;rA;rxyloC;rC;rAs;fluG;omeC; rG;fluU;omeA;fluA;omeA;rUs;rG;rAs;rGs;omeCSup-3' | 7795.01 | 626 |
| 621 | 5'-HO;rG;omeC;rU;rC;rA;fluU;rU;rUs;rA;fluC;rxyloC;rAs;fluG;omeC; rG;fluU;omeA;fluA;omeA;rUs;rG;rAs;rGs;omeCSup-3' | 7797.00 | 627 |
| 622 | 5'-HO;rG;omeC;rU;rC;rA;fluU;rU;rUs;rA;fluC;rC;rxyloAs;fluG;omeC; rG;fluU;omeA;fluA;omeA;rUs;rG;rAs;rGs;omeCSup-3' | 7797.00 | 628 |
| 623 | 5'-HO;rG;omeC;rU;rC;rA;fluU;rU;rUs;rA;fluC;rC;rAs;rxyloG;omeC; rG;fluU;omeA;fluA;omeA;rUs;rG;rAs;rGs;omeCSup-3' | 7795.01 | 629 |
| 624 | 5'-HO;rG;omeC;rU;rC;rA;fluU;rU;rUs;rA;fluC;rC;rAs;fluG;rxyloC;rG; fluU;omeA;fluA;omeA;rUs;rG;rAs;rGs;omeCSup-3' | 7782.98 | 630 |
| 625 | 5'-HO;rG;omeC;rU;rC;rA;fluU;rU;rUs;rA;fluC;rC;rAs;fluG;omeC;rxyloG; fluU;omeA;fluA;omeA;rUs;rG;rAs;rGs;omeCSup-3' | 7797.00 | 631 |
| 626 | 5'-HO;rG;omeC;rU;rC;rA;fluU;rU;rUs;rA;fluC;rC;rAs;fluG;omeC;rG; rxyloU;omeA;fluA;omeA;rUs;rG;rAs;rGs;omeCSup-3' | 7795.01 | 632 |
| 627 | 5'-HO;rG;omeC;rU;rC;rA;fluU;rU;rUs;rA;fluC;rC;rAs;fluG;omeC;rG; fluU;rxyloA;fluA;omeA;rUs;rG;rAs;rGs;omeCSup-3' | 7782.98 | 633 |
| 628 | 5'-HO;rG;omeC;rU;rC;rA;fluU;rU;rUs;rA;fluC;rC;rAs;fluG;omeC;rG; fluU;omeA;rxyloA;omeA;rUs;rG;rAs;rGs;omeCSup-3' | 7795.01 | 634 |
| 629 | 5'-HO;rG;omeC;rU;rC;rA;fluU;rU;rUs;rA;fluC;rC;rAs;fluG;omeC;rG; fluU;omeA;fluA;rxyloA;rUs;rG;rAs;rGs;omeCSup-3' | 7782.98 | 635 |

TABLE 5-continued

| Ex | Sequence | MW | SEQ ID No. |
|---|---|---|---|
| 630 | 5'-HO;rG;omeC;rU;rC;rA;fluU;rU;rUs;rA;fluC;rC;rAs;fluG;omeC;rG; fluU;omeA;fluA;omeA;rxyloUs;rG;rAs;rGs;omeCSup-3' | 7797.00 | 636 |
| 631 | 5'-HO;rG;omeC;rU;rC;rA;fluU;rU;rUs;rA;fluC;rC;rAs;fluG;omeC;rG; fluU;omeA;fluA;omeA;rUs;rxyloG;rAs;rGs;omeCSup-3' | 7797.00 | 637 |
| 632 | 5'-HO;rG;omeC;rU;rC;rA;fluU;rU;rUs;rA;fluC;rC;rAs;fluG;omeC;rG; fluU;omeA;fluA;omeA;rUs;rG;rxyloAs;rGs;omeCSup-3' | 7797.00 | 638 |
| 633 | 5'-HO;rG;omeC;rU;rC;rA;fluU;rU;rUs;rA;fluC;rC;rAs;fluG;omeC;rG; fluU;omeA;fluA;omeA;rUs;rG;rAs;rxyloGs;omeCSup-3' | 7797.00 | 639 |
| 634 | 5'-HO;4S8azG;rC;rUs;fluC;omeA;fluU;rU;rUs;fluA;omeC;omeC;rAs; omeG;omeC;omeG;omeU;rA;fluA;fluA;omeUs;fluG;omeAs;rGs;fluCSup-3' | 7890.21 | 118 |
| 635 | 5'-HO;rG;araC;rUs;fluC;omeA;fluU;rU;rUs;fluA;omeC;omeC;rAs;omeG; omeC;omeG;omeU;rA;fluA;fluA;omeUs;fluG;omeAs;rGs;fluCSup-3' | 7873.16 | 640 |
| 636 | 5'-HO;rG;rC;araUs;fluC;omeA;fluU;rU;rUs;fluA;omeC;omeC;rAs;omeG; omeC;omeG;omeU;rA;fluA;fluA;omeUs;fluG;omeAs;rGs;fluCSup-3' | 7873.16 | 641 |
| 637 | 5'-HO;rG;rC;rUs;araC;omeA;fluU;rU;rUs;fluA;omeC;omeC;rAs;omeG; omeC;omeG;omeU;rA;fluA;fluA;omeUs;fluG;omeAs;rGs;fluCSup-3' | 7871.17 | 642 |
| 638 | 5'-HO;rG;rC;rUs;fluC;araA;fluU;rU;rUs;fluA;omeC;omeC;rAs;omeG; omeC;omeG;omeU;rA;fluA;fluA;omeUs;fluG;omeAs;rGs;fluCSup-3' | 7859.13 | 643 |
| 639 | 5'-HO;rG;rC;rUs;fluC;omeA;araU;rU;rUs;fluA;omeC;omeC;rAs;omeG; omeC;omeG;omeU;rA;fluA;fluA;omeUs;fluG;omeAs;rGs;fluCSup-3' | 7871.17 | 644 |
| 640 | 5'-HO;rG;rC;rUs;fluC;omeA;fluU;araU;rUs;fluA;omeC;omeC;rAs;omeG; omeC;omeG;omeU;rA;fluA;fluA;omeUs;fluG;omeAs;rGs;fluCSup-3' | 7873.16 | 645 |
| 641 | 5'-HO;rG;rC;rUs;fluC;omeA;fluU;rU;araUs;fluA;omeC;omeC;rAs;omeG; omeC;omeG;omeU;rA;fluA;fluA;omeUs;fluG;omeAs;rGs;fluCSup-3' | 7873.16 | 646 |
| 642 | 5'-HO;rG;rC;rUs;fluC;omeA;fluU;rU;rUs;araA;omeC;omeC;rAs;omeG; omeC;omeG;omeU;rA;fluA;fluA;omeUs;fluG;omeAs;rGs;fluCSup-3' | 7871.17 | 647 |
| 643 | 5'-HO;rG;rC;rUs;fluC;omeA;fluU;rU;rUs;fluA;araC;omeC;rAs;omeG; omeC;omeG;omeU;rA;fluA;fluA;omeUs;fluG;omeAs;rGs;fluCSup-3' | 7859.13 | 648 |
| 644 | 5'-HO;rG;rC;rUs;fluC;omeA;fluU;rU;rUs;fluA;omeC;araC;rAs;omeG; omeC;omeG;omeU;rA;fluA;fluA;omeUs;fluG;omeAs;rGs;fluCSup-3' | 7859.13 | 649 |
| 645 | 5'-HO;rG;rC;rUs;fluC;omeA;fluU;rU;rUs;fluA;omeC;omeC;araAs;omeG; omeC;omeG;omeU;rA;fluA;fluA;omeUs;fluG;omeAs;rGs;fluCSup-3' | 7873.16 | 650 |
| 646 | 5'-HO;rG;rC;rUs;fluC;omeA;fluU;rU;rUs;fluA;omeC;omeC;rAs;4S8azG; omeC;omeG;omeU;rA;fluA;fluA;omeUs;fluG;omeAs;rGs;fluCSup-3' | 7876.18 | 119 |
| 647 | 5'-HO;rG;rC;rUs;fluC;omeA;fluU;rU;rUs;fluA;omeC;omeC;rAs;omeG; araC;omeG;omeU;rA;fluA;fluA;omeUs;fluG;omeAs;rGs;fluCSup-3' | 7859.13 | 651 |
| 648 | 5'-HO;rG;rC;rUs;fluC;omeA;fluU;rU;rUs;fluA;omeC;omeC;rAs;omeG; omeC;4S8azG;omeU;rA;fluA;fluA;omeUs;fluG;omeAs;rGs;fluCSup-3' | 7876.18 | 120 |
| 649 | 5'-HO;rG;rC;rUs;fluC;omeA;fluU;rU;rUs;fluA;omeC;omeC;rAs;omeG; omeC;omeG;araU;rA;fluA;fluA;omeUs;fluG;omeAs;rGs;fluCSup-3' | 7859.13 | 652 |
| 650 | 5'-HO;rG;rC;rUs;fluC;omeA;fluU;rU;rUs;fluA;omeC;omeC;rAs;omeG; omeC;omeG;omeU;araA;fluA;fluA;omeUs;fluG;omeAs;rGs;fluCSup-3' | 7873.16 | 653 |
| 651 | 5'-HO;rG;rC;rUs;fluC;omeA;fluU;rU;rUs;fluA;omeC;omeC;rAs;omeG; omeC;omeG;omeU;rA;araA;fluA;omeUs;fluG;omeAs;rGs;fluCSup-3' | 7871.17 | 654 |
| 652 | 5'-HO;rG;rC;rUs;fluC;omeA;fluU;rU;rUs;fluA;omeC;omeC;rAs;omeG; omeC;omeG;omeU;rA;fluA;araA;omeUs;fluG;omeAs;rGs;fluCSup-3' | 7871.17 | 655 |
| 653 | 5'-HO;rG;rC;rUs;fluC;omeA;fluU;rU;rUs;fluA;omeC;omeC;rAs;omeG; omeC;omeG;omeU;rA;fluA;fluA;araUs;fluG;omeAs;rGs;fluCSup-3' | 7859.13 | 656 |
| 654 | 5'-HO;rG;rC;rUs;fluC;omeA;fluU;rU;rUs;fluA;omeC;omeC;rAs;omeG; omeC;omeG;omeU;rA;fluA;fluA;omeUs;4S8azG;omeAs;rGs;fluCSup-3' | 7888.22 | 121 |
| 655 | 5'-HO;rG;rC;rUs;fluC;omeA;fluU;rU;rUs;fluA;omeC;omeC;rAs;omeG; omeC;omeG;omeU;rA;fluA;fluA;omeUs;fluG;araAs;rGs;fluCSup-3' | 7859.13 | 657 |
| 656 | 5'-HO;rG;rC;rUs;fluC;omeA;fluU;rU;rUs;fluA;omeC;omeC;rAs;omeG; omeC;omeG;omeU;rA;fluA;fluA;omeUs;fluG;omeAs;4S8azGs;fluCSup-3' | 7890.20 | 122 |
| 657 | 5'-HO;rG;rC;rUs;fluC;omeA;rxyloU;rU;rUs;fluA;omeC;omeC;rAs;omeG; omeC;omeG;omeU;rA;fluA;fluA;omeUs;fluG;omeAs;rGs;fluCSup-3' | 7871.17 | 658 |
| 658 | 5'-HO;rG;rC;rUs;fluC;omeA;fluU;rxyloU;rUs;fluA;omeC;omeC;rAs;omeG; omeC;omeG;omeU;rA;fluA;fluA;omeUs;fluG;omeAs;rGs;fluCSup-3' | 7873.16 | 659 |
| 659 | 5'-HO;rG;rC;rUs;fluC;omeA;fluU;rU;rxyloUs;fluA;omeC;omeC;rAs;omeG; omeC;omeG;omeU;rA;fluA;fluA;omeUs;fluG;omeAs;rGs;fluCSup-3' | 7873.16 | 660 |
| 660 | 5'-HO;rG;rC;rUs;fluC;omeA;fluU;rU;rUs;fluA;omeC;rxyloC;rAs;omeG; omeC;omeG;omeU;rA;fluA;fluA;omeUs;fluG;omeAs;rGs;fluCSup-3' | 7859.13 | 661 |
| 661 | 5'-HO;rG;rC;rUs;fluC;omeA;fluU;rU;rUs;fluA;omeC;omeC;rxyloAs; omeG;omeC;omeG;omeU;rA;fluA;fluA;omeUs;fluG;omeAs;rGs;fluCSup-3' | 7873.16 | 662 |
| 662 | 5'-HO;rG;rC;rUs;fluC;omeA;fluU;rU;rUs;fluA;omeC;omeC;rAs;rxyloG; omeC;omeG;omeU;rA;fluA;fluA;omeUs;fluG;omeAs;rGs;fluCSup-3' | 7859.13 | 663 |
| 663 | 5'-HO;rG;rC;rUs;fluC;omeA;fluU;rU;rUs;fluA;omeC;omeC;rAs;omeG; rxyloC;omeG;omeU;rA;fluA;fluA;omeUs;fluG;omeAs;rGs;fluCSup-3' | 7859.13 | 664 |
| 664 | 5'-HO;rG;rC;rUs;fluC;omeA;fluU;rU;rUs;fluA;omeC;omeC;rAs;omeG; omeC;rxyloG;omeU;rA;fluA;fluA;omeUs;fluG;omeAs;rGs;fluCSup-3' | 7859.13 | 665 |
| 665 | 5'-HO;rG;rC;rUs;fluC;omeA;fluU;rU;rUs;fluA;omeC;omeC;rAs;omeG; omeC;omeG;rxyloU;rA;fluA;fluA;omeUs;fluG;omeAs;rGs;fluCSup-3' | 7859.13 | 666 |
| 666 | 5'-HO;rG;rC;rUs;fluC;omeA;fluU;rU;rUs;fluA;omeC;omeC;rAs;omeG; omeC;omeG;omeU;rxyloA;fluA;fluA;omeUs;fluG;omeAs;rGs;fluCSup-3' | 7873.16 | 667 |
| 667 | 5'-HO;rG;rC;rUs;fluC;omeA;fluU;rU;rUs;fluA;omeC;omeC;rAs;omeG; omeC;omeG;omeU;rA;rxyloA;fluA;omeUs;fluG;omeAs;rGs;fluCSup-3' | 7871.17 | 668 |

TABLE 5-continued

| Ex | Sequence | MW | SEQ ID No. |
|---|---|---|---|
| 668 | 5'-HO;rG;rC;rUs;fluC;omeA;fluU;rU;rUs;fluA;omeC;omeC;rAs;omeG; omeC;omeG;omeU;rA;fluA;rxyloA;omeUs;fluG;omeAs;rGs;fluCSup-3' | 7871.17 | 669 |
| 669 | 5'-HO;rG;rC;rUs;fluC;omeA;fluU;rU;rUs;fluA;omeC;omeC;rAs;omeG; omeC;omeG;omeU;rA;fluA;fluA;rxyloUs;fluG;omeAs;rGs;fluCSup-3' | 7859.13 | 670 |
| 670 | 5'-HO;rG;rC;rUs;fluC;omeA;fluU;rU;rUs;fluA;omeC;omeC;rAs;omeG; omeC;omeG;omeU;rA;fluA;fluA;omeUs;rxyloG;omeAs;rGs;fluCSup-3' | 7871.17 | 671 |
| 671 | 5'-HO;rG;rC;rUs;fluC;omeA;fluU;rU;rUs;fluA;omeC;omeC;rAs;omeG; omeC;omeG;omeU;rA;fluA;fluA;omeUs;fluG;rxyloAs;rGs;fluCSup-3' | 7859.13 | 672 |
| 672 | 5'-HO;rG;rC;rUs;fluC;omeA;fluU;rU;rUs;fluA;omeC;omeC;rAs;omeG; omeC;omeG;omeU;rA;fluA;fluA;omeUs;fluG;omeAs;rxyloGs;fluCSup-3' | 7873.16 | 673 |
| 673 | 5'-HO;amiG;omeC;rU;rC;rA;fluU;rU;rUs;rA;fluC;rC;rAs;fluG;omeC; rG;fluU;omeA;fluA;omeA;rUs;rG;rAs;rGs;omeCSup-3' | 7796.02 | 674 |
| 674 | 5'-HO;rG;amiC;rU;rC;rA;fluU;rU;rUs;rA;fluC;rC;rAs;fluG;omeC;rG; fluU;omeA;fluA;omeA;rUs;rG;rAs;rGs;omeCSup-3' | 7781.99 | 675 |
| 675 | 5'-HO;rG;omeC;amiU;rC;rA;fluU;rU;rUs;rA;fluC;rC;rAs;fluG;omeC; rG;fluU;omeA;fluA;omeA;rUs;rG;rAs;rGs;omeCSup-3' | 7796.02 | 676 |
| 676 | 5'-HO;rG;omeC;rU;rC;amiA;fluU;rU;rUs;rA;fluC;rC;rAs;fluG;omeC; rG;fluU;omeA;fluA;omeA;rUs;rG;rAs;rGs;omeCSup-3' | 7796.02 | 677 |
| 677 | 5'-HO;rG;omeC;rU;rC;rA;amiU;rU;rUs;rA;fluC;rC;rAs;fluG;omeC;rG; fluU;omeA;fluA;omeA;rUs;rG;rAs;rGs;omeCSup-3' | 7794.03 | 678 |
| 678 | 5'-HO;rG;omeC;rU;rC;rA;fluU;amiU;rUs;rA;fluC;rC;rAs;fluG;omeC; rG;fluU;omeA;fluA;omeA;rUs;rG;rAs;rGs;omeCSup-3' | 7796.02 | 679 |
| 679 | 5'-HO;rG;omeC;rU;rC;rA;fluU;rU;amiUs;rA;fluC;rC;rAs;fluG;omeC; rG;fluU;omeA;fluA;omeA;rUs;rG;rAs;rGs;omeCSup-3' | 7796.02 | 680 |
| 680 | 5'-HO;rG;omeC;rU;rC;rA;fluU;rU;rUs;rA;amiC;rC;rAs;fluG;omeC;rG; fluU;omeA;fluA;omeA;rUs;rG;rAs;rGs;omeCSup-3' | 7794.03 | 681 |
| 681 | 5'-HO;rG;omeC;rU;rC;rA;fluU;rU;rUs;rA;fluC;rC;amiAs;fluG;omeC; rG;fluU;omeA;fluA;omeA;rUs;rG;rAs;rGs;omeCSup-3' | 7796.02 | 682 |
| 682 | 5'-HO;rG;omeC;rU;rC;rA;fluU;rU;rUs;rA;fluC;rC;rAs;amiG;omeC;rG; fluU;omeA;fluA;omeA;rUs;rG;rAs;rGs;omeCSup-3' | 7794.03 | 683 |
| 683 | 5'-HO;rG;omeC;rU;rC;rA;fluU;rU;rUs;rA;fluC;rC;rAs;fluG;amiC;rG; fluU;omeA;fluA;omeA;rUs;rG;rAs;rGs;omeCSup-3' | 7781.99 | 684 |
| 684 | 5'-HO;rG;omeC;rU;rC;rA;fluU;rU;rUs;rA;fluC;rC;rAs;fluG;omeC;rG; amiU;omeA;fluA;omeA;rUs;rG;rAs;rGs;omeCSup-3' | 7794.03 | 685 |
| 685 | 5'-HO;rG;omeC;rU;rC;rA;fluU;rU;rUs;rA;fluC;rC;rAs;fluG;omeC;rG; fluU;omeA;amiA;omeA;rUs;rG;rAs;rGs;omeCSup-3' | 7794.03 | 686 |
| 686 | 5'-HO;rG;omeC;rU;rC;rA;fluU;rU;rUs;rA;fluC;rC;rAs;fluG;omeC;rG; fluU;omeA;fluA;amiA;rUs;rG;rAs;rGs;omeCSup-3' | 7781.99 | 687 |
| 687 | 5'-HO;rG;omeC;rU;rC;rA;fluU;rU;rUs;rA;fluC;rC;rAs;fluG;omeC;rG; fluU;omeA;fluA;omeA;amiUs;rG;rAs;rGs;omeCSup-3' | 7796.02 | 688 |
| 688 | 5'-HO;rG;omeC;rU;rC;rA;fluU;rU;rUs;rA;fluC;rC;rAs;fluG;omeC;rG; fluU;omeA;fluA;omeA;rUs;amiG;rAs;rGs;omeCSup-3' | 7796.02 | 689 |
| 689 | 5'-HO;rG;omeC;rU;rC;rA;fluU;rU;rUs;rA;fluC;rC;rAs;fluG;omeC;rG; fluU;omeA;fluA;omeA;rUs;rG;amiAs;rGs;omeCSup-3' | 7796.02 | 690 |
| 690 | 5'-HO;rG;omeC;rU;rC;rA;fluU;rU;rUs;rA;fluC;rC;rAs;fluG;omeC;rG; fluU;omeA;fluA;omeA;rUs;rG;rAs;amiGs;omeCSup-3' | 7796.02 | 691 |
| 691 | 5'-HO;rG;unaC;rU;rC;rA;fluU;rU;rUs;rA;fluC;rC;rAs;fluG;omeC;rG; fluU;omeA;fluA;omeA;rUs;rG;rAs;rGs;omeCSup-3' | 7784.99 | 692 |
| 692 | 5'-HO;rG;omeC;unaU;rC;rA;fluU;rU;rUs;rA;fluC;rC;rAs;fluG;omeC; rG;fluU;omeA;fluA;omeA;rUs;rG;rAs;rGs;omeCSup-3' | 7799.02 | 693 |
| 693 | 5'-HO;rG;omeC;rU;unaC;rA;fluU;rU;rUs;rA;fluC;rC;rAs;fluG;omeC; rG;fluU;omeA;fluA;omeA;rUs;rG;rAs;rGs;omeCSup-3' | 7799.02 | 694 |
| 694 | 5'-HO;rG;omeC;rU;rC;unaA;fluU;rU;rUs;rA;fluC;rC;rAs;fluG;omeC; rG;fluU;omeA;fluA;omeA;rUs;rG;rAs;rGs;omeCSup-3' | 7799.02 | 695 |
| 695 | 5'-HO;rG;omeC;rU;rC;rA;unaU;rU;rUs;rA;fluC;rC;rAs;fluG;omeC;rG; fluU;omeA;fluA;omeA;rUs;rG;rAs;rGs;omeCSup-3' | 7797.03 | 696 |
| 696 | 5'-HO;rG;omeC;rU;rC;rA;fluU;unaU;rUs;rA;fluC;rC;rAs;fluG;omeC; rG;fluU;omeA;fluA;omeA;rUs;rG;rAs;rGs;omeCSup-3' | 7799.02 | 697 |
| 697 | 5'-HO;rG;omeC;rU;rC;rA;fluU;rU;unaUs;rA;fluC;rC;rAs;fluG;omeC; rG;fluU;omeA;fluA;omeA;rUs;rG;rAs;rGs;omeCSup-3' | 7799.02 | 698 |
| 698 | 5'-HO;rG;omeC;rU;rC;rA;fluU;rU;rUs;unaA;fluC;rC;rAs;fluG;omeC; rG;fluU;omeA;fluA;omeA;rUs;rG;rAs;rGs;omeCSup-3' | 7799.02 | 699 |
| 699 | 5'-HO;rG;omeC;rU;rC;rA;fluU;rU;rUs;rA;unaC;rC;rAs;fluG;omeC;rG; fluU;omeA;fluA;omeA;rUs;rG;rAs;rGs;omeCSup-3' | 7797.03 | 700 |
| 700 | 5'-HO;rG;omeC;rU;rC;rA;fluU;rU;rUs;rA;fluC;unaC;rAs;fluG;omeC; rG;fluU;omeA;fluA;omeA;rUs;rG;rAs;rGs;omeCSup-3' | 7799.02 | 701 |
| 701 | 5'-HO;rG;omeC;rU;rC;rA;fluU;rU;rUs;rA;fluC;rC;unaAs;fluG;omeC; rG;fluU;omeA;fluA;omeA;rUs;rG;rAs;rGs;omeCSup-3' | 7799.02 | 702 |
| 702 | 5'-HO;rG;omeC;rU;rC;rA;fluU;rU;rUs;rA;fluC;rC;rAs;unaG;omeC;rG; fluU;omeA;fluA;omeA;rUs;rG;rAs;rGs;omeCSup-3' | 7797.03 | 703 |
| 703 | 5'-HO;rG;omeC;rU;rC;rA;fluU;rU;rUs;rA;fluC;rC;rAs;fluG;unaC;rG; fluU;omeA;fluA;omeA;rUs;rG;rAs;rGs;omeCSup-3' | 7784.99 | 704 |
| 704 | 5'-HO;rG;omeC;rU;rC;rA;fluU;rU;rUs;rA;fluC;rC;rAs;fluG;omeC;unaG; fluU;omeA;fluA;omeA;rUs;rG;rAs;rGs;omeCSup-3' | 7799.02 | 705 |
| 705 | 5'-HO;rG;omeC;rU;rC;rA;fluU;rU;rUs;rA;fluC;rC;rAs;fluG;omeC;rG; unaU;omeA;fluA;omeA;rUs;rG;rAs;rGs;omeCSup-3' | 7797.03 | 706 |

TABLE 5-continued

| Ex | Sequence | MW | SEQ ID No. |
|---|---|---|---|
| 706 | 5'-HO;rG;omeC;rU;rC;rA;fluU;rU;rUs;rA;fluC;rC;rAs;fluG;omeC;rG; fluU;unaA;fluA;omeA;rUs;rG;rAs;rGs;omeCSup-3' | 7784.99 | 707 |
| 707 | 5'-HO;rG;omeC;rU;rC;rA;fluU;rU;rUs;rA;fluC;rC;rAs;fluG;omeC;rG; fluU;omeA;unaA;omeA;rUs;rG;rAs;rGs;omeCSup-3' | 7797.03 | 708 |
| 708 | 5'-HO;rG;omeC;rU;rC;rA;fluU;rU;rUs;rA;fluC;rC;rAs;fluG;omeC;rG; fluU;omeA;fluA;unaA;rUs;rG;rAs;rGs;omeCSup-3' | 7784.99 | 709 |
| 709 | 5'-HO;rG;omeC;rU;rC;rA;fluU;rU;rUs;rA;fluC;rC;rAs;fluG;omeC;rG; fluU;omeA;fluA;omeA;unaUs;rG;rAs;rGs;omeCSup-3' | 7799.02 | 710 |
| 710 | 5'-HO;rG;omeC;rU;rC;rA;fluU;rU;rUs;rA;fluC;rC;rAs;fluG;omeC;rG; fluU;omeA;fluA;omeA;rUs;unaG;rAs;rGs;omeCSup-3' | 7799.02 | 711 |
| 711 | 5'-HO;rG;omeC;rU;rC;rA;fluU;rU;rUs;rA;fluC;rC;rAs;fluG;omeC;rG; fluU;omeA;fluA;omeA;rUs;rG;unaAs;rGs;omeCSup-3' | 7799.02 | 712 |
| 712 | 5'-HO;rG;omeC;rU;rC;rA;fluU;rU;rUs;rA;fluC;rC;rAs;fluG;omeC;rG; fluU;omeA;fluA;omeA;rUs;rG;rAs;unaGs;omeCSup-3' | 7799.02 | 713 |
| 713 | 5'-HO;amiG;rC;rUs;fluC;omeA;fluU;rU;rUs;fluA;omeC;omeC;rAs;omeG; omeC;omeG;omeU;rA;fluA;fluA;omeUs;fluG;omeAs;rGs;fluCSup-3' | 7872.17 | 714 |
| 714 | 5'-HO;rG;amiC;rUs;fluC;omeA;fluU;rU;rUs;fluA;omeC;omeC;rAs;omeG; omeC;omeG;omeU;rA;fluA;fluA;omeUs;fluG;omeAs;rGs;fluCSup-3' | 7872.17 | 715 |
| 715 | 5'-HO;rG;rC;amiUs;fluC;omeA;fluU;rU;rUs;fluA;omeC;omeC;rAs;omeG; omeC;omeG;omeU;rA;fluA;fluA;omeUs;fluG;omeAs;rGs;fluCSup-3' | 7872.17 | 716 |
| 716 | 5'-HO;rG;rC;rUs;amiC;omeA;fluU;rU;rUs;fluA;omeC;omeC;rAs;omeG; omeC;omeG;omeU;rA;fluA;fluA;omeUs;fluG;omeAs;rGs;fluCSup-3' | 7870.18 | 717 |
| 717 | 5'-HO;rG;rC;rUs;fluC;amiA;fluU;rU;rUs;fluA;omeC;omeC;rAs;omeG; omeC;omeG;omeU;rA;fluA;fluA;omeUs;fluG;omeAs;rGs;fluCSup-3' | 7858.15 | 718 |
| 718 | 5'-HO;rG;rC;rUs;fluC;omeA;amiU;rU;rUs;fluA;omeC;omeC;rAs;omeG; omeC;omeG;omeU;rA;fluA;fluA;omeUs;fluG;omeAs;rGs;fluCSup-3' | 7870.18 | 719 |
| 719 | 5'-HO;rG;rC;rUs;fluC;omeA;fluU;amiU;rUs;fluA;omeC;omeC;rAs;omeG; omeC;omeG;omeU;rA;fluA;fluA;omeUs;fluG;omeAs;rGs;fluCSup-3' | 7872.17 | 720 |
| 720 | 5'-HO;rG;rC;rUs;fluC;omeA;fluU;rU;amiUs;fluA;omeC;omeC;rAs;omeG; omeC;omeG;omeU;rA;fluA;fluA;omeUs;fluG;omeAs;rGs;fluCSup-3' | 7872.17 | 721 |
| 721 | 5'-HO;rG;rC;rUs;fluC;omeA;fluU;rU;rUs;fluA;amiC;omeC;rAs;omeG; omeC;omeG;omeU;rA;fluA;fluA;omeUs;fluG;omeAs;rGs;fluCSup-3' | 7858.15 | 722 |
| 722 | 5'-HO;rG;rC;rUs;fluC;omeA;fluU;rU;rUs;fluA;omeC;amiC;rAs;omeG; omeC;omeG;omeU;rA;fluA;fluA;omeUs;fluG;omeAs;rGs;fluCSup-3' | 7858.15 | 723 |
| 723 | 5'-HO;rG;rC;rUs;fluC;omeA;fluU;rU;rUs;fluA;omeC;omeC;amiAs;omeG; omeC;omeG;omeU;rA;fluA;fluA;omeUs;fluG;omeAs;rGs;fluCSup-3' | 7872.17 | 724 |
| 724 | 5'-HO;rG;rC;rUs;fluC;omeA;fluU;rU;rUs;fluA;omeC;omeC;rAs;amiG; omeC;omeG;omeU;rA;fluA;fluA;omeUs;fluG;omeAs;rGs;fluCSup-3' | 7858.15 | 725 |
| 725 | 5'-HO;rG;rC;rUs;fluC;omeA;fluU;rU;rUs;fluA;omeC;omeC;rAs;omeG; amiC;omeG;omeU;rA;fluA;fluA;omeUs;fluG;omeAs;rGs;fluCSup-3' | 7858.15 | 726 |
| 726 | 5'-HO;rG;rC;rUs;fluC;omeA;fluU;rU;rUs;fluA;omeC;omeC;rAs;omeG; omeC;amiG;omeU;rA;fluA;fluA;omeUs;fluG;omeAs;rGs;fluCSup-3' | 7858.15 | 727 |
| 727 | 5'-HO;rG;rC;rUs;fluC;omeA;fluU;rU;rUs;fluA;omeC;omeC;rAs;omeG; omeC;omeG;amiU;rA;fluA;fluA;omeUs;fluG;omeAs;rGs;fluCSup-3' | 7858.15 | 728 |
| 728 | 5'-HO;rG;rC;rUs;fluC;omeA;fluU;rU;rUs;fluA;omeC;omeC;rAs;omeG; omeC;omeG;omeU;amiA;fluA;fluA;omeUs;fluG;omeAs;rGs;fluCSup-3' | 7872.17 | 729 |
| 729 | 5'-HO;rG;rC;rUs;fluC;omeA;fluU;rU;rUs;fluA;omeC;omeC;rAs;omeG; omeC;omeG;omeU;rA;amiA;fluA;omeUs;fluG;omeAs;rGs;fluCSup-3' | 7870.18 | 730 |
| 730 | 5'-HO;rG;rC;rUs;fluC;omeA;fluU;rU;rUs;fluA;omeC;omeC;rAs;omeG; omeC;omeG;omeU;rA;fluA;amiA;omeUs;fluG;omeAs;rGs;fluCSup-3' | 7870.18 | 731 |
| 731 | 5'-HO;rG;rC;rUs;fluC;omeA;fluU;rU;rUs;fluA;omeC;omeC;rAs;omeG; omeC;omeG;omeU;rA;fluA;fluA;amiUs;fluG;omeAs;rGs;fluCSup-3' | 7858.15 | 732 |
| 732 | 5'-HO;rG;rC;rUs;fluC;omeA;fluU;rU;rUs;fluA;omeC;omeC;rAs;omeG; omeC;omeG;omeU;rA;fluA;fluA;omeUs;fluG;amiAs;rGs;fluCSup-3' | 7858.15 | 733 |
| 733 | 5'-HO;rG;rC;rUs;fluC;omeA;fluU;rU;rUs;fluA;omeC;omeC;rAs;omeG; omeC;omeG;omeU;rA;fluA;fluA;omeUs;fluG;omeAs;amiGs;fluCSup-3' | 7872.17 | 734 |
| 734 | 5'-HO;unaG;rC;rUs;fluC;omeA;fluU;rU;rUs;fluA;omeC;omeC;rAs;omeG; omeC;omeG;omeU;rA;fluA;fluA;omeUs;fluG;omeAs;rGs;fluCSup-3' | 7875.17 | 735 |
| 735 | 5'-HO;rG;unaC;rUs;fluC;omeA;fluU;rU;rUs;fluA;omeC;omeC;rAs;omeG; omeC;omeG;omeU;rA;fluA;fluA;omeUs;fluG;omeAs;rGs;fluCSup-3' | 7875.17 | 736 |
| 736 | 5'-HO;rG;rC;unaUs;fluC;omeA;fluU;rU;rUs;fluA;omeC;omeC;rAs;omeG; omeC;omeG;omeU;rA;fluA;fluA;omeUs;fluG;omeAs;rGs;fluCSup-3' | 7875.17 | 737 |
| 737 | 5'-HO;rG;rC;rUs;unaC;omeA;fluU;rU;rUs;fluA;omeC;omeC;rAs;omeG; omeC;omeG;omeU;rA;fluA;fluA;omeUs;fluG;omeAs;rGs;fluCSup-3' | 7873.18 | 738 |
| 738 | 5'-HO;rG;rC;rUs;fluC;unaA;fluU;rU;rUs;fluA;omeC;omeC;rAs;omeG; omeC;omeG;omeU;rA;fluA;fluA;omeUs;fluG;omeAs;rGs;fluCSup-3' | 7861.15 | 739 |
| 739 | 5'-HO;rG;rC;rUs;fluC;omeA;unaU;rU;rUs;fluA;omeC;omeC;rAs;omeG; omeC;omeG;omeU;rA;fluA;fluA;omeUs;fluG;omeAs;rGs;fluCSup-3' | 7873.18 | 740 |
| 740 | 5'-HO;rG;rC;rUs;fluC;omeA;fluU;unaU;rUs;fluA;omeC;omeC;rAs;omeG; omeC;omeG;omeU;rA;fluA;fluA;omeUs;fluG;omeAs;rGs;fluCSup-3' | 7875.17 | 741 |
| 741 | 5'-HO;rG;rC;rUs;fluC;omeA;fluU;rU;unaUs;fluA;omeC;omeC;rAs;omeG; omeC;omeG;omeU;rA;fluA;fluA;omeUs;fluG;omeAs;rGs;fluCSup-3' | 7875.17 | 742 |
| 742 | 5'-HO;rG;rC;rUs;fluC;omeA;fluU;rU;rUs;unaA;omeC;omeC;rAs;omeG; omeC;omeG;omeU;rA;fluA;fluA;omeUs;fluG;omeAs;rGs;fluCSup-3' | 7873.18 | 743 |
| 743 | 5'-HO;rG;rC;rUs;fluC;omeA;fluU;rU;rUs;fluA;unaC;omeC;rAs;omeG; omeC;omeG;omeU;rA;fluA;fluA;omeUs;fluG;omeAs;rGs;fluCSup-3' | 7861.15 | 744 |

TABLE 5-continued

| Ex | Sequence | MW | SEQ ID No. |
|---|---|---|---|
| 744 | 5'-HO;rG;rC;rUs;fluC;omeA;fluU;rU;rUs;fluA;omeC;unaC;rAs;omeG; omeC;omeG;omeU;rA;fluA;fluA;omeUs;fluG;omeAs;rGs;fluCSup-3' | 7861.15 | 745 |
| 745 | 5'-HO;rG;rC;rUs;fluC;omeA;fluU;rU;rUs;fluA;omeC;omeC;rAs;unaG; omeC;omeG;omeU;rA;fluA;fluA;omeUs;fluG;omeAs;rGs;fluCSup-3' | 7861.15 | 746 |
| 746 | 5'-HO;rG;rC;rUs;fluC;omeA;fluU;rU;rUs;fluA;omeC;omeC;rAs;omeG; omeC;unaU;rA;fluA;fluA;omeUs;fluG;omeAs;rGs;fluCSup-3' | 7861.15 | 747 |
| 747 | 5'-HO;rG;rC;rUs;fluC;omeA;fluU;rU;rUs;fluA;omeC;omeC;rAs;omeG; omeC;omeG;omeU;unaA;fluA;fluA;omeUs;fluG;omeAs;rGs;fluCSup-3' | 7875.17 | 748 |
| 748 | 5'-HO;rG;rC;rUs;fluC;omeA;fluU;rU;rUs;fluA;omeC;omeC;rAs;omeG; omeC;omeG;omeU;rA;unaA;fluA;omeUs;fluG;omeAs;rGs;fluCSup-3' | 7873.18 | 749 |
| 749 | 5'-HO;rG;rC;rUs;fluC;omeA;fluU;rU;rUs;fluA;omeC;omeC;rAs;omeG; omeC;omeG;omeU;rA;fluA;unaA;omeUs;fluG;omeAs;rGs;fluCSup-3' | 7873.18 | 750 |
| 750 | 5'-HO;rG;rC;rUs;fluC;omeA;fluU;rU;rUs;fluA;omeC;omeC;rAs;omeG; omeC;omeG;omeU;rA;fluA;fluA;unaUs;fluG;omeAs;rGs;fluCSup-3' | 7861.15 | 751 |
| 751 | 5'-HO;rG;rC;rUs;fluC;omeA;fluU;rU;rUs;fluA;omeC;omeC;rAs;omeG; omeC;omeG;omeU;rA;fluA;fluA;omeUs;unaG;omeAs;rGs;fluCSup-3' | 7873.18 | 752 |
| 752 | 5'-HO;rG;rC;rUs;fluC;omeA;fluU;rU;rUs;fluA;omeC;omeC;rAs;omeG; omeC;omeG;omeU;rA;fluA;fluA;omeUs;fluG;unaAs;rGs;fluCSup-3' | 7861.15 | 753 |
| 753 | 5'-HO;rG;rC;rUs;fluC;omeA;fluU;rU;rUs;fluA;omeC;omeC;rAs;omeG; omeC;omeG;omeU;rA;fluA;fluA;omeUs;fluG;omeAs;unaGs;fluCSup-3' | 7875.17 | 754 |
| 754 | 5'-HO;4alk-dG;omeC;rU;rC;rA;fluU;rU;rUs;rA;fluC;rC;rAs;fluG;omeC;rG;fluU; omeA;fluA;omeA;rUs;rG;rAs;rGs;omeCSup-3' | 7805.03 | 755 |
| 755 | 5'-HO;rG;4alk-dC;rU;rC;rA;fluU;rU;rUs;rA;fluC;rC;rAs;fluG;omeC;rG;fluU;omeA; fluA;omeA;rUs;rG;rAs;rGs;omeCSup-3' | 7791.00 | 756 |
| 756 | 5'-HO;rG;omeC;4alk-dU;rC;rA;fluU;rU;rUs;rA;fluC;rC;rAs;fluG;omeC;rG;fluU;omeA; fluA;omeA;rUs;rG;rAs;rGs;omeCSup-3' | 7805.03 | 757 |
| 757 | 5'-HO;rG;omeC;rU;4alk-dC;rA;fluU;rU;rUs;rA;fluC;rC;rAs;fluG;omeC;rG;fluU;omeA;fluA; omeA;rUs;rG;rAs;rGs;omeCSup-3' | 7805.03 | 758 |
| 758 | 5'-HO;rG;omeC;rU;rC;4alk-dA;fluU;rU;rUs;rA;fluC;rC;rAs;fluG;omeC;rG;fluU;omeA;fluA;omeA; rUs;rG;rAs;rGs;omeCSup-3' | 7805.03 | 759 |
| 759 | 5'-HO;rG;omeC;rU;rC;rA;4alk-dU;rU;rUs;rA;fluC;rC;rAs;fluG;omeC;rG;fluU;omeA;fluA;omeA; rUs;rG;rAs;rGs;omeCSup-3' | 7803.04 | 760 |
| 760 | 5'-HO;rG;omeC;rU;rC;rA;fluU;4alk-dU;rUs;rA;fluC;rC;rAs;fluG;omeC;rG;fluU;omeA;fluA;omeA;rUs; rG;rAs;rGs;omeCSup-3' | 7805.03 | 761 |
| 761 | 5'-HO;rG;omeC;rU;rC;rA;fluU;rU;4alk-dUs;rA;fluC;rC;rAs;fluG;omeC;rG;fluU;omeA;fluA;omeA;rUs;rG; rAs;rGs;omeCSup-3' | 7805.02 | 762 |
| 762 | 5'-HO;rG;omeC;rU;rC;rA;fluU;rU;rUs;4alk-dA;fluC;rC;rAs;fluG;omeC;rG;fluU;omeA;fluA;omeA;rUs;rG;rAs; rGs;omeCSup-3' | 7805.03 | 763 |
| 763 | 5'-HO;rG;omeC;rU;rC;rA;fluU;rU;rUs;rA;4alk-dC;rC;rAs;fluG;omeC;rG;fluU;omeA;fluA;omeA;rUs;rG;rAs;rGs; omeCSup-3' | 7803.04 | 764 |
| 764 | 5'-HO;rG;omeC;rU;rC;rA;fluU;rU;rUs;rA;fluC;rC;4alk-dAs;fluG;omeC;rG;fluU;omeA;fluA;omeA;rUs;rG;rAs;rGs;omeCSup-3' | 7805.02 | 765 |
| 765 | 5'-HO;rG;omeC;rU;rC;rA;fluU;rU;rUs;rA;fluC;rC;rAs;fluG;4alk-dC;rG;fluU;omeA;fluA;omeA;rUs;rG;rAs;rGs;omeCSup-3' | 7791.00 | 766 |
| 766 | 5'-HO;rG;omeC;rU;rC;rA;fluU;rU;rUs;rA;fluC;rC;rAs;fluG;omeC; 4alk-dG;fluU;omeA;fluA;omeA;rUs;rG;rAs;rGs;omeCSup-3' | 7805.03 | 767 |
| 767 | 5'-HO;rG;omeC;rU;rC;rA;fluU;rU;rUs;rA;fluC;rC;rAs;fluG;omeC; rG;4alk-dU;omeA;fluA;omeA;rUs;rG;rAs;rGs;omeCSup-3' | 7803.04 | 768 |
| 768 | 5'-HO;rG;omeC;rU;rC;rA;fluU;rU;rUs;rA;fluC;rC;rAs;fluG;omeC;rG; fluU;4alk-dA;fluA;omeA;rUs;rG;rAs;rGs;omeCSup-3' | 7791.00 | 769 |
| 769 | 5'-HO;rG;omeC;rU;rC;rA;fluU;rU;rUs;rA;fluC;rC;rAs;fluG;omeC;rG; fluU;omeA;4alk-dA;rAs;rUs;rG;rAs;rGs;omeCSup-3' | 7803.04 | 770 |
| 770 | 5'-HO;rG;omeC;rU;rC;rA;fluU;rU;rUs;rA;fluC;rC;rAs;fluG;omeC;rG; fluU;omeA;fluA;4alk-dA;rUs;rG;rAs;rGs;omeCSup-3' | 7791.00 | 771 |
| 771 | 5'-HO;rG;omeC;rU;rC;rA;fluU;rU;rUs;rA;fluC;rC;rAs;fluG;omeC;rG; fluU;omeA;fluA;omeA;4alk-dUs;rG;rAs;rGs;omeCSup-3' | 7805.02 | 772 |
| 772 | 5'-HO;rG;omeC;rU;rC;rA;fluU;rU;rUs;rA;fluC;rC;rAs;fluG;omeC;rG; fluU;omeA;fluA;omeA;rUs;rG;4alk-dAs;rGs;omeCSup-3' | 7805.02 | 773 |
| 773 | 5'-HO;ome4SG;omeC;rU;rC;rA;fluU;rU;rUs;rA;fluC;rC;rAs;fluG;omeC; rG;fluU;omeA;fluA;omeA;rUs;rG;rAs;rGs;omeCSup-3' | 7827.09 | 774 |
| 774 | 5'-HO;rG;ome4SC;rU;rC;rA;fluU;rU;rUs;rA;fluC;rC;rAs;fluG;omeC; rG;fluU;omeA;fluA;omeA;rUs;rG;rAs;rGs;omeCSup-3' | 7813.07 | 775 |
| 775 | 5'-HO;rG;omeC;ome4SU;rC;rA;fluU;rU;rUs;rA;fluC;rC;rAs;fluG;omeC; rG;fluU;omeA;fluA;omeA;rUs;rG;rAs;rGs;omeCSup-3' | 7827.09 | 776 |
| 776 | 5'-HO;rG;omeC;rU;ome4SC;rA;fluU;rU;rUs;rA;fluC;rC;rAs;fluG;omeC; rG;fluU;omeA;fluA;omeA;rUs;rG;rAs;rGs;omeCSup-3' | 7827.09 | 777 |

TABLE 5-continued

| Ex | Sequence | MW | SEQ ID No. |
|---|---|---|---|
| 777 | 5'-HO;rG;omeC;rU;rC;ome4SA;fluU;rU;rUs;rA;fluC;rC;rAs;fluG;omeC; rG;fluU;omeA;fluA;omeA;rUs;rG;rAs;rGs;omeCSup-3' | 7827.09 | 778 |
| 778 | 5'-HO;rG;omeC;rU;rC;rA;ome4SU;rU;rUs;rA;fluC;rC;rAs;fluG;omeC; rG;fluU;omeA;fluA;omeA;rUs;rG;rAs;rGs;omeCSup-3' | 7825.10 | 779 |
| 779 | 5'-HO;rG;omeC;rU;rC;rA;fluU;ome4SU;rUs;rA;fluC;rC;rAs;fluG;omeC; rG;fluU;omeA;fluA;omeA;rUs;rG;rAs;rGs;omeCSup-3' | 7827.09 | 780 |
| 780 | 5'-HO;rG;omeC;rU;rC;rA;fluU;rU;ome4SUs;rA;fluC;rC;rAs;fluG;omeC; rG;fluU;omeA;fluA;omeA;rUs;rG;rAs;rGs;omeCSup-3' | 7827.09 | 781 |
| 781 | 5'-HO;rG;omeC;rU;rC;rA;fluU;rU;rUs;rA;ome4SC;rC;rAs;fluG;omeC; rG;fluU;omeA;fluA;omeA;rUs;rG;rAs;rGs;omeCSup-3' | 7825.10 | 782 |
| 782 | 5'-HO;rG;omeC;rU;rC;rA;fluU;rU;rUs;rA;fluC;rC;rAs;ome4SG;omeC; rG;fluU;omeA;fluA;omeA;rUs;rG;rAs;rGs;omeCSup-3' | 7825.10 | 783 |
| 783 | 5'-HO;rG;omeC;rU;rC;rA;fluU;rU;rUs;rA;fluC;rC;rAs;fluG;ome4SC; rG;fluU;omeA;fluA;omeA;rUs;rG;rAs;rGs;omeCSup-3' | 7813.07 | 784 |
| 784 | 5'-HO;rG;omeC;rU;rC;rA;fluU;rU;rUs;rA;fluC;rC;rAs;fluG;omeC;ome4SG; fluU;omeA;fluA;omeA;rUs;rG;rAs;rGs;omeCSup-3' | 7827.09 | 785 |
| 785 | 5'-HO;rG;omeC;rU;rC;rA;fluU;rU;rUs;rA;fluC;rC;rAs;fluG;omeC;rG; ome4SU;omeA;fluA;omeA;rUs;rG;rAs;rGs;omeCSup-3' | 7825.10 | 786 |
| 786 | 5'-HO;rG;omeC;rU;rC;rA;fluU;rU;rUs;rA;fluC;rC;rAs;fluG;omeC;rG; fluU;ome4SA;fluA;omeA;rUs;rG;rAs;rGs;omeCSup-3' | 7813.07 | 787 |
| 787 | 5'-HO;rG;omeC;rU;rC;rA;fluU;rU;rUs;rA;fluC;rC;rAs;fluG;omeC;rG; fluU;omeA;ome4SA;omeA;rUs;rG;rAs;rGs;omeCSup-3' | 7825.10 | 788 |
| 788 | 5'-HO;rG;omeC;rU;rC;rA;fluU;rU;rUs;rA;fluC;rC;rAs;fluG;omeC;rG; fluU;omeA;fluA;ome4SA;rUs;rG;rAs;rGs;omeCSup-3' | 7813.07 | 789 |
| 789 | 5'-HO;rG;omeC;rU;rC;rA;fluU;rU;rUs;rA;fluC;rC;rAs;fluG;omeC;rG; fluU;omeA;fluA;omeA;ome4SUs;rG;rAs;rGs;omeCSup-3' | 7827.09 | 790 |
| 790 | 5'-HO;rG;omeC;rU;rC;rA;fluU;rU;rUs;rA;fluC;rC;rAs;fluG;omeC;rG; fluU;omeA;fluA;omeA;rUs;ome4SG;rAs;rGs;omeCSup-3' | 7827.09 | 791 |
| 791 | 5'-HO;rG;omeC;rU;rC;rA;fluU;rU;rUs;rA;fluC;rC;rAs;fluG;omeC;rG; fluU;omeA;fluA;omeA;rUs;rG;rAs;ome4SGs;omeCSup-3' | 7827.09 | 792 |
| 792 | 5'-HO;4alk- dG;rC;rUs;fluC;omeA;fluU;rU;rUs;fluA;omeC;omeC;rAs;omeG;omeC; omeG;omeU;rA;fluA;fluA;omeUs;fluG;omeAs;rGs;fluCSup-3' | 7881.18 | 793 |
| 793 | 5'-HO;rG;4alk- dC;rUs;fluC;omeA;fluU;rU;rUs;fluA;omeC;omeC;rAs;omeG;omeC; omeG;omeU;rA;fluA;fluA;omeUs;fluG;omeAs;rGs;fluCSup-3' | 7881.18 | 794 |
| 794 | 5'-HO;rG;rC;4alk- dUs;fluC;omeA;fluU;rU;rUs;fluA;omeC;omeC;rAs;omeG;omeC; omeG;omeU;rA;fluA;fluA;omeUs;fluG;omeAs;rGs;fluCSup-3' | 7881.18 | 795 |
| 795 | 5'-HO;rG;rC;rUs;4alk- dC;omeA;fluU;rU;rUs;fluA;omeC;omeC;rAs;omeG;omeC;omeG; omeU;rA;fluA;fluA;omeUs;fluG;omeAs;rGs;fluCSup-3' | 7879.19 | 844 |
| 796 | 5'-HO;rG;rC;rUs;fluC;4alk- dA;fluU;rU;rUs;fluA;omeC;omeC;rAs;omeG;omeC;omeG;omeU; rA;fluA;fluA;omeUs;fluG;omeAs;rGs;fluCSup-3' | 7867.16 | 796 |
| 797 | 5'-HO;rG;rC;rUs;fluC;omeA;4alk- dU;rU;rUs;fluA;omeC;omeC;rAs;omeG;omeC;omeG;omeU;rA;fluA; fluA;omeUs;fluG;omeAs;rGs;fluCSup-3' | 7879.19 | 797 |
| 798 | 5'-HO;rG;rC;rUs;fluC;omeA;fluU;4alk- dU;rUs;fluA;omeC;omeC;rAs;omeG;omeC;omeG;omeU;rA;fluA; fluA;omeUs;fluG;omeAs;rGs;fluCSup-3' | 7881.18 | 798 |
| 799 | 5'-HO;rG;rC;rUs;fluC;omeA;fluU;rU;4alk- dUs;fluA;omeC;omeC;rAs;omeG;omeC;omeG;omeU;rA;fluA;fluA; omeUs;fluG;omeAs;rGs;fluCSup-3' | 7881.18 | 799 |
| 800 | 5'-HO;rG;rC;rUs;fluC;omeA;fluU;rU;rUs;4alk- dA;omeC;omeC;rAs;omeG;omeC;omeG;omeU;rA;fluA;fluA;ome Us;fluG;omeAs;rGs;fluCSup-3' | 7879.19 | 800 |
| 801 | 5'-HO;rG;rC;rUs;fluC;omeA;fluU;rU;rUs;fluA;omeC;omeC;4alk- dAs;omeG;omeC;omeG;omeU;rA;fluA;fluA;omeUs;fluG;omeAs; rGs;fluCSup-3' | 7881.18 | 801 |
| 802 | 5'-HO;rG;rC;rUs;fluC;omeA;fluU;rU;rUs;fluA;omeC;omeC;rAs;omeG; omeC;4alk-dG;omeU;rA;fluA;fluA;omeUs;fluG;omeAs;rGs;fluCSup-3' | 7867.16 | 802 |
| 803 | 5'-HO;rG;rC;rUs;fluC;omeA;fluU;rU;rUs;fluA;omeC;omeC;rAs;omeG; omeC;omeG;4alk-dU;rA;fluA;fluA;omeUs;fluG;omeAs;rGs;fluCSup-3' | 7867.15 | 803 |
| 804 | 5'-HO;rG;rC;rUs;fluC;omeA;fluU;rU;rUs;fluA;omeC;omeC;rAs;omeG; omeC;omeG;omeU;4alk-dA;fluA;fluA;omeUs;fluG;omeAs;rGs;fluCSup-3' | 7881.18 | 804 |
| 805 | 5'-HO;rG;rC;rUs;fluC;omeA;fluU;rU;rUs;fluA;omeC;omeC;rAs;omeG; omeC;omeG;omeU;rA;4alk-dA;fluA;omeUs;fluG;omeAs;rGs;fluCSup-3' | 7879.19 | 805 |
| 806 | 5'-HO;rG;rC;rUs;fluC;omeA;fluU;rU;rUs;fluA;omeC;omeC;rAs;omeG; omeC;omeG;omeU;rA;fluA;4alk-dA;omeUs;fluG;omeAs;rGs;fluCSup-3' | 7879.19 | 806 |
| 807 | 5'-HO;rG;rC;rUs;fluC;omeA;fluU;rU;rUs;fluA;omeC;omeC;rAs;omeG; omeC;omeG;omeU;rA;fluA;fluA;4alk-dUs;fluG;omeAs;rGs;fluCSup-3' | 7867.15 | 807 |
| 808 | 5'-HO;rG;rC;rUs;fluC;omeA;fluU;rU;rUs;fluA;omeC;omeC;rAs;omeG; omeC;omeG;omeU;rA;fluA;fluA;omeUs;4alk-dG;omeAs;rGs;fluCSup-3' | 7879.19 | 808 |
| 809 | 5'-HO;rG;rC;rUs;fluC;omeA;fluU;rU;rUs;fluA;omeC;omeC;rAs;omeG; omeC;omeG;omeU;rA;fluA;fluA;omeUs;fluG;4alk-dAs;rGs;fluCSup-3' | 7867.15 | 809 |

TABLE 5-continued

| Ex | Sequence | MW | SEQ ID No. |
|---|---|---|---|
| 810 | 5'-HO;rG;rC;rUs;fluC;omeA;fluU;rU;rUs;fluA;omeC;omeC;rAs;omeG; omeC;omeG;omeU;rA;fluA;fluA;omeUs;fluG;omeAs;4alk-dGs;fluCSup-3' | 7881.18 | 810 |
| 811 | 5'-HO;ome4SG;rC;rUs;fluC;omeA;fluU;rU;rUs;fluA;omeC;omeC;rAs; omeG;omeC;omeG;omeU;rA;fluA;fluA;omeUs;fluG;omeAs;rGs;fluCSup-3' | 7903.25 | 811 |
| 812 | 5'-HO;rG;ome4SC;rUs;fluC;omeA;fluU;rU;rUs;fluA;omeC;omeC;rAs; omeC;omeC;omeG;omeU;rA;fluA;fluA;omeUs;fluG;omeAs;rGs;fluCSup-3' | 7903.25 | 812 |
| 813 | 5'-HO;rG;rC;ome4SUs;fluC;omeA;fluU;rU;rUs;fluA;omeC;omeC;rAs; omeG;omeC;omeG;omeU;rA;fluA;fluA;omeUs;fluG;omeAs;rGs;fluCSup-3' | 7903.24 | 813 |
| 814 | 5'-HO;rG;rC;rUs;ome4SC;omeA;fluU;rU;rUs;fluA;omeC;omeC;rAs; omeG;omeC;omeG;omeU;rA;fluA;fluA;omeUs;fluG;omeAs;rGs;fluCSup-3' | 7901.26 | 814 |
| 815 | 5'-HO;rG;rC;rUs;fluC;omeA;ome4SU;rU;rUs;fluA;omeC;omeC;rAs; omeC;omeC;omeG;omeU;rA;fluA;fluA;omeUs;fluG;omeAs;rGs;fluCSup-3' | 7901.25 | 815 |
| 816 | 5'-HO;rG;rC;rUs;fluC;omeA;fluU;ome4SU;rUs;fluA;omeC;omeC;rAs; omeC;omeC;omeG;omeU;rA;fluA;fluA;omeUs;fluG;omeAs;rGs;fluCSup-3' | 7903.25 | 816 |
| 817 | 5'-HO;rG;rC;rUs;fluC;omeA;fluU;rU;ome4SUs;fluA;omeC;omeC;rAs; omeC;omeC;omeG;omeU;rA;fluA;fluA;omeUs;fluG;omeAs;rGs;fluCSup-3' | 7903.24 | 817 |
| 818 | 5'-HO;rG;rC;rUs;fluC;omeA;fluU;rU;rUs;fluA;ome4SC;omeC;rAs;omeG; omeC;omeG;omeU;rA;fluA;omeUs;fluG;omeAs;rGs;fluCSup-3' | 7889.22 | 818 |
| 819 | 5'-HO;rG;rC;rUs;fluC;omeA;fluU;rU;rUs;fluA;omeC;omeC;ome4SAs; omeC;omeC;omeG;omeU;rA;fluA;fluA;omeUs;fluG;omeAs;rGs;fluCSup-3' | 7903.24 | 819 |
| 820 | 5'-HO;rG;rC;rUs;fluC;omeA;fluU;rU;rUs;fluA;omeC;omeC;rAs;ome4SG; omeC;omeG;omeU;rA;fluA;fluA;omeUs;fluG;omeAs;rGs;fluCSup-3' | 7889.22 | 820 |
| 821 | 5'-HO;rG;rC;rUs;fluC;omeA;fluU;rU;rUs;fluA;omeC;omeC;rAs;omeG; ome4SC;omeG;omeU;rA;fluA;fluA;omeUs;fluG;omeAs;rGs;fluCSup-3' | 7889.22 | 821 |
| 822 | 5'-HO;rG;rC;rUs;fluC;omeA;fluU;rU;rUs;fluA;omeC;omeC;rAs;omeG; omeC;ome4SG;omeU;rA;fluA;fluA;omeUs;fluG;omeAs;rGs;fluCSup-3' | 7889.22 | 822 |
| 823 | 5'-HO;rG;rC;rUs;fluC;omeA;fluU;rU;rUs;fluA;omeC;omeC;rAs;omeG; omeC;omeG;ome4SU;rA;fluA;fluA;omeUs;fluG;omeAs;rGs;fluCSup-3' | 7889.22 | 823 |
| 824 | 5'-HO;rG;rC;rUs;fluC;omeA;fluU;rU;rUs;fluA;omeC;omeC;rAs;omeG; omeC;omeG;omeU;ome4SA;fluA;fluA;omeUs;fluG;omeAs;rGs;fluCSup-3' | 7903.25 | 824 |
| 825 | 5'-HO;rG;rC;rUs;fluC;omeA;fluU;rU;rUs;fluA;omeC;omeC;rAs;omeG; omeC;omeG;omeU;rA;ome4SA;fluA;omeUs;fluG;omeAs;rGs;fluCSup-3' | 7901.26 | 825 |
| 826 | 5'-HO;rG;rC;rUs;fluC;omeA;fluU;rU;rUs;fluA;omeC;omeC;rAs;omeG; omeC;omeG;omeU;rA;fluA;fluA;ome4SUs;fluG;omeAs;rGs;fluCSup-3' | 7889.21 | 826 |
| 827 | 5'-HO;rG;rC;rUs;fluC;omeA;fluU;rU;rUs;fluA;omeC;omeC;rAs;omeG; omeC;omeG;omeU;rA;fluA;fluA;omeUs;ome4SG;omeAs;rGs;fluCSup-3' | 7901.26 | 827 |
| 828 | 5'-HO;rG;rC;rUs;fluC;omeA;fluU;rU;rUs;fluA;omeC;omeC;rAs;omeG; omeC;omeG;omeU;rA;fluA;fluA;omeUs;fluG;ome4SAs;rGs;fluCSup-3' | 7889.22 | 828 |
| 829 | 5'-HO;rG;rC;rUs;fluC;omeA;fluU;rU;rUs;fluA;omeC;omeC;rAs;omeG; omeC;omeG;omeU;rA;fluA;fluA;omeUs;fluG;omeAs;ome4SGs;fluCSup-3' | 7903.24 | 829 |

Example 830

5,-ppp;rG;rC;rU;rC;rA;rU;rU;rU;rA;rC;rC;rA;rG;rC;rG;rU; rA;rA;rA;rU;rG;rA;rG;rCSu p-3' (SEQ ID No. 839)

To fully protected CPG-bound 5'-O-dimethoxytrityl-oligoribonucleotide (44 µmol), 3% dichloroacetic acid (DCA) in methylene chloride (20 mL) was added and aged at room temperature. The DCA solution was removed after 30 min and the solid support rinsed with acetonitrile (20 mL). After removal of the acetonitrile, solutions of 5-benzylthio-1H-tetrazole (3504 µL, 0.876 µmol) and 6-chloro-N,N-diisopropyl-4H-benzo[d][1,3,2]dioxaphosphinin-2-amine (4380 µL, 0.876 µmol) in acetonitrile were added and the reaction was aged at room temperature overnight. The solution was removed from the solid support and 0.02 M I$_2$ in THF/H$_2$O/pyridine (Glen Research, cat: 40-4330-52) was added and the reaction was aged for 5 min. The oxidizer reagent was removed and the solid support was rinsed with acetonitrile (20 mL). After removal of acetonitrile, the CPG was dried under vacuum for 4 h. To the solid support was added 0.5 M tetrabutylammonium dihydrogendiphosphate in dry DMF (3.5 mL) and the mixture was aged at 45° C. for 3 days. The solid was filtered and washed with DMF, water (3×), and acetonitrile. The solid support then was treated with 8 mL AMA (40% aqueous methylamine:concentrated aqueous ammonia hydroxide, 1:1 v/v) for 2.5 h. The CPG was filtered and washed with an additional 5 mL AMA. The combined filtrates were placed in a GeneVac (ambient temperature) overnight to remove all solvent. The resulting pellet was treated with 5 mL dry THF and TBAF (tetra-n-butylammonium fluoride) in dry THF (8 mL, 1.0 M), and the mixture was aged at room temperature overnight. The reaction was quenched with 2 mL concentrated aqueous ammonia hydroxide. The solvent was removed from the reaction with a GeneVac evaporator (ambient temperature) for 5 h. The resulting viscous material was diluted with 40 mL water and dialyzed by spin filtration (3000 MWCO). The solution was further washed by spin dialysis with water (4×40 mL). The retained solution was collected, diluted with water to 15 mL and purified by ion pairing reversed phase (IP-RP) HPLC using a YMC column, 19×150 mm, 5 µm, to give the desired product.

HR LC-MS: (m/z)$^-$(z=4) 1969.2855 (exp); 1969.2442 (theor).

Examples 830-837 as shown in Table 6 below were prepared according to the procedures analogous to those outlined in Example 830 above

TABLE 6

| Ex# | Sequence | MW | SEQ ID No. |
|---|---|---|---|
| 830 | ppp;rG;rC;rU;rC;rA; rU;rU;rU;rA;rC;rC;rA; rG;rC;rG;rU;rA;rA;rA; rU;rG;rA;rG;rCSup | 7876.52 | 1 |

TABLE 6-continued

| Ex# | Sequence | MW | SEQ ID No. |
|---|---|---|---|
| 831 | ppp;rG;omeC,rU;rC;rA; fluU;rU;rU;rA;fluC;rC; rA;fluG;omeC;rG;fluU; omeA,fluA;omeA;rU;rG; rA;rG;omeCSup | 7956.61 | 1 |
| 832 | ppp;rG;omeCs;rUs;rCs; rA;fluU;rU;rUs;rA; fluC;rC;rAs;fluGs; omeCs;rG;fluU;omeA; fluAs;omeA;rU;rG;rA; rG;omeCSup | 8085.13 | 1 |
| 833 | ppp,rG;omeC;rU;rC;rA; fluU;rU;rUs;rA;fluC; rC,rAs;fluG,omeC;rG; fluU;omeA;fluA;omeA; rUs;rG;rAs;rGs;omeCSup | 8036.94 | 1 |
| 834 | ppp;rGs;rCs;omeUs;rCs; fluAs;rUs;omeUs;rUs; rAs;rCs;omeC;rA;fluG; omeC;rG;omeU;omeA; fluA;fluA;rU;rGs; omeA,rGs;fluCSup | 8177.45 | 1 |
| 835 | ppp;rG;rC;rU;fluC, omeA;fluU;rU;rUs;fluA; omeG;omeC;rAs;omeG; omeC,omeG;omeU;rA; fluA;fluA;omeUs;fluG, omeAs;rGs;fluCSup | 8097.03 | 1 |
| 836 | ppp,rG;rC;rU;fluC; omeA;fluU;rU;rU;fluA; omeC;omeC;rA;omeG; omeC;omeG;omeU;rA; fluA;fluA;omeU;fluG; omeA;rG;fluCSup | 8016.70 | 1 |
| 837 | ppp;rG;rC;rUs;fluC; omeA;fluU;rU;rUs;fluA; omeC;omeC;rAs;omeG; OmeC;omeG;omeU;rA; fluA,fluA;omeUs;fluG; omeAs;rGs;fluCSup | 8113.09 | 1 |

Example 838

5'-PcP;rG;rC;rUs;fluC;omeA;fluU;rU;rUs;fluA;omeC; omeC;rAs;omeG;omeC;omeG;omeU;r A;fluA;fluA; omeUs;fluG;omeAs;rGs;fluCSup-3' (SEQ ID No. 840)

Fully protected CPG-bound 5'-O-dimethoxytrityl-oligoribonucleotide (5'-DMT-O;rG;rC;rUs;fluC;omeA;fluU;rU; rUs;fluA;omeC;omeC;rAs;omeG;omeC;omeG;omeU;rA; fluA;f luA;omeUs;fluG;omeAs;rGs;fluCSup-3' (SEQ ID NO: 842); 10 µmol) was treated with 3% 2',2'-dichloroacetic acid in dichloromethane for 5 min (2×5 mL). Then, the solid phase was washed with acetonitrile (3×3 mL) and dichloromethane (3×3 mL). To the solid phase, $N_2$ was passed through for 2 min and it was kept under vacuum for 1 h.

The solid phase was treated with diethyl ((((diisopropylamino)(methoxy)phosphaneyl)methyl)phosphonate (0.125 g, 0.400 mmol), acetonitrile (2.5 mL), and 5-(ethylthio)-2H-tetrazole (20 mg, 0.15 mmol) in acetonitrile (0.5 mL). The mixture was shaken at room temperature for 18 h. Then, the solid phase was filtered, rinsed with acetonitrile (2×1 mL), and treated with 12 in acetonitrile/pyridine/water (0.025 M, 9/9/2, 3 mL) for 5 min. The resin was further rinsed with acetonitrile (4×3 mL) and dichloromethane (2×3 mL). The solid phase was dried by passing a stream of $N_2$ through it for 1 min and kept under vacuum for 1 h.

The resulting solid phase was treated with TMSI (20 mg, 0.10 mmol) in pyridine/acetonitrile (v/v 1/50, 3 mL) for 30 min. Then, the solid phase was filtered, rinsed with acetonitrile (2×3 mL) and treated with 2-mercaptoethanol in $Et_3N$/acetonitrile (1 M, v/v 1/1, 0.5 mL) for 1 min. The CPG was washed again with acetonitrile (5×5 mL) and then treated with 40% aq $MeNH_2$ (2 mL) for 20 min. The solid support was filtered off and rinsed with 40% aq $MeNH_2$ (2×2 mL). The combined filtrate was shaken at ambient temperature for 2 h and then partly concentrated to ca. 2 mL under reduced pressure. The resulting solution lyophilized to give a solid.

The solid was dissolved in water (4 mL) and $Et_3N$-3HF (0.32 mL, 2.0 mmol) in water (1 mL) was added. The mixture was shaken at 40° C. for 6 h, after which aqueous sodium acetate (6 mL, 1 M) was added. The resulting mixture was purified by preparative HPLC (C18), eluting with 5 to 40% acetonitrile in water (0.1 M triethylammonium acetate) to provide the desired product.

LC-MS: (m/z)$^-$(z=5) 1605.7 (exp), 1605.2 (theor); (z=6) 1338.0 (exp), 1337.5 (theor); (z=7) 1146.3 (exp), 1146.3 (theor); (z=8) 1002.9 (exp), 1002.9 (theor).

The oligonucleotides of the invention based on SEQ ID No. 1 comprises at least one 5' group selected from L in Table 2a; 24 unmodified nucleobases consisting of (Adenine (A), Guanine (G), Cytosine (C) and Uracil (U), and when read from left to right, is presented as 5'-GCU-CAUUUACCAGCGUAAAUGAGC-3' (SEQ ID NO: 841) without the L group. Certain oligonucleotides of the invention based on SEQ ID No. 1 further comprise optionally modified sugar groups and optionally modified phosphodiester groups. One or more of the sugar groups optionally comprises modifications at one or more of the 2' and/or 4' positions selected from Table 2 for the first position nucleotide, Tables 3 and 3a for positions 2-23 nucleotides, and Table 4 for position 24 nucleotide. Exemplary modifications at the 2' position are selected from the group consisting of OH, $CH_3$, $OCH_3$, $OCF_3$, OP(O)OH, $O(CH_2)_2OCH_3$, fluoro, $NH_2$, locked nucleosides, or 2'-3' seco-nucleosides. Exemplary modifications of the 4' position are selected from halogen, $C_{1-6}$ alkyl, or $C_{2-6}$ alkynyl. The oligonucleotides of the invention may also comprise modified phosphodiester backbone groups also depicted in Tables 3 and 3a.

An embodiment of the invention of Formula Ia and Formula I is realized when greater than 10 independently selected modified nucleobases from Table 3 are incorporated into the nucleotide sequence. A subembodiment of this aspect of the invention is realized when 10 to 20, 10 to 15, or 10 to 12 independently selected modified nucleobases from Table 3 are incorporated into the nucleotide sequence. Another subembodiment of this aspect of the invention is realized when the nucleotide sequence comprises optionally modified sugar groups and optionally modified phosphodiester backbones. A further aspect of this subembodiment of the invention is realized when one or more of the sugar groups optionally comprises modifications at one or more of the 2' and/or 4' positions selected from Table 2 for the first position nucleotide, Table 3 for positions 2-23 nucleotides, and Table 4 for position 24 nucleotide. Still a further aspect of this subembodiment of the invention is realized when modifications at the 2' position are selected from the group consisting of OH, $CH_3$, $OCH_3$, $OCF_3$, OP(O)OH, $O(CH_2)_2OCH_3$, fluoro, $NH_2$, locked nucleosides, 2'-3' seco-nucleosides and modifications of the 4' position are selected from halogen, $C_{1-6}$ alkyl, or $C_{2-6}$ alkynyl.

An embodiment of the invention of Formula Ia and Formula I is realized when one or more of the sugar moieties at nucleotide positions 1, 2, 3, 7, 8, 12, and/or 17 optionally comprise a natural nucleobase; one or more of the sugar moieties at nucleotide positions 4, 6, 9, 18, 19, 21 and/or 24 optionally comprise a modified nucleobase containing a 2' fluoro group; one or more of the sugar moieties at nucleotide positions 5, 10, 11, 13, 14, 15,16, 20, and/or 22 optionally comprise a modified nucleobase containing 2' OMe group; and Formula Ia and Formula I optionally comprises a modified phosphodiester backbone between positions 3-4, 8-9, 20-21, 22-23 and/or 23-24.

Another embodiment of the invention of Formula Ia and Formula I is realized when SEQ ID No. 1 optionally comprises an 2'-OH at one or more of the sugar moieties at nucleotide positions 1, 3, 4, 5, 7, 8, 9, 11, 12, 15, 20, 22, and/or 23; optionally comprises fluoro at one or more of the sugar moieties at nucleotide positions 6, 10, 13, 16, and/or 18; optionally comprises 2'-OMe at one or more of the sugar moieties at nucleotide positions 2, 14, 17, 19, and/or 24; and optionally comprises a modified phosphodiester backbone between positions 8-9, 12-13, 20-21, 22-23 and/or 23-24.

An embodiment of the invention of Formula Ia and Formula I is realized when the position 8 nucleotide is selected from the group consisting of rUs, thiorUs, araU, and d5propUs.

Another embodiment of the invention of Formula Ia and Formula I is realized when the position 12 nucleotide is selected from rAs, d7dzAs, cf3As, and d2aminoAs.

Another embodiment of the invention of Formula Ia and Formula I is realized when the position 2 nucleotide is rC.

Another embodiment of the invention of Formula Ia and Formula I is realized when the position 3 nucleotide is selected from the group consisting of rUs and thiorUs.

Another embodiment of the invention of Formula Ia and Formula I is realized when the position 7 nucleotide is selected from the group consisting of rU and thiorU.

Another embodiment of the invention of Formula Ia and Formula I is realized when the position 22 nucleotide is selected from the group consisting of omeAs and araAs.

Still another embodiment of the invention of Formula Ia and Formula I is realized when the terminal 5' substituent is selected from OH and triphosphate. A subembodiment of this aspect of the invention is realized when the terminal 5' substituent is OH. Another subembodiment of this aspect of the invention is realized when the terminal 5' substituent is triphosphate.

Yet another embodiment of the invention of Formula Ia and Formula I is realized when the terminal 5' end is OH or triphosphate, nucleotide positions 1, 4, 5, 6, 9, 10, 11, 13, 14, 15, 16, 17, 18, 19, 20, 21, 23 and 24, respectively, is:

rG;rC;rUs;fluC;omeA;fluU;rU;ome4SUs;fluA;omeC;
omeC;rAs;omeG;omeC;omeG;omeU;rA;fluA;fluA;
omeUs;fluG;omeAs;rGs;fluCSup (SEQ ID NO: 843). A subembodiment of this aspect of the invention is realized when nucleotide position 8 is selected from the group consisting of rUs, thiorUs, araUs, and d5propUs. Another subembodiment of this aspect of the invention is realized when nucleotide position 12 is selected from the group consisting of rAs, d7dzAs, cf3As, and d2aminoAs. Another subembodiment of this aspect of the invention is realized when nucleotide position 2 is selected from the group consisting of rC. Another subembodiment of this aspect of the invention is realized when nucleotide position 3 is selected from the group consisting of rUs and thiorUs. Another subembodiment of this aspect of the invention is realized when nucleotide position 7 is selected from the group consisting of rU and thiorU.

Biological Data

The oligonucleotides described here are RIG-I agonists which demonstrate interferon production with an $EC_{50}$ of <1.7 μM. Preferred oligonucleotides of the invention demonstrate EC50 values of <1.0 μM, <0.5 μM, <0.25 μM, <0.1 μM, or <0.05 μM in the A549 Dual cell assay when transfected using LyoVec. The methods below describe each of these assays.

Annealing Hairpin RNA

All hairpin RNA samples were annealed and snap cooled prior to testing. RNA samples (100 uM) were prepared in phosphate buffered saline (PBS) and transferred to a PCR plate. The RNA containing plate was sealed, placed in a thermocycler and heated at 95° C. for 1 minute followed by immediate transfer to wet ice. The plate was incubated on ice for 10 minutes and then allowed to return to room temperature prior to subsequent reformatting.

A549 Dual Cell Assay

Equilibrate a 96-well source plate(s) containing 10 nmol of lyophilized RNA in each well to room temperature. Centrifuge the plate(s) at 800×g for 5 minutes at room temperature to pellet material to the bottom of the wells. Carefully remove plate seal(s) and resuspend the RNA using 100 μL of molecular biology grade 1×PBS, hereafter referred to as 1×PBS (Thermo Fisher; Cat. No. AM9624). Mix thoroughly to ensure complete solvation of RNA. Allow the RNA plate(s) to stand for 5-10 minutes at room temperature to aid complete dissolution of all RNA. At this point the final concentration of RNA after dissolution is 100 μM in 100 μL.

To prepare dilution series of the RNA, briefly mix then transfer 60 μL of 10 μM positive control RNA (ppp-SLR10, Pyle et al. Sci. Adv. 2018 February; 4 (2): e1701854) previously prepared in 1×PBS, or test RNA solution from the 96-well source plate(s) to the appropriate wells in columns 3 and 13 of 384-well DNA Lo-Bind destination plate(s) (Eppendorf, Cat. No. 951040546). To columns 4-12 and 14-22 of the destination plate(s) add 30 μL of 1×PBS. Transfer 15 μL of RNA solution from columns 3 and 13 to adjacent wells in columns 4 and 14 and mix by aspiration. Using fresh pipette tips each time, repeat this process a further 8 times until columns 12 and 22 are reached to generate 10-point, 3-fold serial dilutions. In wells A1 to H2 and I23 to P24 add 45 μL 10 μM control RNA to define maximum effect. In wells I1 to P2 and I23 to P24 add 45 μL 1×PBS to define minimum effect. At this point these serial dilution plates can be stored at −20° C. until required.

To further dilute the RNA samples transfer 3 μL of RNA solution from all wells of the serial dilution plate(s) to fresh 384-well DNA LoBind plate(s). To these new plate(s) add 27 μL of molecular biology grade 1×PBS and mix. These plates can be stored at −20° C. until required. These 1:10 dilution daughter plates are used as the RNA source plates in this assay and can be sealed and kept at room temperature if being used on the same day or sealed and stored at −20° C. until needed.

Transfer 5 μL from each well of the 1:10 dilution daughter plate(s) to equivalent wells of 384-well assay plate(s) (Corning; Cat. No. 3764). The plates are sealed and kept at room temperature for up to 2 hours. Dissolve LyoVec transfection reagent (Invivogen; Cat. No. lyec-2) to 0.078 mg/mL using 1×PBS. Dispense 5 μL of LyoVec solution into each well of 384-well assay plate(s). Briefly centrifuge the plate(s) to ensure the RNA/LyoVec mixture is brought down to the bottom of the wells and incubate for a minimum of 15 minutes before adding cells. Rapidly thaw A549-Dual cells (originally obtained from Invivogen; Cat. No. a549d-nfisi), dilute in 5 volumes of prewarmed assay buffer (DMEM, Thermo Fisher Cat. No. 21063-029; supplemented with 10% FBS, Thermo Fisher, Cat. No. 10091148), perform a cell count on a small sample of the cell suspension and centrifuge the remainder at 200×g for 5 minutes at room temperature. Resuspend the cell pellet to a density of 2 million viable cells per mL in assay buffer. Add 20 μL of cells per well to all wells of the 384-well assay plate(s). Briefly, centrifuge the plates to ensure that the cell suspension is brought down to the bottom of the wells. Incubate the plates at 37° C., 5% $CO_2$ in a humidified chamber for 18 hours.

Protecting the reagent from light, reconstitute the Quanti-Luc detection reagent (Invivogen; Cat. No. rep-qlc2) with 25 mL of deionized water per reagent sachet. Remove assay plate(s) from the incubator and transfer 10 μL of supernatant from the assay plate(s) to 384-well AlphaPlate(s) (Perkin Elmer; Cat. No. 6005359). Then add 25 μL of Quanti-Luc reagent to each well of the AlphaPlate(s) and mix thoroughly. Incubate each AlphaPlate for 60 minutes at room temperature then read plate on an Envision Multilabel Plate Reader (Perkin Elmer) using a 384-L1 aperture, an integration time of 0.2 seconds and reading by rows bi-directionally.

Data is normalized to the maximum and minimum effect control wells and then subjected to a 4 parameter logistic fit based on the Levenberg-Marquardt algorithm to provide measures of potency and relative efficacy.

Examples 1 through 838 were evaluated in cell based assay as described above. Table 7 gives the biological data (RIG-I $EC_{50}$) collected for each example using the methodology described above.

Compounds of the disclosure were evaluated for interferon β production in A549 cell culture with LyoVec as described above. The following Table 7 tabulates the biological data for these compounds as $EC_{50}$.

TABLE 7

| Ex | $EC_{50}$ (μM) |
|---|---|
| 1 | 0.002 |
| 2 | 0.007 |
| 3 | 0.012 |
| 4 | 0.104 |
| 5 | 0.197 |
| 6 | 0.003 |
| 7 | 0.069 |
| 8 | 0.007 |
| 9 | 0.006 |
| 10 | 0.139 |
| 11 | 0.007 |
| 12 | 0.037 |
| 13 | 0.029 |
| 14 | 0.010 |
| 15 | 0.049 |
| 16 | 0.039 |
| 17 | 0.016 |
| 18 | 0.014 |
| 19 | 0.061 |
| 20 | 0.099 |
| 21 | 0.009 |
| 22 | 0.066 |
| 23 | 0.176 |
| 24 | 0.214 |
| 15 | 0.058 |
| 26 | 0.148 |
| 27 | 0.016 |
| 28 | 0.016 |
| 29 | 0.018 |
| 30 | 0.023 |
| 31 | 0.005 |
| 32 | 0.273 |
| 33 | 0.005 |
| 34 | 0.481 |
| 35 | 0.029 |
| 36 | 0.247 |
| 37 | 0.048 |
| 38 | 0.018 |
| 39 | 0.008 |
| 40 | 0.118 |
| 41 | 0.169 |
| 42 | 0.011 |
| 43 | 0.172 |
| 44 | 0.219 |
| 45 | 0.038 |
| 46 | 0.239 |
| 47 | 0.066 |
| 48 | 0.024 |
| 49 | 0.101 |
| 50 | 0.195 |
| 51 | 0.080 |
| 51 | 0.056 |
| 53 | 0.350 |
| 54 | 0.075 |
| 55 | 0.022 |
| 56 | 0.219 |
| 57 | 0.011 |
| 58 | 0.039 |
| 59 | 0.375 |
| 60 | 0.074 |
| 61 | 0.121 |
| 62 | 0.012 |
| 63 | 0.008 |
| 64 | 0.231 |
| 65 | 0.006 |
| 66 | 0.028 |
| 67 | 0.036 |
| 68 | 0.295 |
| 69 | 0.084 |
| 70 | 0.075 |
| 71 | 0.422 |
| 72 | 0.243 |
| 73 | 0.250 |
| 74 | 0.339 |
| 75 | 0.194 |
| 76 | 0.158 |
| 77 | 0.038 |
| 78 | 0.392 |
| 79 | 0.121 |
| 80 | 0.381 |
| 81 | 0.310 |
| 82 | 0.092 |
| 83 | 0.280 |
| 84 | 0.083 |
| 85 | 0.011 |
| 86 | 0.284 |
| 87 | 0.012 |
| 88 | 0.211 |
| 89 | 0.295 |
| 90 | 0.080 |
| 91 | 1.122 |
| 92 | 0.014 |
| 93 | 0.011 |
| 94 | 0.013 |
| 95 | 0.013 |
| 96 | 0.008 |
| 97 | 0.012 |
| 98 | 0.109 |
| 99 | 0.018 |
| 100 | 0.011 |
| 101 | 0.014 |
| 102 | 0.017 |
| 103 | 0.128 |
| 104 | 1.177 |
| 105 | 0.104 |
| 106 | 0.235 |
| 107 | 0.240 |
| 108 | 0.014 |
| 109 | 0.021 |
| 110 | 0.084 |
| 111 | 0.014 |
| 112 | 0.021 |
| 113 | 0.073 |
| 114 | 0.469 |
| 115 | 0.292 |
| 116 | 0.054 |

TABLE 7-continued

| Ex | EC$_{50}$ (μM) |
|---|---|
| 117 | 0.137 |
| 118 | 0.005 |
| 119 | 0.026 |
| 120 | 0.010 |
| 121 | 0.029 |
| 122 | 0.112 |
| 123 | 0.139 |
| 124 | 0.235 |
| 125 | 0.322 |
| 126 | 1.091 |
| 127 | 0.253 |
| 128 | 0.291 |
| 129 | 0.077 |
| 130 | 0.042 |
| 131 | 0.120 |
| 132 | 0.038 |
| 133 | 0.368 |
| 134 | 0.070 |
| 135 | 0.114 |
| 136 | 1.238 |
| 137 | 0.160 |
| 138 | 0.070 |
| 139 | 0.065 |
| 140 | 0.092 |
| 141 | 0.319 |
| 142 | 0.027 |
| 143 | 0.272 |
| 144 | 0.374 |
| 145 | 0.055 |
| 146 | 0.144 |
| 147 | 0.121 |
| 148 | 0.422 |
| 149 | 0.013 |
| 150 | 0.029 |
| 151 | 0.551 |
| 152 | 0.042 |
| 153 | 0.022 |
| 154 | 0.262 |
| 155 | 0.377 |
| 156 | 0.167 |
| 157 | 0.200 |
| 158 | 0.465 |
| 159 | 0.065 |
| 160 | 0.157 |
| 161 | 0.143 |
| 162 | 0.043 |
| 163 | 0.384 |
| 164 | 0.442 |
| 165 | 0.246 |
| 166 | 0.017 |
| 167 | 0.442 |
| 168 | 0.387 |
| 169 | 0.076 |
| 170 | 0.028 |
| 171 | 0.538 |
| 172 | 0.361 |
| 173 | 0.206 |
| 174 | 0.463 |
| 175 | 1.101 |
| 176 | 0.592 |
| 177 | 0.502 |
| 178 | 0.796 |
| 179 | 0.002 |
| 180 | 0.002. |
| 181 | 0.002 |
| 182 | 0.001 |
| 183 | 0.001 |
| 184 | 0.001 |
| 185 | 0.002 |
| 186 | 0.001 |
| 187 | 0.001 |
| 188 | 0.002 |
| 189 | 0.002 |
| 190 | 0.001 |
| 191 | 0.001 |
| 192 | 0.005 |
| 193 | 0.001 |
| 194 | 0.001 |
| 195 | 0.001 |
| 196 | 0.001 |
| 197 | 0.002 |
| 198 | 0.002 |
| 199 | 0.003 |
| 200 | 0.002 |
| 201 | 0.001 |
| 202 | 0.012 |
| 203 | 0.003 |
| 204 | 0.001 |
| 205 | 0.003 |
| 206 | 0.001 |
| 207 | 0.001 |
| 208 | 0.001 |
| 209 | 0.001 |
| 210 | 0.003 |
| 211 | 0.004 |
| 212 | 0.001 |
| 213 | 0.005 |
| 214 | 0.004 |
| 215 | 0.002 |
| 216 | 0.004 |
| 217 | 0.003 |
| 218 | 0.004 |
| 219 | 0.001 |
| 220 | 0.001 |
| 221 | 0.002 |
| 222 | 0.003 |
| 223 | 0.035 |
| 224 | 0.005 |
| 225 | 0.002 |
| 226 | 0.002. |
| 227 | 0.003 |
| 228 | 0.005 |
| 229 | 0.010 |
| 230 | 0.003 |
| 231 | 0.005 |
| 232 | 0.018 |
| 233 | 0.002 |
| 234 | 0.004 |
| 235 | 0.017 |
| 236 | 0.004 |
| 237 | 0.008 |
| 238 | 0.006 |
| 239 | 0.005 |
| 240 | 0.001 |
| 241 | 0.001 |
| 242 | 0.041 |
| 243 | 0.017 |
| 244 | <0.001 |
| 245 | <0.001 |
| 246 | 0.001 |
| 247 | 0.001 |
| 248 | 0.001 |
| 249 | <0.001 |
| 250 | 0.001 |
| 251 | 0.001 |
| 252 | 0.001 |
| 253 | 0.001 |
| 254 | 0.001 |
| 255 | 0.005 |
| 256 | 0.002 |
| 257 | 0.001 |
| 258 | 0.003 |
| 259 | 0.002 |
| 260 | 0.002 |
| 261 | 0.001 |
| 262 | 0.003 |
| 263 | 0.002 |
| 264 | 0.001 |
| 265 | 0.001 |
| 266 | 0.001 |
| 267 | 0.002 |
| 268 | 0.001 |
| 269 | 0.002 |
| 270 | 0.001 |
| 271 | 0.001 |
| /72 | 0.002 |

TABLE 7-continued

| Ex | EC$_{50}$ (μM) |
|---|---|
| 273 | 0.006 |
| 274 | 0.004 |
| 275 | 0.001 |
| 276 | 0.012 |
| 277 | 0.004 |
| 278 | 0.005 |
| 279 | 0.003 |
| 280 | 0.003 |
| 281 | 0.004 |
| 282 | 0.013 |
| 283 | 0.002 |
| 284 | 0.002 |
| 285 | 0.001 |
| 286 | 0.001 |
| 287 | 0.004 |
| 288 | 0.012 |
| 289 | 0.002 |
| 290 | 0.003 |
| 291 | 0.005 |
| 292 | 0.002 |
| 293 | 0.007 |
| 294 | 0.006 |
| 295 | 0.002 |
| 296 | 0.006 |
| 297 | 0.004 |
| 298 | 0.003 |
| 299 | 0.006 |
| 300 | 0.002 |
| 301 | 0.002 |
| 302 | 0.002 |
| 303 | 0.002 |
| 304 | 0.002 |
| 305 | 0.002 |
| 306 | 0.006 |
| 307 | 0.002 |
| 308 | 0.023 |
| 309 | 0.051 |
| 310 | 0.004 |
| 311 | 0.001 |
| 312 | 0.003 |
| 313 | 0.008 |
| 314 | 0.004 |
| 315 | 0.004 |
| 316 | 0.864 |
| 317 | 0.007 |
| 318 | 0.040 |
| 319 | 0.006 |
| 320 | 0.016 |
| 321 | 0.007 |
| 322 | 0.010 |
| 323 | 0.003 |
| 324 | 0.009 |
| 325 | 0.001 |
| 326 | 0.005 |
| 327 | 0.004 |
| 328 | 0.012 |
| 329 | 0.018 |
| 330 | 0.015 |
| 331 | 0.095 |
| 332 | 0.009 |
| 333 | 0.005 |
| 334 | 0.003 |
| 335 | <0.001 |
| 336 | 0.008 |
| 337 | 0.004 |
| 338 | 0.003 |
| 339 | 0.005 |
| 340 | 0.003 |
| 341 | 0.003 |
| 342 | 0.005 |
| 343 | 0.019 |
| 344 | <0.001 |
| 345 | 0.003 |
| 346 | 0.001 |
| 347 | 0.006 |
| 348 | 0.002 |
| 349 | 0.002 |
| 350 | 0.001 |

TABLE 7-continued

| Ex | EC$_{50}$ (μM) |
|---|---|
| 351 | 0.002 |
| 352 | 0.015 |
| 353 | 0.006 |
| 354 | 0.004 |
| 355 | 0.004 |
| 356 | 0.005 |
| 357 | 0.003 |
| 358 | 0.016 |
| 359 | 0.004 |
| 360 | 0.008 |
| 361 | 0.028 |
| 362 | 0.003 |
| 363 | 0.003 |
| 364 | 0.006 |
| 365 | 0.037 |
| 366 | 0.021 |
| 367 | 0.055 |
| 368 | 0.005 |
| 369 | 0.012 |
| 370 | 0.004 |
| 371 | 0.001 |
| 372 | <0.001 |
| 373 | 0.003 |
| 374 | 0.002 |
| 375 | 0.002 |
| 376 | 0.004 |
| 377 | 0.002 |
| 378 | 0.001 |
| 379 | 0.001 |
| 380 | 0.011 |
| 381 | 0.002 |
| 382 | 0.004 |
| 383 | <0.001 |
| 384 | 0.005 |
| 385 | 0.007 |
| 386 | 0.005 |
| 387 | 0.001 |
| 388 | 0.005 |
| 389 | 0.013 |
| 390 | 0.020 |
| 391 | 0.011 |
| 392 | 0.015 |
| 393 | 0.010 |
| 394 | 0.003 |
| 395 | 0.012 |
| 396 | 0.005 |
| 397 | 0.005 |
| 398 | 0.010 |
| 399 | 0.008 |
| 400 | 0.006 |
| 401 | 0.011 |
| 402 | 0.007 |
| 403 | 0.006 |
| 404 | 0.011 |
| 405 | 0.004 |
| 406 | 0.005 |
| 407 | 0.008 |
| 408 | 0.004 |
| 409 | 0.003 |
| 410 | 0.005 |
| 411 | 0.005 |
| 412 | 0.006 |
| 413 | 0.004 |
| 414 | 0.005 |
| 415 | 0.004 |
| 416 | 0.005 |
| 417 | 0.005 |
| 418 | 0.004 |
| 419 | 0.004 |
| 420 | 0.003 |
| 421 | 0.004 |
| 422 | 0.006 |
| 423 | 0.002 |
| 424 | 0.006 |
| 425 | 0.007 |
| 426 | 0.010 |
| 417 | 0.008 |
| 428 | 0.004 |

TABLE 7-continued

| Ex | EC$_{50}$ (μM) |
|---|---|
| 429 | 0.009 |
| 430 | 0.005 |
| 431 | 0.009 |
| 432 | 0.003 |
| 433 | 0.002 |
| 434 | 0.004 |
| 435 | 0.004 |
| 436 | 0.010 |
| 437 | 0.006 |
| 438 | 0.006 |
| 439 | 0.005 |
| 440 | 0.008 |
| 441 | 0.011 |
| 442 | 0.007 |
| 443 | 0.010 |
| 444 | 0.012 |
| 445 | 0.006 |
| 446 | 0.004 |
| 447 | 0.004 |
| 448 | 0.001 |
| 449 | 0.004 |
| 450 | 0.003 |
| 451 | 0.002 |
| 452 | 0.002 |
| 453 | 0.007 |
| 454 | 0.029 |
| 455 | 0.004 |
| 456 | 0.003 |
| 457 | 0.005 |
| 458 | 0.004 |
| 459 | 0.003 |
| 460 | 0.004 |
| 461 | 0.003 |
| 462 | 0.004 |
| 463 | 0.002. |
| 464 | 0.005 |
| 465 | 0.005 |
| 466 | 0.009 |
| 467 | 0.004 |
| 468 | 0.003 |
| 469 | 0.006 |
| 470 | 0.007 |
| 471 | 0.011 |
| 472 | 0.011 |
| 473 | 0.005 |
| 474 | 0.011 |
| 475 | <0.001 |
| 476 | 0.002 |
| 477 | 0.004 |
| 478 | 0.002 |
| 479 | 0.008 |
| 480 | 0.004 |
| 481 | 0.004 |
| 482 | 0.004 |
| 483 | 0.004 |
| 484 | 0.004 |
| 485 | 0.004 |
| 486 | 0.003 |
| 487 | 0.003 |
| 488 | 0.004 |
| 489 | 0.003 |
| 490 | 0.002 |
| 491 | 0.004 |
| 492 | 0.003 |
| 493 | 0.002 |
| 494 | 0.003 |
| 495 | 0.002 |
| 496 | 0.003 |
| 497 | <0.001 |
| 498 | 0.002 |
| 499 | 0.004 |
| 500 | 0.003 |
| 501 | 0.003 |
| 502 | 0.004 |
| 503 | 0.003 |
| 504 | 0.003 |
| 505 | 0.003 |
| 506 | 0.008 |

TABLE 7-continued

| Ex | EC$_{50}$ (μM) |
|---|---|
| 507 | 0.003 |
| 508 | 0.003 |
| 509 | 0.003 |
| 510 | 0.004 |
| 511 | 0.004 |
| 512 | 0.003 |
| 513 | 0.017 |
| 514 | <0.001 |
| 515 | 0.003 |
| 516 | 0.002 |
| 517 | 0.003 |
| 518 | 0.001 |
| 519 | 0.005 |
| 520 | 0.010 |
| 521 | 0.009 |
| 522 | 0.026 |
| 523 | 0.033 |
| 524 | 1.111 |
| 525 | 1.667 |
| 526 | 0.009 |
| 527 | 0.008 |
| 528 | 0.008 |
| 529 | 0.004 |
| 530 | 0.005 |
| 531 | 0.005 |
| 532 | 0.004 |
| 533 | 0.004 |
| 534 | 0.003 |
| 535 | 0.004 |
| 536 | 0.002 |
| 537 | 0.004 |
| 538 | 0.022 |
| 539 | 0.004 |
| 540 | 0.004 |
| 541 | 0.005 |
| 542 | 0.004 |
| 543 | 0.003 |
| 544 | 0.004 |
| 545 | 0.005 |
| 546 | 0.004 |
| 547 | 0.004 |
| 548 | 0.004 |
| 549 | 0.008 |
| 550 | 0.005 |
| 551 | 0.004 |
| 552 | 0.011 |
| 553 | 0.004 |
| 554 | 0.004 |
| 555 | 0.008 |
| 556 | 0.382 |
| 557 | 0.007 |
| 558 | 0.010 |
| 559 | 0.004 |
| 560 | 0.004 |
| 561 | 0.004 |
| 562 | 0.004 |
| 563 | 0.018 |
| 564 | 0.013 |
| 565 | 0.006 |
| 566 | 0.007 |
| 567 | 0.004 |
| 568 | 0.006 |
| 569 | 0.004 |
| 570 | 0.011 |
| 571 | 0.009 |
| 572 | 0.004 |
| 573 | 0.034 |
| 574 | 0.008 |
| 575 | 0.012 |
| 576 | 0.004 |
| 577 | 0.009 |
| 578 | 0.012 |
| 579 | 0.007 |
| 580 | 0.010 |
| 581 | 0.010 |
| 582 | 0.007 |
| 583 | 0.005 |
| 584 | 0.005 |

TABLE 7-continued

| Ex | EC$_{50}$ (μM) |
|---|---|
| 585 | 0.004 |
| 586 | 0.008 |
| 587 | 0.004 |
| 588 | 0.012 |
| 589 | 0.009 |
| 590 | 0.009 |
| 591 | 0.010 |
| 592 | 0.013 |
| 593 | 0.005 |
| 594 | 0.014 |
| 595 | 0.011 |
| 596 | 0.012 |
| 597 | 0.037 |
| 598 | 0.040 |
| 599 | 0.037 |
| 600 | 0.029 |
| 601 | 0.037 |
| 602 | 0.018 |
| 603 | <0.001 |
| 604 | 0.007 |
| 605 | 0.006 |
| 606 | 0.006 |
| 607 | 0.004 |
| 608 | 0.006 |
| 609 | 0.029 |
| 610 | 0.028 |
| 611 | 0.027 |
| 612 | 0.032 |
| 613 | 0.037 |
| 614 | 0.011 |
| 615 | 0.005 |
| 616 | 0.005 |
| 617 | 0.049 |
| 618 | 0.043 |
| 619 | 0.003 |
| 620 | 0.004 |
| 621 | 0.003 |
| 622 | 0.011 |
| 623 | 0.010 |
| 624 | 0.009 |
| 625 | 0.013 |
| 626 | 0.054 |
| 627 | 0.025 |
| 628 | 0.036 |
| 629 | 0.038 |
| 630 | 0.002 |
| 631 | <0.001 |
| 632 | 0.001 |
| 633 | 0.001 |
| 634 | 0.006 |
| 635 | 0.011 |
| 636 | 0.012 |
| 637 | 0.036 |
| 638 | 0.031 |
| 639 | 0.032 |
| 640 | 0.024 |
| 641 | <0.001 |
| 642 | 0.002 |
| 643 | 0.001 |
| 644 | 0.009 |
| 645 | 0.004 |
| 646 | 0.004 |
| 647 | 0.006 |
| 648 | 0.005 |
| 649 | 0.023 |
| 650 | 0.019 |
| 651 | 0.026 |
| 652 | 0.033 |
| 653 | 0.002 |
| 654 | 0.003 |
| 655 | <0.001 |
| 656 | 0.002 |
| 657 | 0.040 |
| 658 | 0.042 |
| 659 | 0.006 |
| 660 | 0.002 |
| 661 | 0.009 |
| 662 | 0.007 |
| 663 | 0.011 |
| 664 | 0.011 |
| 665 | 0.036 |
| 666 | 0.037 |
| 667 | 0.033 |
| 668 | 0.038 |
| 669 | <0.001 |
| 670 | 0.002 |
| 671 | 0.002 |
| 672 | 0.007 |
| 673 | 0.015 |
| 674 | 0.007 |
| 675 | 0.004 |
| 676 | 0.003 |
| 677 | 0.006 |
| 678 | 0.003 |
| 679 | 0.008 |
| 680 | 0.012 |
| 681 | 0.004 |
| 682 | 0.003 |
| 683 | 0.005 |
| 684 | 0.006 |
| 685 | 0.006 |
| 686 | 0.003 |
| 687 | 0.012 |
| 688 | 0.005 |
| 689 | 0.006 |
| 690 | 0.009 |
| 691 | 0.167 |
| 692 | 0.009 |
| 693 | 0.017 |
| 694 | 0.005 |
| 695 | 0.009 |
| 696 | 0.005 |
| 697 | 0.011 |
| 698 | 0.014 |
| 699 | 0.012 |
| 700 | 0.002 |
| 701 | 0.002 |
| 702 | 0.001 |
| 703 | <0.001 |
| 704 | 0.005 |
| 705 | 0.013 |
| 706 | 0.011 |
| 707 | 0.006 |
| 708 | 0.006 |
| 709 | 0.008 |
| 710 | 0.007 |
| 711 | 0.010 |
| 712 | 0.014 |
| 713 | 0.011 |
| 714 | 0.003 |
| 715 | 0.003 |
| 716 | 0.004 |
| 717 | 0.004 |
| 718 | 0.005 |
| 719 | 0.007 |
| 720 | 0.003 |
| 721 | 0.008 |
| 722 | 0.005 |
| 723 | 0.003 |
| 724 | 0.004 |
| 725 | 0.003 |
| 726 | 0.007 |
| 727 | 0.003 |
| 728 | 0.004 |
| 729 | 0.004 |
| 730 | 0.005 |
| 731 | 0.007 |
| 732 | 0.010 |
| 733 | 0.006 |
| 734 | 0.010 |
| 735 | 0.111 |
| 736 | 0.014 |
| 737 | 0.142 |
| 738 | 0.007 |
| 739 | 0.013 |
| 740 | 0.009 |

TABLE 7-continued

| Ex | EC$_{50}$ (µM) |
|---|---|
| 741 | 0.009 |
| 742 | 0.012 |
| 743 | 0.007 |
| 744 | 0.006 |
| 745 | 0.001 |
| 746 | 0.015 |
| 747 | 0.012 |
| 748 | 0.005 |
| 749 | 0.010 |
| 750 | 0.007 |
| 751 | 0.011 |
| 752 | 0.004 |
| 753 | 0.009 |
| 754 | 0.014 |
| 755 | 0.012 |
| 756 | 0.003 |
| 757 | 0.007 |
| 758 | 0.002 |
| 759 | 0.005 |
| 760 | 0.015 |
| 761 | 0.011 |
| 761 | 0.019 |
| 763 | 0.009 |
| 764 | 0.016 |
| 765 | 0.007 |
| 766 | 0.004 |
| 767 | 0.009 |
| 768 | 0.035 |
| 769 | 0.007 |
| 770 | 0.088 |
| 771 | 0.019 |
| 772 | 0.022 |
| 773 | 0.062 |
| 774 | 0.004 |
| 775 | 0.002 |
| 776 | 0.010 |
| 777 | 0.003 |
| 778 | 0.005 |
| 779 | 0.008 |
| 780 | 0.042 |
| 781 | 0.009 |
| 782 | 0.003 |
| 783 | 0.003 |
| 784 | 0.002 |
| 785 | 0.006 |
| 786 | 0.005 |
| 787 | 0.007 |
| 788 | 0.011 |
| 789 | 0.011 |
| 790 | 0.007 |
| 791 | 0.023 |
| 792 | 0.007 |
| 793 | 0.010 |
| 794 | 0.009 |
| 795 | 0.006 |
| 796 | 0.004 |
| 797 | 0.009 |
| 798 | 0.041 |
| 799 | 0.017 |
| 800 | 0.013 |
| 801 | 0.004 |
| 802 | 0.009 |
| 803 | 0.006 |
| 804 | 0.015 |
| 805 | 0.009 |
| 806 | 0.015 |
| 807 | 0.009 |
| 808 | 0.008 |
| 809 | 0.013 |
| 810 | 0.013 |
| 811 | 0.013 |
| 812 | 0.011 |
| 813 | 0.011 |
| 814 | 0.005 |
| 815 | 0.008 |
| 816 | 0.012 |
| 817 | 0.007 |
| 818 | 0.013 |
| 819 | 0.003 |
| 820 | 0.008 |
| 821 | 0.006 |
| 822 | 0.009 |
| 823 | 0.004 |
| 824 | 0.009 |
| 825 | 0.009 |
| 826 | 0.007 |
| 827 | 0.016 |
| 828 | 0.011 |
| 829 | 0.025 |
| 830 | <0.001 |
| 831 | <0.001 |
| 832 | 0.001 |
| 833 | <0.001 |
| 834 | NA |
| 835 | NA |
| 836 | 0.002 |
| 837 | 0.004 |
| 838 | 0.001 |

Human Peripheral Blood Mononuclear Cell (PBMC) Assay

The cell-based potencies of representative compounds of the disclosure were evaluated for interferon α production in human PBMC cell culture with LyoVec as described above compared to known literature RIG-I agonist, 5'ppp-GGACGUACGUUUCGACGUACGUCC-3', referred to as SEQ ID No. 123 herein, and as SEQ ID No. 12 in US2016/0046943 A (5ppp 10 L); also in Linehand et al. Sci Adv. 2018 February; as 4(2) (ppp-SLR10)) were ascertained by measuring the increase of the type I interferon, IFN-α, secreted by human peripheral blood mononuclear cells (PBMCs) following transfection of the test RNAs.

The test RNAs were serially diluted in calcium/magnesium-free 1×DPBS (Gibco Cat. No. 14190136) across 10 points with 5 µL per dilution point added to the wells of a flat-bottom tissue-culture treated 384-well plate (Corning Cat. No. 3764). Five microliters per well of 1:50 diluted transfection reagent Lipofectamine 2000 (Invitrogen Cat. No. 11668019) were added to each RNA-containing. The RNA/Lipofectamine 2000 mixtures were incubated at room temperature for 10 minutes to enable complexation. Frozen human PBMCs (AllCells Cat. No. C-PB102F-001) were thawed, resuspended to a density of 2.5×10$^6$/mL in assay medium (RPMI 1640 (Gibco Cat. No. 11875-085) supplemented with 10% fetal bovine serum (Gibco Cat. No. 10091148)) then 40 µL was added to each well containing the complexed RNA.

After 18 hours of incubation at 37° C., 5% CO$_2$, 5 µL of undiluted cell supernatant was transferred from each well into a 384-well AlphaPlate (Perkin Elmer Cat. No. 6005359). Interferon alpha levels were measured using a human IFN-α AlphaLISA Kit (Perkin Elmer Cat. No. AL297F) following the manufacturer's protocol. Briefly, 10 µL of 5× AlphaLISA anti-IFN-α acceptor beads were added to each supernatant-containing well followed by a 30 minute room temperature incubation. Ten microliters of 5× biotinylated anti-IFN-α antibody were then added to each well followed by a 60 minute room temperature incubation. Twenty-five microliters of light-sensitive 2× Streptavidin donor beads were added to each well followed by a final incubation of 30 minutes at room temperature in the dark. A Perkin Elmer Envision Multilabel Plate Reader with a 384-A1 aperture was used to scan the plates at an excitation wavelength of 680 nM and emission wavelength of 615 nM. The data were analyzed using a nonlinear regression model, log(agonist) vs. response—Variable Slope, in Prism 7.05

(GraphPad Software, La Jolla, Calif., USA). The following Table 8 tabulates the biological data for these compounds as $EC_{50}$.

Table 8: Biological activities of unmodified example 830 and modified example 833 compared to literature RIG-I agonist 5ppp 10 L (pppSLR10) in human PBMC assay.

TABLE 8

| | | 95% CI | | |
|---|---|---|---|---|
| | EC50 (nM) | Lower Limit | Upper Limit | |
| 5ppp 10L (pppSLR10) | | | | |
| Donor 1 | 6.84 | 5.65 | 8.22 | Mean EC50 (95% CI) |
| Donor 2 | 7.79 | 5.41 | 10.74 | nM = 6.07 (4,72, 7.75) |
| Donor 3 | 4.23 | 3.63 | 4.98 | |
| Donor 4 | 6.04 | 4.48 | 8.21 | |

TABLE 8-continued

| | | 95% CI | | |
|---|---|---|---|---|
| | EC50 (nM) | Lower Limit | Upper Limit | |
| Example 830 | | | | |
| Donor 1 | 0.41 | 0.32 | 0.54 | Mean EC50 (95% CI) |
| Donor 2 | 0.34 | 0.25 | 0.46 | nM = 0.36 (0.25, 0.51) |
| Donor 3 | 0.37 | 0.22 | 0.59 | |
| Donor 4 | 0.32 | 0.22 | 0.46 | |
| Example 833 | | | | |
| Donor 1 | 0.80 | 0.61 | 1.07 | Mean EC50 (95% CI) |
| Donor 2 | 0.49 | 0.38 | 0.65 | nM = 0.64 (0.46, 0.93) |
| Donor 3 | 0.67 | 0.48 | 0.94 | |
| Donor 4 | 0.63 | 0.39 | 1.14 | |

What is claimed is:

1. A compound of formula Ia:

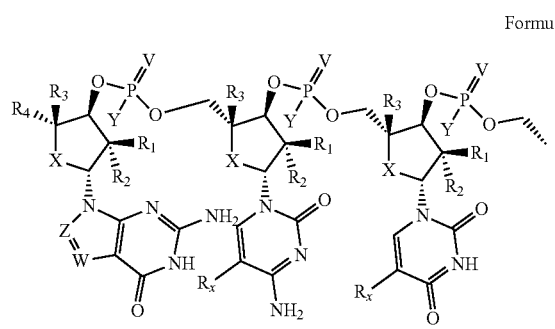

Formula Ia

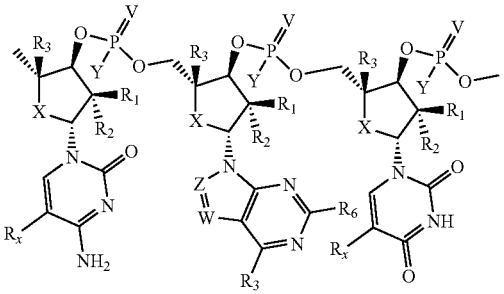

-continued

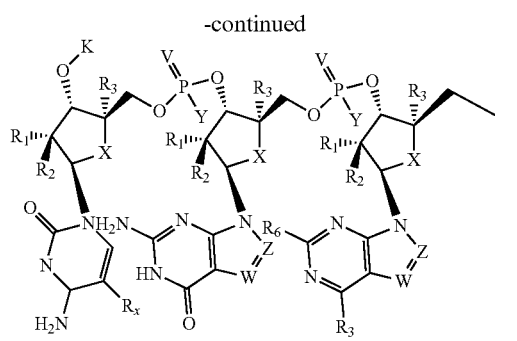

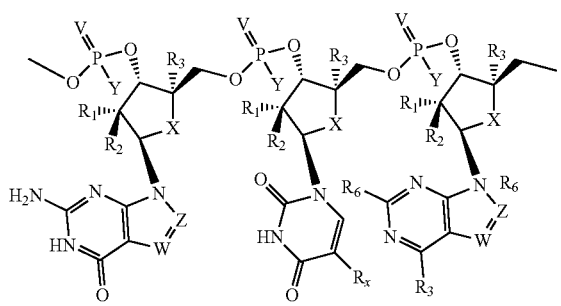

-continued

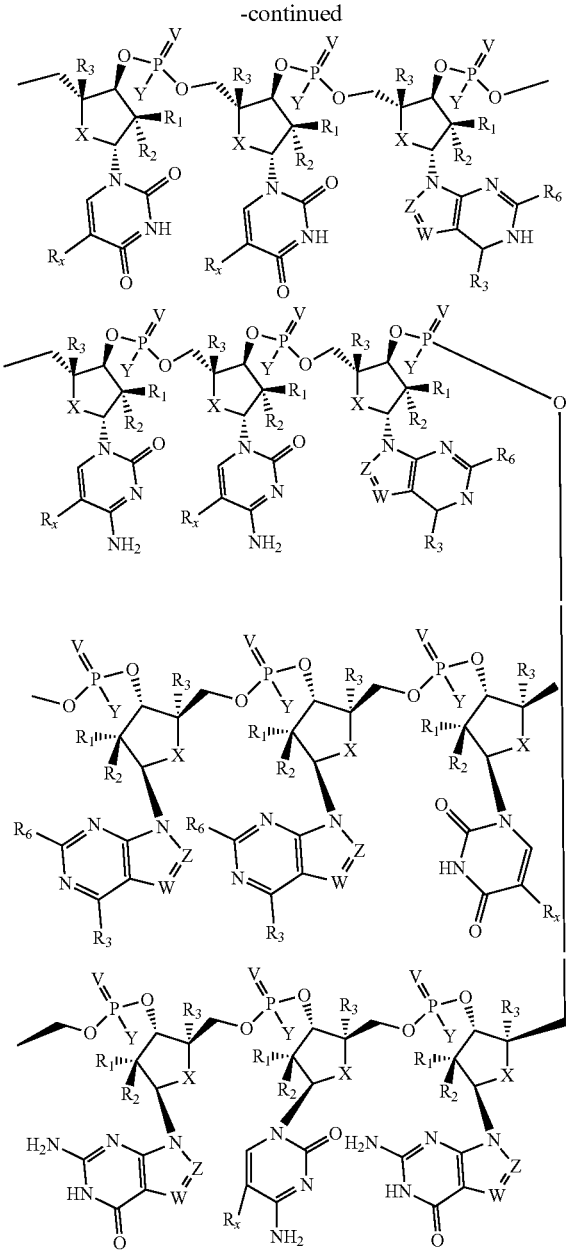

or a pharmaceutically acceptable salt thereof, wherein:

each X is independently selected from the group consisting of O, S, —CH$_2$—, and —NH—;

each Y is independently selected from the group consisting of —OH, —SH, and

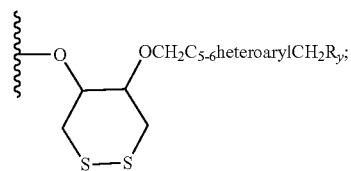

each V is independently O, or S;

K is H, or

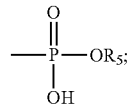

each W is independently N, —CH—, or —C(F)—;

each Z is independently N, or —CH—;

each R$_1$ is independently selected from the group consisting of H, halogen, —OH, —OC$_{1-6}$ alkyl, C$_{1-6}$ alkyl, —OC$_{1-3}$ haloalkyl, —OC$_{2-6}$ alkenyl, —OC$_{2-6}$ alkynyl, —NH$_2$, and —OCH$_2$C$_{5-6}$ heteroarylCH$_2$R$_y$, said alkyl, alkenyl, alkynyl and heteroaryl optionally substituted with 1 to 3 groups of R$_b$;

each R$_2$ is independently selected from the group consisting of H, halogen, —OH, —OC$_{1-6}$ alkyl, C$_{1-6}$ alkyl, —OC$_{1-3}$ haloalkyl;

or one or more adjacent R$_1$ and R$_2$ can combine to form =CH$_2$;

each R$_3$ is independently H, halogen, C$_{1-6}$ alkyl, or C$_{2-6}$ alkynyl;

or R$_1$ and R$_3$ on a sugar moiety can be linked to form —CH$_2$O, provided R$_2$ is hydrogen;

R$_4$ is selected from the group consisting of —CH$_2$OH,

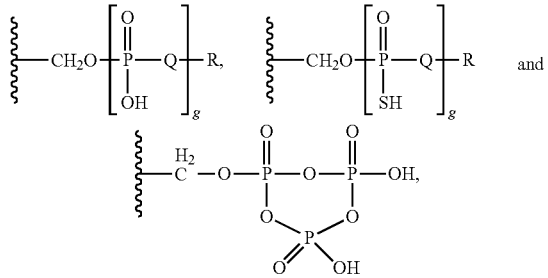

R$_5$ is selected from the group consisting of H, C$_{1-6}$ alkyl, —(CH$_2$CH$_2$O)$_p$CH$_2$CH$_3$, and —CH$_2$CH(OH)CH$_2$(O(CH$_2$)$_2$)$_n$CH$_2$NHC(O)R$_z$;

each R$_6$ is independently selected from H and NH$_2$;

R$_b$ is selected from C$_{1-6}$ alkyl, —OC$_{1-6}$ alkyl, halo, OH, CN, NO, NH$_2$, NHC$_{1-6}$alkyl, N(C$_{1-6}$alkyl)$_2$, SO$_3$H, SO$_4$, PO$_4$, C$_{1-3}$ haloalkyl, C$_{1-3}$ haloalkoxy, carboxyl, oxo, and S(O)$_g$alkyl;

R is H or —P(O)(OH)$_2$;

Q is independently selected from the group consisting of O, CH$_2$, and NH;

R$_s$ is NH$_2$ or —C(O)—;

R$_x$ is hydrogen or —C≡CH;

R$_y$ is —CH$_2$(O(CH$_2$)$_2$)$_n$(CH$_2$)$_k$NHC(O)—R$_z$, or —(CH$_2$OCH$_2$)$_n$CH$_2$C(O)N((CH$_2$)$_k$NHC(O)R$_z$)$_2$;

R$_z$ is cholesterol;

g is 1, 2, or 3;

k and n are independently selected from 1, 2, 3, 4, 5, and 6; and p is an integer from 1 to 50.

2. A compound according to claim 1 of Formula Ia represented by Formula I:

Formula Ia
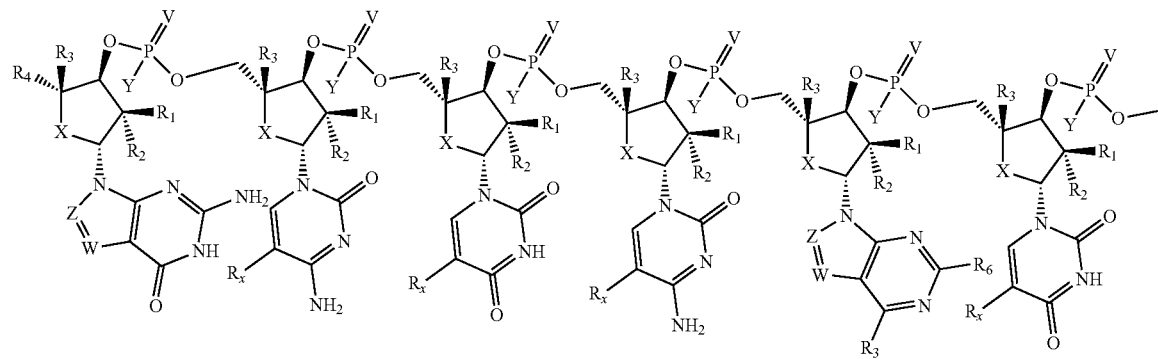
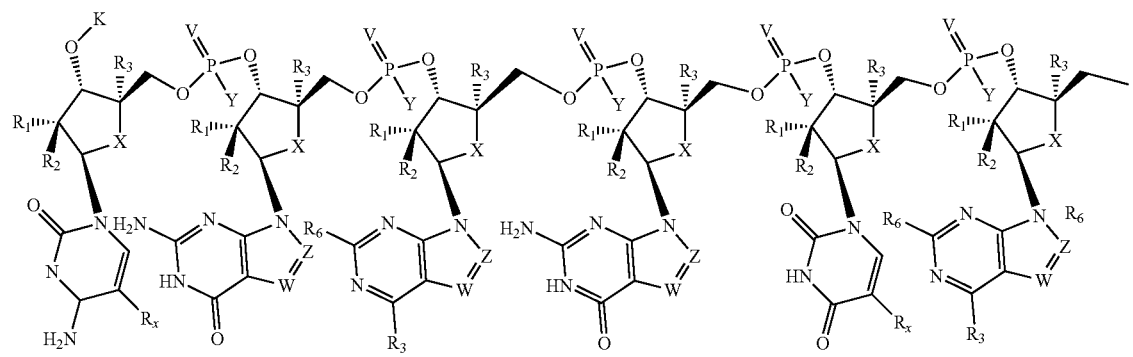
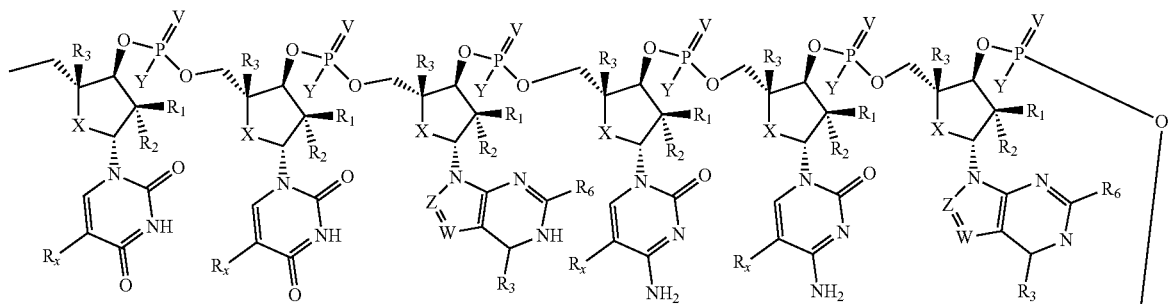
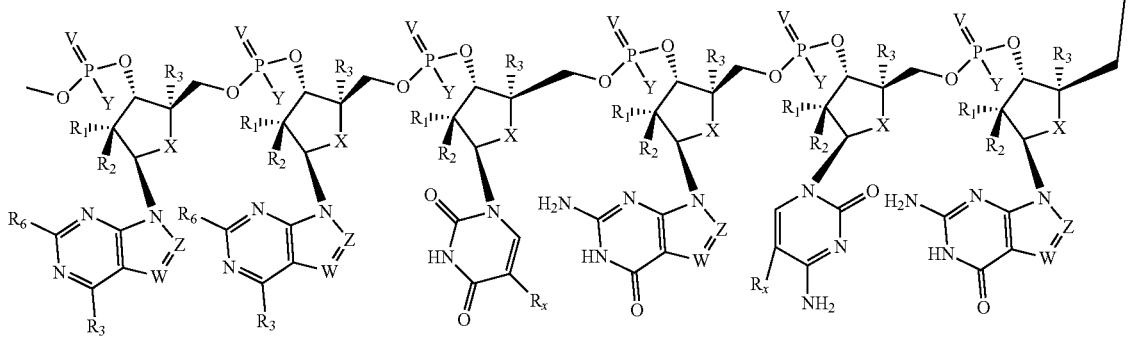

or a pharmaceutically acceptable salt thereof, wherein:
each X is independently selected from the group consisting of O, S, —CH$_2$—, and —NH—;
each Y is independently selected from the group consisting of —OH, —SH, and

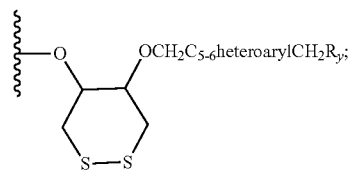

each V is independently O, or S;
K is H, or

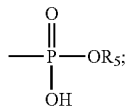

each W is independently N, —CH—, or —C(F)—;
each Z is independently N, or —CH—;
each R$_1$ is independently selected from the group consisting of H, halogen, —OH, —OC$_{1-6}$ alkyl, C$_{1-6}$ alkyl, —OC$_{1-3}$ haloalkyl, —OC$_{2-6}$ alkenyl, —OC$_{2-6}$ alkynyl, —NH$_2$, and —OCH$_2$C$_{5-6}$ heteroarylCH$_2$R$_y$, said alkyl, alkenyl, alkynyl and heteroaryl optionally substituted with 1 to 3 groups of R$_b$;
each R$_2$ is independently selected from the group consisting of H, halogen, —OH, —OC$_{1-6}$ alkyl, C$_{1-6}$ alkyl, —OC$_{1-3}$ haloalkyl;
or one or more adjacent R$_1$ and R$_2$ can combine to form =CH$_2$;
each R$_3$ is independently H, halogen, C$_{1-6}$ alkyl, or C$_{2-6}$ alkynyl;
or R$_1$ and R$_3$ on a sugar moiety can be linked to form —CH$_2$O, provided R$_2$ is hydrogen;
R$_4$ is selected from the group consisting of —CH$_2$OH,

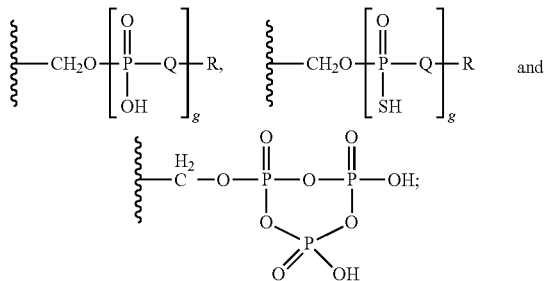

R$_5$ is selected from the group consisting of H, C$_{1-6}$ alkyl, —(CH$_2$CH$_2$O)$_p$CH$_2$CH$_3$, and —CH$_2$CH(OH)CH$_2$(O(CH$_2$)$_2$)$_n$CH$_2$NHC(O)R$_z$;
each R$_6$ is independently selected from H and NH$_2$;
R$_b$ is selected from C$_{1-6}$ alkyl, —OC$_{1-6}$ alkyl, halo, OH, CN, NO, NH$_2$, NHC$_{1-6}$alkyl, N(C$_{1-6}$alkyl)$_2$, SO$_3$H, SO$_4$, PO$_4$, C$_{1-3}$ haloalkyl, C$_{1-3}$ haloalkoxy, carboxyl, oxo, and S(O)$_g$alkyl;
R is H or —P(O)(OH)$_2$;

Q is independently selected from the group consisting of O, CH$_2$, and NH;
R$_y$ is —CH$_2$(O(CH$_2$)$_2$)$_n$(CH$_2$)$_k$NHC(O)—R$_z$, or —(CH$_2$OCH$_2$)$_n$CH$_2$C(O)N((CH$_2$)$_k$NHC(O)R$_z$)$_2$;
R$_z$ is cholesterol;
g is 1, 2, or 3;
k and n are independently selected from 1, 2, 3, 4, 5, and 6; and
p is an integer from 1 to 50.

3. The compound according to claim 1, or a pharmaceutically acceptable salt thereof, wherein: any X is independently selected from O and S, any Y is independently selected from OH and SH, any V is independently selected from O and S, and any K is independently selected from H and

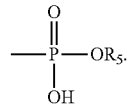

4. The compound according to claim 1, or a pharmaceutically acceptable salt thereof, wherein: any R$_1$ is selected from the group consisting of H, halogen, —OH, —OMe, Me, —OCF$_3$, O(CH$_2$)$_2$OCH$_3$, NH$_2$, and —OCH$_2$C≡CH; any R$_2$ is independently selected from the group consisting of H, halogen, —OH, —OMe, Me, and —OCF$_3$; and Rx is hydrogen.

5. The compound according to claim 1, or a pharmaceutically acceptable salt thereof, wherein: any X is independently selected from O and S; any Y is independently selected from OH and SH; any V is independently selected from O and S; K is H; any W and Z within a single nine membered bicycle is independently selected from W=N and Z=—CH—, W=—CH— and Z=N and W=—CH— and Z is CH; any R$_1$ selected from the group consisting of H, halogen, —OH, —OMe, Me, —OCF$_3$, —O(CH$_2$)$_2$OCH$_3$, —NH$_2$, and —OCH$_2$C≡CH; any R$_2$ is independently selected from the group consisting of H, halogen, —OH, —OMe, -Me, and —OCF$_3$; R$_x$ is hydrogen; R$_s$ is NH$_2$; and any R$_3$ is independently selected from the group consisting of H, halogen, C$_{1-6}$ alkyl, and —C≡CH.

6. A compound selected from Examples 1 through 838, or a pharmaceutically acceptable salt thereof.

7. A pharmaceutical composition comprising a compound according to claim 6, or a pharmaceutically acceptable salt thereof, and a pharmaceutically acceptable carrier or diluent.

8. The composition according to claim 7, wherein the compound comprises a hairpin or stem loop oligonucleotide further comprising a blunt end.

9. A viral vector encoding a compound according to claim 6.

10. An oligonucleotide capable of inducing interferon production, wherein the oligonucleotide comprises 5'-GCU-CAUUUACCAGCGUAAAUGAGC-3' (SEQ ID NO: 841), and wherein the oligonucleotide further comprises a self complementary base pairing region of less than 12 base pairs which are capable of forming a double-stranded section of the oligonucleotide.

11. The oligonucleotide of claim 10, which forms a hairpin structure comprising the double-stranded section and a loop.

12. The oligonucleotide of claim 10, which comprises a blunt end.

13. The oligonucleotide of claim 10, which comprises a 5'-OH, a 5'-triphosphate, or a 5'-diphosphate.

14. The oligonucleotide of claim 10, wherein at least one nucleotide comprises a sugar group modified at its 2' position, wherein the 2' modification is selected from the group consisting of: 2'-OH, 2'-methyl, 2'-OCF$_3$, 2'-OCH$_2$C≡CH, NH$_2$, 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyl-oxyethyl (2'-O-DMAEOE), and 2'-O—N-methylacetamido (2'-O-NMA).

15. A pharmaceutical composition comprising an oligonucleotide of claim 10, wherein the oligonucleotide comprises at least one phosphorothioate group.

16. The oligonucleotide of claim 10, wherein the molecule comprises at least one modified nucleobase.

17. The compound according to claim 2, or a pharmaceutically acceptable salt thereof, wherein: any X is independently selected from O and S, any Y is independently selected from OH and SH, any V is independently selected from O and S, and any K is independently selected from H and

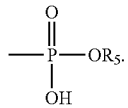

18. The compound according to claim 2, or a pharmaceutically acceptable salt thereof, wherein: any $R_1$ is selected from the group consisting of H, halogen, —OH, —OMe, Me, —OCF$_3$, O(CH$_2$)$_2$OCH$_3$, NH$_2$, and —OCH$_2$C≡CH; any $R_2$ is independently selected from the group consisting of H, halogen, —OH, —OMe, Me, and —OCF$_3$; and Rx is hydrogen.

19. The compound according to claim 2, or a pharmaceutically acceptable salt thereof, wherein: any X is independently selected from O and S; any Y is independently selected from OH and SH; any V is independently selected from O and S; K is H; any W and Z within a single nine membered bicycle is independently selected from W=N and Z=—CH—, W=—CH— and Z=N and W=—CH— and Z is CH; any $R_1$ is selected from the group consisting of H, halogen, —OH, —OMe, Me, —OCF$_3$, —O(CH$_2$)$_2$OCH$_3$, —NH$_2$, and —OCH$_2$C≡CH; any $R_2$ is independently selected from the group consisting of H, halogen, —OH, —OMe, -Me, and —OCF$_3$; $R_x$ is hydrogen; $R_s$ is NH$_2$; and any $R_3$ is independently selected from the group consisting of H, halogen, C$_{1-6}$ alkyl, and —C≡CH.

* * * * *

SEQUENCE LISTING

```
<160> NUMBER OF SEQ ID NOS: 844

<210> SEQ ID NO 1
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gcucauuuac cagcguaaau gagc                                            24

<210> SEQ ID NO 2
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: ribose-2,6-diamino-purine (r2AP)

<400> SEQUENCE: 2
gcucnuuuac cagcguaaau gagc                                            24

<210> SEQ ID NO 3
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: ribose-2,6-diamino-purine (r2AP)

<400> SEQUENCE: 3
gcucauuuac cngcguaaau gagc                                            24

<210> SEQ ID NO 4
<211> LENGTH: 24
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: ribose-2,6-diamino-purine (r2AP)

<400> SEQUENCE: 4
gcucauuuac cagcgunaau gagc                                              24

<210> SEQ ID NO 5
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: ribose-2,6-diamino-purine (r2AP)

<400> SEQUENCE: 5
gcucauuuac cagcguanau gagc                                              24

<210> SEQ ID NO 6
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: ribose-2,6-diamino-purine (r2AP)

<400> SEQUENCE: 6
gcucauuuac cagcguaanu gagc                                              24

<210> SEQ ID NO 7
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: ribose-2,6-diamino-purine (r2AP)

<400> SEQUENCE: 7
gcucnuuuac cagcguaaau gagc                                              24

<210> SEQ ID NO 8
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: ribose-2,6-diamino-purine (r2AP)

<400> SEQUENCE: 8
gcucauuunc cagcguaaau gagc                                              24
```

```
<210> SEQ ID NO 9
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: ribose-2,6-diamino-purine (r2AP)

<400> SEQUENCE: 9
gcucauuuac cngcguaaau gagc                                          24

<210> SEQ ID NO 10
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: ribose-2,6-diamino-purine (r2AP)

<400> SEQUENCE: 10
gcucauuuac cagcgunaau gagc                                          24

<210> SEQ ID NO 11
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: ribose-2,6-diamino-purine (r2AP)

<400> SEQUENCE: 11
gcucauuuac cagcguanau gagc                                          24

<210> SEQ ID NO 12
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: ribose-2,6-diamino-purine (r2AP)

<400> SEQUENCE: 12
gcucauuuac cagcguaanu gagc                                          24

<210> SEQ ID NO 13
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
```

<223> OTHER INFORMATION: ribose-2,6-diamino-purine (r2AP)

<400> SEQUENCE: 13
gcucauuuac cagcguaaau gngc                                              24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-deoxyribose-5-alkynyl-cytidine (d5propC)

<400> SEQUENCE: 14
gcucauuuac cagcguaaau gagc                                              24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: 2'-deoxyribose-5-alkynyl-uridine (d5propU)

<400> SEQUENCE: 15
gcucauuuac cagcguaaau gagc                                              24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (4)..(4)
<223> OTHER INFORMATION: 2'-deoxyribose-5-alkynyl-cytidine (d5propC)

<400> SEQUENCE: 16
gcucauuuac cagcguaaau gagc                                              24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base

```
<222> LOCATION: (6)..(6)
<223> OTHER INFORMATION: 2'-deoxyribose-5-alkynyl-uridine (d5propU)

<400> SEQUENCE: 17
gcucauuuac cagcguaaau gagc                                            24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(7)
<223> OTHER INFORMATION: 2'-deoxyribose-5-alkynyl-uridine (d5propU)

<400> SEQUENCE: 18
gcucauuuac cagcguaaau gagc                                            24

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (8)..(8)
<223> OTHER INFORMATION: 2'-deoxyribose-5-alkynyl-uridine (d5propU)

<400> SEQUENCE: 19
gcucauuuac cagcguaaau gagc                                            24

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (10)..(10)
<223> OTHER INFORMATION: 2'-deoxyribose-5-alkynyl-cytidine (d5propC)

<400> SEQUENCE: 20
gcucauuuac cagcguaaau gagc                                            24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
```

```
<221> NAME/KEY: modified_base
<222> LOCATION: (11)..(11)
<223> OTHER INFORMATION: 2'-deoxyribose-5-alkynyl-cytidine (d5propC)

<400> SEQUENCE: 21
gcucauuuac cagcguaaau gagc                                              24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (14)..(14)
<223> OTHER INFORMATION: 2'-deoxyribose-5-alkynyl-cytidine (d5propC)

<400> SEQUENCE: 22
gcucauuuac cagcguaaau gagc                                              24

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (16)..(16)
<223> OTHER INFORMATION: 2'-deoxyribose-5-alkynyl-uridine (d5propU)

<400> SEQUENCE: 23
gcucauuuac cagcguaaau gagc                                              24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(20)
<223> OTHER INFORMATION: 2'-deoxyribose-5-alkynyl-uridine (d5propU)

<400> SEQUENCE: 24
gcucauuuac cagcguaaau gagc                                              24

<210> SEQ ID NO 25
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
```

<223> OTHER INFORMATION: ribose-7-deaza-8-aza-adenosine (r7dz8azA)

<400> SEQUENCE: 25
gcucauuuac cagcguaaau gagc                                          24

<210> SEQ ID NO 26
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: ribose-7-deaza-8-aza-adenosine (r7dz8azA)

<400> SEQUENCE: 26
gcucauuuac cagcguaaau gagc                                          24

<210> SEQ ID NO 27
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: ribose-7-deaza-8-aza-adenosine (r7dz8azA)

<400> SEQUENCE: 27
gcucauuuac cagcguaaau gagc                                          24

<210> SEQ ID NO 28
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: ribose-7-deaza-8-aza-adenosine (r7dz8azA)

<400> SEQUENCE: 28
gcucauuuac cagcguaaau gagc                                          24

<210> SEQ ID NO 29
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: ribose-7-deaza-8-aza-adenosine (r7dz8azA)

<400> SEQUENCE: 29
gcucauuuac cagcguaaau gagc                                          24

<210> SEQ ID NO 30
<211> LENGTH: 24
<212> TYPE: RNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: ribose-7-deaza-8-aza-adenosine (r7dz8azA)

<400> SEQUENCE: 30
gcucauuuac cagcguaaau gagc                                              24

<210> SEQ ID NO 31
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: ribose-7-deaza-8-aza-adenosine (r7dz8azA)

<400> SEQUENCE: 31
gcucauuuac cagcguaaau gagc                                              24

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(5)
<223> OTHER INFORMATION: 2'-deoxy-ribose-2-amino-adenosine (d2aminoA)

<400> SEQUENCE: 32
gcucauuuac cagcguaaau gagc                                              24

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (9)..(9)
<223> OTHER INFORMATION: 2'-deoxy-ribose-2-amino-adenosine (d2aminoA)

<400> SEQUENCE: 33
gcucauuuac cagcguaaau gagc                                              24

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

```
        Synthetic oligonucleotide
<220> FEATURE:
<221> NAME/KEY: modified_base
<222> LOCATION: (12)..(12)
<223> OTHER INFORMATION: 2'-deoxy-ribose-2-amino-adenosine (d2aminoA)

<400> SEQUENCE: 34
gcucauuuac cagcguaaau gagc                                              24

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (17)..(17)
<223> OTHER INFORMATION: 2'-deoxy-ribose-2-amino-adenosine (d2aminoA)

<400> SEQUENCE: 35
gcucauuuac cagcguaaau gagc                                              24

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (18)..(18)
<223> OTHER INFORMATION: 2'-deoxy-ribose-2-amino-adenosine (d2aminoA)

<400> SEQUENCE: 36
gcucauuuac cagcguaaau gagc                                              24

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (19)..(19)
<223> OTHER INFORMATION: 2'-deoxy-ribose-2-amino-adenosine (d2aminoA)

<400> SEQUENCE: 37
gcucauuuac cagcguaaau gagc                                              24

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: Description of Combined DNA/RNA Molecule:
      Synthetic oligonucleotide
<220> FEATURE:
<221> NAME/KEY: modified_base
<222> LOCATION: (22)..(22)
<223> OTHER INFORMATION: 2'-deoxy-ribose-2-amino-adenosine (d2aminoA)

<400> SEQUENCE: 38
gcucauuuac cagcguaaau gagc                                               24

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(5)
<223> OTHER INFORMATION: 2'-fluoro-2'-deoxy-arabinose-8-aza-adenosine
      (fara8azA)

<400> SEQUENCE: 39
gcucauuuac cagcguaaau gagc                                               24

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (9)..(9)
<223> OTHER INFORMATION: 2'-fluoro-2'-deoxy-arabinose-8-aza-adenosine
      (fara8azA)

<400> SEQUENCE: 40
gcucauuuac cagcguaaau gagc                                               24

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (12)..(12)
<223> OTHER INFORMATION: 2'-fluoro-2'-deoxy-arabinose-8-aza-adenosine
      (fara8azA)

<400> SEQUENCE: 41
gcucauuuac cagcguaaau gagc                                               24

<210> SEQ ID NO 42
<211> LENGTH: 24
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (17)..(17)
<223> OTHER INFORMATION: 2'-fluoro-2'-deoxy-arabinose-8-aza-adenosine
      (fara8azA)

<400> SEQUENCE: 42
gcucauuuac cagcguaaau gagc                                          24

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (18)..(18)
<223> OTHER INFORMATION: 2'-fluoro-2'-deoxy-arabinose-8-aza-adenosine
      (fara8azA)

<400> SEQUENCE: 43
gcucauuuac cagcguaaau gagc                                          24

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (19)..(19)
<223> OTHER INFORMATION: 2'-fluoro-2'-deoxy-arabinose-8-aza-adenosine
      (fara8azA)

<400> SEQUENCE: 44
gcucauuuac cagcguaaau gagc                                          24

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-deoxyribose-5-alkynyl-cytidine (d5propC)

<400> SEQUENCE: 45
gcucauuuac cagcguaaau gagc                                          24
```

```
<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: 2'-deoxyribose-5-alkynyl-uridine (d5propU)

<400> SEQUENCE: 46
gcucauuuac cagcguaaau gagc                                              24

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (4)..(4)
<223> OTHER INFORMATION: 2'-deoxyribose-5-alkynyl-cytidine (d5propC)

<400> SEQUENCE: 47
gcucauuuac cagcguaaau gagc                                              24

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxyribose-5-alkynyl-uridine (d5propU)

<400> SEQUENCE: 48
gcucauuuac cagcguaaau gagc                                              24

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(7)
<223> OTHER INFORMATION: 2'-deoxyribose-5-alkynyl-uridine (d5propU)

<400> SEQUENCE: 49
gcucauuuac cagcguaaau gagc                                              24
```

```
<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (8)..(8)
<223> OTHER INFORMATION: 2'-deoxyribose-5-alkynyl-uridine (d5propU)

<400> SEQUENCE: 50
gcucauuuac cagcguaaau gagc                                          24

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (10)..(10)
<223> OTHER INFORMATION: 2'-deoxyribose-5-alkynyl-cytidine (d5propC)

<400> SEQUENCE: 51
gcucauuuac cagcguaaau gagc                                          24

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (11)..(11)
<223> OTHER INFORMATION: 2'-deoxyribose-5-alkynyl-cytidine (d5propC)

<400> SEQUENCE: 52
gcucauuuac cagcguaaau gagc                                          24

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (14)..(14)
<223> OTHER INFORMATION: 2'-deoxyribose-5-alkynyl-cytidine (d5propC)

<400> SEQUENCE: 53
gcucauuuac cagcguaaau gagc                                          24
```

```
<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (16)..(16)
<223> OTHER INFORMATION: 2'-deoxyribose-5-alkynyl-uridine (d5propU)

<400> SEQUENCE: 54
gcucauuuac cagcguaaau gagc                                          24

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(20)
<223> OTHER INFORMATION: 2'-deoxyribose-5-alkynyl-uridine (d5propU)

<400> SEQUENCE: 55
gcucauuuac cagcguaaau gagc                                          24

<210> SEQ ID NO 56
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: ribose-7-deaza-8-aza-adenosine (r7dz8azA)

<400> SEQUENCE: 56
gcucauuuac cagcguaaau gagc                                          24

<210> SEQ ID NO 57
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: ribose-7-deaza-8-aza-adenosine (r7dz8azA)

<400> SEQUENCE: 57
gcucauuuac cagcguaaau gagc                                          24

<210> SEQ ID NO 58
<211> LENGTH: 24
<212> TYPE: RNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: ribose-7-deaza-8-aza-adenosine (r7dz8azA)

<400> SEQUENCE: 58
gcucauuuac cagcguaaau gagc                                              24

<210> SEQ ID NO 59
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: ribose-7-deaza-8-aza-adenosine (r7dz8azA)

<400> SEQUENCE: 59
gcucauuuac cagcguaaau gagc                                              24

<210> SEQ ID NO 60
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: ribose-7-deaza-8-aza-adenosine (r7dz8azA)

<400> SEQUENCE: 60
gcucauuuac cagcguaaau gagc                                              24

<210> SEQ ID NO 61
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: ribose-7-deaza-8-aza-adenosine (r7dz8azA)

<400> SEQUENCE: 61
gcucauuuac cagcguaaau gagc                                              24

<210> SEQ ID NO 62
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: ribose-7-deaza-8-aza-adenosine (r7dz8azA)

<400> SEQUENCE: 62
```
gcucauuuac cagcguaaau gagc                                    24

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(5)
<223> OTHER INFORMATION: 2'-deoxy-ribose-2-amino-adenosine (d2aminoA)

<400> SEQUENCE: 63
gcucauuuac cagcguaaau gagc                                    24

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (9)..(9)
<223> OTHER INFORMATION: 2'-deoxy-ribose-2-amino-adenosine (d2aminoA)

<400> SEQUENCE: 64
gcucauuuac cagcguaaau gagc                                    24

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (12)..(12)
<223> OTHER INFORMATION: 2'-deoxy-ribose-2-amino-adenosine (d2aminoA)

<400> SEQUENCE: 65
gcucauuuac cagcguaaau gagc                                    24

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (17)..(17)
<223> OTHER INFORMATION: 2'-deoxy-ribose-2-amino-adenosine (d2aminoA)

<400> SEQUENCE: 66
gcucauuuac cagcguaaau gagc                                    24

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (18)..(18)
<223> OTHER INFORMATION: 2'-deoxy-ribose-2-amino-adenosine (d2aminoA)

<400> SEQUENCE: 67
gcucauuuac cagcguaaau gagc                                    24

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (19)..(19)
<223> OTHER INFORMATION: 2'-deoxy-ribose-2-amino-adenosine (d2aminoA)

<400> SEQUENCE: 68
gcucauuuac cagcguaaau gagc                                    24

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (22)..(22)
<223> OTHER INFORMATION: 2'-deoxy-ribose-2-amino-adenosine (d2aminoA)

<400> SEQUENCE: 69
gcucauuuac cagcguaaau gagc                                    24

<210> SEQ ID NO 70
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(5)
<223> OTHER INFORMATION: 2'-fluoro-2'-deoxy-arabinose-8-aza-adenosine
      (fara8azA)

```
<400> SEQUENCE: 70
gcucauuuac cagcguaaau gagc                                              24

<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (9)..(9)
<223> OTHER INFORMATION: 2'-fluoro-2'-deoxy-arabinose-8-aza-adenosine
      (fara8azA)

<400> SEQUENCE: 71
gcucauuuac cagcguaaau gagc                                              24

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (12)..(12)
<223> OTHER INFORMATION: 2'-fluoro-2'-deoxy-arabinose-8-aza-adenosine
      (fara8azA)

<400> SEQUENCE: 72
gcucauuuac cagcguaaau gagc                                              24

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (17)..(17)
<223> OTHER INFORMATION: 2'-fluoro-2'-deoxy-arabinose-8-aza-adenosine
      (fara8azA)

<400> SEQUENCE: 73
gcucauuuac cagcguaaau gagc                                              24

<210> SEQ ID NO 74
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<220> FEATURE:
<221> NAME/KEY: modified_base
<222> LOCATION: (18)..(18)
<223> OTHER INFORMATION: 2'-fluoro-2'-deoxy-arabinose-8-aza-adenosine
      (fara8azA)

<400> SEQUENCE: 74
gcucauuuac cagcguaaau gagc                                          24

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (19)..(19)
<223> OTHER INFORMATION: 2'-fluoro-2'-deoxy-arabinose-8-aza-adenosine
      (fara8azA)

<400> SEQUENCE: 75
gcucauuuac cagcguaaau gagc                                          24

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (22)..(22)
<223> OTHER INFORMATION: 2'-fluoro-2'-deoxy-arabinose-8-aza-adenosine
      (fara8azA)

<400> SEQUENCE: 76
gcucauuuac cagcguaaau gagc                                          24

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(5)
<223> OTHER INFORMATION: 2'-fluoro-2'-deoxy-arabinose-7-deaza-adenosine
      (fara7dzA)

<400> SEQUENCE: 77
gcucauuuac cagcguaaau gagc                                          24

<210> SEQ ID NO 78
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (9)..(9)
<223> OTHER INFORMATION: 2'-fluoro-2'-deoxy-arabinose-7-deaza-adenosine
      (fara7dzA)

<400> SEQUENCE: 78
gcucauuuac cagcguaaau gagc                                           24

<210> SEQ ID NO 79
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (12)..(12)
<223> OTHER INFORMATION: 2'-fluoro-2'-deoxy-arabinose-7-deaza-adenosine
      (fara7dzA)

<400> SEQUENCE: 79
gcucauuuac cagcguaaau gagc                                           24

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (17)..(17)
<223> OTHER INFORMATION: 2'-fluoro-2'-deoxy-arabinose-7-deaza-adenosine
      (fara7dzA)

<400> SEQUENCE: 80
gcucauuuac cagcguaaau gagc                                           24

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (18)..(18)
<223> OTHER INFORMATION: 2'-fluoro-2'-deoxy-arabinose-7-deaza-adenosine
      (fara7dzA)

<400> SEQUENCE: 81
gcucauuuac cagcguaaau gagc                                           24
```

```
<210> SEQ ID NO 82
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (19)..(19)
<223> OTHER INFORMATION: 2'-fluoro-2'-deoxy-arabinose-7-deaza-adenosine
      (fara7dzA)

<400> SEQUENCE: 82
gcucauuuac cagcguaaau gagc                                            24

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (22)..(22)
<223> OTHER INFORMATION: 2'-fluoro-2'-deoxy-arabinose-7-deaza-adenosine
      (fara7dzA)

<400> SEQUENCE: 83
gcucauuuac cagcguaaau gagc                                            24

<210> SEQ ID NO 84
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(5)
<223> OTHER INFORMATION: 2'-deoxy-ribose-7-deaza-adenosine (d7dzA)

<400> SEQUENCE: 84
gcucauuuac cagcguaaau gagc                                            24

<210> SEQ ID NO 85
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (9)..(9)
<223> OTHER INFORMATION: 2'-deoxy-ribose-7-deaza-adenosine (d7dzA)

<400> SEQUENCE: 85
```
gcucauuuac cagcguaaau gagc                                              24

<210> SEQ ID NO 86
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (12)..(12)
<223> OTHER INFORMATION: 2'-deoxy-ribose-7-deaza-adenosine (d7dzA)

<400> SEQUENCE: 86
gcucauuuac cagcguaaau gagc                                              24

<210> SEQ ID NO 87
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (17)..(17)
<223> OTHER INFORMATION: 2'-deoxy-ribose-7-deaza-adenosine (d7dzA)

<400> SEQUENCE: 87
gcucauuuac cagcguaaau gagc                                              24

<210> SEQ ID NO 88
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (18)..(18)
<223> OTHER INFORMATION: 2'-deoxy-ribose-7-deaza-adenosine (d7dzA)

<400> SEQUENCE: 88
gcucauuuac cagcguaaau gagc                                              24

<210> SEQ ID NO 89
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (19)..(19)
<223> OTHER INFORMATION: 2'-deoxy-ribose-7-deaza-adenosine (d7dzA)

<400> SEQUENCE: 89

-continued gcucauuuac cagcguaaau gagc                                              24

<210> SEQ ID NO 90
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (22)..(22)
<223> OTHER INFORMATION: 2'-deoxy-ribose-7-deaza-adenosine (d7dzA)

<400> SEQUENCE: 90
gcucauuuac cagcguaaau gagc                                              24

<210> SEQ ID NO 91
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: ribose-7-deaza-adenosine (r7dzA)

<400> SEQUENCE: 91
gcucauuuac cagcguaaau gagc                                              24

<210> SEQ ID NO 92
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: ribose-7-deaza-adenosine (r7dzA)

<400> SEQUENCE: 92
gcucauuuac cagcguaaau gagc                                              24

<210> SEQ ID NO 93
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: ribose-7-deaza-adenosine (r7dzA)

<400> SEQUENCE: 93
gcucauuuac cagcguaaau gagc                                              24

<210> SEQ ID NO 94
<211> LENGTH: 24
<212> TYPE: RNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: ribose-7-deaza-adenosine (r7dzA)

<400> SEQUENCE: 94
gcucauuuac cagcguaaau gagc                                              24

<210> SEQ ID NO 95
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: ribose-7-deaza-adenosine (r7dzA)

<400> SEQUENCE: 95
gcucauuuac cagcguaaau gagc                                              24

<210> SEQ ID NO 96
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: ribose-7-deaza-adenosine (r7dzA)

<400> SEQUENCE: 96
gcucauuuac cagcguaaau gagc                                              24

<210> SEQ ID NO 97
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: ribose-7-deaza-adenosine (r7dzA)

<400> SEQUENCE: 97
gcucauuuac cagcguaaau gagc                                              24

<210> SEQ ID NO 98
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(5)
<223> OTHER INFORMATION: 2'-fluoro-2'-deoxy-arabinose-7-deaza-adenosine
      (fara7dzA)
```

<400> SEQUENCE: 98
gcucauuuac cagcguaaau gagc                                          24

<210> SEQ ID NO 99
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (9)..(9)
<223> OTHER INFORMATION: 2'-fluoro-2'-deoxy-arabinose-7-deaza-adenosine
      (fara7dzA)

<400> SEQUENCE: 99
gcucauuuac cagcguaaau gagc                                          24

<210> SEQ ID NO 100
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (12)..(12)
<223> OTHER INFORMATION: 2'-fluoro-2'-deoxy-arabinose-7-deaza-adenosine
      (fara7dzA)

<400> SEQUENCE: 100
gcucauuuac cagcguaaau gagc                                          24

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (17)..(17)
<223> OTHER INFORMATION: 2'-fluoro-2'-deoxy-arabinose-7-deaza-adenosine
      (fara7dzA)

<400> SEQUENCE: 101
gcucauuuac cagcguaaau gagc                                          24

<210> SEQ ID NO 102
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide <220> FEATURE:
<221> NAME/KEY: modified_base
<222> LOCATION: (18)..(18)
<223> OTHER INFORMATION: 2'-fluoro-2'-deoxy-arabinose-7-deaza-adenosine
    (fara7dzA)

<400> SEQUENCE: 102
gcucauuuac cagcguaaau gagc                                      24

<210> SEQ ID NO 103
<211> LENGTH: 24
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide
<220> FEATURE:
<221> NAME/KEY: modified_base
<222> LOCATION: (19)..(19)
<223> OTHER INFORMATION: 2'-fluoro-2'-deoxy-arabinose-7-deaza-adenosine
    (fara7dzA)

<400> SEQUENCE: 103
gcucauuuac cagcguaaau gagc                                      24

<210> SEQ ID NO 104
<211> LENGTH: 24
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide
<220> FEATURE:
<221> NAME/KEY: modified_base
<222> LOCATION: (22)..(22)
<223> OTHER INFORMATION: 2'-fluoro-2'-deoxy-arabinose-7-deaza-adenosine
    (fara7dzA)

<400> SEQUENCE: 104
gcucauuuac cagcguaaau gagc                                      24

<210> SEQ ID NO 105
<211> LENGTH: 24
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide
<220> FEATURE:
<221> NAME/KEY: modified_base
<222> LOCATION: (5)..(5)
<223> OTHER INFORMATION: 2'-deoxy-ribose-7-deaza-adenosine (d7dzA)

<400> SEQUENCE: 105
gcucauuuac cagcguaaau gagc                                      24

<210> SEQ ID NO 106
<211> LENGTH: 24
<212> TYPE: DNA
<213> ORGANISM: Artificial Sequence
<220> FEATURE:
<223> OTHER INFORMATION: Description of Artificial Sequence: Synthetic

```
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (9)..(9)
<223> OTHER INFORMATION: 2'-deoxy-ribose-7-deaza-adenosine (d7dzA)

<400> SEQUENCE: 106
gcucauuuac cagcguaaau gagc                                          24

<210> SEQ ID NO 107
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (12)..(12)
<223> OTHER INFORMATION: 2'-deoxy-ribose-7-deaza-adenosine (d7dzA)

<400> SEQUENCE: 107
gcucauuuac cagcguaaau gagc                                          24

<210> SEQ ID NO 108
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (17)..(17)
<223> OTHER INFORMATION: 2'-deoxy-ribose-7-deaza-adenosine (d7dzA)

<400> SEQUENCE: 108
gcucauuuac cagcguaaau gagc                                          24

<210> SEQ ID NO 109
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (18)..(18)
<223> OTHER INFORMATION: 2'-deoxy-ribose-7-deaza-adenosine (d7dzA)

<400> SEQUENCE: 109
gcucauuuac cagcguaaau gagc                                          24

<210> SEQ ID NO 110
<211> LENGTH: 24
<212> TYPE: DNA
<213> ORGANISM: Artificial Sequence
<220> FEATURE:
```

<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide
<220> FEATURE:
<221> NAME/KEY: modified_base
<222> LOCATION: (19)..(19)
<223> OTHER INFORMATION: 2'-deoxy-ribose-7-deaza-adenosine (d7dzA)

<400> SEQUENCE: 110
gcucauuuac cagcguaaau gagc                                          24

<210> SEQ ID NO 111
<211> LENGTH: 24
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide
<220> FEATURE:
<221> NAME/KEY: modified_base
<222> LOCATION: (22)..(22)
<223> OTHER INFORMATION: 2'-deoxy-ribose-7-deaza-adenosine (d7dzA)

<400> SEQUENCE: 111
gcucauuuac cagcguaaau gagc                                          24

<210> SEQ ID NO 112
<211> LENGTH: 24
<212> TYPE: RNA
<213> ORGANISM: Artificial Sequence
<220> FEATURE:
<223> OTHER INFORMATION: Description of Artificial Sequence: Synthetic
     oligonucleotide
<220> FEATURE:
<221> NAME/KEY: modified_base
<222> LOCATION: (9)..(9)
<223> OTHER INFORMATION: ribose-7-deaza-adenosine (r7dzA)

<400> SEQUENCE: 112
gcucauuuac cagcguaaau gagc                                          24

<210> SEQ ID NO 113
<211> LENGTH: 24
<212> TYPE: RNA
<213> ORGANISM: Artificial Sequence
<220> FEATURE:
<223> OTHER INFORMATION: Description of Artificial Sequence: Synthetic
     oligonucleotide
<220> FEATURE:
<221> NAME/KEY: modified_base
<222> LOCATION: (1)..(1)
<223> OTHER INFORMATION: 4'-thio-ribose-8-aza-guanosine (4S8azG)

<400> SEQUENCE: 113
gcucauuuac cagcguaaau gagc                                          24

<210> SEQ ID NO 114
<211> LENGTH: 24
<212> TYPE: RNA
<213> ORGANISM: Artificial Sequence
<220> FEATURE:
<223> OTHER INFORMATION: Description of Artificial Sequence: Synthetic
     oligonucleotide
<220> FEATURE:
<221> NAME/KEY: modified_base
<222> LOCATION: (13)..(13)

```
<223> OTHER INFORMATION: 4'-thio-ribose-8-aza-guanosine (4S8azG)

<400> SEQUENCE: 114
gcucauuuac cagcguaaau gagc                                              24

<210> SEQ ID NO 115
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(15)
<223> OTHER INFORMATION: 4'-thio-ribose-8-aza-guanosine (4S8azG)

<400> SEQUENCE: 115
gcucauuuac cagcguaaau gagc                                              24

<210> SEQ ID NO 116
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: 4'-thio-ribose-8-aza-guanosine (4S8azG)

<400> SEQUENCE: 116
gcucauuuac cagcguaaau gagc                                              24

<210> SEQ ID NO 117
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(23)
<223> OTHER INFORMATION: 4'-thio-ribose-8-aza-guanosine (4S8azG)

<400> SEQUENCE: 117
gcucauuuac cagcguaaau gagc                                              24

<210> SEQ ID NO 118
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 4'-thio-ribose-8-aza-guanosine (4S8azG)

<400> SEQUENCE: 118
gcucauuuac cagcguaaau gagc                                              24

<210> SEQ ID NO 119
<211> LENGTH: 24
<212> TYPE: RNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: 4'-thio-ribose-8-aza-guanosine (4S8azG)

<400> SEQUENCE: 119
gcucauuuac cagcguaaau gagc                                               24

<210> SEQ ID NO 120
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(15)
<223> OTHER INFORMATION: 4'-thio-ribose-8-aza-guanosine (4S8azG)

<400> SEQUENCE: 120
gcucauuuac cagcguaaau gagc                                               24

<210> SEQ ID NO 121
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: 4'-thio-ribose-8-aza-guanosine (4S8azG)

<400> SEQUENCE: 121
gcucauuuac cagcguaaau gagc                                               24

<210> SEQ ID NO 122
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(23)
<223> OTHER INFORMATION: 4'-thio-ribose-8-aza-guanosine (4S8azG)

<400> SEQUENCE: 122
gcucauuuac cagcguaaau gagc                                               24

<210> SEQ ID NO 123
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
ggacguacgu uucgacguac gucc                                               24

<210> SEQ ID NO 124
<211> LENGTH: 24
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
gcucauuuac cagcguaaau gagc                                           24

<210> SEQ ID NO 125
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
gcucauuuac cagcguaaau gagc                                           24

<210> SEQ ID NO 126
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
gcucauuuac cagcguaaau gagc                                           24

<210> SEQ ID NO 127
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
gcucauuuac cagcguaaau gagc                                           24

<210> SEQ ID NO 128
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
gcucauuuac cagcguaaau gagc                                           24

<210> SEQ ID NO 129
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
gcucauuuac cagcguaaau gagc                                           24

<210> SEQ ID NO 130
<211> LENGTH: 24
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 130
gcucauuuac cagcguaaau gagc                                           24

<210> SEQ ID NO 131
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
gcucauuuac cagcguaaau gagc                                           24

<210> SEQ ID NO 132
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
gcucauuuac cagcguaaau gagc                                           24

<210> SEQ ID NO 133
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
gcucauuuac cagcguaaau gagc                                           24

<210> SEQ ID NO 134
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
gcucauuuac cagcguaaau gagc                                           24

<210> SEQ ID NO 135
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
gcucauuuac cagcguaaau gagc                                           24

<210> SEQ ID NO 136
<211> LENGTH: 24
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 136
gcucauuuac cagcguaaau gagc                                              24

<210> SEQ ID NO 137
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
gcucauuuac cagcguaaau gagc                                              24

<210> SEQ ID NO 138
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
gcucauuuac cagcguaaau gagc                                              24

<210> SEQ ID NO 139
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
gcucauuuac cagcguaaau gagc                                              24

<210> SEQ ID NO 140
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
gcucauuuac cagcguaaau gagc                                              24

<210> SEQ ID NO 141
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
gcucauuuac cagcguaaau gagc                                              24

<210> SEQ ID NO 142
<211> LENGTH: 24
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 142
gcucauuuac cagcguaaau gagc                                              24

<210> SEQ ID NO 143
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
gcucauuuac cagcguaaau gagc                                              24

<210> SEQ ID NO 144
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
gcucauuuac cagcguaaau gagc                                              24

<210> SEQ ID NO 145
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
gcucauuuac cagcguaaau gagc                                              24

<210> SEQ ID NO 146
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
gcucauuuac cagcguaaau gagc                                              24

<210> SEQ ID NO 147
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
gcucauuuac cagcguaaau gagc                                              24

<210> SEQ ID NO 148
<211> LENGTH: 24
<212> TYPE: RNA
<213> ORGANISM: Artificial Sequence
<220> FEATURE:
<223> OTHER INFORMATION: Description of Artificial Sequence: Synthetic
```

-continued

```
      oligonucleotide

<400> SEQUENCE: 148
gcucauuuac cagcguaaau gagc                                            24

<210> SEQ ID NO 149
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
gcucauuuac cagcguaaau gagc                                            24

<210> SEQ ID NO 150
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
gcucauuuac cagcguaaau gagc                                            24

<210> SEQ ID NO 151
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
gcucauuuac cagcguaaau gagc                                            24

<210> SEQ ID NO 152
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
gcucauuuac cagcguaaau gagc                                            24

<210> SEQ ID NO 153
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
gcucauuuac cagcguaaau gagc                                            24

<210> SEQ ID NO 154
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 154
gcucauuuac cagcguaaau gagc        24

<210> SEQ ID NO 155
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
gcucauuuac cagcguaaau gagc        24

<210> SEQ ID NO 156
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
gcucauuuac cagcguaaau gagc        24

<210> SEQ ID NO 157
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
gcucauuuac cagcguaaau gagc        24

<210> SEQ ID NO 158
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
gcucauuuac cagcguaaau gagc        24

<210> SEQ ID NO 159
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
gcucauuuac cagcguaaau gagc        24

<210> SEQ ID NO 160
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 160
gcucauuuac cagcguaaau gagc                                          24

<210> SEQ ID NO 161
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
gcucauuuac cagcguaaau gagc                                          24

<210> SEQ ID NO 162
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
gcucauuuac cagcguaaau gagc                                          24

<210> SEQ ID NO 163
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
gcucauuuac cagcguaaau gagc                                          24

<210> SEQ ID NO 164
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
gcucauuuac cagcguaaau gagc                                          24

<210> SEQ ID NO 165
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
gcucauuuac cagcguaaau gagc                                          24

<210> SEQ ID NO 166
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
```
gcucauuuac cagcguaaau gagc                                              24

<210> SEQ ID NO 167
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
gcucauuuac cagcguaaau gagc                                              24

<210> SEQ ID NO 168
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
gcucauuuac cagcguaaau gagc                                              24

<210> SEQ ID NO 169
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
gcucauuuac cagcguaaau gagc                                              24

<210> SEQ ID NO 170
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
gcucauuuac cagcguaaau gagc                                              24

<210> SEQ ID NO 171
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
gcucauuuac cagcguaaau gagc                                              24

<210> SEQ ID NO 172
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172

```
gcucauuuac cagcguaaau gagc                                              24
```

<210> SEQ ID NO 173
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173

```
gcucauuuac cagcguaaau gagc                                              24
```

<210> SEQ ID NO 174
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174

```
gcucauuuac cagcguaaau gagc                                              24
```

<210> SEQ ID NO 175
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175

```
gcucauuuac cagcguaaau gagc                                              24
```

<210> SEQ ID NO 176
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176

```
gcucauuuac cagcguaaau gagc                                              24
```

<210> SEQ ID NO 177
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177

```
gcucauuuac cagcguaaau gagc                                              24
```

<210> SEQ ID NO 178
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178

```
gcucauuuac cagcguaaau gagc                                              24
```

<210> SEQ ID NO 179
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
gcucauuuac cagcguaaau gagc                                          24

<210> SEQ ID NO 180
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
gcucauuuac cagcguaaau gagc                                          24

<210> SEQ ID NO 181
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
gcucauuuac cagcguaaau gagc                                          24

<210> SEQ ID NO 182
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
gcucauuuac cagcguaaau gagc                                          24

<210> SEQ ID NO 183
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
gcucauuuac cagcguaaau gagc                                          24

<210> SEQ ID NO 184
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
gcucauuuac cagcguaaau gagc                                          24

```
<210> SEQ ID NO 185
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
gcucauuuac cagcguaaau gagc                                          24

<210> SEQ ID NO 186
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
gcucauuuac cagcguaaau gagc                                          24

<210> SEQ ID NO 187
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
gcucauuuac cagcguaaau gagc                                          24

<210> SEQ ID NO 188
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
gcucauuuac cagcguaaau gagc                                          24

<210> SEQ ID NO 189
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
gcucauuuac cagcguaaau gagc                                          24

<210> SEQ ID NO 190
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
gcucauuuac cagcguaaau gagc                                          24
```

```
<210> SEQ ID NO 191
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
gcucauuuac cagcguaaau gagc                                              24

<210> SEQ ID NO 192
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192
gcucauuuac cagcguaaau gagc                                              24

<210> SEQ ID NO 193
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
gcucauuuac cagcguaaau gagc                                              24

<210> SEQ ID NO 194
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
gcucauuuac cagcguaaau gagc                                              24

<210> SEQ ID NO 195
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
gcucauuuac cagcguaaau gagc                                              24

<210> SEQ ID NO 196
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
gcucauuuac cagcguaaau gagc                                              24

<210> SEQ ID NO 197
```

```
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
gcucauuuac cagcguaaau gagc                                          24

<210> SEQ ID NO 198
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
gcucauuuac cagcguaaau gagc                                          24

<210> SEQ ID NO 199
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
gcucauuuac cagcguaaau gagc                                          24

<210> SEQ ID NO 200
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
gcucauuuac cagcguaaau gagc                                          24

<210> SEQ ID NO 201
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
gcucauuuac cagcguaaau gagc                                          24

<210> SEQ ID NO 202
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
gcucauuuac cagcguaaau gagc                                          24

<210> SEQ ID NO 203
<211> LENGTH: 24
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
gcucauuuac cagcguaaau gagc                                            24

<210> SEQ ID NO 204
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
gcucauuuac cagcguaaau gagc                                            24

<210> SEQ ID NO 205
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
gcucauuuac cagcguaaau gagc                                            24

<210> SEQ ID NO 206
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
gcucauuuac cagcguaaau gagc                                            24

<210> SEQ ID NO 207
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
gcucauuuac cagcguaaau gagc                                            24

<210> SEQ ID NO 208
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
gcucauuuac cagcguaaau gagc                                            24

<210> SEQ ID NO 209
<211> LENGTH: 24
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 209
gcucauuuac cagcguaaau gagc                                            24

<210> SEQ ID NO 210
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 210
gcucauuuac cagcguaaau gagc                                            24

<210> SEQ ID NO 211
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
gcucauuuac cagcguaaau gagc                                            24

<210> SEQ ID NO 212
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
gcucauuuac cagcguaaau gagc                                            24

<210> SEQ ID NO 213
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
gcucauuuac cagcguaaau gagc                                            24

<210> SEQ ID NO 214
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
gcucauuuac cagcguaaau gagc                                            24

<210> SEQ ID NO 215
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
gcucauuuac cagcguaaau gagc                                              24

<210> SEQ ID NO 216
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216
gcucauuuac cagcguaaau gagc                                              24

<210> SEQ ID NO 217
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
gcucauuuac cagcguaaau gagc                                              24

<210> SEQ ID NO 218
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
gcucauuuac cagcguaaau gagc                                              24

<210> SEQ ID NO 219
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
gcucauuuac cagcguaaau gagc                                              24

<210> SEQ ID NO 220
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
gcucauuuac cagcguaaau gagc                                              24

<210> SEQ ID NO 221
<211> LENGTH: 24
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 221
gcucauuuac cagcguaaau gagc                                              24

<210> SEQ ID NO 222
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
gcucauuuac cagcguaaau gagc                                              24

<210> SEQ ID NO 223
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
gcucauuuac cagcguaaau gagc                                              24

<210> SEQ ID NO 224
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
gcucauuuac cagcguaaau gagc                                              24

<210> SEQ ID NO 225
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
gcucauuuac cagcguaaau gagc                                              24

<210> SEQ ID NO 226
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
gcucauuuac cagcguaaau gagc                                              24

<210> SEQ ID NO 227
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 227
gcucauuuac cagcguaaau gagc                                              24

<210> SEQ ID NO 228
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
gcucauuuac cagcguaaau gagc                                              24

<210> SEQ ID NO 229
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
gcucauuuac cagcguaaau gagc                                              24

<210> SEQ ID NO 230
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
gcucauuuac cagcguaaau gagc                                              24

<210> SEQ ID NO 231
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
gcucauuuac cagcguaaau gagc                                              24

<210> SEQ ID NO 232
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
gcucauuuac cagcguaaau gagc                                              24

<210> SEQ ID NO 233
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
gcucauuuac cagcguaaau gagc                                              24

<210> SEQ ID NO 234
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
gcucauuuac cagcguaaau gagc                                              24

<210> SEQ ID NO 235
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
gcucauuuac cagcguaaau gagc                                              24

<210> SEQ ID NO 236
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
gcucauuuac cagcguaaau gagc                                              24

<210> SEQ ID NO 237
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
gcucauuuac cagcguaaau gagc                                              24

<210> SEQ ID NO 238
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
gcucauuuac cagcguaaau gagc                                              24

<210> SEQ ID NO 239
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 239
gcucauuuac cagcguaaau gagc                                              24

<210> SEQ ID NO 240
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
gcucauuuac cagcguaaau gagc                                              24

<210> SEQ ID NO 241
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
gcucauuuac cagcguaaau gagc                                              24

<210> SEQ ID NO 242
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
gcucauuuac cagcguaaau gagc                                              24

<210> SEQ ID NO 243
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
gcucauuuac cagcguaaau gagc                                              24

<210> SEQ ID NO 244
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
gcucauuuac cagcguaaau gagc                                              24

<210> SEQ ID NO 245
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
```
gcucauuuac cagcguaaau gagc                                              24

<210> SEQ ID NO 246
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246
gcucauuuac cagcguaaau gagc                                              24

<210> SEQ ID NO 247
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
gcucauuuac cagcguaaau gagc                                              24

<210> SEQ ID NO 248
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
gcucauuuac cagcguaaau gagc                                              24

<210> SEQ ID NO 249
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
gcucauuuac cagcguaaau gagc                                              24

<210> SEQ ID NO 250
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
gcucauuuac cagcguaaau gagc                                              24

<210> SEQ ID NO 251
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251
gcucauuuac cagcguaaau gagc 24

<210> SEQ ID NO 252
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252
gcucauuuac cagcguaaau gagc 24

<210> SEQ ID NO 253
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
gcucauuuac cagcguaaau gagc 24

<210> SEQ ID NO 254
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
gcucauuuac cagcguaaau gagc 24

<210> SEQ ID NO 255
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
gcucauuuac cagcguaaau gagc 24

<210> SEQ ID NO 256
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 256
gcucauuuac cagcguaaau gagc 24

<210> SEQ ID NO 257
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 257
gcucauuuac cagcguaaau gagc 24

<210> SEQ ID NO 258
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 258
gcucauuuac cagcguaaau gagc                                           24

<210> SEQ ID NO 259
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 259
gcucauuuac cagcguaaau gagc                                           24

<210> SEQ ID NO 260
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 260
gcucauuuac cagcguaaau gagc                                           24

<210> SEQ ID NO 261
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 261
gcucauuuac cagcguaaau gagc                                           24

<210> SEQ ID NO 262
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 262
gcucauuuac cagcguaaau gagc                                           24

<210> SEQ ID NO 263
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 263
gcucauuuac cagcguaaau gagc                                           24

```
<210> SEQ ID NO 264
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 264
gcucauuuac cagcguaaau gagc                                              24

<210> SEQ ID NO 265
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 265
gcucauuuac cagcguaaau gagc                                              24

<210> SEQ ID NO 266
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 266
gcucauuuac cagcguaaau gagc                                              24

<210> SEQ ID NO 267
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 267
gcucauuuac cagcguaaau gagc                                              24

<210> SEQ ID NO 268
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 268
gcucauuuac cagcguaaau gagc                                              24

<210> SEQ ID NO 269
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 269
gcucauuuac cagcguaaau gagc                                              24
```

```
<210> SEQ ID NO 270
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270
gcucauuuac cagcguaaau gagc                                              24

<210> SEQ ID NO 271
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 271
gcucauuuac cagcguaaau gagc                                              24

<210> SEQ ID NO 272
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 272
gcucauuuac cagcguaaau gagc                                              24

<210> SEQ ID NO 273
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
gcucauuuac cagcguaaau gagc                                              24

<210> SEQ ID NO 274
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 274
gcucauuuac cagcguaaau gagc                                              24

<210> SEQ ID NO 275
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 275
gcucauuuac cagcguaaau gagc                                              24

<210> SEQ ID NO 276
```

```
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 276
gcucauuuac cagcguaaau gagc                                              24

<210> SEQ ID NO 277
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 277
gcucauuuac cagcguaaau gagc                                              24

<210> SEQ ID NO 278
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 278
gcucauuuac cagcguaaau gagc                                              24

<210> SEQ ID NO 279
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
gcucauuuac cagcguaaau gagc                                              24

<210> SEQ ID NO 280
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 280
gcucauuuac cagcguaaau gagc                                              24

<210> SEQ ID NO 281
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
gcucauuuac cagcguaaau gagc                                              24

<210> SEQ ID NO 282
<211> LENGTH: 24
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 282
gcucauuuac cagcguaaau gagc                                           24

<210> SEQ ID NO 283
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
gcucauuuac cagcguaaau gagc                                           24

<210> SEQ ID NO 284
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
gcucauuuac cagcguaaau gagc                                           24

<210> SEQ ID NO 285
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
gcucauuuac cagcguaaau gagc                                           24

<210> SEQ ID NO 286
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
gcucauuuac cagcguaaau gagc                                           24

<210> SEQ ID NO 287
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
gcucauuuac cagcguaaau gagc                                           24

<210> SEQ ID NO 288
<211> LENGTH: 24
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 288
gcucauuuac cagcguaaau gagc                                              24

<210> SEQ ID NO 289
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 289
gcucauuuac cagcguaaau gagc                                              24

<210> SEQ ID NO 290
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290
gcucauuuac cagcguaaau gagc                                              24

<210> SEQ ID NO 291
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291
gcucauuuac cagcguaaau gagc                                              24

<210> SEQ ID NO 292
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 292
gcucauuuac cagcguaaau gagc                                              24

<210> SEQ ID NO 293
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 293
gcucauuuac cagcguaaau gagc                                              24

<210> SEQ ID NO 294
<211> LENGTH: 24
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 294
gcucauuuac cagcguaaau gagc                                              24

<210> SEQ ID NO 295
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 295
gcucauuuac cagcguaaau gagc                                              24

<210> SEQ ID NO 296
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296
gcucauuuac cagcguaaau gagc                                              24

<210> SEQ ID NO 297
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297
gcucauuuac cagcguaaau gagc                                              24

<210> SEQ ID NO 298
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298
gcucauuuac cagcguaaau gagc                                              24

<210> SEQ ID NO 299
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299
gcucauuuac cagcguaaau gagc                                              24

<210> SEQ ID NO 300
<211> LENGTH: 24
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 300
gcucauuuac cagcguaaau gagc                                           24

<210> SEQ ID NO 301
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 301
gcucauuuac cagcguaaau gagc                                           24

<210> SEQ ID NO 302
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 302
gcucauuuac cagcguaaau gagc                                           24

<210> SEQ ID NO 303
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 303
gcucauuuac cagcguaaau gagc                                           24

<210> SEQ ID NO 304
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 304
gcucauuuac cagcguaaau gagc                                           24

<210> SEQ ID NO 305
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 305
gcucauuuac cagcguaaau gagc                                              24

<210> SEQ ID NO 306
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 306
gcucauuuac cagcguaaau gagc                                              24

<210> SEQ ID NO 307
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 307
gcucauuuac cagcguaaau gagc                                              24

<210> SEQ ID NO 308
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 308
gcucauuuac cagcguaaau gagc                                              24

<210> SEQ ID NO 309
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 309
gcucauuuac cagcguaaau gagc                                              24

<210> SEQ ID NO 310
<211> LENGTH: 24
<212> TYPE: DNA
<213> ORGANISM: Artificial Sequence
<220> FEATURE:
<223> OTHER INFORMATION: Description of Artificial Sequence: Synthetic
```

```
            oligonucleotide
<220> FEATURE:
<223> OTHER INFORMATION: Description of Combined DNA/RNA Molecule:
      Synthetic oligonucleotide

<400> SEQUENCE: 310
gcucauuuac cagcguaaau gagc                                            24

<210> SEQ ID NO 311
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 311
gcucauuuac cagcguaaau gagc                                            24

<210> SEQ ID NO 312
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 312
gcucauuuac cagcguaaau gagc                                            24

<210> SEQ ID NO 313
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 313
gcucauuuac cagcguaaau gagc                                            24

<210> SEQ ID NO 314
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 314
gcucauuuac cagcguaaau gagc                                            24

<210> SEQ ID NO 315
<211> LENGTH: 24
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 315
gcucauuuac cagcguaaau gagc                                            24

<210> SEQ ID NO 316
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 316
gcucauuuac cagcguaaau gagc                                            24

<210> SEQ ID NO 317
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 317
gcucauuuac cagcguaaau gagc                                            24

<210> SEQ ID NO 318
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 318
gcucauuuac cagcguaaau gagc                                            24

<210> SEQ ID NO 319
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 319
gcucauuuac cagcguaaau gagc                                            24

<210> SEQ ID NO 320
<211> LENGTH: 24
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 320
gcucauuuac cagcguaaau gagc                                          24

<210> SEQ ID NO 321
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 321
gcucauuuac cagcguaaau gagc                                          24

<210> SEQ ID NO 322
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-fluoro-2'-deoxy-arabinose cytidine (faraC)

<400> SEQUENCE: 322
gcucauuuac cagcguaaau gagc                                          24

<210> SEQ ID NO 323
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: 2'-fluoro-2'-deoxy-arabinose uridine (faraU)

<400> SEQUENCE: 323
gcucauuuac cagcguaaau gagc                                          24

<210> SEQ ID NO 324
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
```

<221> NAME/KEY: modified_base
<222> LOCATION: (4)..(4)
<223> OTHER INFORMATION: 2'-fluoro-2'-deoxy-arabinose cytidine (faraC)

<400> SEQUENCE: 324
gcucauuuac cagcguaaau gagc                                              24

<210> SEQ ID NO 325
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-fluoro-2'-deoxy-arabinose uridine (faraU)

<400> SEQUENCE: 325
gcucauuuac cagcguaaau gagc                                              24

<210> SEQ ID NO 326
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(7)
<223> OTHER INFORMATION: 2'-fluoro-2'-deoxy-arabinose uridine (faraU)

<400> SEQUENCE: 326
gcucauuuac cagcguaaau gagc                                              24

<210> SEQ ID NO 327
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (8)..(8)
<223> OTHER INFORMATION: 2'-fluoro-2'-deoxy-arabinose uridine (faraU)

<400> SEQUENCE: 327
gcucauuuac cagcguaaau gagc                                              24

<210> SEQ ID NO 328
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<220> FEATURE:
<221> NAME/KEY: modified_base
<222> LOCATION: (10)..(10)
<223> OTHER INFORMATION: 2'-fluoro-2'-deoxy-arabinose cytidine (faraC)

<400> SEQUENCE: 328
gcucauuuac cagcguaaau gagc                                              24

<210> SEQ ID NO 329
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (11)..(11)
<223> OTHER INFORMATION: 2'-fluoro-2'-deoxy-arabinose cytidine (faraC)

<400> SEQUENCE: 329
gcucauuuac cagcguaaau gagc                                              24

<210> SEQ ID NO 330
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (14)..(14)
<223> OTHER INFORMATION: 2'-fluoro-2'-deoxy-arabinose cytidine (faraC)

<400> SEQUENCE: 330
gcucauuuac cagcguaaau gagc                                              24

<210> SEQ ID NO 331
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (16)..(16)
<223> OTHER INFORMATION: 2'-fluoro-2'-deoxy-arabinose uridine (faraU)

<400> SEQUENCE: 331
gcucauuuac cagcguaaau gagc                                              24

<210> SEQ ID NO 332
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide
<220> FEATURE:
<221> NAME/KEY: modified_base
<222> LOCATION: (20)..(20)
<223> OTHER INFORMATION: 2'-fluoro-2'-deoxy-arabinose uridine (faraU)

<400> SEQUENCE: 332
gcucauuuac cagcguaaau gagc                                          24

<210> SEQ ID NO 333
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 333
gcucauuuac cagcguaaau gagc                                          24

<210> SEQ ID NO 334
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 334
gcucauuuac cagcguaaau gagc                                          24

<210> SEQ ID NO 335
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 335
gcucauuuac cagcguaaau gagc                                          24

<210> SEQ ID NO 336
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 336
gcucauuuac cagcguaaau gagc                                          24

<210> SEQ ID NO 337
<211> LENGTH: 24
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 337
gcucauuuac cagcguaaau gagc                                          24

<210> SEQ ID NO 338
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 338
gcucauuuac cagcguaaau gagc                                          24

<210> SEQ ID NO 339
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 339
gcucauuuac cagcguaaau gagc                                          24

<210> SEQ ID NO 340
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 340
gcucauuuac cagcguaaau gagc                                          24

<210> SEQ ID NO 341
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 341
gcucauuuac cagcguaaau gagc                                          24

<210> SEQ ID NO 342
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 342
gcucauuuac cagcguaaau gagc                                          24

<210> SEQ ID NO 343
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 343
gcucauuuac cagcguaaau gagc                                          24

<210> SEQ ID NO 344
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 344
gcucauuuac cagcguaaau gagc                                          24

<210> SEQ ID NO 345
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 345
gcucauuuac cagcguaaau gagc                                          24

<210> SEQ ID NO 346
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 346
gcucauuuac cagcguaaau gagc                                          24

<210> SEQ ID NO 347
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 347
gcucauuuac cagcguaaau gagc                                              24

<210> SEQ ID NO 348
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 348
gcucauuuac cagcguaaau gagc                                              24

<210> SEQ ID NO 349
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 349
gcucauuuac cagcguaaau gagc                                              24

<210> SEQ ID NO 350
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 350
gcucauuuac cagcguaaau gagc                                              24

<210> SEQ ID NO 351
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 351
gcucauuuac cagcguaaau gagc                                              24

<210> SEQ ID NO 352
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 352
gcucauuuac cagcguaaau gagc                                             24

<210> SEQ ID NO 353
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 353
gcucauuuac cagcguaaau gagc                                             24

<210> SEQ ID NO 354
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-fluoro-2'-deoxy-arabinose cytidine (faraC)

<400> SEQUENCE: 354
gcucauuuac cagcguaaau gagc                                             24

<210> SEQ ID NO 355
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: 2'-fluoro-2'-deoxy-arabinose uridine (faraU)

<400> SEQUENCE: 355
gcucauuuac cagcguaaau gagc                                             24

<210> SEQ ID NO 356
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: Description of Combined DNA/RNA Molecule:
      Synthetic oligonucleotide
<220> FEATURE:
<221> NAME/KEY: modified_base
<222> LOCATION: (4)..(4)
<223> OTHER INFORMATION: 2'-fluoro-2'-deoxy-arabinose cytidine (faraC)

<400> SEQUENCE: 356
gcucauuuac cagcguaaau gagc                                                 24

<210> SEQ ID NO 357
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-fluoro-2'-deoxy-arabinose uridine (faraU)

<400> SEQUENCE: 357
gcucauuuac cagcguaaau gagc                                                 24

<210> SEQ ID NO 358
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(7)
<223> OTHER INFORMATION: 2'-fluoro-2'-deoxy-arabinose uridine (faraU)

<400> SEQUENCE: 358
gcucauuuac cagcguaaau gagc                                                 24

<210> SEQ ID NO 359
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (8)..(8)
<223> OTHER INFORMATION: 2'-fluoro-2'-deoxy-arabinose uridine (faraU)

<400> SEQUENCE: 359
gcucauuuac cagcguaaau gagc                                                 24

<210> SEQ ID NO 360
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (10)..(10)
<223> OTHER INFORMATION: 2'-fluoro-2'-deoxy-arabinose cytidine (faraC)

<400> SEQUENCE: 360
gcucauuuac cagcguaaau gagc                                            24

<210> SEQ ID NO 361
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (11)..(11)
<223> OTHER INFORMATION: 2'-fluoro-2'-deoxy-arabinose cytidine (faraC)

<400> SEQUENCE: 361
gcucauuuac cagcguaaau gagc                                            24

<210> SEQ ID NO 362
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (12)..(12)
<223> OTHER INFORMATION: 2'-fluoro-2'-deoxy-arabinose adenosine (faraA)

<400> SEQUENCE: 362
gcucauuuac cagcguaaau gagc                                            24

<210> SEQ ID NO 363
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (14)..(14)
<223> OTHER INFORMATION: 2'-fluoro-2'-deoxy-arabinose cytidine (faraC)

<400> SEQUENCE: 363
gcucauuuac cagcguaaau gagc                                            24

<210> SEQ ID NO 364
<211> LENGTH: 24
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (16)..(16)
<223> OTHER INFORMATION: 2'-fluoro-2'-deoxy-arabinose uridine (faraU)

<400> SEQUENCE: 364
gcucauuuac cagcguaaau gagc                                          24

<210> SEQ ID NO 365
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(20)
<223> OTHER INFORMATION: 2'-fluoro-2'-deoxy-arabinose uridine (faraU)

<400> SEQUENCE: 365
gcucauuuac cagcguaaau gagc                                          24

<210> SEQ ID NO 366
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 366
gcucauuuac cagcguaaau gagc                                          24

<210> SEQ ID NO 367
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 367
gcucauuuac cagcguaaau gagc                                          24

<210> SEQ ID NO 368
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 368
gcucauuuac cagcguaaau gagc                                          24

<210> SEQ ID NO 369
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 369
gcucauuuac cagcguaaau gagc                                              24

<210> SEQ ID NO 370
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 370
gcucauuuac cagcguaaau gagc                                              24

<210> SEQ ID NO 371
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 371
gcucauuuac cagcguaaau gagc                                              24

<210> SEQ ID NO 372
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 372
gcucauuuac cagcguaaau gagc                                              24

<210> SEQ ID NO 373
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 373
gcucauuuac cagcguaaau gagc                                              24

<210> SEQ ID NO 374
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 374
gcucauuuac cagcguaaau gagc                                              24

<210> SEQ ID NO 375
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 375
gcucauuuac cagcguaaau gagc                                          24

<210> SEQ ID NO 376
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 376
gcucauuuac cagcguaaau gagc                                          24

<210> SEQ ID NO 377
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 377
gcucauuuac cagcguaaau gagc                                          24

<210> SEQ ID NO 378
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 378
gcucauuuac cagcguaaau gagc                                          24

<210> SEQ ID NO 379
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 379
gcucauuuac cagcguaaau gagc                                          24

<210> SEQ ID NO 380
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 380
gcucauuuac cagcguaaau gagc                                          24

<210> SEQ ID NO 381
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 381
gcucauuuac cagcguaaau gagc                                          24

<210> SEQ ID NO 382
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 382
gcucauuuac cagcguaaau gagc                                          24

<210> SEQ ID NO 383
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 383
gcucauuuac cagcguaaau gagc                                          24

<210> SEQ ID NO 384
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 384
gcucauuuac cagcguaaau gagc                                          24

<210> SEQ ID NO 385
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 385
gcucauuuac cagcguaaau gagc                                          24

<210> SEQ ID NO 386
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 386
gcucauuuac cagcguaaau gagc                                          24

<210> SEQ ID NO 387
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 387
```
gcucauuuac cagcguaaau gagc                                              24

<210> SEQ ID NO 388
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 388
gcucauuuac cagcguaaau gagc                                              24

<210> SEQ ID NO 389
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 389
gcucauuuac cagcguaaau gagc                                              24

<210> SEQ ID NO 390
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 390
gcucauuuac cagcguaaau gagc                                              24

<210> SEQ ID NO 391
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 391
gcucauuuac cagcguaaau gagc                                              24

<210> SEQ ID NO 392
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 392
gcucauuuac cagcguaaau gagc                                              24

<210> SEQ ID NO 393
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 393
gcucauuuac cagcguaaau gagc                                              24

<210> SEQ ID NO 394
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 394
gcucauuuac cagcguaaau gagc                                              24

<210> SEQ ID NO 395
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 395
gcucauuuac cagcguaaau gagc                                              24

<210> SEQ ID NO 396
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-5'-linked-cytidine (25C)

<400> SEQUENCE: 396
gcucauuuac cagcguaaau gagc                                              24

<210> SEQ ID NO 397
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 2'-5'-linked-uridine (25U)

<400> SEQUENCE: 397
gcucauuuac cagcguaaau gagc                                              24

<210> SEQ ID NO 398
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: 2'-5'-linked-cytidine (25C)

<400> SEQUENCE: 398
gcucauuuac cagcguaaau gagc                                              24

```
<210> SEQ ID NO 399
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: 2'-5'-linked-adenosine (25A)

<400> SEQUENCE: 399
gcucauuuac cagcguaaau gagc                                              24

<210> SEQ ID NO 400
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: 2'-5'-linked-uridine (25U)

<400> SEQUENCE: 400
gcucauuuac cagcguaaau gagc                                              24

<210> SEQ ID NO 401
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 2'-5'-linked-uridine (25U)

<400> SEQUENCE: 401
gcucauuuac cagcguaaau gagc                                              24

<210> SEQ ID NO 402
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: 2'-5'-linked-uridine (25U)

<400> SEQUENCE: 402
gcucauuuac cagcguaaau gagc                                              24

<210> SEQ ID NO 403
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
```

```
<223> OTHER INFORMATION: 2'-5'-linked-adenosine (25A)

<400> SEQUENCE: 403
gcucauuuac cagcguaaau gagc                                              24

<210> SEQ ID NO 404
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: 2'-5'-linked-cytidine (25C)

<400> SEQUENCE: 404
gcucauuuac cagcguaaau gagc                                              24

<210> SEQ ID NO 405
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: 2'-5'-linked-cytidine (25C)

<400> SEQUENCE: 405
gcucauuuac cagcguaaau gagc                                              24

<210> SEQ ID NO 406
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: 2'-5'-linked-adenosine (25A)

<400> SEQUENCE: 406
gcucauuuac cagcguaaau gagc                                              24

<210> SEQ ID NO 407
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: 2'-5'-linked-guanosine (25G)

<400> SEQUENCE: 407
gcucauuuac cagcguaaau gagc                                              24

<210> SEQ ID NO 408
<211> LENGTH: 24
<212> TYPE: RNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: 2'-5'-linked-cytidine (25C)

<400> SEQUENCE: 408
gcucauuuac cagcguaaau gagc                                              24

<210> SEQ ID NO 409
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: 2'-5'-linked-uridine (25U)

<400> SEQUENCE: 409
gcucauuuac cagcguaaau gagc                                              24

<210> SEQ ID NO 410
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: 2'-5'-linked-adenosine (25A)

<400> SEQUENCE: 410
gcucauuuac cagcguaaau gagc                                              24

<210> SEQ ID NO 411
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: 2'-5'-linked-adenosine (25A)

<400> SEQUENCE: 411
gcucauuuac cagcguaaau gagc                                              24

<210> SEQ ID NO 412
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: 2'-5'-linked-adenosine (25A)

<400> SEQUENCE: 412
gcucauuuac cagcguaaau gagc                                              24
```

```
<210> SEQ ID NO 413
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: 2'-5'-linked-uridine (25U)

<400> SEQUENCE: 413
gcucauuuac cagcguaaau gagc                                              24

<210> SEQ ID NO 414
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: 2'-5'-linked-adenosine (25A)

<400> SEQUENCE: 414
gcucauuuac cagcguaaau gagc                                              24

<210> SEQ ID NO 415
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 415
gcucauuuac cagcguaaau gagc                                              24

<210> SEQ ID NO 416
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 416
gcucauuuac cagcguaaau gagc                                              24

<210> SEQ ID NO 417
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 417
gcucauuuac cagcguaaau gagc                                              24

<210> SEQ ID NO 418
<211> LENGTH: 24
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 418
gcucauuuac cagcguaaau gagc                                                24

<210> SEQ ID NO 419
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 419
gcucauuuac cagcguaaau gagc                                                24

<210> SEQ ID NO 420
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 420
gcucauuuac cagcguaaau gagc                                                24

<210> SEQ ID NO 421
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 421
gcucauuuac cagcguaaau gagc                                                24

<210> SEQ ID NO 422
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 422
gcucauuuac cagcguaaau gagc                                                24

<210> SEQ ID NO 423
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 423
gcucauuuac cagcguaaau gagc                                                24

<210> SEQ ID NO 424
<211> LENGTH: 24
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 424
gcucauuuac cagcguaaau gagc                                              24

<210> SEQ ID NO 425
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 425
gcucauuuac cagcguaaau gagc                                              24

<210> SEQ ID NO 426
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 426
gcucauuuac cagcguaaau gagc                                              24

<210> SEQ ID NO 427
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 427
gcucauuuac cagcguaaau gagc                                              24

<210> SEQ ID NO 428
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 428
gcucauuuac cagcguaaau gagc                                              24

<210> SEQ ID NO 429
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 429
gcucauuuac cagcguaaau gagc                                              24

<210> SEQ ID NO 430
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 430
gcucauuuac cagcguaaau gagc						24

<210> SEQ ID NO 431
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 431
gcucauuuac cagcguaaau gagc						24

<210> SEQ ID NO 432
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 432
gcucauuuac cagcguaaau gagc						24

<210> SEQ ID NO 433
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 433
gcucauuuac cagcguaaau gagc						24

<210> SEQ ID NO 434
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 434
gcucauuuac cagcguaaau gagc						24

<210> SEQ ID NO 435
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 435
gcucauuuac cagcguaaau gagc						24

<210> SEQ ID NO 436
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: modified_base
<222> LOCATION: (2)..(2)
<223> OTHER INFORMATION: 2'-5'-linked-cytidine (25C)

<400> SEQUENCE: 436
gcucauuuac cagcguaaau gagc                                              24

<210> SEQ ID NO 437
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 2'-5'-linked-uridine (25U)

<400> SEQUENCE: 437
gcucauuuac cagcguaaau gagc                                              24

<210> SEQ ID NO 438
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: 2'-5'-linked-cytidine (25C)

<400> SEQUENCE: 438
gcucauuuac cagcguaaau gagc                                              24

<210> SEQ ID NO 439
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: 2'-5'-linked-adenosine (25A)

<400> SEQUENCE: 439
gcucauuuac cagcguaaau gagc                                              24

<210> SEQ ID NO 440
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: 2'-5'-linked-uridine (25U)

<400> SEQUENCE: 440
gcucauuuac cagcguaaau gagc                                              24

<210> SEQ ID NO 441
```

```
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 2'-5'-linked-uridine (25U)

<400> SEQUENCE: 441
gcucauuuac cagcguaaau gagc                                          24

<210> SEQ ID NO 442
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: 2'-5'-linked-uridine (25U)

<400> SEQUENCE: 442
gcucauuuac cagcguaaau gagc                                          24

<210> SEQ ID NO 443
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: 2'-5'-linked-adenosine (25A)

<400> SEQUENCE: 443
gcucauuuac cagcguaaau gagc                                          24

<210> SEQ ID NO 444
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: 2'-5'-linked-cytidine (25C)

<400> SEQUENCE: 444
gcucauuuac cagcguaaau gagc                                          24

<210> SEQ ID NO 445
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: 2'-5'-linked-cytidine (25C)
```

```
<400> SEQUENCE: 445
gcucauuuac cagcguaaau gagc                                              24

<210> SEQ ID NO 446
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: 2'-5'-linked-adenosine (25A)

<400> SEQUENCE: 446
gcucauuuac cagcguaaau gagc                                              24

<210> SEQ ID NO 447
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: 2'-5'-linked-guanosine (25G)

<400> SEQUENCE: 447
gcucauuuac cagcguaaau gagc                                              24

<210> SEQ ID NO 448
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: 2'-5'-linked-cytidine (25C)

<400> SEQUENCE: 448
gcucauuuac cagcguaaau gagc                                              24

<210> SEQ ID NO 449
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(15)
<223> OTHER INFORMATION: 2'-5'-linked-guanosine (25G)

<400> SEQUENCE: 449
gcucauuuac cagcguaaau gagc                                              24

<210> SEQ ID NO 450
<211> LENGTH: 24
<212> TYPE: RNA
<213> ORGANISM: Artificial Sequence
<220> FEATURE:
<223> OTHER INFORMATION: Description of Artificial Sequence: Synthetic
``` oligonucleotide
<220> FEATURE:
<221> NAME/KEY: modified_base
<222> LOCATION: (16)..(16)
<223> OTHER INFORMATION: 2'-5'-linked-uridine (25U)

<400> SEQUENCE: 450
gcucauuuac cagcguaaau gagc                                           24

<210> SEQ ID NO 451
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: 2'-5'-linked-adenosine (25A)

<400> SEQUENCE: 451
gcucauuuac cagcguaaau gagc                                           24

<210> SEQ ID NO 452
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: 2'-5'-linked-adenosine (25A)

<400> SEQUENCE: 452
gcucauuuac cagcguaaau gagc                                           24

<210> SEQ ID NO 453
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: 2'-5'-linked-adenosine (25A)

<400> SEQUENCE: 453
gcucauuuac cagcguaaau gagc                                           24

<210> SEQ ID NO 454
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: 2'-5'-linked-uridine (25U)

<400> SEQUENCE: 454
gcucauuuac cagcguaaau gagc                                           24

```
<210> SEQ ID NO 455
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: 2'-5'-linked-adenosine (25A)

<400> SEQUENCE: 455
gcucauuuac cagcguaaau gagc                                              24

<210> SEQ ID NO 456
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 456
gcucauuuac cagcguaaau gagc                                              24

<210> SEQ ID NO 457
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 457
gcucauuuac cagcguaaau gagc                                              24

<210> SEQ ID NO 458
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 458
gcucauuuac cagcguaaau gagc                                              24

<210> SEQ ID NO 459
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 459
gcucauuuac cagcguaaau gagc                                              24

<210> SEQ ID NO 460
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 460
```

-continued gcucauuuac cagcguaaau gagc 24

<210> SEQ ID NO 461
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 461
gcucauuuac cagcguaaau gagc 24

<210> SEQ ID NO 462
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 462
gcucauuuac cagcguaaau gagc 24

<210> SEQ ID NO 463
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 463
gcucauuuac cagcguaaau gagc 24

<210> SEQ ID NO 464
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 464
gcucauuuac cagcguaaau gagc 24

<210> SEQ ID NO 465
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 465
gcucauuuac cagcguaaau gagc 24

<210> SEQ ID NO 466
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 466
gcucauuuac cagcguaaau gagc 24

<210> SEQ ID NO 467
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 467
gcucauuuac cagcguaaau gagc                                          24

<210> SEQ ID NO 468
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 468
gcucauuuac cagcguaaau gagc                                          24

<210> SEQ ID NO 469
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 469
gcucauuuac cagcguaaau gagc                                          24

<210> SEQ ID NO 470
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 470
gcucauuuac cagcguaaau gagc                                          24

<210> SEQ ID NO 471
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 471
gcucauuuac cagcguaaau gagc                                          24

<210> SEQ ID NO 472
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 472
gcucauuuac cagcguaaau gagc                                          24

<210> SEQ ID NO 473
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 473
gcucauuuac cagcguaaau gagc                                            24

<210> SEQ ID NO 474
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 474
gcucauuuac cagcguaaau gagc                                            24

<210> SEQ ID NO 475
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 475
gcucauuuac cagcguaaau gagc                                            24

<210> SEQ ID NO 476
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 476
gcucauuuac cagcguaaau gagc                                            24

<210> SEQ ID NO 477
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 477
gcucauuuac cagcguaaau gagc                                            24

<210> SEQ ID NO 478
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 478
gcucauuuac cagcguaaau gagc                                            24

-continued

<210> SEQ ID NO 479
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 479
gcucauuuac cagcguaaau gagc                                          24

<210> SEQ ID NO 480
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 480
gcucauuuac cagcguaaau gagc                                          24

<210> SEQ ID NO 481
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 481
gcucauuuac cagcguaaau gagc                                          24

<210> SEQ ID NO 482
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 482
gcucauuuac cagcguaaau gagc                                          24

<210> SEQ ID NO 483
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 483
gcucauuuac cagcguaaau gagc                                          24

<210> SEQ ID NO 484
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 484
gcucauuuac cagcguaaau gagc                                          24

<210> SEQ ID NO 485

```
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 485
gcucauuuac cagcguaaau gagc                                              24

<210> SEQ ID NO 486
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 486
gcucauuuac cagcguaaau gagc                                              24

<210> SEQ ID NO 487
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 487
gcucauuuac cagcguaaau gagc                                              24

<210> SEQ ID NO 488
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 488
gcucauuuac cagcguaaau gagc                                              24

<210> SEQ ID NO 489
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 489
gcucauuuac cagcguaaau gagc                                              24

<210> SEQ ID NO 490
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 490
gcucauuuac cagcguaaau gagc                                              24

<210> SEQ ID NO 491
<211> LENGTH: 24
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 491
gcucauuuac cagcguaaau gagc                                            24

<210> SEQ ID NO 492
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 492
gcucauuuac cagcguaaau gagc                                            24

<210> SEQ ID NO 493
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 493
gcucauuuac cagcguaaau gagc                                            24

<210> SEQ ID NO 494
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 494
gcucauuuac cagcguaaau gagc                                            24

<210> SEQ ID NO 495
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 495
gcucauuuac cagcguaaau gagc                                            24

<210> SEQ ID NO 496
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 496
gcucauuuac cagcguaaau gagc                                            24

<210> SEQ ID NO 497
<211> LENGTH: 24
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 497
gcucauuuac cagcguaaau gagc                                           24

<210> SEQ ID NO 498
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 498
gcucauuuac cagcguaaau gagc                                           24

<210> SEQ ID NO 499
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 499
gcucauuuac cagcguaaau gagc                                           24

<210> SEQ ID NO 500
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 500
gcucauuuac cagcguaaau gagc                                           24

<210> SEQ ID NO 501
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 501
gcucauuuac cagcguaaau gagc                                           24

<210> SEQ ID NO 502
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 502
gcucauuuac cagcguaaau gagc                                           24

<210> SEQ ID NO 503
<211> LENGTH: 24
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 503
gcucauuuac cagcguaaau gagc                                            24

<210> SEQ ID NO 504
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 504
gcucauuuac cagcguaaau gagc                                            24

<210> SEQ ID NO 505
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 505
gcucauuuac cagcguaaau gagc                                            24

<210> SEQ ID NO 506
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 506
gcucauuuac cagcguaaau gagc                                            24

<210> SEQ ID NO 507
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 507
gcucauuuac cagcguaaau gagc                                            24

<210> SEQ ID NO 508
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: Inosine (rI)

<400> SEQUENCE: 508
gcucnuuuac cagcguaaau gagc                                            24

<210> SEQ ID NO 509
```

```
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: Inosine  (rI)

<400> SEQUENCE: 509
gcucauuunc cagcguaaau gagc                                              24

<210> SEQ ID NO 510
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: Inosine  (rI)

<400> SEQUENCE: 510
gcucauuuac cngcguaaau gagc                                              24

<210> SEQ ID NO 511
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: Inosine  (rI)

<400> SEQUENCE: 511
gcucauuuac cagcgunaau gagc                                              24

<210> SEQ ID NO 512
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: Inosine  (rI)

<400> SEQUENCE: 512
gcucauuuac cagcguanau gagc                                              24

<210> SEQ ID NO 513
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: Inosine  (rI)
```

```
<400> SEQUENCE: 513
gcucauuuac cagcguaanu gagc                                                24

<210> SEQ ID NO 514
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: Inosine  (rI)

<400> SEQUENCE: 514
gcucauuuac cagcguaaau gngc                                                24

<210> SEQ ID NO 515
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: Inosine  (rI)

<400> SEQUENCE: 515
gcucnuuuac cagcguaaau gagc                                                24

<210> SEQ ID NO 516
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: Inosine  (rI)

<400> SEQUENCE: 516
gcucauuunc cagcguaaau gagc                                                24

<210> SEQ ID NO 517
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: Inosine  (rI)

<400> SEQUENCE: 517
gcucauuuac cngcguaaau gagc                                                24

<210> SEQ ID NO 518
<211> LENGTH: 24
<212> TYPE: RNA
<213> ORGANISM: Artificial Sequence
<220> FEATURE:
<223> OTHER INFORMATION: Description of Artificial Sequence: Synthetic
```

```
        oligonucleotide
<220> FEATURE:
<221> NAME/KEY: modified_base
<222> LOCATION: (17)..(17)
<223> OTHER INFORMATION: Inosine (rI)

<400> SEQUENCE: 518
gcucauuuac cagcgunaau gagc                                              24

<210> SEQ ID NO 519
<211> LENGTH: 24
<212> TYPE: RNA
<213> ORGANISM: Artificial Sequence
<220> FEATURE:
<223> OTHER INFORMATION: Description of Artificial Sequence: Synthetic
        oligonucleotide
<220> FEATURE:
<221> NAME/KEY: modified_base
<222> LOCATION: (18)..(18)
<223> OTHER INFORMATION: Inosine (rI)

<400> SEQUENCE: 519
gcucauuuac cagcguanau gagc                                              24

<210> SEQ ID NO 520
<211> LENGTH: 24
<212> TYPE: RNA
<213> ORGANISM: Artificial Sequence
<220> FEATURE:
<223> OTHER INFORMATION: Description of Artificial Sequence: Synthetic
        oligonucleotide
<220> FEATURE:
<221> NAME/KEY: modified_base
<222> LOCATION: (19)..(19)
<223> OTHER INFORMATION: Inosine (rI)

<400> SEQUENCE: 520
gcucauuuac cagcguaanu gagc                                              24

<210> SEQ ID NO 521
<211> LENGTH: 24
<212> TYPE: RNA
<213> ORGANISM: Artificial Sequence
<220> FEATURE:
<223> OTHER INFORMATION: Description of Artificial Sequence: Synthetic
        oligonucleotide
<220> FEATURE:
<221> NAME/KEY: modified_base
<222> LOCATION: (22)..(22)
<223> OTHER INFORMATION: Inosine (rI)

<400> SEQUENCE: 521
gcucauuuac cagcguaaau gngc                                              24

<210> SEQ ID NO 522
<211> LENGTH: 24
<212> TYPE: RNA
<213> ORGANISM: Artificial Sequence
<220> FEATURE:
<223> OTHER INFORMATION: Description of Artificial Sequence: Synthetic
        oligonucleotide

<400> SEQUENCE: 522
gcucauuuac cagcguaaau gagc                                              24

<210> SEQ ID NO 523
<211> LENGTH: 24
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 523
gcucauuuac cagcguaaau gagc                                            24

<210> SEQ ID NO 524
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 524
gcucauuuac cagcguaaau gagc                                            24

<210> SEQ ID NO 525
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 525
gcucauuuac cagcguaaau gagc                                            24

<210> SEQ ID NO 526
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 526
gcucauuuac cagcguaaau gagc                                            24

<210> SEQ ID NO 527
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 527
gcucauuuac cagcguaaau gagc                                            24

<210> SEQ ID NO 528
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 528
gcucauuuac cagcguaaau gagc                                            24

<210> SEQ ID NO 529
<211> LENGTH: 24
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 529
gcucauuuac cagcguaaau gagc                                                24

<210> SEQ ID NO 530
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 4'-thio-guanosine (thiorG)

<400> SEQUENCE: 530
gcucauuuac cagcguaaau gagc                                                24

<210> SEQ ID NO 531
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 4'-thio-uridine (thiorU)

<400> SEQUENCE: 531
gcucauuuac cagcguaaau gagc                                                24

<210> SEQ ID NO 532
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: 4'-thio-cytidine (thiorC)

<400> SEQUENCE: 532
gcucauuuac cagcguaaau gagc                                                24

<210> SEQ ID NO 533
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: 4'-thio-adenosine (thiorA)

<400> SEQUENCE: 533
gcucauuuac cagcguaaau gagc                                                24

<210> SEQ ID NO 534
<211> LENGTH: 24
<212> TYPE: RNA

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: 4'-thio-uridine (thiorU)

<400> SEQUENCE: 534
gcucauuuac cagcguaaau gagc                                              24

<210> SEQ ID NO 535
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 4'-thio-uridine (thiorU)

<400> SEQUENCE: 535
gcucauuuac cagcguaaau gagc                                              24

<210> SEQ ID NO 536
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: 4'-thio-uridine (thiorU)

<400> SEQUENCE: 536
gcucauuuac cagcguaaau gagc                                              24

<210> SEQ ID NO 537
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: 4'-thio-adenosine (thiorA)

<400> SEQUENCE: 537
gcucauuuac cagcguaaau gagc                                              24

<210> SEQ ID NO 538
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: 4'-thio-cytidine (thiorC)

<400> SEQUENCE: 538
```
gcucauuuac cagcguaaau gagc                                              24

<210> SEQ ID NO 539
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: 4'-thio-cytidine (thiorC)

<400> SEQUENCE: 539
gcucauuuac cagcguaaau gagc                                              24

<210> SEQ ID NO 540
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: 4'-thio-adenosine (thiorA)

<400> SEQUENCE: 540
gcucauuuac cagcguaaau gagc                                              24

<210> SEQ ID NO 541
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: 4'-thio-guanosine (thiorG)

<400> SEQUENCE: 541
gcucauuuac cagcguaaau gagc                                              24

<210> SEQ ID NO 542
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: 4'-thio-cytidine (thiorC)

<400> SEQUENCE: 542
gcucauuuac cagcguaaau gagc                                              24

<210> SEQ ID NO 543
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:

<221> NAME/KEY: modified_base
<222> LOCATION: (15)..(15)
<223> OTHER INFORMATION: 4'-thio-guanosine (thiorG)

<400> SEQUENCE: 543
gcucauuuac cagcguaaau gagc                                              24

<210> SEQ ID NO 544
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: 4'-thio-uridine (thiorU)

<400> SEQUENCE: 544
gcucauuuac cagcguaaau gagc                                              24

<210> SEQ ID NO 545
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: 4'-thio-adenosine (thiorA)

<400> SEQUENCE: 545
gcucauuuac cagcguaaau gagc                                              24

<210> SEQ ID NO 546
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: 4'-thio-adenosine (thiorA)

<400> SEQUENCE: 546
gcucauuuac cagcguaaau gagc                                              24

<210> SEQ ID NO 547
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: 4'-thio-adenosine (thiorA)

<400> SEQUENCE: 547
gcucauuuac cagcguaaau gagc                                              24

<210> SEQ ID NO 548
<211> LENGTH: 24

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: 4'-thio-uridine (thiorU)

<400> SEQUENCE: 548
gcucauuuac cagcguaaau gagc                                          24

<210> SEQ ID NO 549
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: 4'-thio-guanosine (thiorG)

<400> SEQUENCE: 549
gcucauuuac cagcguaaau gagc                                          24

<210> SEQ ID NO 550
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: 4'-thio-adenosine (thiorA)

<400> SEQUENCE: 550
gcucauuuac cagcguaaau gagc                                          24

<210> SEQ ID NO 551
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(23)
<223> OTHER INFORMATION: 4'-thio-guanosine (thiorG)

<400> SEQUENCE: 551
gcucauuuac cagcguaaau gagc                                          24

<210> SEQ ID NO 552
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-trifluoromethoxy-cytidine (cf3C)

<400> SEQUENCE: 552
```
gcucauuuac cagcguaaau gagc                                              24

<210> SEQ ID NO 553
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 2'-trifluoromethoxy-uridine (cf3U)

<400> SEQUENCE: 553
gcucauuuac cagcguaaau gagc                                              24

<210> SEQ ID NO 554
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: 2'-trifluoromethoxy-cytidine (cf3C)

<400> SEQUENCE: 554
gcucauuuac cagcguaaau gagc                                              24

<210> SEQ ID NO 555
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: 2'-trifluoromethoxy-uridine (cf3U)

<400> SEQUENCE: 555
gcucauuuac cagcguaaau gagc                                              24

<210> SEQ ID NO 556
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 2'-trifluoromethoxy-uridine (cf3U)

<400> SEQUENCE: 556
gcucauuuac cagcguaaau gagc                                              24

<210> SEQ ID NO 557
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: modified_base
<222> LOCATION: (8)..(8)
<223> OTHER INFORMATION: 2'-trifluoromethoxy-uridine (cf3U)

<400> SEQUENCE: 557
gcucauuuac cagcguaaau gagc                                              24

<210> SEQ ID NO 558
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: 2'-trifluoromethoxy-cytidine (cf3C)

<400> SEQUENCE: 558
gcucauuuac cagcguaaau gagc                                              24

<210> SEQ ID NO 559
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: 2'-trifluoromethoxy-cytidine (cf3C)

<400> SEQUENCE: 559
gcucauuuac cagcguaaau gagc                                              24

<210> SEQ ID NO 560
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: 2'-trifluoromethoxy-adenosine (cf3A)

<400> SEQUENCE: 560
gcucauuuac cagcguaaau gagc                                              24

<210> SEQ ID NO 561
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: 2'-trifluoromethoxy-cytidine (cf3C)

<400> SEQUENCE: 561
gcucauuuac cagcguaaau gagc                                              24

<210> SEQ ID NO 562
```

```
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: 2'-trifluoromethoxy-uridine (cf3U)

<400> SEQUENCE: 562
gcucauuuac cagcguaaau gagc                                             24

<210> SEQ ID NO 563
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: 2'-trifluoromethoxy-adenosine (cf3A)

<400> SEQUENCE: 563
gcucauuuac cagcguaaau gagc                                             24

<210> SEQ ID NO 564
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: 2'-trifluoromethoxy-adenosine (cf3A)

<400> SEQUENCE: 564
gcucauuuac cagcguaaau gagc                                             24

<210> SEQ ID NO 565
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: 2'-trifluoromethoxy-uridine (cf3U)

<400> SEQUENCE: 565
gcucauuuac cagcguaaau gagc                                             24

<210> SEQ ID NO 566
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: 2'-trifluoromethoxy-adenosine (cf3A)
```

-continued

<400> SEQUENCE: 566
gcucauuuac cagcguaaau gagc                                         24

<210> SEQ ID NO 567
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(23)
<223> OTHER INFORMATION: 2'-trifluoromethoxy-guanosine (cf3G)

<400> SEQUENCE: 567
gcucauuuac cagcguaaau gagc                                         24

<210> SEQ ID NO 568
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 4'-thio-guanosine (thiorG)

<400> SEQUENCE: 568
gcucauuuac cagcguaaau gagc                                         24

<210> SEQ ID NO 569
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 4'-thio-cytidine (thiorC)

<400> SEQUENCE: 569
gcucauuuac cagcguaaau gagc                                         24

<210> SEQ ID NO 570
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 4'-thio-uridine (thiorU)

<400> SEQUENCE: 570
gcucauuuac cagcguaaau gagc                                         24

<210> SEQ ID NO 571
<211> LENGTH: 24
<212> TYPE: RNA
<213> ORGANISM: Artificial Sequence
<220> FEATURE:
<223> OTHER INFORMATION: Description of Artificial Sequence: Synthetic

```
                oligonucleotide
<220> FEATURE:
<221> NAME/KEY: modified_base
<222> LOCATION: (6)..(6)
<223> OTHER INFORMATION: 4'-thio-uridine (thiorU)

<400> SEQUENCE: 571
gcucauuuac cagcguaaau gagc                                              24

<210> SEQ ID NO 572
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 4'-thio-uridine (thiorU)

<400> SEQUENCE: 572
gcucauuuac cagcguaaau gagc                                              24

<210> SEQ ID NO 573
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: 4'-thio-uridine (thiorU)

<400> SEQUENCE: 573
gcucauuuac cagcguaaau gagc                                              24

<210> SEQ ID NO 574
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: 4'-thio-adenosine (thiorA)

<400> SEQUENCE: 574
gcucauuuac cagcguaaau gagc                                              24

<210> SEQ ID NO 575
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: 4'-thio-cytidine (thiorC)

<400> SEQUENCE: 575
gcucauuuac cagcguaaau gagc                                              24
```

```
<210> SEQ ID NO 576
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: 4'-thio-cytidine (thiorC)

<400> SEQUENCE: 576
gcucauuuac cagcguaaau gagc                                          24

<210> SEQ ID NO 577
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: 4'-thio-adenosine (thiorA)

<400> SEQUENCE: 577
gcucauuuac cagcguaaau gagc                                          24

<210> SEQ ID NO 578
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: 4'-thio-guanosine (thiorG)

<400> SEQUENCE: 578
gcucauuuac cagcguaaau gagc                                          24

<210> SEQ ID NO 579
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: 4'-thio-cytidine (thiorC)

<400> SEQUENCE: 579
gcucauuuac cagcguaaau gagc                                          24

<210> SEQ ID NO 580
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(15)
<223> OTHER INFORMATION: 4'-thio-guanosine (thiorG)
```

-continued

```
<400> SEQUENCE: 580
gcucauuuac cagcguaaau gagc                                              24

<210> SEQ ID NO 581
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: 4'-thio-uridine (thiorU)

<400> SEQUENCE: 581
gcucauuuac cagcguaaau gagc                                              24

<210> SEQ ID NO 582
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: 4'-thio-adenosine (thiorA)

<400> SEQUENCE: 582
gcucauuuac cagcguaaau gagc                                              24

<210> SEQ ID NO 583
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: 4'-thio-adenosine (thiorA)

<400> SEQUENCE: 583
gcucauuuac cagcguaaau gagc                                              24

<210> SEQ ID NO 584
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: 4'-thio-adenosine (thiorA)

<400> SEQUENCE: 584
gcucauuuac cagcguaaau gagc                                              24

<210> SEQ ID NO 585
<211> LENGTH: 24
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: 4'-thio-uridine (thiorU)

<400> SEQUENCE: 585
gcucauuuac cagcguaaau gagc                                            24

<210> SEQ ID NO 586
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: 4'-thio-guanosine (thiorG)

<400> SEQUENCE: 586
gcucauuuac cagcguaaau gagc                                            24

<210> SEQ ID NO 587
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: 4'-thio-adenosine (thiorA)

<400> SEQUENCE: 587
gcucauuuac cagcguaaau gagc                                            24

<210> SEQ ID NO 588
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(23)
<223> OTHER INFORMATION: 4'-thio-guanosine (thiorG)

<400> SEQUENCE: 588
gcucauuuac cagcguaaau gagc                                            24

<210> SEQ ID NO 589
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-trifluoromethoxy-cytidine (cf3C)

<400> SEQUENCE: 589
gcucauuuac cagcguaaau gagc                                            24
```

```
<210> SEQ ID NO 590
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 2'-trifluoromethoxy-uridine (cf3U)

<400> SEQUENCE: 590
gcucauuuac cagcguaaau gagc                                            24

<210> SEQ ID NO 591
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: 2'-trifluoromethoxy-cytidine (cf3C)

<400> SEQUENCE: 591
gcucauuuac cagcguaaau gagc                                            24

<210> SEQ ID NO 592
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: 2'-trifluoromethoxy-uridine (cf3U)

<400> SEQUENCE: 592
gcucauuuac cagcguaaau gagc                                            24

<210> SEQ ID NO 593
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 2'-trifluoromethoxy-uridine (cf3U)

<400> SEQUENCE: 593
gcucauuuac cagcguaaau gagc                                            24

<210> SEQ ID NO 594
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
```

<223> OTHER INFORMATION: 2'-trifluoromethoxy-uridine (cf3U)

<400> SEQUENCE: 594
gcucauuuac cagcguaaau gagc                                                    24

<210> SEQ ID NO 595
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: 2'-trifluoromethoxy-adenosine (cf3A)

<400> SEQUENCE: 595
gcucauuuac cagcguaaau gagc                                                    24

<210> SEQ ID NO 596
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: 2'-trifluoromethoxy-cytidine (cf3C)

<400> SEQUENCE: 596
gcucauuuac cagcguaaau gagc                                                    24

<210> SEQ ID NO 597
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: 2'-trifluoromethoxy-cytidine (cf3C)

<400> SEQUENCE: 597
gcucauuuac cagcguaaau gagc                                                    24

<210> SEQ ID NO 598
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: 2'-trifluoromethoxy-adenosine (cf3A)

<400> SEQUENCE: 598
gcucauuuac cagcguaaau gagc                                                    24

<210> SEQ ID NO 599
<211> LENGTH: 24
<212> TYPE: RNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: 2'-trifluoromethoxy-cytidine (cf3C)

<400> SEQUENCE: 599
gcucauuuac cagcguaaau gagc                                            24

<210> SEQ ID NO 600
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: 2'-trifluoromethoxy-uridine (cf3U)

<400> SEQUENCE: 600
gcucauuuac cagcguaaau gagc                                            24

<210> SEQ ID NO 601
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: 2'-trifluoromethoxy-adenosine (cf3A)

<400> SEQUENCE: 601
gcucauuuac cagcguaaau gagc                                            24

<210> SEQ ID NO 602
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: 2'-trifluoromethoxy-adenosine (cf3A)

<400> SEQUENCE: 602
gcucauuuac cagcguaaau gagc                                            24

<210> SEQ ID NO 603
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: 2'-trifluoromethoxy-uridine (cf3U)

<400> SEQUENCE: 603
gcucauuuac cagcguaaau gagc                                            24
```

```
<210> SEQ ID NO 604
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: 2'-trifluoromethoxy-adenosine (cf3A)

<400> SEQUENCE: 604
gcucauuuac cagcguaaau gagc                                          24

<210> SEQ ID NO 605
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: arabinose cytidine (araC)

<400> SEQUENCE: 605
gcucauuuac cagcguaaau gagc                                          24

<210> SEQ ID NO 606
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: arabinose uridine (araU)

<400> SEQUENCE: 606
gcucauuuac cagcguaaau gagc                                          24

<210> SEQ ID NO 607
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: arabinose cytidine (araC)

<400> SEQUENCE: 607
gcucauuuac cagcguaaau gagc                                          24

<210> SEQ ID NO 608
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (5)..(5)
<223> OTHER INFORMATION: arabinose adenosine (araA)

<400> SEQUENCE: 608
gcucauuuac cagcguaaau gagc                                            24

<210> SEQ ID NO 609
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: arabinose uridine (araU)

<400> SEQUENCE: 609
gcucauuuac cagcguaaau gagc                                            24

<210> SEQ ID NO 610
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: arabinose uridine (araU)

<400> SEQUENCE: 610
gcucauuuac cagcguaaau gagc                                            24

<210> SEQ ID NO 611
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: arabinose uridine (araU)

<400> SEQUENCE: 611
gcucauuuac cagcguaaau gagc                                            24

<210> SEQ ID NO 612
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: arabinose adenosine (araA)

<400> SEQUENCE: 612
gcucauuuac cagcguaaau gagc                                            24

<210> SEQ ID NO 613
<211> LENGTH: 24
<212> TYPE: RNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: arabinose cytidine (araC)

<400> SEQUENCE: 613
gcucauuuac cagcguaaau gagc                                              24

<210> SEQ ID NO 614
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: arabinose cytidine (araC)

<400> SEQUENCE: 614
gcucauuuac cagcguaaau gagc                                              24

<210> SEQ ID NO 615
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: arabinose adenosine (araA)

<400> SEQUENCE: 615
gcucauuuac cagcguaaau gagc                                              24

<210> SEQ ID NO 616
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: arabinose cytidine (araC)

<400> SEQUENCE: 616
gcucauuuac cagcguaaau gagc                                              24

<210> SEQ ID NO 617
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: arabinose uridine (araU)

<400> SEQUENCE: 617
```
gcucauuuac cagcguaaau gagc                                              24

<210> SEQ ID NO 618
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: arabinose adenosine (araA)

<400> SEQUENCE: 618
gcucauuuac cagcguaaau gagc                                              24

<210> SEQ ID NO 619
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: arabinose adenosine (araA)

<400> SEQUENCE: 619
gcucauuuac cagcguaaau gagc                                              24

<210> SEQ ID NO 620
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: arabinose adenosine (araA)

<400> SEQUENCE: 620
gcucauuuac cagcguaaau gagc                                              24

<210> SEQ ID NO 621
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: arabinose uridine (araU)

<400> SEQUENCE: 621
gcucauuuac cagcguaaau gagc                                              24

<210> SEQ ID NO 622
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:

<221> NAME/KEY: modified_base
<222> LOCATION: (22)..(22)
<223> OTHER INFORMATION: arabinose adenosine (araA)

<400> SEQUENCE: 622
gcucauuuac cagcguaaau gagc                                              24

<210> SEQ ID NO 623
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: xylose uridine (rxyloU)

<400> SEQUENCE: 623
gcucauuuac cagcguaaau gagc                                              24

<210> SEQ ID NO 624
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: xylose uridine (rxyloU)

<400> SEQUENCE: 624
gcucauuuac cagcguaaau gagc                                              24

<210> SEQ ID NO 625
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: xylose uridine (rxyloU)

<400> SEQUENCE: 625
gcucauuuac cagcguaaau gagc                                              24

<210> SEQ ID NO 626
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: xylose cytidine (rxyloC)

<400> SEQUENCE: 626
gcucauuuac cagcguaaau gagc                                              24

<210> SEQ ID NO 627
<211> LENGTH: 24

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: xylose cytidine (rxyloC)

<400> SEQUENCE: 627
gcucauuuac cagcguaaau gagc                                           24

<210> SEQ ID NO 628
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: xylose adenosine (rxyloA)

<400> SEQUENCE: 628
gcucauuuac cagcguaaau gagc                                           24

<210> SEQ ID NO 629
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: xylose guanosine (rxyloG)

<400> SEQUENCE: 629
gcucauuuac cagcguaaau gagc                                           24

<210> SEQ ID NO 630
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: xylose cytidine (rxyloC)

<400> SEQUENCE: 630
gcucauuuac cagcguaaau gagc                                           24

<210> SEQ ID NO 631
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(15)
<223> OTHER INFORMATION: xylose guanosine (rxyloG)

<400> SEQUENCE: 631
```
gcucauuuac cagcguaaau gagc                                          24

<210> SEQ ID NO 632
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: xylose uridine (rxyloU)

<400> SEQUENCE: 632
gcucauuuac cagcguaaau gagc                                          24

<210> SEQ ID NO 633
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: xylose adenosine (rxyloA)

<400> SEQUENCE: 633
gcucauuuac cagcguaaau gagc                                          24

<210> SEQ ID NO 634
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: xylose adenosine (rxyloA)

<400> SEQUENCE: 634
gcucauuuac cagcguaaau gagc                                          24

<210> SEQ ID NO 635
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: xylose adenosine (rxyloA)

<400> SEQUENCE: 635
gcucauuuac cagcguaaau gagc                                          24

<210> SEQ ID NO 636
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: modified_base
<222> LOCATION: (20)..(20)
<223> OTHER INFORMATION: xylose uridine (rxyloU)

<400> SEQUENCE: 636
gcucauuuac cagcguaaau gagc                                              24

<210> SEQ ID NO 637
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: xylose guanosine (rxyloG)

<400> SEQUENCE: 637
gcucauuuac cagcguaaau gagc                                              24

<210> SEQ ID NO 638
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: xylose adenosine (rxyloA)

<400> SEQUENCE: 638
gcucauuuac cagcguaaau gagc                                              24

<210> SEQ ID NO 639
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(23)
<223> OTHER INFORMATION: xylose guanosine (rxyloG)

<400> SEQUENCE: 639
gcucauuuac cagcguaaau gagc                                              24

<210> SEQ ID NO 640
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: arabinose cytidine (araC)

<400> SEQUENCE: 640
gcucauuuac cagcguaaau gagc                                              24

<210> SEQ ID NO 641
```

-continued

```
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: arabinose uridine (araU)

<400> SEQUENCE: 641
gcucauuuac cagcguaaau gagc                                            24

<210> SEQ ID NO 642
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: arabinose cytidine (araC)

<400> SEQUENCE: 642
gcucauuuac cagcguaaau gagc                                            24

<210> SEQ ID NO 643
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: arabinose adenosine (araA)

<400> SEQUENCE: 643
gcucauuuac cagcguaaau gagc                                            24

<210> SEQ ID NO 644
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: arabinose uridine (araU)

<400> SEQUENCE: 644
gcucauuuac cagcguaaau gagc                                            24

<210> SEQ ID NO 645
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: arabinose uridine (araU)
```

-continued

```
<400> SEQUENCE: 645
gcucauuuac cagcguaaau gagc                                          24

<210> SEQ ID NO 646
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: arabinose uridine (araU)

<400> SEQUENCE: 646
gcucauuuac cagcguaaau gagc                                          24

<210> SEQ ID NO 647
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: arabinose adenosine (araA)

<400> SEQUENCE: 647
gcucauuuac cagcguaaau gagc                                          24

<210> SEQ ID NO 648
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: arabinose cytidine (araC)

<400> SEQUENCE: 648
gcucauuuac cagcguaaau gagc                                          24

<210> SEQ ID NO 649
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: arabinose cytidine (araC)

<400> SEQUENCE: 649
gcucauuuac cagcguaaau gagc                                          24

<210> SEQ ID NO 650
<211> LENGTH: 24
<212> TYPE: RNA
<213> ORGANISM: Artificial Sequence
<220> FEATURE:
<223> OTHER INFORMATION: Description of Artificial Sequence: Synthetic
```

```
            oligonucleotide
<220> FEATURE:
<221> NAME/KEY: modified_base
<222> LOCATION: (12)..(12)
<223> OTHER INFORMATION: arabinose adenosine (araA)

<400> SEQUENCE: 650
gcucauuuac cagcguaaau gagc                                          24

<210> SEQ ID NO 651
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: arabinose cytidine (araC)

<400> SEQUENCE: 651
gcucauuuac cagcguaaau gagc                                          24

<210> SEQ ID NO 652
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: arabinose uridine (araU)

<400> SEQUENCE: 652
gcucauuuac cagcguaaau gagc                                          24

<210> SEQ ID NO 653
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: arabinose adenosine (araA)

<400> SEQUENCE: 653
gcucauuuac cagcguaaau gagc                                          24

<210> SEQ ID NO 654
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: arabinose adenosine (araA)

<400> SEQUENCE: 654
gcucauuuac cagcguaaau gagc                                          24
```

```
<210> SEQ ID NO 655
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: arabinose adenosine (araA)

<400> SEQUENCE: 655
gcucauuuac cagcguaaau gagc                                              24

<210> SEQ ID NO 656
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: arabinose uridine (araU)

<400> SEQUENCE: 656
gcucauuuac cagcguaaau gagc                                              24

<210> SEQ ID NO 657
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: arabinose adenosine (araA)

<400> SEQUENCE: 657
gcucauuuac cagcguaaau gagc                                              24

<210> SEQ ID NO 658
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: xylose uridine (rxyloU)

<400> SEQUENCE: 658
gcucauuuac cagcguaaau gagc                                              24

<210> SEQ ID NO 659
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: xylose uridine (rxyloU)
```

```
<400> SEQUENCE: 659
gcucauuuac cagcguaaau gagc                                          24

<210> SEQ ID NO 660
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: xylose uridine (rxyloU)

<400> SEQUENCE: 660
gcucauuuac cagcguaaau gagc                                          24

<210> SEQ ID NO 661
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: xylose cytidine (rxyloC)

<400> SEQUENCE: 661
gcucauuuac cagcguaaau gagc                                          24

<210> SEQ ID NO 662
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: xylose adenosine (rxyloA)

<400> SEQUENCE: 662
gcucauuuac cagcguaaau gagc                                          24

<210> SEQ ID NO 663
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: xylose guanosine (rxyloG)

<400> SEQUENCE: 663
gcucauuuac cagcguaaau gagc                                          24

<210> SEQ ID NO 664
<211> LENGTH: 24
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: xylose cytidine (rxyloC)

<400> SEQUENCE: 664
gcucauuuac cagcguaaau gagc                                          24

<210> SEQ ID NO 665
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(15)
<223> OTHER INFORMATION: xylose guanosine (rxyloG)

<400> SEQUENCE: 665
gcucauuuac cagcguaaau gagc                                          24

<210> SEQ ID NO 666
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: xylose uridine (rxyloU)

<400> SEQUENCE: 666
gcucauuuac cagcguaaau gagc                                          24

<210> SEQ ID NO 667
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: xylose adenosine (rxyloA)

<400> SEQUENCE: 667
gcucauuuac cagcguaaau gagc                                          24

<210> SEQ ID NO 668
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: xylose adenosine (rxyloA)

<400> SEQUENCE: 668
gcucauuuac cagcguaaau gagc                                          24
```

<210> SEQ ID NO 669
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (19)..(19)
<223> OTHER INFORMATION: xylose adenosine (rxyloA)

<400> SEQUENCE: 669
gcucauuuac cagcguaaau gagc    24

<210> SEQ ID NO 670
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (20)..(20)
<223> OTHER INFORMATION: xylose uridine (rxyloU)

<400> SEQUENCE: 670
gcucauuuac cagcguaaau gagc    24

<210> SEQ ID NO 671
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (21)..(21)
<223> OTHER INFORMATION: xylose guanosine (rxyloG)

<400> SEQUENCE: 671
gcucauuuac cagcguaaau gagc    24

<210> SEQ ID NO 672
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (22)..(22)
<223> OTHER INFORMATION: xylose adenosine (rxyloA)

<400> SEQUENCE: 672
gcucauuuac cagcguaaau gagc    24

<210> SEQ ID NO 673
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (23)..(23)

<223> OTHER INFORMATION: xylose guanosine (rxyloG)

<400> SEQUENCE: 673
gcucauuuac cagcguaaau gagc                                              24

<210> SEQ ID NO 674
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-amino-guanosine (amiG)

<400> SEQUENCE: 674
gcucauuuac cagcguaaau gagc                                              24

<210> SEQ ID NO 675
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-amino-cytidine (amiC)

<400> SEQUENCE: 675
gcucauuuac cagcguaaau gagc                                              24

<210> SEQ ID NO 676
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 2'-amino-uridine (amiU)

<400> SEQUENCE: 676
gcucauuuac cagcguaaau gagc                                              24

<210> SEQ ID NO 677
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: 2'-amino-adenosine (amiA)

<400> SEQUENCE: 677
gcucauuuac cagcguaaau gagc                                              24

<210> SEQ ID NO 678
<211> LENGTH: 24
<212> TYPE: RNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: 2'-amino-uridine (amiU)

<400> SEQUENCE: 678
gcucauuuac cagcguaaau gagc                                              24

<210> SEQ ID NO 679
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 2'-amino-uridine (amiU)

<400> SEQUENCE: 679
gcucauuuac cagcguaaau gagc                                              24

<210> SEQ ID NO 680
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: 2'-amino-uridine (amiU)

<400> SEQUENCE: 680
gcucauuuac cagcguaaau gagc                                              24

<210> SEQ ID NO 681
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: 2'-amino-cytidine (amiC)

<400> SEQUENCE: 681
gcucauuuac cagcguaaau gagc                                              24

<210> SEQ ID NO 682
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: 2'-amino-adenosine (amiA)

<400> SEQUENCE: 682
gcucauuuac cagcguaaau gagc                                              24
```

<210> SEQ ID NO 683
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: 2'-amino-guanosine (amiG)

<400> SEQUENCE: 683
gcucauuuac cagcguaaau gagc                                           24

<210> SEQ ID NO 684
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: 2'-amino-cytidine (amiC)

<400> SEQUENCE: 684
gcucauuuac cagcguaaau gagc                                           24

<210> SEQ ID NO 685
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: 2'-amino-uridine (amiU)

<400> SEQUENCE: 685
gcucauuuac cagcguaaau gagc                                           24

<210> SEQ ID NO 686
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: 2'-amino-adenosine (amiA)

<400> SEQUENCE: 686
gcucauuuac cagcguaaau gagc                                           24

<210> SEQ ID NO 687
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base

```
<222> LOCATION: (19)..(19)
<223> OTHER INFORMATION: 2'-amino-adenosine (amiA)

<400> SEQUENCE: 687
gcucauuuac cagcguaaau gagc                                          24

<210> SEQ ID NO 688
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: 2'-amino-uridine (amiU)

<400> SEQUENCE: 688
gcucauuuac cagcguaaau gagc                                          24

<210> SEQ ID NO 689
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: 2'-amino-guanosine (amiG)

<400> SEQUENCE: 689
gcucauuuac cagcguaaau gagc                                          24

<210> SEQ ID NO 690
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: 2'-amino-adenosine (amiA)

<400> SEQUENCE: 690
gcucauuuac cagcguaaau gagc                                          24

<210> SEQ ID NO 691
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(23)
<223> OTHER INFORMATION: 2'-amino-guanosine (amiG)

<400> SEQUENCE: 691
gcucauuuac cagcguaaau gagc                                          24

<210> SEQ ID NO 692
<211> LENGTH: 24
<212> TYPE: RNA
```

<213> ORGANISM: Artificial Sequence
<220> FEATURE:
<223> OTHER INFORMATION: Description of Artificial Sequence: Synthetic
oligonucleotide

<400> SEQUENCE: 692
gcucauuuac cagcguaaau gagc                                          24

<210> SEQ ID NO 693
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 693
gcucauuuac cagcguaaau gagc                                          24

<210> SEQ ID NO 694
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 694
gcucauuuac cagcguaaau gagc                                          24

<210> SEQ ID NO 695
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 695
gcucauuuac cagcguaaau gagc                                          24

<210> SEQ ID NO 696
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 696
gcucauuuac cagcguaaau gagc                                          24

<210> SEQ ID NO 697
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 697
gcucauuuac cagcguaaau gagc                                          24

<210> SEQ ID NO 698
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 698
gcucauuuac cagcguaaau gagc                                              24

<210> SEQ ID NO 699
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 699
gcucauuuac cagcguaaau gagc                                              24

<210> SEQ ID NO 700
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 700
gcucauuuac cagcguaaau gagc                                              24

<210> SEQ ID NO 701
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 701
gcucauuuac cagcguaaau gagc                                              24

<210> SEQ ID NO 702
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 702
gcucauuuac cagcguaaau gagc                                              24

<210> SEQ ID NO 703
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 703
gcucauuuac cagcguaaau gagc                                              24

<210> SEQ ID NO 704
<211> LENGTH: 24
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 704
gcucauuuac cagcguaaau gagc                                              24

<210> SEQ ID NO 705
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 705
gcucauuuac cagcguaaau gagc                                              24

<210> SEQ ID NO 706
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 706
gcucauuuac cagcguaaau gagc                                              24

<210> SEQ ID NO 707
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 707
gcucauuuac cagcguaaau gagc                                              24

<210> SEQ ID NO 708
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 708
gcucauuuac cagcguaaau gagc                                              24

<210> SEQ ID NO 709
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 709
gcucauuuac cagcguaaau gagc                                              24

<210> SEQ ID NO 710
<211> LENGTH: 24
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 710
gcucauuuac cagcguaaau gagc                                          24

<210> SEQ ID NO 711
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 711
gcucauuuac cagcguaaau gagc                                          24

<210> SEQ ID NO 712
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 712
gcucauuuac cagcguaaau gagc                                          24

<210> SEQ ID NO 713
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 713
gcucauuuac cagcguaaau gagc                                          24

<210> SEQ ID NO 714
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-amino-guanosine (amiG)

<400> SEQUENCE: 714
gcucauuuac cagcguaaau gagc                                          24

<210> SEQ ID NO 715
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-amino-cytidine (amiC)

<400> SEQUENCE: 715
gcucauuuac cagcguaaau gagc                                          24

```
<210> SEQ ID NO 716
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 2'-amino-uridine (amiU)

<400> SEQUENCE: 716
gcucauuuac cagcguaaau gagc                                          24

<210> SEQ ID NO 717
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: 2'-amino-cytidine (amiC)

<400> SEQUENCE: 717
gcucauuuac cagcguaaau gagc                                          24

<210> SEQ ID NO 718
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: 2'-amino-adenosine (amiA)

<400> SEQUENCE: 718
gcucauuuac cagcguaaau gagc                                          24

<210> SEQ ID NO 719
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: 2'-amino-uridine (amiU)

<400> SEQUENCE: 719
gcucauuuac cagcguaaau gagc                                          24

<210> SEQ ID NO 720
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
```

<223> OTHER INFORMATION: 2'-amino-uridine (amiU)

<400> SEQUENCE: 720
gcucauuuac cagcguaaau gagc                                              24

<210> SEQ ID NO 721
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: 2'-amino-uridine (amiU)

<400> SEQUENCE: 721
gcucauuuac cagcguaaau gagc                                              24

<210> SEQ ID NO 722
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: 2'-amino-cytidine (amiC)

<400> SEQUENCE: 722
gcucauuuac cagcguaaau gagc                                              24

<210> SEQ ID NO 723
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: 2'-amino-cytidine (amiC)

<400> SEQUENCE: 723
gcucauuuac cagcguaaau gagc                                              24

<210> SEQ ID NO 724
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: 2'-amino-adenosine (amiA)

<400> SEQUENCE: 724
gcucauuuac cagcguaaau gagc                                              24

<210> SEQ ID NO 725
<211> LENGTH: 24
<212> TYPE: RNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: 2'-amino-guanosine (amiG)

<400> SEQUENCE: 725
gcucauuuac cagcguaaau gagc                                          24

<210> SEQ ID NO 726
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: 2'-amino-cytidine (amiC)

<400> SEQUENCE: 726
gcucauuuac cagcguaaau gagc                                          24

<210> SEQ ID NO 727
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(15)
<223> OTHER INFORMATION: 2'-amino-guanosine (amiG)

<400> SEQUENCE: 727
gcucauuuac cagcguaaau gagc                                          24

<210> SEQ ID NO 728
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: 2'-amino-uridine (amiU)

<400> SEQUENCE: 728
gcucauuuac cagcguaaau gagc                                          24

<210> SEQ ID NO 729
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: 2'-amino-adenosine (amiA)

<400> SEQUENCE: 729
gcucauuuac cagcguaaau gagc                                          24
```

<210> SEQ ID NO 730
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: 2'-amino-adenosine (amiA)

<400> SEQUENCE: 730
gcucauuuac cagcguaaau gagc                                           24

<210> SEQ ID NO 731
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: 2'-amino-adenosine (amiA)

<400> SEQUENCE: 731
gcucauuuac cagcguaaau gagc                                           24

<210> SEQ ID NO 732
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: 2'-amino-uridine (amiU)

<400> SEQUENCE: 732
gcucauuuac cagcguaaau gagc                                           24

<210> SEQ ID NO 733
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: 2'-amino-adenosine (amiA)

<400> SEQUENCE: 733
gcucauuuac cagcguaaau gagc                                           24

<210> SEQ ID NO 734
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base

```
<222> LOCATION: (23)..(23)
<223> OTHER INFORMATION: 2'-amino-guanosine (amiG)

<400> SEQUENCE: 734
gcucauuuac cagcguaaau gagc                                              24

<210> SEQ ID NO 735
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 735
gcucauuuac cagcguaaau gagc                                              24

<210> SEQ ID NO 736
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 736
gcucauuuac cagcguaaau gagc                                              24

<210> SEQ ID NO 737
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 737
gcucauuuac cagcguaaau gagc                                              24

<210> SEQ ID NO 738
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 738
gcucauuuac cagcguaaau gagc                                              24

<210> SEQ ID NO 739
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 739
gcucauuuac cagcguaaau gagc                                              24

<210> SEQ ID NO 740
<211> LENGTH: 24
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 740
gcucauuuac cagcguaaau gagc                                               24

<210> SEQ ID NO 741
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 741
gcucauuuac cagcguaaau gagc                                               24

<210> SEQ ID NO 742
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 742
gcucauuuac cagcguaaau gagc                                               24

<210> SEQ ID NO 743
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 743
gcucauuuac cagcguaaau gagc                                               24

<210> SEQ ID NO 744
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 744
gcucauuuac cagcguaaau gagc                                               24

<210> SEQ ID NO 745
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 745
gcucauuuac cagcguaaau gagc                                               24

<210> SEQ ID NO 746
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 746
gcucauuuac cagcguaaau gagc                                          24

<210> SEQ ID NO 747
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 747
gcucauuuac cagcguaaau gagc                                          24

<210> SEQ ID NO 748
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 748
gcucauuuac cagcguaaau gagc                                          24

<210> SEQ ID NO 749
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 749
gcucauuuac cagcguaaau gagc                                          24

<210> SEQ ID NO 750
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 750
gcucauuuac cagcguaaau gagc                                          24

<210> SEQ ID NO 751
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 751
gcucauuuac cagcguaaau gagc                                          24

<210> SEQ ID NO 752
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 752
gcucauuuac cagcguaaau gagc                                              24

<210> SEQ ID NO 753
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 753
gcucauuuac cagcguaaau gagc                                              24

<210> SEQ ID NO 754
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 754
gcucauuuac cagcguaaau gagc                                              24

<210> SEQ ID NO 755
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 4'-alkynyl, 2'-deoxy-guanosine (4alk-dG)

<400> SEQUENCE: 755
gcucauuuac cagcguaaau gagc                                              24

<210> SEQ ID NO 756
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 4'-alkynyl, 2'-deoxy-cytidine (4alk-dC)

<400> SEQUENCE: 756
gcucauuuac cagcguaaau gagc                                              24

<210> SEQ ID NO 757
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: 4'-alkynyl, 2'-deoxy-uridine (4alk-dU)

<400> SEQUENCE: 757
gcucauuuac cagcguaaau gagc                                              24

<210> SEQ ID NO 758
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (4)..(4)
<223> OTHER INFORMATION: 4'-alkynyl, 2'-deoxy-cytidine (4alk-dC)

<400> SEQUENCE: 758
gcucauuuac cagcguaaau gagc                                              24

<210> SEQ ID NO 759
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(5)
<223> OTHER INFORMATION: 4'-alkynyl, 2'-deoxy-adenosine (4alk-dA)

<400> SEQUENCE: 759
gcucauuuac cagcguaaau gagc                                              24

<210> SEQ ID NO 760
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 4'-alkynyl, 2'-deoxy-uridine (4alk-dU)

<400> SEQUENCE: 760
gcucauuuac cagcguaaau gagc                                              24

<210> SEQ ID NO 761
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(7)
<223> OTHER INFORMATION: 4'-alkynyl, 2'-deoxy-uridine (4alk-dU)

<400> SEQUENCE: 761
gcucauuuac cagcguaaau gagc                                           24

<210> SEQ ID NO 762
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (8)..(8)
<223> OTHER INFORMATION: 4'-alkynyl, 2'-deoxy-uridine (4alk-dU)

<400> SEQUENCE: 762
gcucauuuac cagcguaaau gagc                                           24

<210> SEQ ID NO 763
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (9)..(9)
<223> OTHER INFORMATION: 4'-alkynyl, 2'-deoxy-adenosine (4alk-dA)

<400> SEQUENCE: 763
gcucauuuac cagcguaaau gagc                                           24

<210> SEQ ID NO 764
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (10)..(10)
<223> OTHER INFORMATION: 4'-alkynyl, 2'-deoxy-cytidine (4alk-dC)

<400> SEQUENCE: 764
gcucauuuac cagcguaaau gagc                                           24

<210> SEQ ID NO 765
<211> LENGTH: 24
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (12)..(12)
<223> OTHER INFORMATION: 4'-alkynyl, 2'-deoxy-adenosine (4alk-dA)

<400> SEQUENCE: 765
gcucauuuac cagcguaaau gagc                                              24

<210> SEQ ID NO 766
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (14)..(14)
<223> OTHER INFORMATION: 4'-alkynyl, 2'-deoxy-cytidine (4alk-dC)

<400> SEQUENCE: 766
gcucauuuac cagcguaaau gagc                                              24

<210> SEQ ID NO 767
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (15)..(15)
<223> OTHER INFORMATION: 4'-alkynyl, 2'-deoxy-guanosine (4alk-dG)

<400> SEQUENCE: 767
gcucauuuac cagcguaaau gagc                                              24

<210> SEQ ID NO 768
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (16)..(16)
<223> OTHER INFORMATION: 4'-alkynyl, 2'-deoxy-uridine (4alk-dU)

<400> SEQUENCE: 768
gcucauuuac cagcguaaau gagc                                              24

<210> SEQ ID NO 769
<211> LENGTH: 24
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (17)..(17)
<223> OTHER INFORMATION: 4'-alkynyl, 2'-deoxy-adenosine (4alk-dA)

<400> SEQUENCE: 769
gcucauuuac cagcguaaau gagc                                          24

<210> SEQ ID NO 770
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (18)..(18)
<223> OTHER INFORMATION: 4'-alkynyl, 2'-deoxy-adenosine (4alk-dA)

<400> SEQUENCE: 770
gcucauuuac cagcguaaau gagc                                          24

<210> SEQ ID NO 771
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (19)..(19)
<223> OTHER INFORMATION: 4'-alkynyl, 2'-deoxy-adenosine (4alk-dA)

<400> SEQUENCE: 771
gcucauuuac cagcguaaau gagc                                          24

<210> SEQ ID NO 772
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(20)
<223> OTHER INFORMATION: 4'-alkynyl, 2'-deoxy-uridine (4alk-dU)

<400> SEQUENCE: 772
gcucauuuac cagcguaaau gagc                                          24

<210> SEQ ID NO 773
<211> LENGTH: 24
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (22)..(22)
<223> OTHER INFORMATION: 4'-alkynyl, 2'-deoxy-adenosine (4alk-dA)

<400> SEQUENCE: 773
gcucauuuac cagcguaaau gagc                                             24

<210> SEQ ID NO 774
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-methoxy-4'-thio-guanosine (ome4SG)

<400> SEQUENCE: 774
gcucauuuac cagcguaaau gagc                                             24

<210> SEQ ID NO 775
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-methoxy-4'-thio-cytidine (ome4SC)

<400> SEQUENCE: 775
gcucauuuac cagcguaaau gagc                                             24

<210> SEQ ID NO 776
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 2'-methoxy-4'-thio-uridine (ome4SU)

<400> SEQUENCE: 776
gcucauuuac cagcguaaau gagc                                             24

<210> SEQ ID NO 777
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: 2'-methoxy-4'-thio-cytidine (ome4SC)
```

```
<400> SEQUENCE: 777
gcucauuuac cagcguaaau gagc                                              24

<210> SEQ ID NO 778
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: 2'-methoxy-4'-thio-adenosine (ome4SA)

<400> SEQUENCE: 778
gcucauuuac cagcguaaau gagc                                              24

<210> SEQ ID NO 779
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: 2'-methoxy-4'-thio-uridine (ome4SU)

<400> SEQUENCE: 779
gcucauuuac cagcguaaau gagc                                              24

<210> SEQ ID NO 780
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 2'-methoxy-4'-thio-uridine (ome4SU)

<400> SEQUENCE: 780
gcucauuuac cagcguaaau gagc                                              24

<210> SEQ ID NO 781
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: 2'-methoxy-4'-thio-uridine (ome4SU)

<400> SEQUENCE: 781
gcucauuuac cagcguaaau gagc                                              24

<210> SEQ ID NO 782
<211> LENGTH: 24
<212> TYPE: RNA
<213> ORGANISM: Artificial Sequence
<220> FEATURE:
<223> OTHER INFORMATION: Description of Artificial Sequence: Synthetic
```

```
    oligonucleotide
<220> FEATURE:
<221> NAME/KEY: modified_base
<222> LOCATION: (10)..(10)
<223> OTHER INFORMATION: 2'-methoxy-4'-thio-cytidine (ome4SC)

<400> SEQUENCE: 782
gcucauuuac cagcguaaau gagc                                              24

<210> SEQ ID NO 783
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: 2'-methoxy-4'-thio-guanosine (ome4SG)

<400> SEQUENCE: 783
gcucauuuac cagcguaaau gagc                                              24

<210> SEQ ID NO 784
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: 2'-methoxy-4'-thio-cytidine (ome4SC)

<400> SEQUENCE: 784
gcucauuuac cagcguaaau gagc                                              24

<210> SEQ ID NO 785
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(15)
<223> OTHER INFORMATION: 2'-methoxy-4'-thio-guanosine (ome4SG)

<400> SEQUENCE: 785
gcucauuuac cagcguaaau gagc                                              24

<210> SEQ ID NO 786
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: 2'-methoxy-4'-thio-uridine (ome4SU)

<400> SEQUENCE: 786
gcucauuuac cagcguaaau gagc                                              24
```

```
<210> SEQ ID NO 787
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: 2'-methoxy-4'-thio-adenosine (ome4SA)

<400> SEQUENCE: 787
gcucauuuac cagcguaaau gagc                                            24

<210> SEQ ID NO 788
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: 2'-methoxy-4'-thio-adenosine (ome4SA)

<400> SEQUENCE: 788
gcucauuuac cagcguaaau gagc                                            24

<210> SEQ ID NO 789
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: 2'-methoxy-4'-thio-adenosine (ome4SA)

<400> SEQUENCE: 789
gcucauuuac cagcguaaau gagc                                            24

<210> SEQ ID NO 790
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: 2'-methoxy-4'-thio-uridine (ome4SU)

<400> SEQUENCE: 790
gcucauuuac cagcguaaau gagc                                            24

<210> SEQ ID NO 791
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: 2'-methoxy-4'-thio-guanosine (ome4SG)
```

```
<400> SEQUENCE: 791
gcucauuuac cagcguaaau gagc                                           24

<210> SEQ ID NO 792
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(23)
<223> OTHER INFORMATION: 2'-methoxy-4'-thio-guanosine (ome4SG)

<400> SEQUENCE: 792
gcucauuuac cagcguaaau gagc                                           24

<210> SEQ ID NO 793
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 4'-alkynyl, 2'-deoxy-guanosine (4alk-dG)

<400> SEQUENCE: 793
gcucauuuac cagcguaaau gagc                                           24

<210> SEQ ID NO 794
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 4'-alkynyl, 2'-deoxy-cytidine (4alk-dC)

<400> SEQUENCE: 794
gcucauuuac cagcguaaau gagc                                           24

<210> SEQ ID NO 795
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: 4'-alkynyl, 2'-deoxy-uridine (4alk-dU)

<400> SEQUENCE: 795
```
gcucauuuac cagcguaaau gagc                                              24

<210> SEQ ID NO 796
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(5)
<223> OTHER INFORMATION: 4'-alkynyl, 2'-deoxy-adenosine (4alk-dA)

<400> SEQUENCE: 796
gcucauuuac cagcguaaau gagc                                              24

<210> SEQ ID NO 797
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 4'-alkynyl, 2'-deoxy-uridine (4alk-dU)

<400> SEQUENCE: 797
gcucauuuac cagcguaaau gagc                                              24

<210> SEQ ID NO 798
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(7)
<223> OTHER INFORMATION: 4'-alkynyl, 2'-deoxy-uridine (4alk-dU)

<400> SEQUENCE: 798
gcucauuuac cagcguaaau gagc                                              24

<210> SEQ ID NO 799
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (8)..(8)
<223> OTHER INFORMATION: 4'-alkynyl, 2'-deoxy-uridine (4alk-dU)

```
<400> SEQUENCE: 799
gcucauuuac cagcguaaau gagc                                           24

<210> SEQ ID NO 800
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (9)..(9)
<223> OTHER INFORMATION: 4'-alkynyl, 2'-deoxy-adenosine (4alk-dA)

<400> SEQUENCE: 800
gcucauuuac cagcguaaau gagc                                           24

<210> SEQ ID NO 801
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (12)..(12)
<223> OTHER INFORMATION: 4'-alkynyl, 2'-deoxy-adenosine (4alk-dA)

<400> SEQUENCE: 801
gcucauuuac cagcguaaau gagc                                           24

<210> SEQ ID NO 802
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (15)..(15)
<223> OTHER INFORMATION: 4'-alkynyl, 2'-deoxy-guanosine (4alk-dG)

<400> SEQUENCE: 802
gcucauuuac cagcguaaau gagc                                           24

<210> SEQ ID NO 803
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (16)..(16)
<223> OTHER INFORMATION: 4'-alkynyl, 2'-deoxy-uridine (4alk-dU)
```

<400> SEQUENCE: 803
gcucauuuac cagcguaaau gagc                                              24

<210> SEQ ID NO 804
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (17)..(17)
<223> OTHER INFORMATION: 4'-alkynyl, 2'-deoxy-adenosine (4alk-dA)

<400> SEQUENCE: 804
gcucauuuac cagcguaaau gagc                                              24

<210> SEQ ID NO 805
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (18)..(18)
<223> OTHER INFORMATION: 4'-alkynyl, 2'-deoxy-adenosine (4alk-dA)

<400> SEQUENCE: 805
gcucauuuac cagcguaaau gagc                                              24

<210> SEQ ID NO 806
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (19)..(19)
<223> OTHER INFORMATION: 4'-alkynyl, 2'-deoxy-adenosine (4alk-dA)

<400> SEQUENCE: 806
gcucauuuac cagcguaaau gagc                                              24

<210> SEQ ID NO 807
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(20)

<223> OTHER INFORMATION: 4'-alkynyl, 2'-deoxy-uridine (4alk-dU)

<400> SEQUENCE: 807
gcucauuuac cagcguaaau gagc                                                24

<210> SEQ ID NO 808
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (21)..(21)
<223> OTHER INFORMATION: 4'-alkynyl, 2'-deoxy-guanosine (4alk-dG)

<400> SEQUENCE: 808
gcucauuuac cagcguaaau gagc                                                24

<210> SEQ ID NO 809
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (22)..(22)
<223> OTHER INFORMATION: 4'-alkynyl, 2'-deoxy-adenosine (4alk-dA)

<400> SEQUENCE: 809
gcucauuuac cagcguaaau gagc                                                24

<210> SEQ ID NO 810
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (23)..(23)
<223> OTHER INFORMATION: 4'-alkynyl, 2'-deoxy-guanosine (4alk-dG)

<400> SEQUENCE: 810
gcucauuuac cagcguaaau gagc                                                24

<210> SEQ ID NO 811
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-methoxy-4'-thio-guanosine (ome4SG)

-continued

```
<400> SEQUENCE: 811
gcucauuuac cagcguaaau gagc                                          24

<210> SEQ ID NO 812
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-methoxy-4'-thio-cytidine (ome4SC)

<400> SEQUENCE: 812
gcucauuuac cagcguaaau gagc                                          24

<210> SEQ ID NO 813
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 2'-methoxy-4'-thio-uridine (ome4SU)

<400> SEQUENCE: 813
gcucauuuac cagcguaaau gagc                                          24

<210> SEQ ID NO 814
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: 2'-methoxy-4'-thio-cytidine (ome4SC)

<400> SEQUENCE: 814
gcucauuuac cagcguaaau gagc                                          24

<210> SEQ ID NO 815
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: 2'-methoxy-4'-thio-uridine (ome4SU)

<400> SEQUENCE: 815
gcucauuuac cagcguaaau gagc                                          24

<210> SEQ ID NO 816
<211> LENGTH: 24
<212> TYPE: RNA
<213> ORGANISM: Artificial Sequence
<220> FEATURE:
<223> OTHER INFORMATION: Description of Artificial Sequence: Synthetic
```

```
                          oligonucleotide
<220> FEATURE:
<221> NAME/KEY: modified_base
<222> LOCATION: (7)..(7)
<223> OTHER INFORMATION: 2'-methoxy-4'-thio-uridine (ome4SU)

<400> SEQUENCE: 816
gcucauuuac cagcguaaau gagc                                            24

<210> SEQ ID NO 817
<211> LENGTH: 24
<212> TYPE: RNA
<213> ORGANISM: Artificial Sequence
<220> FEATURE:
<223> OTHER INFORMATION: Description of Artificial Sequence: Synthetic
                          oligonucleotide
<220> FEATURE:
<221> NAME/KEY: modified_base
<222> LOCATION: (8)..(8)
<223> OTHER INFORMATION: 2'-methoxy-4'-thio-uridine (ome4SU)

<400> SEQUENCE: 817
gcucauuuac cagcguaaau gagc                                            24

<210> SEQ ID NO 818
<211> LENGTH: 24
<212> TYPE: RNA
<213> ORGANISM: Artificial Sequence
<220> FEATURE:
<223> OTHER INFORMATION: Description of Artificial Sequence: Synthetic
                          oligonucleotide
<220> FEATURE:
<221> NAME/KEY: modified_base
<222> LOCATION: (10)..(10)
<223> OTHER INFORMATION: 2'-methoxy-4'-thio-cytidine (ome4SC)

<400> SEQUENCE: 818
gcucauuuac cagcguaaau gagc                                            24

<210> SEQ ID NO 819
<211> LENGTH: 24
<212> TYPE: RNA
<213> ORGANISM: Artificial Sequence
<220> FEATURE:
<223> OTHER INFORMATION: Description of Artificial Sequence: Synthetic
                          oligonucleotide
<220> FEATURE:
<221> NAME/KEY: modified_base
<222> LOCATION: (12)..(12)
<223> OTHER INFORMATION: 2'-methoxy-4'-thio-adenosine (ome4SA)

<400> SEQUENCE: 819
gcucauuuac cagcguaaau gagc                                            24

<210> SEQ ID NO 820
<211> LENGTH: 24
<212> TYPE: RNA
<213> ORGANISM: Artificial Sequence
<220> FEATURE:
<223> OTHER INFORMATION: Description of Artificial Sequence: Synthetic
                          oligonucleotide
<220> FEATURE:
<221> NAME/KEY: modified_base
<222> LOCATION: (13)..(13)
<223> OTHER INFORMATION: 2'-methoxy-4'-thio-guanosine (ome4SG)

<400> SEQUENCE: 820
gcucauuuac cagcguaaau gagc                                            24
```

```
<210> SEQ ID NO 821
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: 2'-methoxy-4'-thio-cytidine (ome4SC)

<400> SEQUENCE: 821
gcucauuuac cagcguaaau gagc                                              24

<210> SEQ ID NO 822
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(15)
<223> OTHER INFORMATION: 2'-methoxy-4'-thio-guanosine (ome4SG)

<400> SEQUENCE: 822
gcucauuuac cagcguaaau gagc                                              24

<210> SEQ ID NO 823
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: 2'-methoxy-4'-thio-uridine (ome4SU)

<400> SEQUENCE: 823
gcucauuuac cagcguaaau gagc                                              24

<210> SEQ ID NO 824
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: 2'-methoxy-4'-thio-adenosine (ome4SA)

<400> SEQUENCE: 824
gcucauuuac cagcguaaau gagc                                              24

<210> SEQ ID NO 825
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: 2'-methoxy-4'-thio-adenosine (ome4SA)
```

-continued

```
<400> SEQUENCE: 825
gcucauuuac cagcguaaau gagc                                              24

<210> SEQ ID NO 826
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: 2'-methoxy-4'-thio-uridine (ome4SU)

<400> SEQUENCE: 826
gcucauuuac cagcguaaau gagc                                              24

<210> SEQ ID NO 827
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: 2'-methoxy-4'-thio-guanosine (ome4SG)

<400> SEQUENCE: 827
gcucauuuac cagcguaaau gagc                                              24

<210> SEQ ID NO 828
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: 2'-methoxy-4'-thio-adenosine (ome4SA)

<400> SEQUENCE: 828
gcucauuuac cagcguaaau gagc                                              24

<210> SEQ ID NO 829
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(23)
<223> OTHER INFORMATION: 2'-methoxy-4'-thio-guanosine (ome4SG)

<400> SEQUENCE: 829
gcucauuuac cagcguaaau gagc                                              24

<210> SEQ ID NO 830
<211> LENGTH: 24
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 830
gcucauuuac cagcguaaau gagc                                              24

<210> SEQ ID NO 831
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 831
gcucauuuac cagcguaaau gagc                                              24

<210> SEQ ID NO 832
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 832
gcucauuuac cagcguaaau gagc                                              24

<210> SEQ ID NO 833
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 833
gcucauuuac cagcguaaau gagc                                              24

<210> SEQ ID NO 834
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 834
gcucauuuac cagcguaaau gagc                                              24

<210> SEQ ID NO 835
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 835
gcucauuuac cagcguaaau gagc                                              24

<210> SEQ ID NO 836
<211> LENGTH: 24
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 836
gcucauuuac cagcguaaau gagc                                          24

<210> SEQ ID NO 837
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 837
gcucauuuac cagcguaaau gagc                                          24

<210> SEQ ID NO 838
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 838
gcucauuuac cagcguaaau gagc                                          24

<210> SEQ ID NO 839
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 839
gcucauuuac cagcguaaau gagc                                          24

<210> SEQ ID NO 840
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 840
gcucauuuac cagcguaaau gagc                                          24

<210> SEQ ID NO 841
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 841
gcucauuuac cagcguaaau gagc                                          24

<210> SEQ ID NO 842
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide -continued

```
<220> FEATURE:
<223> OTHER INFORMATION: Description of Combined DNA/RNA Molecule:
      Synthetic oligonucleotide

<400> SEQUENCE: 842
gcucauuuac cagcguaaau gagc                                          24

<210> SEQ ID NO 843
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: 2'-methoxy-4'-thio-uridine (ome4SU)

<400> SEQUENCE: 843
gcucauuuac cagcguaaau gagc                                          24

<210> SEQ ID NO 844
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (4)..(4)
<223> OTHER INFORMATION: 4'-alkynyl, 2'-deoxy-cytidine (4alk-dC)

<400> SEQUENCE: 844
gcucauuuac cagcguaaau gagc                                          24
```